United States Patent
Weiner et al.

(10) Patent No.: US 7,439,034 B2
(45) Date of Patent: Oct. 21, 2008

(54) ALGINASES, SYSTEMS CONTAINING ALGINASES AND METHODS OF CLONING, PURIFYING AND/OR UTILIZING ALGINASES

(75) Inventors: Ronald M. Weiner, Potomac, MD (US); Steven W. Hutcheson, Columbia, MD (US); Ahmed Abdel-Wahab Abdel-Hafez, Nasr (EG); Michael Howard, Diamondhead, MS (US); Larry Edmund Taylor, II, Palmyra, PA (US); Nathan A. Ekborg, Annapolis, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 11/141,691

(22) Filed: Jun. 1, 2005

(65) Prior Publication Data
US 2006/0128946 A1 Jun. 15, 2006

Related U.S. Application Data

(60) Provisional application No. 60/576,000, filed on Jun. 1, 2004.

(51) Int. Cl.
| | |
|---|---|
| *C12Q 1/34* | (2006.01) |
| *C12N 1/20* | (2006.01) |
| *C12N 9/14* | (2006.01) |
| *C12P 21/06* | (2006.01) |
| *C07H 21/04* | (2006.01) |

(52) U.S. Cl. ............... 435/18; 435/69.1; 435/252.3; 435/195; 536/23.2; 536/23.7

(58) Field of Classification Search ............... None
See application file for complete search history.

(56) References Cited

U.S. PATENT DOCUMENTS 5,348,875 A * 9/1994 Murata et al. ............ 435/200

FOREIGN PATENT DOCUMENTS

WO  WO 99/14312 A1  3/1999

OTHER PUBLICATIONS

Franklin et al., Identification of algF in the alginate biosynthetic gene cluster of Pseudomonas aeruginosa which is required for alginate acetylaton. J. Bacteriol., 1993, vol. 175 (16): 5057-5065.*
Witkowski et al., Conversion of b-ketoacyl synthase to a malonyl decarboxylase by replacement of the active-site cysteine with glutamate. Biochemistry, 1999, vol. 38: 11643-11650.*
Seffernick et al., Melamine deaminase and atrazine chlorohydrolase: 98 percent identical but functionally different. J. Bacteriol., 2001, vol. 183 (8): 2405-2410.*
Whisstock et al., Prediction of protein function from protein sequence and structure. Q. Rev. Biophys., 2003, Vil. 36 (3): 307-340.*

* cited by examiner

*Primary Examiner*—Rebecca E. Prouty
*Assistant Examiner*—Ganapathirama Raghu
(74) *Attorney, Agent, or Firm*—Arent Fox LLP

(57) ABSTRACT

The present invention relates to cell wall degradative systems, in particular to systems containing enzymes that bind to and/or depolymerize cellulose. These systems have a number of applications.

2 Claims, 34 Drawing Sheets

```
Class 1

AlgA    110  TFYTSPQTGAMVFNCPTHGSTTSSATKYSRTELREMLRGLNTRPSTKGIGRNNWVLSTAP
AlgD    381  YFYTG-SDGGMVFKCPISGYKTSTGTSYTRTELREMLRAGNTSIATSGVNKNNWVFGSAP
AlgE    291  FFYTA-ADGGMVFKCPVAGFKTSTNTSYTRVELREMLRRGNSSISTQGVNGNNWVFGSAP
AlgK     48  YFYVN-SEGGIVEATPNQATTTS-GSSNSRSELRQMIRGTNTRIGTKSPG-NNEALASHP

AlgA    170  HQNQVSAGGIDCTLEAVLSVDYVSQT-GP--AHMIGRVIVGQIHGEDD------------
AlgD    440  SSAQAAAGGVDGNMKATLAVNYVTTT-GD--SSQVGRVITGQIHAEKN------------
AlgE    350  QSDLNAAGGIDGNLRATLAVNKVTTTHGDGFEYQVGRVITGQIHANDD------------
AlgK    106  QA--KAFGDIGGNLKATLAVNHVALNAKYTDKFPAYSVVVGQIHAGKDKDLIAKGEGYGW

AlgA    215  --EPVRTYYRKLPHNIKGSVYFASEH------PGGEDVHYPMIGSSSNSAADPED-GIAL
AlgD    185  --EPIRLYYRKLPGNSKGGIYYAHED------ADGGEVWVDMIGSRSSSASNPSD-GIAL
AlgE    390  --EPIRLYYRKLPSNSKGSTYFAHEL------LDGDDTWHEMIGSRGDNASDPAD-GIAL
AlgK    164  GNEPIKTYYKKWPDHKTGSVEWTYERNLEKANPDRTDIAYPVWGNTWDNSENPGDKGIAL

AlgA    266  GEKWGYRIHIEGRQLSVRIIREDGRYVEQSLTIG---EAY---N---------NDWFYFK
AlgD    536  NEVFSYEIDVTNNMLTVKIYRDGKSTVTSQYNMVN--SGY---DDS-------DDWMYFK
AlgE    449  DEIFSYEIDVRGNTLTVTIMREGKPDVTKVLDMSA--SGY---DEG-------GQYMYFK
AlgK    224  DESFSYEINVYKDIMHLTFTAANKPTVKYSINLANNVNAYGKVDEKDHPKGYLGDWLYFK

AlgA    311  AGVYNQ---NND---------GNPD--------EYAQASFEKLATHKQYNKQ
AlgD    584  AGVYNQ---NNT---------GNGS--------DYVQATFYSLTHTHD-----
AlgE    497  AGVYNQ---NNS---------GDPD--------DYVQATFYALEATHN-----
AlgK    284  AGAYDQCSVKDDPGFWYPACAGTGDWETDKKNGDYTRVTFTKLELGKGYSVSK

Class 2

AlgC      45  ASWESYDAYAEQLNADKTN-EDAF---MAEGVVVPMPKDAGGYTHEQHKRNYKAIRNAGF
AlgF-2  1101  ATLAASAGDTIEIGAGDYANMGTVVTDGVTITRAEGSNAVISGEFCLQVSGDGARITGL
AlgG     532  AIYKPIAGHVYEITAYVYG-HGTIGTQDLGSDNVYETSTAHGNSWQQISVTYVSTGSPAM

AlgC     103  LYQVTG----DEKYLTF-AKD---LLLAYAK-MYP-SLGEHPNRKEQSPGR-LFWQS---
AlgF-2  1161  EEADLIVP-ADSANHCRSNGDGNIVITGDDVVFDHNLLSGDAEFPIPVDDDDHNWLVLKG
AlgG     591  LYAKYGPGSGDSYFDVFDAKD---ISTAEDLSKQP-PAPIMR-YASQVIDL-SWWKITLP

AlgC     149  IN--EAVW----LVYSIQGYDAII---DGIAAFEKQ----EIESGVFLPMAKF------L
AlgF-2  1220  SN--ALVER---NTEQNRRGIAA----DGVS-QVRCGFISIYVNGSATGNTVQ------Y
AlgG     645  INNAMEIYTPELLTYEIDPIFKLVEDEDGYAVQFRANHGGSTTGGSSNPRSELRELTQNY

AlgC     190  SVESPETFNKIHN----HCTWAVAAVGMTGYVL----------GNDE---LVEISL-MG
AlgF-2  1264  NFFKDMLLNDQST---AYAIMFGRTTGLDSMED----------GFNTIQYNRFDNIDSKT
AlgG     705  HYRNSKSAAAWSNTSGTHEMWIKQKVTHLIYVKPHVVVGQIHDSGDDVTVFRVEGHLGQG

AlgC     231  --IDKTCKAGFMKQLDKLESP---D--GYYTEGPVYQRYAL-MPFIWFAKAIETNEPERK
AlgF-2  1311  RVIRVQGSSNTIS-HNTVVNS---Q--GMLALESGQNNVVS-YNVILPSG-TDSNDGCIS
AlgG     765  GDWDNNGTVGVMDTHANEWIINGNDRHGYLVDDNYELGTVFTVKFIARDGKVEYEYNGRK

AlgC     283  I----FEYRNNILEKA-VYTI---------IDESYAG-YFRP--INDAL-
AlgF-2  1363  AAP-YGHTIVGNYIAGSNTISSERGAIYLNNDVDEPGNLAAT--PSAVEI
AlgG     825  EDYVHEESFSGAYFKLGNYTQSHNGTAPGETDDAYAETYVYDYYIKHTE-
```

Figure 9a

```
Class 3

AlgB  220  ETLRIGTSHFSLSDSFTLVENNYFDR---CNGELEIISNKSGSNKFIGNTFFESRGTLTMR
algH  288  EGIRIGTSDSHTGDSFSVIEHNYFER--IQGEAEVISNKSGNNRIEHNTVRNSYGSTTTR
algI  217  EALLVGDSNMQHVDAKVTVANNLFYDASILGEPEVISNKSSSNIYRSNTVRNTTASLTLR AlgB  278  HGHGNVIENNVFFGNGKDHTGGIRVINERQTVRNNYMSDLAGYRFGG----GLVVMNGV-
algH  346  HGSSATITNNFIIGDGHPYAGGLRIIDDGHTVINNYIQGARYLATTHH---GGIVLMGS-
algI  277  HGNRNTMENNWFLQDQTEGSGGIRVIGDDNIIHNNYIAGSAGGGKSAAYRPALGIAAGYS AlgB  333  ---PNSAINRYHQVKNAVIENNTLVNVDH-IQLAAGSDKE---RTATPVDSKFSNNLIVN
algH  402  ---DGSTTNGYQQLTNVLVAHNTVVDSVN-SLNVDGGQK----STNPNNVYLVNNIIAN
algI  337  KKDDDANINGYQLSERNVLSNNSVIQSAQPVMLSTWYDRGKLSMTRPPMQTTFINNLVYQ AlgB  386  DDK--------RNPFTVYDDVSGITFSNNSISAASKELKKGFEVDAAKIAKNDQGMVFDA
algH  453  GIG--------PVITEAADGMPGSSVIAGNIFYGQSFSDSSSLTSVDGITWLDVAFAADM
algI  397  LDVAPSTADWVRGLAISVDYTPDSEYGNNYGIDKAEYVPSFAKVKGNITDGKVSPLVSKG AlgB  438  SGTYG--------ASKS----LKPVRKQDVGASWFVKS-EDRKAFQSGKIVKAGAGQNS-
algH  505  QGVMR--------ATGS----SPDLTAAAADTGDFAAVTEDMDGLARAAITQAGADDDIG
algI  457  TKAESKKELKGCDAFGTGDIVYLPLKKAGADLSKMDEPLVWTDTVKSARLGPDWLNANWG AlgB       ---------
algH  553  GNPVRGI--
algI  517  GEKKAYKGC
```

Figure 9b (A)
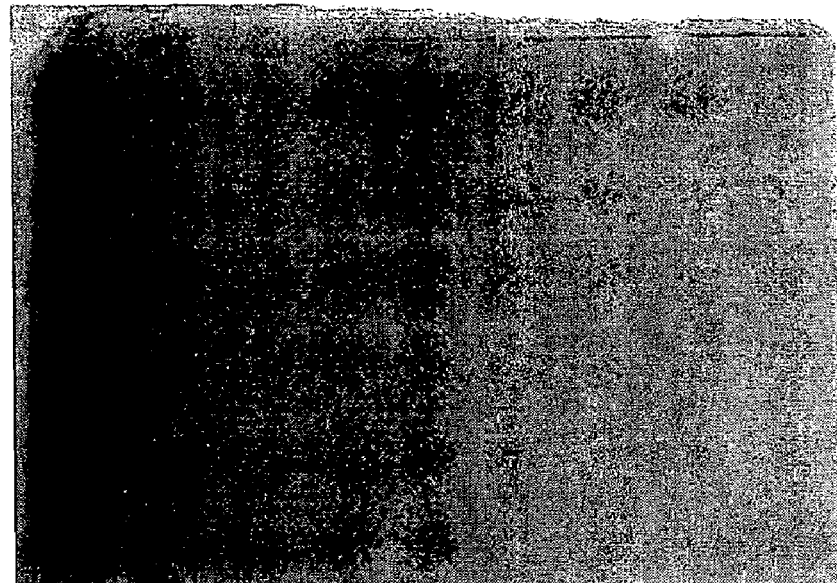
(B)
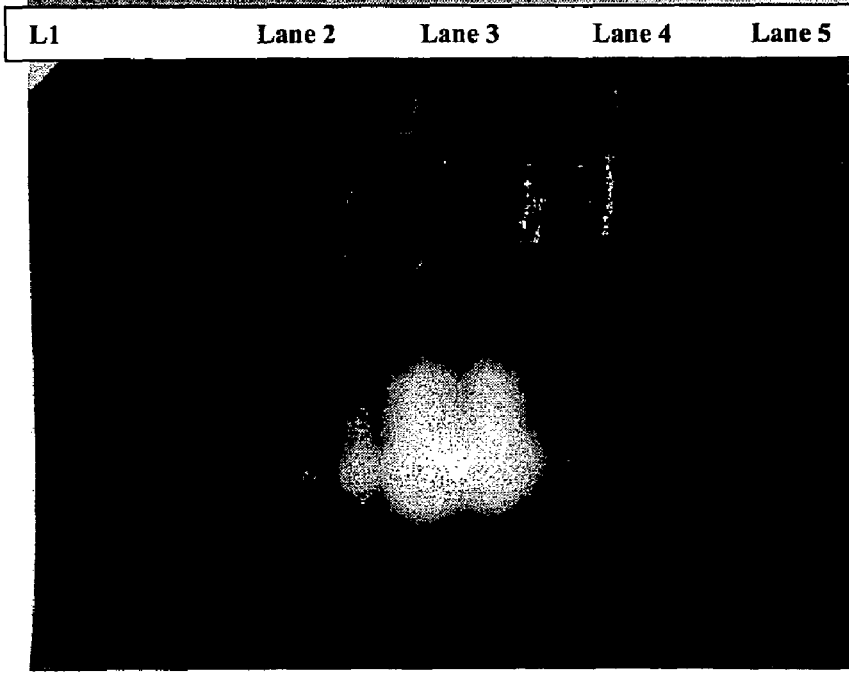
Figure 17

SEQUENCE LISTING

<160> NUMBER OF SEQ ID NOS: 70

<210> SEQ ID NO 1
<211> LENGTH: 234
<212> TYPE: PRT
<213> ORGANISM: Microbulbifer degradans 2-40

<400> SEQUENCE: 1

```
Thr Phe Tyr Thr Ser Pro Gln Thr Gly Ala Met Val Phe Asn Cys Pro
  1               5                  10                  15

Thr His Gly Ser Thr Thr Ser Ser Ala Thr Lys Tyr Ser Arg Thr Glu
             20                  25                  30

Leu Arg Glu Met Leu Arg Gly Leu Asn Thr Arg Pro Ser Thr Lys Gly
         35                  40                  45

Ile Gly Arg Asn Asn Trp Val Leu Ser Thr Ala Pro His Gln Asn Gln
     50                  55                  60

Val Ser Ala Gly Gly Ile Asp Gly Thr Leu Glu Ala Val Leu Ser Val
 65                  70                  75                  80

Asp Tyr Val Ser Gln Thr Gly Pro Ala His Met Ile Gly Arg Val Ile
                 85                  90                  95

Val Gly Gln Ile His Gly Glu Asp Asp Glu Pro Val Arg Ile Tyr Tyr
            100                 105                 110

Arg Lys Leu Pro His Asn Thr Lys Gly Ser Val Tyr Phe Ala Ser Glu
        115                 120                 125

His Pro Gly Gly Glu Asp Val Phe Tyr Pro Met Ile Gly Ser Ser Ser
    130                 135                 140

Asn Ser Ala Ala Asp Pro Glu Asp Gly Ile Ala Leu Gly Glu Lys Trp
145                 150                 155                 160

Gly Tyr Arg Ile His Ile Glu Gly Arg Gln Leu Ser Val Arg Ile Ile
                165                 170                 175

Arg Glu Asp Gly Arg Tyr Val Glu Gln Ser Leu Thr Ile Gly Glu Ala
            180                 185                 190

Tyr Asn Asn Asp Trp Phe Tyr Phe Lys Ala Gly Val Tyr Asn Gln Asn
        195                 200                 205

Asn Asp Gly Asn Pro Asp Glu Tyr Ala Gln Ala Ser Phe Phe Lys Leu
    210                 215                 220

Lys Ala Thr His Lys Gln Tyr Asn Lys Gln
225                 230
```

<210> SEQ ID NO 2
<211> LENGTH: 231
<212> TYPE: PRT
<213> ORGANISM: Microbulbifer degradans 2-40

<400> SEQUENCE: 2

```
Tyr Phe Tyr Thr Gly Ser Asp Gly Gly Met Val Phe Lys Cys Pro Ile
  1               5                  10                  15

Ser Gly Tyr Lys Thr Ser Thr Gly Thr Ser Tyr Thr Arg Thr Glu Leu
             20                  25                  30

Arg Glu Met Leu Arg Ala Gly Asn Thr Ser Ile Ala Thr Ser Gly Val
         35                  40                  45

Asn Lys Asn Asn Trp Val Phe Gly Ser Ala Pro Ser Ser Ala Gln Ala
     50                  55                  60

Ala Ala Gly Gly Val Asp Gly Asn Met Lys Ala Thr Leu Ala Val Asn
 65                  70                  75                  80
```

```
Tyr Val Thr Thr Thr Gly Asp Ser Ser Gln Val Gly Arg Val Ile Ile
                85                  90                  95

Gly Gln Ile His Ala Glu Lys Asn Glu Pro Ile Arg Leu Tyr Tyr Arg
            100                 105                 110

Lys Leu Pro Gly Asn Ser Lys Gly Ile Tyr Tyr Ala His Glu Asp
        115                 120                 125

Ala Asp Gly Gly Glu Val Trp Val Asp Met Ile Gly Ser Arg Ser Ser
    130                 135                 140

Ser Ala Ser Asn Pro Ser Asp Gly Ile Ala Leu Asn Glu Val Phe Ser
145                 150                 155                 160

Tyr Glu Ile Asp Val Thr Asn Asn Met Leu Thr Val Lys Ile Tyr Arg
                165                 170                 175

Asp Gly Lys Ser Thr Val Thr Ser Gln Tyr Asn Met Val Asn Ser Gly
            180                 185                 190

Tyr Asp Asp Ser Asp Asp Trp Met Tyr Phe Lys Ala Gly Val Tyr Asn
        195                 200                 205

Gln Asn Asn Thr Gly Asn Gly Ser Asp Tyr Val Gln Ala Thr Phe Tyr
    210                 215                 220

Ser Leu Thr His Thr His Asp
225                 230

<210> SEQ ID NO 3
<211> LENGTH: 234
<212> TYPE: PRT
<213> ORGANISM: Microbulbifer degradans 2-40

<400> SEQUENCE: 3

Phe Phe Tyr Thr Ala Ala Asp Gly Gly Met Val Phe Lys Cys Pro Val
 1               5                  10                  15

Ala Gly Phe Lys Thr Ser Thr Asn Thr Ser Tyr Thr Arg Val Glu Leu
                20                  25                  30

Arg Glu Met Leu Arg Arg Gly Asn Ser Ser Ile Ser Thr Gln Gly Val
            35                  40                  45

Asn Gly Asn Asn Trp Val Phe Gly Ser Ala Pro Gln Ser Asp Leu Asn
        50                  55                  60

Ala Ala Gly Gly Ile Asp Gly Asn Leu Arg Ala Thr Leu Ala Val Asn
65                  70                  75                  80

Lys Val Thr Thr Thr His Gly Asp Gly Phe Glu Tyr Gln Val Gly Arg
                85                  90                  95

Val Ile Ile Gly Gln Ile His Ala Asn Asp Asp Glu Pro Ile Arg Leu
            100                 105                 110

Tyr Tyr Arg Lys Leu Pro Ser Asn Ser Lys Gly Ser Ile Tyr Phe Ala
        115                 120                 125

His Glu Leu Leu Asp Gly Asp Asp Thr Trp His Glu Met Ile Gly Ser
    130                 135                 140

Arg Gly Asp Asn Ala Ser Asp Pro Ala Asp Gly Ile Ala Leu Asp Glu
145                 150                 155                 160

Thr Phe Ser Tyr Glu Ile Asp Val Arg Gly Asn Thr Leu Thr Val Thr
                165                 170                 175

Ile Met Arg Glu Gly Lys Pro Asp Val Thr Lys Val Leu Asp Met Ser
            180                 185                 190

Ala Ser Gly Tyr Asp Glu Gly Gly Gln Tyr Met Tyr Phe Lys Ala Gly
        195                 200                 205

Val Tyr Asn Gln Asn Asn Ser Gly Asp Pro Asp Asp Tyr Val Gln Ala
```

```
            210                 215                 220
Thr Phe Tyr Ala Leu Glu Ala Thr His Asn
225                 230

<210> SEQ ID NO 4
<211> LENGTH: 288
<212> TYPE: PRT
<213> ORGANISM: Microbulbifer degradans 2-40

<400> SEQUENCE: 4

Tyr Phe Tyr Val Asn Ser Glu Gly Gly Leu Val Phe Ala Thr Pro Asn
  1               5                  10                  15

Gln Ala Thr Thr Thr Ser Gly Ser Ser Asn Ser Arg Ser Glu Leu Arg
                 20                  25                  30

Gln Met Ile Arg Gly Thr Asn Thr Arg Ile Gly Thr Lys Ser Pro Gly
             35                  40                  45

Asn Asn Phe Ala Leu Ala Ser His Pro Gln Ala Lys Ala Phe Gly Asp
         50                  55                  60

Ile Gly Gly Asn Leu Lys Ala Thr Leu Ala Val Asn His Val Ala Leu
 65                  70                  75                  80

Asn Ala Lys Tyr Thr Asp Lys Phe Pro Ala Tyr Ser Val Val Gly
                 85                  90                  95

Gln Ile His Ala Gly Lys Asp Lys Asp Leu Ile Ala Lys Gly Glu Gly
                100                 105                 110

Tyr Gly Trp Gly Asn Glu Pro Ile Lys Ile Tyr Tyr Lys Lys Trp Pro
            115                 120                 125

Asp His Lys Thr Gly Ser Val Phe Trp Thr Tyr Glu Arg Asn Leu Glu
        130                 135                 140

Lys Ala Asn Pro Asp Arg Thr Asp Ile Ala Tyr Pro Val Trp Gly Asn
145                 150                 155                 160

Thr Trp Asp Asn Ser Glu Asn Pro Gly Asp Lys Gly Ile Ala Leu Asp
                165                 170                 175

Glu Ser Phe Ser Tyr Glu Ile Asn Val Tyr Lys Asp Ile Met His Leu
            180                 185                 190

Thr Phe Thr Ala Ala Asn Lys Pro Thr Val Lys Tyr Ser Ile Asn Leu
        195                 200                 205

Ala Asn Asn Val Asn Ala Tyr Gly Lys Val Asp Glu Lys Asp His Pro
    210                 215                 220

Lys Gly Tyr Leu Gly Asp Trp Leu Tyr Phe Lys Ala Gly Ala Tyr Asp
225                 230                 235                 240

Gln Cys Ser Val Lys Asp Asp Pro Gly Phe Trp Tyr Pro Ala Cys Ala
                245                 250                 255

Gly Thr Gly Asp Trp Glu Thr Asp Lys Lys Asn Gly Asp Tyr Thr Arg
            260                 265                 270

Val Thr Phe Thr Lys Leu Glu Leu Gly Lys Gly Tyr Ser Val Ser Lys
        275                 280                 285

<210> SEQ ID NO 5
<211> LENGTH: 269
<212> TYPE: PRT
<213> ORGANISM: Microbulbifer degradans 2-40

<400> SEQUENCE: 5

Ala Ser Trp Glu Ser Tyr Asp Ala Tyr Ala Glu Gln Leu Asn Ala Asp
  1               5                  10                  15

Lys Thr Asn Leu Asp Ala Phe Met Ala Glu Gly Val Val Val Pro Met
```

```
                  20                  25                  30
Pro Lys Asp Ala Gly Gly Tyr Thr His Glu Gln His Lys Arg Asn
             35                  40                  45

Tyr Lys Ala Ile Arg Asn Ala Gly Phe Leu Tyr Gln Val Thr Gly Asp
     50                  55                  60

Glu Lys Tyr Leu Thr Phe Ala Lys Asp Leu Leu Ala Tyr Ala Lys
 65                  70                  75                  80

Met Tyr Pro Ser Leu Gly Glu His Pro Asn Arg Lys Glu Gln Ser Pro
                 85                  90                  95

Gly Arg Leu Phe Trp Gln Ser Leu Asn Glu Ala Val Trp Leu Val Tyr
             100                 105                 110

Ser Ile Gln Gly Tyr Asp Ala Ile Asp Gly Leu Ala Ala Glu Glu
             115                 120                 125

Lys Gln Glu Ile Glu Ser Gly Val Phe Leu Pro Met Ala Lys Phe Leu
130                 135                 140

Ser Val Glu Ser Pro Glu Thr Phe Asn Lys Ile His Asn His Gly Thr
145                 150                 155                 160

Trp Ala Val Ala Ala Val Gly Met Thr Gly Tyr Val Leu Gly Asn Asp
                 165                 170                 175

Glu Leu Val Glu Ile Ser Leu Met Gly Leu Asp Lys Thr Gly Lys Ala
             180                 185                 190

Gly Phe Met Lys Gln Leu Asp Lys Leu Phe Ser Pro Asp Gly Tyr Tyr
             195                 200                 205

Thr Glu Gly Pro Tyr Tyr Gln Arg Tyr Ala Leu Met Pro Phe Ile Trp
     210                 215                 220

Phe Ala Lys Ala Ile Glu Thr Asn Glu Pro Glu Arg Lys Ile Phe Glu
225                 230                 235                 240

Tyr Arg Asn Asn Ile Leu Leu Lys Ala Val Tyr Thr Thr Ile Asp Leu
                 245                 250                 255

Ser Tyr Ala Gly Tyr Phe Phe Pro Ile Asn Asp Ala Leu
             260                 265

<210> SEQ ID NO 6
<211> LENGTH: 309
<212> TYPE: PRT
<213> ORGANISM: Microbulbifer degradans 2-40

<400> SEQUENCE: 6

Ala Ile Leu Ala Ala Ser Ala Gly Asp Thr Ile Glu Ile Gly Ala Gly
 1               5                  10                  15

Asp Tyr Ala Asn Met Gly Thr Val Val Val Thr Asp Gly Val Thr Ile
                 20                  25                  30

Thr Arg Ala Glu Gly Ser Asn Ala Val Ile Ser Gly Glu Phe Cys Leu
             35                  40                  45

Gln Val Ser Gly Asp Gly Ala Arg Ile Thr Gly Leu Glu Phe Ala Asp
     50                  55                  60

Leu Ile Val Pro Ala Asp Ser Ala Asn His Cys Arg Ser Asn Gly Asp
 65                  70                  75                  80

Gly Asn Ile Val Ile Thr Gly Asp Asp Val Val Phe Asp His Asn Leu
                 85                  90                  95

Leu Ser Gly Asp Ala Glu Phe Pro Thr Pro Val Asp Asp Asp His
             100                 105                 110

Asn Trp Leu Val Leu Lys Gly Ser Asn Ala Leu Val Glu Arg Asn Thr
             115                 120                 125
```

```
Phe Gln Asn Arg Arg Gly Ile Ala Ala Asp Gly Val Ser Gln Val Arg
        130                 135                 140

Gly Gly Phe Ile Ser Ile Tyr Val Asn Gly Ser Ala Thr Gly Asn Thr
145                 150                 155                 160

Val Gln Tyr Asn Leu Phe Lys Asp Met Leu Leu Asn Asp Gln Ser Thr
                165                 170                 175

Ala Tyr Ala Ile Met Leu Gly Arg Thr Thr Gly Leu Asp Ser Met Leu
            180                 185                 190

Asp Gly Phe Asn Thr Ile Gln Tyr Asn Arg Phe Asp Asn Ile Asp Ser
        195                 200                 205

Lys Thr Arg Val Ile Arg Val Gln Gly Ser Ser Asn Thr Ile Ser His
210                 215                 220

Asn Thr Val Val Asn Ser Gln Gly Met Leu Ala Leu Glu Ser Gly Gln
225                 230                 235                 240

Asn Asn Val Val Ser Tyr Asn Val Ile Leu Pro Ser Gly Thr Asp Ser
                245                 250                 255

Asn Asp Gly Gly Ile Ser Ala Ala Pro Tyr Gly His Thr Ile Val Gly
            260                 265                 270

Asn Tyr Ile Ala Gly Ser Asn Thr Thr Ser Ser Glu Arg Gly Ala Ile
        275                 280                 285

Tyr Leu Asn Asn Asp Val Asp Glu Pro Gly Asn Leu Ala Ala Thr Pro
290                 295                 300

Ser Ala Val Glu Ile
305

<210> SEQ ID NO 7
<211> LENGTH: 342
<212> TYPE: PRT
<213> ORGANISM: Microbulbifer degradans 2-40

<400> SEQUENCE: 7

Ala Ile Tyr Lys Pro Ile Ala Gly His Val Tyr Glu Ile Thr Ala Tyr
  1               5                  10                  15

Val Tyr Gly His Gly Thr Ile Gly Ile Gln Asp Leu Gly Ser Asp Asn
             20                  25                  30

Val Tyr Glu Thr Ser Thr Ala His Gly Asn Ser Trp Gln Gln Ile Ser
         35                  40                  45

Val Thr Tyr Val Ser Thr Gly Ser Pro Ala Met Leu Tyr Ala Lys Tyr
     50                  55                  60

Gly Pro Gly Ser Gly Asp Ser Tyr Phe Asp Val Phe Asp Ala Lys Asp
 65                  70                  75                  80

Ile Ser Thr Ala Glu Asp Leu Ser Lys Gln Pro Pro Ala Pro Ile Met
                 85                  90                  95

Arg Tyr Ala Ser Gln Val Ile Asp Leu Ser Trp Trp Lys Ile Thr Leu
            100                 105                 110

Pro Ile Asn Asn Ala Met Glu Ile Tyr Thr Pro Glu Leu Leu Thr Tyr
        115                 120                 125

Glu Ile Asp Pro Trp Phe Lys Leu Val Glu Asp Glu Asp Gly Tyr Ala
    130                 135                 140

Val Gln Phe Arg Ala Asn His Gly Gly Ser Thr Thr Gly Gly Ser Ser
145                 150                 155                 160

Asn Pro Arg Ser Glu Leu Arg Glu Leu Thr Gln Asn Tyr His Tyr Arg
                165                 170                 175

Asn Ser Lys Ser Ala Ala Ala Trp Ser Asn Thr Ser Gly Thr His Glu
            180                 185                 190
```

```
Met Trp Ile Lys Gln Lys Val Thr His Leu Thr Tyr Val Lys Pro His
            195                 200                 205

Val Val Val Gly Gln Ile His Asp Ser Gly Asp Val Thr Val Phe
    210                 215                 220

Arg Val Glu Gly His Leu Gly Gln Gly Gly Asp Trp Asp Asn Asn Gly
225                 230                 235                 240

Thr Val Gly Val Met Asp Thr His Ala Asn Ile Trp Ile Thr Asn Gly
                245                 250                 255

Asn Asp Arg His Gly Tyr Leu Val Asp Asp Asn Tyr Glu Leu Gly Thr
                260                 265                 270

Val Phe Thr Val Lys Phe Ile Ala Arg Asp Gly Lys Val Glu Tyr Glu
    275                 280                 285

Tyr Asn Gly Arg Lys Leu Asp Tyr Val His Glu Glu Ser Phe Ser Gly
    290                 295                 300

Ala Tyr Phe Lys Leu Gly Asn Tyr Thr Gln Ser His Asn Gly Thr Ala
305                 310                 315                 320

Pro Gly Glu Thr Asp Asp Ala Tyr Ala Glu Thr Tyr Val Tyr Asp Tyr
                325                 330                 335

Tyr Ile Lys His Thr Glu
                340

<210> SEQ ID NO 8
<211> LENGTH: 264
<212> TYPE: PRT
<213> ORGANISM: Microbulbifer degradans 2-40

<400> SEQUENCE: 8

Glu Thr Leu Arg Ile Gly Thr Ser His Phe Ser Leu Ser Asp Ser Phe
1               5                   10                  15

Thr Leu Val Glu Asn Asn Tyr Phe Asp Arg Cys Asn Gly Glu Leu Glu
                20                  25                  30

Ile Ile Ser Asn Lys Ser Gly Ser Asn Lys Phe Ile Gly Asn Thr Phe
            35                  40                  45

Phe Glu Ser Arg Gly Thr Leu Thr Met Arg His Gly His Gly Asn Val
    50                  55                  60

Ile Glu Asn Asn Val Phe Phe Gly Asn Gly Lys Asp His Thr Gly Gly
65                  70                  75                  80

Ile Arg Val Ile Asn Glu Arg Gln Thr Val Arg Asn Asn Tyr Met Ser
                85                  90                  95

Asp Leu Ala Gly Tyr Arg Phe Gly Gly Gly Leu Val Val Met Asn Gly
                100                 105                 110

Val Pro Asn Ser Ala Ile Asn Arg Tyr His Gln Val Lys Asn Ala Val
            115                 120                 125

Ile Glu Asn Asn Thr Leu Val Asn Val Asp His Ile Gln Leu Ala Ala
130                 135                 140

Gly Ser Asp Lys Glu Arg Thr Ala Thr Pro Val Asp Ser Lys Phe Ser
145                 150                 155                 160

Asn Asn Leu Ile Val Asn Asp Lys Arg Asn Pro Phe Thr Val Tyr
                165                 170                 175

Asp Asp Val Ser Gly Ile Thr Phe Ser Asn Asn Ser Ile Ser Ala Ala
            180                 185                 190

Ser Lys Glu Leu Lys Lys Gly Phe Glu Val Asp Ala Ala Lys Ile Ala
    195                 200                 205

Lys Asn Asp Gln Gly Met Val Phe Asp Ala Ser Gly Thr Tyr Gly Ala
```

```
            210                 215                 220
Ser Lys Ser Leu Lys Pro Val Arg Lys Gln Asp Val Gly Ala Ser Trp
225                 230                 235                 240

Phe Val Lys Ser Glu Asp Arg Lys Ala Phe Gln Ser Gly Lys Thr Val
                245                 250                 255

Lys Ala Gly Ala Gly Gln Asn Ser
            260

<210> SEQ ID NO 9
<211> LENGTH: 272
<212> TYPE: PRT
<213> ORGANISM: Microbulbifer degradans 2-40

<400> SEQUENCE: 9

Glu Gly Ile Arg Ile Gly Thr Ser Asp Ser His Thr Gly Asp Ser Phe
  1               5                  10                  15

Ser Val Ile Glu His Asn Tyr Phe Glu Arg Ile Gln Gly Glu Ala Glu
                 20                  25                  30

Val Ile Ser Asn Lys Ser Gly Asn Asn Arg Ile Glu His Asn Thr Val
             35                  40                  45

Arg Asn Ser Tyr Gly Ser Ile Thr Thr Arg His Gly Ser Ser Ala Thr
         50                  55                  60

Ile Thr Asn Asn Phe Ile Ile Gly Asp Gly His Pro Tyr Ala Gly Gly
 65                  70                  75                  80

Leu Arg Ile Ile Asp Asp Gly His Thr Val Thr Asn Asn Tyr Ile Gln
                 85                  90                  95

Gly Ala Arg Tyr Leu Ala Thr Thr His His Gly Gly Ile Val Leu Met
            100                 105                 110

Gly Ser Asp Gly Ser Thr Thr Asn Gly Tyr Gln Gln Leu Thr Asn Val
        115                 120                 125

Leu Val Ala His Asn Thr Val Val Asp Ser Val Asn Ser Leu Asn Val
    130                 135                 140

Asp Gly Gly Gln Lys Ser Thr Asn Pro Asn Asn Val Tyr Leu Val Asn
145                 150                 155                 160

Asn Ile Ile Ala Asn Gly Ile Gly Pro Val Ile Thr Glu Ala Ala Asp
                165                 170                 175

Gly Met Pro Gly Ser Ser Val Ile Ala Gly Asn Ile Phe Tyr Gly Gln
            180                 185                 190

Ser Phe Ser Asp Ser Ser Leu Thr Ser Val Asp Gly Ile Thr Trp
        195                 200                 205

Leu Asp Val Ala Phe Ala Ala Asp Met Gln Gly Val Met Arg Ala Thr
    210                 215                 220

Gly Ser Ser Pro Asp Leu Thr Ala Ala Ala Asp Thr Gly Asp Phe
225                 230                 235                 240

Ala Ala Val Thr Leu Asp Met Asp Gly Leu Ala Arg Ala Ala Thr Thr
                245                 250                 255

Gln Ala Gly Ala Asp Asp Ile Gly Gly Asn Pro Val Arg Gly Ile
            260                 265                 270

<210> SEQ ID NO 10
<211> LENGTH: 309
<212> TYPE: PRT
<213> ORGANISM: Microbulbifer degradans 2-40

<400> SEQUENCE: 10

Glu Ala Leu Leu Val Gly Asp Ser Asn Met Gln His Val Asp Ala Lys
```

-continued

```
                1               5              10              15
        Val Thr Val Ala Asn Asn Leu Phe Tyr Asp Ala Ser Ile Leu Gly Glu
                               20                  25                  30

Pro Glu Val Ile Ser Asn Lys Ser Ser Asn Ile Tyr Arg Ser Asn
                       35                  40                  45

Thr Val Arg Asn Thr Thr Ala Ser Leu Thr Leu Arg His Gly Asn Arg
                       50                  55                  60

Asn Thr Val Glu Asn Asn Trp Phe Leu Gln Asp Gln Thr Glu Gly Ser
         65                  70                  75                  80

Gly Gly Ile Arg Val Ile Gly Asp Asp Asn Ile Ile His Asn Asn Tyr
                           85                  90                  95

Ile Ala Gly Ser Ala Gly Gly Lys Ser Ala Ala Tyr Arg Pro Ala
                       100                 105                 110

Leu Gly Ile Ala Ala Gly Tyr Ser Lys Lys Asp Asp Ala Asn Ile
                       115                 120                 125

Asn Gly Tyr Gln Leu Ser Glu Arg Asn Val Leu Ser Asn Asn Ser Val
                       130                 135                 140

Ile Gln Ser Ala Gln Pro Val Met Leu Ser Thr Trp Tyr Asp Arg Gly
        145                 150                 155                 160

Lys Leu Ser Met Thr Arg Pro Pro Met Gln Thr Thr Phe Ile Asn Asn
                       165                 170                 175

Leu Val Tyr Gln Leu Asp Val Ala Pro Ser Thr Ala Asp Trp Val Arg
                       180                 185                 190

Gly Leu Ala Ile Ser Val Asp Tyr Thr Pro Asp Ser Glu Tyr Gly Asn
                       195                 200                 205

Asn Tyr Gly Ile Asp Lys Ala Glu Tyr Val Pro Ser Phe Ala Lys Val
                       210                 215                 220

Lys Gly Asn Ile Thr Asp Gly Lys Val Ser Pro Leu Val Ser Lys Gly
        225                 230                 235                 240

Thr Lys Ala Glu Ser Lys Lys Glu Leu Lys Gly Cys Asp Ala Phe Gly
                       245                 250                 255

Thr Gly Asp Ile Val Tyr Leu Pro Leu Lys Lys Ala Gly Ala Asp Leu
                       260                 265                 270

Ser Lys Met Asp Glu Pro Leu Val Trp Thr Asp Thr Val Lys Ser Ala
                       275                 280                 285

Arg Leu Gly Pro Asp Trp Leu Asn Ala Asn Trp Gly Gly Glu Lys Lys
                       290                 295                 300

Ala Tyr Lys Gly Cys
        305

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Gly Gly Gly Gly
 1               5

<210> SEQ ID NO 12
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 12

Met Met Met Met Met Met Met Met
  1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Met Gly Met Gly Met Gly Met
  1               5

<210> SEQ ID NO 14
<211> LENGTH: 13
<212> TYPE: PRT
<213> ORGANISM: Microbulbifer degradans 2-40

<400> SEQUENCE: 14

Leu Leu Gly Asp Gly Ala Asp Gly Asp Gln Gly Ala Leu
  1               5                   10

<210> SEQ ID NO 15
<211> LENGTH: 24
<212> TYPE: PRT
<213> ORGANISM: Microbulbifer degradans 2-40

<400> SEQUENCE: 15

Ser Ser Ser Ser Ser Ser Ser Ser Ser Ser Thr Ser Ser Thr Ser Ser
  1               5                   10                  15

Thr Ser Ser Thr Ser Ser Ser Ser
                 20

<210> SEQ ID NO 16
<211> LENGTH: 39
<212> TYPE: PRT
<213> ORGANISM: Microbulbifer degradans 2-40

<400> SEQUENCE: 16

Thr Thr Pro Thr Pro Thr Pro Thr Pro Thr Pro Thr Pro Thr Pro Thr
  1               5                   10                  15

Pro Thr Pro Thr Pro Thr Pro Thr Pro Thr Pro Thr Pro Thr Pro Thr
                 20                  25                  30

Pro Thr Pro Thr Pro Thr Pro
            35

<210> SEQ ID NO 17
<211> LENGTH: 24
<212> TYPE: PRT
<213> ORGANISM: Microbulbifer degradans 2-40

<400> SEQUENCE: 17

Glu Thr Gly Thr Pro Thr Glu Asp Pro Val Val Val Glu Pro Pro Glu
  1               5                   10                  15

Pro Pro Ala Pro Thr Asp Gly Asp
                 20
```

```
<210> SEQ ID NO 18
<211> LENGTH: 19
<212> TYPE: PRT
<213> ORGANISM: Microbulbifer degradans 2-40

<400> SEQUENCE: 18

Ala Asn Gly Leu Leu Asn Asp Ala Asn Ser Leu Ala Gly Ala Asn Ala
 1               5                  10                  15

Ser Ala Leu

<210> SEQ ID NO 19
<211> LENGTH: 22
<212> TYPE: PRT
<213> ORGANISM: Microbulbifer degradans 2-40

<400> SEQUENCE: 19

Pro Val Glu Pro Gly Asn Gly Glu Asp Glu Gly Asn Gly Gly Thr Thr
 1               5                  10                  15

Thr Glu Val Thr Asp Gly
            20

<210> SEQ ID NO 20
<211> LENGTH: 12
<212> TYPE: PRT
<213> ORGANISM: Microbulbifer degradans 2-40

<400> SEQUENCE: 20

Gly Thr Val Val Val Thr Asp Gly Val Thr Ile Thr
 1               5                  10

<210> SEQ ID NO 21
<211> LENGTH: 47
<212> TYPE: PRT
<213> ORGANISM: Microbulbifer degradans 2-40

<400> SEQUENCE: 21

Pro Asp Pro Asp Pro Asp Pro Ile Glu Glu Pro Glu Gly Glu Pro Glu
 1               5                  10                  15

Gly Glu Pro Glu Gly Glu Pro Glu Gly Glu Pro Glu Gly Glu Pro Glu
            20                  25                  30

Gly Glu Pro Glu Gly Glu Pro Glu Gly Glu Pro Glu Gly Glu Pro
        35                  40                  45

<210> SEQ ID NO 22
<211> LENGTH: 16
<212> TYPE: PRT
<213> ORGANISM: Microbulbifer degradans 2-40

<400> SEQUENCE: 22

Asp Leu Thr Ala Ala Ala Ala Asp Thr Gly Asp Phe Ala Ala Val Thr
 1               5                  10                  15

<210> SEQ ID NO 23
<211> LENGTH: 22
<212> TYPE: PRT
<213> ORGANISM: Microbulbifer degradans 2-40

<400> SEQUENCE: 23

Thr Pro Thr Pro Thr Pro Thr Pro Thr Pro Thr Pro Thr Pro Thr Pro
 1               5                  10                  15

Thr Pro Thr Pro Thr Pro
            20
```

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Trp Gln Trp Gln Trp
 1               5

<210> SEQ ID NO 25
<211> LENGTH: 2283
<212> TYPE: DNA
<213> ORGANISM: Microbulbifer degradans 2-40

<400> SEQUENCE: 25

| | | | | | |
|---|---|---|---|---|---|
| atgaaaaaag | agaatgtaaa | catcgcgaag | cagggcttgc | tagttgtttt | ggtaagcttc | 60 |
| tttatgagct | tttccctaat | gggttgcgcc | aaagaaattc | tggtgaactc | gcaggaacaa | 120 |
| tacgcagaag | cattgagttc | agttaagcct | ggcgacacca | ttgtgttggc | taatggcgaa | 180 |
| tggaaagatt | tcgaaattgt | atttacaggt | aagggcactg | aaaaagcgcc | aatcacccta | 240 |
| actgcgcaaa | caaaaggcaa | ggtgttaatt | actggcgagt | caaacttggc | gcttgccggt | 300 |
| gagcatttgg | tggtatctgg | tttggtgttc | actaatggct | acacaccaag | cgatgccgtt | 360 |
| atctcattta | gagctgctaa | acccgtagcg | gaagacgact | acagtacagt | tgcaatgcat | 420 |
| tctcgagtca | ccgaggtggt | gattgataat | tttagcaacc | cagagcgttt | tgaaactgac | 480 |
| tcgtgggtgc | ttatctatgg | caaacacaac | cgtgttgatc | acagtaactt | caccggcaag | 540 |
| cgcaataaag | gtgtgttgat | ggctgtgcgt | ttagatacca | cgcatagccg | cgaaaaccat | 600 |
| catgaaattg | atcacaacta | ctttggtccg | cgcgatattc | ttggctccaa | cggcggagag | 660 |
| actttgcgta | ttggcacgag | ccacttctct | cttttcagact | ctttcacttt | agtagaaaac | 720 |
| aactatttcg | atcgctgtaa | cggtgagtta | gagattattt | ctaacaagtc | tgggtctaac | 780 |
| aagtttattg | gaaataccct | ctttgaatcg | cgtggcacgc | taactatgcg | tcacggtcat | 840 |
| ggaaacgtaa | tcgaaaacaa | tgtgttcttt | ggtaatggca | agatcacac | cggtggtatt | 900 |
| cgtgtaatta | acgagcgcca | aacggtacgc | aacaactaca | tgtctgatct | tgcaggctac | 960 |
| cgctttggtg | gtggtttagt | tgttatgaat | ggcgtgccta | actcagcgat | aaatcgttac | 1020 |
| caccaagtaa | agaatgccgt | tatagaaaac | aacacgctgg | tgaatgtcga | tcacattcag | 1080 |
| ctggcagctg | gtagcgataa | agagcgaaca | gctacacccg | tggattccaa | gttttcaaat | 1140 |
| aacttgatcg | tcaacgatga | taaacgcaac | ccgtttaccg | tatacgacga | tgttagcggc | 1200 |
| ataacctttt | ctaataacag | tattagtgca | gcgtccaaag | agctaaagaa | aggctttgaa | 1260 |
| gttgatgccg | ctaagattgc | taaaaacgat | caaggcatgg | tgtttgatgc | ctccggtact | 1320 |
| tacggtgcaa | gcaagtcgct | aaaacccgtt | cgcaagcaag | atgtgggcgc | tagctggttt | 1380 |
| gttaagtcgg | aagatcgcaa | agcattccaa | tcgggtaaaa | cagttaaagc | tggtgctggc | 1440 |
| caaaactcta | tctacgatgc | agtagagcag | gtagaagatg | gtggcgttgt | cgaactggca | 1500 |
| gcgggtgatt | atgtagaagc | taaacaatc | actattaaca | aaaccgtaac | cgttaaagca | 1560 |
| gcagccggcg | aaaaagtaaa | tattgagttc | tacaaaaagt | cgctgtttga | agtggttgat | 1620 |
| ggcggcagct | acagcttga | aggtttggca | attagcggtg | cgagttcgcc | agacgatgta | 1680 |
| ggtaatgcgg | tcgtgcgtac | atcgcgttat | tccatgttaa | aaaattatcg | cttagagctt | 1740 |

-continued

```
aaaaattgcg agttcacaga cctagatgta aacagattct tcaacgttgt atcggttagc    1800
aagtctacgt tagcagataa cattttgtta gaaaacgtaa gcgttaaaaa ggttactggc    1860
tcagtgttga agttagatct tgagtccgat gattacggta tttataacgc agaatacgtc    1920
acgattaaga atagccagtt tgaagatgta gatggcccat tgattactta ctaccgtggt    1980
ggtaccgatg aaagtacttt cggcccacac tttgaaatga ctggcagcac cttaaaaaat    2040
gtaggtaatg gcagcaagaa caagttgaac gcgtcactgt atttacatgg tgtacaggta    2100
acggctattt caaacaacaa atggctagat agtaagcctg taattattga gcacactgtg    2160
ggtgagcctg taacaagcgt tgtagataac acgtttgtga atacagctaa gttagattta    2220
caagagctgt attctaagaa gacaaccacc gcagtaatta aaataaatac ctataaaaaa    2280
taa                                                                  2283
```

<210> SEQ ID NO 26
<211> LENGTH: 760
<212> TYPE: PRT
<213> ORGANISM: Microbulbifer degradans 2-40

<400> SEQUENCE: 26

```
Met Lys Lys Glu Asn Val Asn Ile Ala Lys Gln Gly Leu Leu Val Val
  1               5                  10                  15

Leu Val Ser Phe Phe Met Ser Phe Ser Leu Met Gly Cys Ala Lys Glu
                 20                  25                  30

Ile Leu Val Asn Ser Gln Glu Gln Tyr Ala Glu Ala Leu Ser Ser Val
             35                  40                  45

Lys Pro Gly Asp Thr Ile Val Leu Ala Asn Gly Glu Trp Lys Asp Phe
         50                  55                  60

Glu Ile Val Phe Thr Gly Lys Gly Thr Glu Lys Ala Pro Ile Thr Leu
 65                  70                  75                  80

Thr Ala Gln Thr Lys Gly Lys Val Leu Ile Thr Gly Glu Ser Asn Leu
                 85                  90                  95

Ala Leu Ala Gly Glu His Leu Val Val Ser Gly Leu Val Phe Thr Asn
            100                 105                 110

Gly Tyr Thr Pro Ser Asp Ala Val Ile Ser Phe Arg Ala Ala Lys Pro
        115                 120                 125

Val Ala Glu Asp Asp Tyr Ser Thr Val Ala Met His Ser Arg Val Thr
    130                 135                 140

Glu Val Val Ile Asp Asn Phe Ser Asn Pro Glu Arg Phe Glu Thr Asp
145                 150                 155                 160

Ser Trp Val Leu Ile Tyr Gly Lys His Asn Arg Val Asp His Ser Asn
                165                 170                 175

Phe Thr Gly Lys Arg Asn Lys Gly Val Leu Met Ala Val Arg Leu Asp
            180                 185                 190

Thr Thr His Ser Arg Glu Asn His Glu Ile Asp His Asn Tyr Phe
        195                 200                 205

Gly Pro Arg Asp Ile Leu Gly Ser Asn Gly Glu Thr Leu Arg Ile
    210                 215                 220

Gly Thr Ser His Phe Ser Leu Ser Asp Ser Phe Thr Leu Val Glu Asn
225                 230                 235                 240

Asn Tyr Phe Asp Arg Cys Asn Gly Glu Leu Glu Ile Ile Ser Asn Lys
                245                 250                 255

Ser Gly Ser Asn Lys Phe Ile Gly Asn Thr Phe Phe Glu Ser Arg Gly
            260                 265                 270
```

```
Thr Leu Thr Met Arg His Gly His Gly Asn Val Ile Glu Asn Asn Val
        275                 280                 285

Phe Phe Gly Asn Gly Lys Asp His Thr Gly Gly Ile Arg Val Ile Asn
        290                 295                 300

Glu Arg Gln Thr Val Arg Asn Asn Tyr Met Ser Asp Leu Ala Gly Tyr
305                 310                 315                 320

Arg Phe Gly Gly Gly Leu Val Val Met Asn Gly Val Pro Asn Ser Ala
                325                 330                 335

Ile Asn Arg Tyr His Gln Val Lys Asn Ala Val Ile Glu Asn Asn Thr
                340                 345                 350

Leu Val Asn Val Asp His Ile Gln Leu Ala Ala Gly Ser Asp Lys Glu
        355                 360                 365

Arg Thr Ala Thr Pro Val Asp Ser Lys Phe Ser Asn Asn Leu Ile Val
        370                 375                 380

Asn Asp Asp Lys Arg Asn Pro Phe Thr Val Tyr Asp Asp Val Ser Gly
385                 390                 395                 400

Ile Thr Phe Ser Asn Asn Ser Ile Ser Ala Ala Ser Lys Glu Leu Lys
                405                 410                 415

Lys Gly Phe Glu Val Asp Ala Ala Lys Ile Ala Lys Asn Asp Gln Gly
                420                 425                 430

Met Val Phe Asp Ala Ser Gly Thr Tyr Gly Ala Ser Lys Ser Leu Lys
        435                 440                 445

Pro Val Arg Lys Gln Asp Val Gly Ala Ser Trp Phe Val Lys Ser Glu
        450                 455                 460

Asp Arg Lys Ala Phe Gln Ser Gly Lys Thr Val Lys Ala Gly Ala Gly
465                 470                 475                 480

Gln Asn Ser Ile Tyr Asp Ala Val Glu Gln Val Glu Asp Gly Gly Val
                485                 490                 495

Val Glu Leu Ala Ala Gly Asp Tyr Val Glu Ala Lys Thr Ile Thr Ile
        500                 505                 510

Asn Lys Thr Val Thr Val Lys Ala Ala Gly Glu Lys Val Asn Ile
        515                 520                 525

Glu Phe Tyr Lys Lys Ser Leu Phe Glu Val Val Asp Gly Gly Ser Leu
        530                 535                 540

Gln Leu Glu Gly Leu Ala Ile Ser Gly Ala Ser Ser Pro Asp Asp Val
545                 550                 555                 560

Gly Asn Ala Val Val Arg Thr Ser Arg Tyr Ser Met Leu Lys Asn Tyr
                565                 570                 575

Arg Leu Glu Leu Lys Asn Cys Glu Phe Thr Asp Leu Asp Val Asn Arg
        580                 585                 590

Phe Phe Asn Val Val Ser Val Ser Lys Ser Thr Leu Ala Asp Asn Ile
        595                 600                 605

Leu Leu Glu Asn Val Ser Val Lys Lys Val Thr Gly Ser Val Leu Lys
        610                 615                 620

Leu Asp Leu Glu Ser Asp Asp Tyr Gly Ile Tyr Asn Ala Glu Tyr Val
625                 630                 635                 640

Thr Ile Lys Asn Ser Gln Phe Glu Asp Val Asp Gly Pro Leu Ile Thr
                645                 650                 655

Tyr Tyr Arg Gly Gly Thr Asp Glu Ser Thr Phe Gly Pro His Phe Glu
                660                 665                 670

Met Thr Gly Ser Thr Leu Lys Asn Val Gly Asn Gly Ser Lys Asn Lys
        675                 680                 685
```

```
Leu Asn Ala Ser Leu Tyr Leu His Gly Val Gln Val Thr Ala Ile Ser
        690                 695                 700
Asn Asn Lys Trp Leu Asp Ser Lys Pro Val Ile Ile Glu His Thr Val
705                 710                 715                 720
Gly Glu Pro Val Thr Ser Val Val Asp Asn Thr Phe Val Asn Thr Ala
                725                 730                 735
Lys Leu Asp Leu Gln Glu Leu Tyr Ser Lys Lys Thr Thr Thr Ala Val
            740                 745                 750
Ile Lys Asn Asn Thr Tyr Lys Lys
        755                 760

<210> SEQ ID NO 27
<211> LENGTH: 2679
<212> TYPE: DNA
<213> ORGANISM: Microbulbifer degradans 2-40

<400> SEQUENCE: 27
atgaagttca aatcattagt ggccctattc ctattgggcc tgcttactgc ttgtggggggc      60 ggtagttcaa atccagaccc agacccagac ccgattgaag aacctgaagg cgaacctgaa     120
ggagagccag aaggagagcc tgaaggagaa ccagaaggag agccagaagg agagccagaa     180
ggggaaccag aaggagagcc agagggtgaa cctcaggagt ctaactttcc gcgtggttca     240
ctcggtgata cgacactgt gccagacgtg gtatgtacgc aaaccgtaaa cagtacgtca     300
gaactagaag acgctgtaag ctacgagatg accccaggta caacgctgtg tttggctgac     360
ggcaactaca ccaacttaga aattcagttc ggtggtattg gtaccgaagc gaaccctatt     420
actgtggcag cagctaaccc cggtatggtt acaattggcg gcgaagttgg gatccgcatg     480
agcggtgaat acgttgtgtt gcaagggctt attttaaag acggtgagag cgcgagtagc     540
gacttaattc aaactcgcgg caactctaac gcgccttgta taactgccg tattaccgaa     600 attgccatta tcgatttcga tcaaaattcc gatagcagcg gcaaatgggt tcacatctac     660
ggtgcacata accgcgtaga ccacagctgg ttttctggca aaactacccg cggcgcatta     720
cttgttgtag atcgttacat tgaagatggt gttgacccac tcgatgccga aatagattac     780
gcgcaaatcg atcacaacta cttcggcgac cgtccaccgg tggatggcaa agcttacgcg     840
agtagcggcg acaacgaata cgaaggtatt cgcattggta ccagtgattc gcacacaggt     900
gattcgttct cggtaatcga gcacaactat tttgagcgca tacaaggcga agccgaagtt     960
atttctaata gtctggcaa caaccgcata gagcacaata ctgtacgtaa cagctatggt    1020
tctattacta cacgtcacgg ctcaagcgcg actattacca ataactttat tattggcgat    1080
ggtcacccat atgcaggcgg cctgcgcatt attgatgacg ccacaccgt aacgaacaac    1140 tacatccaag gtgcgcgtta tttagcaact actcaccatg gcggtattgt gttgatgggc    1200
tccgatggtt caaccaccaa cggttaccag caattaacca atgtacttgt tgcgcacaac    1260
actgtggtag atagcgtgaa cagcttgaac gtagatggcg gccaaaagtc taccaacccc    1320
aataatgttt acctagtgaa taacattatt gctaatggca taggccctgt tattacagaa    1380
gctgcagatg gtatgcctgg tagctctgtg attgcgggca acatttttta cggccaaagc    1440 tttttccgact cctctagcct tacctctgta gacggtatta cttggttaga cgttgcgttc    1500
gcagcagata tgcaaggcgt aatgcgcgct acaggcagca gcccagactt aaccgcggca    1560
gctgcagata ctggcgattt tgccgccgtt actttggata tggatggctt ggcgcgtgca    1620
gcaaccacac aagctggtgc tgacgacgat ataggtggca acccagttcg cggcattctt    1680
```

```
aatagctacg atgttggccc aataagctac cgcccaccaa tgaccacccc acacgttgca    1740
gaagtggatg tcgccaacta tgcgtttgat gaaggtgcag caggttggac tttagttgat    1800
gcagtggtaa acactaacgc tgcagaggtt tttgcccgcg gtgcaagcgt ggaagtaacc    1860
ggtgctaacg gccgcgcttc gcaagttgtt agcttaacgg cgaataccaa ctacacctta    1920
actgcgtttg ttaaaggcac tgcaactctt gcagcagatg taggtggcac ggtttatcgt    1980
tcagatgtga actcttcatt ggagtacaaa ctagcaaccg taagctttaa ttctggtgat    2040
gcaacatcag ccaccattta cggcgaagtt gatgattttg tacttaacta tgccccaatt    2100
ggcgaagcga gcttagacgg cttccctggc gcagacacca ccttttggag tgtgtacgag    2160
ggagcaggta tcggtcaggt tcaaggctct gataactcag cagccggcgc tgatgggtct    2220
gttaagttta aattagaaga cgctacagaa gtgggtaccc gcgtataag ccaagtatta    2280 accggcctag aattaaatac ggactatact ttatctatgt acgcccttta caaaaagtct    2340
gccgatgtga ctgtaactat ggggcgtttt gttggcgaaa cagacactgt actagcaagc    2400
aaagtggttg attttgaaga ccttgttgca gctaatgcgc cgaaaggcga cgacagtttc    2460
cgtcaagaca cactaacgtt taacacgggt agtaactcaa ctattactat ctttgctgaa    2520
tacaacgcca acacaattat tgctgacggc ggcgacgctg gtgatacgga gtttcgtgta    2580
gatgaatttg cattgacata tgaaggtgca cctgctgcgg atgccaaagc atactttgac    2640
gaattccgtc tagtatcgca tgcatcgcta gcagactaa                          2679

<210> SEQ ID NO 28
<211> LENGTH: 892
<212> TYPE: PRT
<213> ORGANISM: Microbulbifer degradans 2-40

<400> SEQUENCE: 28

Met Lys Phe Lys Ser Leu Val Ala Leu Phe Leu Leu Gly Leu Leu Thr
 1               5                  10                  15

Ala Cys Gly Gly Gly Ser Ser Asn Pro Asp Pro Asp Pro Asp Pro Ile
            20                  25                  30

Glu Glu Pro Glu Gly Glu Pro Glu Gly Glu Pro Glu Gly Glu Pro Glu
        35                  40                  45

Gly Glu Pro Glu Gly Glu Pro Glu Gly Glu Pro Glu Gly Glu Pro Glu
    50                  55                  60

Gly Glu Pro Glu Gly Glu Pro Gln Glu Ser Asn Phe Pro Arg Gly Ser
65                  70                  75                  80

Leu Gly Asp Asn Asp Thr Val Pro Asp Val Val Cys Thr Gln Thr Val
                85                  90                  95

Asn Ser Thr Ser Glu Leu Glu Asp Ala Val Ser Tyr Glu Met Thr Pro
            100                 105                 110

Gly Thr Thr Leu Cys Leu Ala Asp Gly Asn Tyr Thr Asn Leu Glu Ile
        115                 120                 125

Gln Phe Gly Gly Ile Gly Thr Glu Ala Asn Pro Ile Thr Val Ala Ala
    130                 135                 140

Ala Asn Pro Gly Met Val Thr Ile Gly Gly Glu Val Gly Ile Arg Met
145                 150                 155                 160

Ser Gly Glu Tyr Val Val Leu Gln Gly Leu Ile Phe Lys Asp Gly Glu
                165                 170                 175

Ser Ala Ser Ser Asp Leu Ile Gln Thr Arg Gly Asn Ser Asn Ala Pro
            180                 185                 190

Cys Asn Asn Cys Arg Ile Thr Glu Ile Ala Ile Ile Asp Phe Asp Gln
```

```
                195                 200                 205
Asn Ser Asp Ser Ser Gly Lys Trp Val His Ile Tyr Gly Ala His Asn
    210                 215                 220
Arg Val Asp His Ser Trp Phe Ser Gly Lys Thr Thr Arg Gly Ala Leu
225                 230                 235                 240
Leu Val Val Asp Arg Tyr Ile Glu Asp Gly Val Asp Pro Leu Asp Ala
                245                 250                 255
Glu Ile Asp Tyr Ala Gln Ile Asp His Asn Tyr Phe Gly Asp Arg Pro
                260                 265                 270
Pro Val Asp Gly Lys Ala Tyr Ala Ser Ser Gly Asp Asn Glu Tyr Glu
            275                 280                 285
Gly Ile Arg Ile Gly Thr Ser Asp Ser His Thr Gly Asp Ser Phe Ser
            290                 295                 300
Val Ile Glu His Asn Tyr Phe Glu Arg Ile Gln Gly Glu Ala Glu Val
305                 310                 315                 320
Ile Ser Asn Lys Ser Gly Asn Asn Arg Ile Glu His Asn Thr Val Arg
                325                 330                 335
Asn Ser Tyr Gly Ser Ile Thr Thr Arg His Gly Ser Ser Ala Thr Ile
            340                 345                 350
Thr Asn Asn Phe Ile Ile Gly Asp Gly His Pro Tyr Ala Gly Gly Leu
            355                 360                 365
Arg Ile Ile Asp Asp Gly His Thr Val Thr Asn Asn Tyr Ile Gln Gly
        370                 375                 380
Ala Arg Tyr Leu Ala Thr Thr His His Gly Gly Ile Val Leu Met Gly
385                 390                 395                 400
Ser Asp Gly Ser Thr Thr Asn Gly Tyr Gln Gln Leu Thr Asn Val Leu
                405                 410                 415
Val Ala His Asn Thr Val Asp Ser Val Asn Ser Leu Asn Val Asp
            420                 425                 430
Gly Gly Gln Lys Ser Thr Asn Pro Asn Asn Val Tyr Leu Val Asn Asn
            435                 440                 445
Ile Ile Ala Asn Gly Ile Gly Pro Val Ile Thr Glu Ala Ala Asp Gly
        450                 455                 460
Met Pro Gly Ser Ser Val Ile Ala Gly Asn Ile Phe Tyr Gly Gln Ser
465                 470                 475                 480
Phe Ser Asp Ser Ser Ser Leu Thr Ser Val Asp Gly Ile Thr Trp Leu
                485                 490                 495
Asp Val Ala Phe Ala Ala Asp Met Gln Gly Val Met Arg Ala Thr Gly
            500                 505                 510
Ser Ser Pro Asp Leu Thr Ala Ala Ala Asp Thr Gly Asp Phe Ala
            515                 520                 525
Ala Val Thr Leu Asp Met Asp Gly Leu Ala Arg Ala Ala Thr Thr Gln
        530                 535                 540
Ala Gly Ala Asp Asp Ile Gly Gly Asn Pro Val Arg Gly Ile Leu
545                 550                 555                 560
Asn Ser Tyr Asp Val Gly Pro Ile Ser Tyr Arg Pro Pro Met Thr Thr
                565                 570                 575
Pro His Val Ala Glu Val Asp Val Ala Asn Tyr Ala Phe Asp Glu Gly
            580                 585                 590
Ala Ala Gly Trp Thr Leu Val Asp Ala Val Val Asn Thr Asn Ala Ala
            595                 600                 605
Glu Val Phe Ala Arg Gly Ala Ser Val Glu Val Thr Gly Ala Asn Gly
        610                 615                 620
```

```
Arg Ala Ser Gln Val Val Ser Leu Thr Ala Asn Thr Asn Tyr Thr Leu
625                 630                 635                 640

Thr Ala Phe Val Lys Gly Thr Ala Thr Leu Ala Ala Asp Val Gly Gly
            645                 650                 655

Thr Val Tyr Arg Ser Asp Val Asn Ser Ser Leu Glu Tyr Lys Leu Ala
            660                 665                 670

Thr Val Ser Phe Asn Ser Gly Asp Ala Thr Ser Ala Thr Ile Tyr Gly
            675                 680                 685

Glu Val Asp Asp Phe Val Leu Asn Tyr Ala Pro Ile Gly Glu Ala Ser
            690                 695                 700

Leu Asp Gly Phe Pro Gly Ala Asp Thr Thr Phe Trp Ser Val Tyr Glu
705                 710                 715                 720

Gly Ala Gly Ile Gly Gln Val Gln Gly Ser Asp Asn Ser Ala Ala Gly
                725                 730                 735

Ala Asp Gly Ser Val Lys Phe Lys Leu Glu Asp Ala Thr Glu Val Gly
            740                 745                 750

Thr Pro Arg Ile Ser Gln Val Leu Thr Gly Leu Glu Leu Asn Thr Asp
            755                 760                 765

Tyr Thr Leu Ser Met Tyr Ala Leu Tyr Lys Lys Ser Ala Asp Val Thr
            770                 775                 780

Val Thr Met Gly Ala Phe Val Gly Glu Thr Asp Thr Val Leu Ala Ser
785                 790                 795                 800

Lys Val Val Asp Phe Glu Asp Leu Val Ala Ala Asn Ala Pro Lys Gly
                805                 810                 815

Asp Asp Ser Phe Arg Gln Asp Thr Leu Thr Phe Asn Thr Gly Ser Asn
            820                 825                 830

Ser Thr Ile Thr Ile Phe Ala Glu Tyr Asn Ala Asn Thr Ile Ile Ala
            835                 840                 845

Asp Gly Gly Asp Ala Gly Asp Thr Glu Phe Arg Val Asp Glu Phe Ala
            850                 855                 860

Leu Thr Tyr Glu Gly Ala Pro Ala Ala Asp Ala Lys Ala Tyr Phe Asp
865                 870                 875                 880

Glu Phe Arg Leu Val Ser His Ala Ser Leu Ala Asp
                885                 890
```

<210> SEQ ID NO 29
<211> LENGTH: 1530
<212> TYPE: DNA
<213> ORGANISM: Microbulbifer degradans 2-40

<400> SEQUENCE: 29

```
gtgtgtgccg aaacgcatat ttacgatggc aaaggtaaag aaacctggac caaaacggac     60
ttaaagccgg gcgatgtggt gattatcccg aatggcacct acgccgactt aaaaattaac    120
gtgcagggca aaggtgagca ggccaagccg attgtactta agcagaaaac acctgggggc    180
gttgtgctta caggtgcatc gtggctgcgc tactggggct atttattgt ggtagatggt    240 ttcgatttta acgacgtaac ctattccatg tataaaaata aagtgcgggc aattattgcc    300
aaccgccgcg cgggttctag cagtgagtcc tctaaggata tgtgccaagc gtgcgtgtta    360
cagcgcgtgc gtatagataa cgagaacgat aaagcgatcg atactgaata taatgggatt    420
gagctatacg ttataacaa cgtggtgagg tacaactact tcggtgctaa aaaatcgggc    480
agccgagttt tacaggttca gttaaagcat gctaatgcgc aaaaattgcc cgtatcccat    540
gttattcagt acaactattt tgcttcgcgt aacgcgggca agctgtagg taatggtggt    600
```

```
gaagcattgt tagtgggcga ttcaaatatg cagcatgttg atgctaaggt taccgtggcc    660
aacaacttat tttacgatgc atccatactt ggcgagccag aggttatttc gaacaaatcc    720
tcctctaata tttatcgcag caatactgtg cgcaatacaa ccgcgagcct cacgctgcgc    780
cacggcaaca gaaacactgt agagaataac tggttttgc aggaccaaac agaaggctct    840
ggtggtatac gtgtcattgg cgacgataat attattcaca acaattacat tgctggctct    900
gccggtggtg gcaaatcggc cgcgtatcgg ccagcacttg gtattgccgc gggttactcc    960
aaaaaagatg acgatgccaa tatcaacggt taccagttaa gtgagcgcaa cgtgctttcg   1020
aataatagcg ttattcaatc tgcacagcct gtaatgcttt ctacttggta cgatcgaggt   1080
aagctaagta tgactcgccc ccctatgcaa accacgttta ttaataactt ggtgtaccaa   1140
ctagatgttg caccatctac tgcagattgg gtgcggggct tagccattag tgtagattac   1200
acgccagact ctgaatacgg taacaactat ggcattgata agcggagta tgtaccgtcg   1260 tttgcaaaag taaaggcaa tattaccgat ggcaaagtgt cgccactggt tagcaaaggc   1320 actaagctg aatcgaaaaa agaacttaaa gggtgcgatg catttggcac tggcgatatc   1380
gtatatttac cccttaaaaa agcaggcgca gacttatcta aaatggatga acccttggtg   1440
tggaccgaca cagtaaaatc tgctcgctta ggaccagatt ggttgaatgc aaattggggc   1500
ggcgagaaaa aagcctataa gggatgttag                                   1530
```

<210> SEQ ID NO 30
<211> LENGTH: 509
<212> TYPE: PRT
<213> ORGANISM: Microbulbifer degradans 2-40

<400> SEQUENCE: 30

```
Met Cys Ala Glu Thr His Ile Tyr Asp Gly Lys Gly Lys Glu Thr Trp
  1               5                  10                  15

Thr Lys Thr Asp Leu Lys Pro Gly Asp Val Val Ile Pro Asn Gly
             20                  25                  30

Thr Tyr Ala Asp Leu Lys Ile Asn Val Gln Gly Lys Gly Glu Gln Ala
         35                  40                  45

Lys Pro Ile Val Leu Lys Ala Glu Thr Pro Gly Gly Val Val Leu Thr
     50                  55                  60

Gly Ala Ser Trp Leu Arg Tyr Trp Gly Tyr Phe Ile Val Val Asp Gly
 65                  70                  75                  80

Phe Asp Phe Asn Asp Val Thr Tyr Ser Met Tyr Lys Asn Lys Val Arg
                 85                  90                  95

Ala Ile Ile Ala Asn Arg Arg Ala Gly Ser Ser Ser Glu Ser Ser Lys
            100                 105                 110

Asp Met Cys Gln Ala Cys Val Leu Gln Arg Val Arg Ile Asp Asn Glu
        115                 120                 125

Asn Asp Lys Ala Ile Asp Thr Glu Tyr Lys Trp Ile Glu Leu Tyr Gly
    130                 135                 140

Tyr Asn Asn Val Val Arg Tyr Asn Tyr Phe Gly Ala Lys Lys Ser Gly
145                 150                 155                 160

Ser Arg Val Leu Gln Val Gln Leu Lys His Ala Asn Ala Gln Lys Leu
                165                 170                 175

Pro Val Ser His Val Ile Gln Tyr Asn Tyr Phe Ala Ser Arg Asn Ala
            180                 185                 190

Gly Lys Ala Val Gly Asn Gly Glu Ala Leu Leu Val Gly Asp Ser
        195                 200                 205
```

Asn Met Gln His Val Asp Ala Lys Val Thr Val Ala Asn Asn Leu Phe
    210                 215                 220

Tyr Asp Ala Ser Ile Leu Gly Glu Pro Glu Val Ile Ser Asn Lys Ser
225                 230                 235                 240

Ser Ser Asn Ile Tyr Arg Ser Asn Thr Val Arg Asn Thr Ala Ser
                245                 250                 255

Leu Thr Leu Arg His Gly Asn Arg Asn Thr Val Glu Asn Trp Phe
            260                 265                 270

Leu Gln Asp Gln Thr Glu Gly Ser Gly Gly Ile Arg Val Ile Gly Asp
        275                 280                 285

Asp Asn Ile Ile His Asn Asn Tyr Ile Ala Gly Ser Ala Gly Gly Gly
    290                 295                 300

Lys Ser Ala Ala Tyr Arg Pro Ala Leu Gly Ile Ala Ala Gly Tyr Ser
305                 310                 315                 320

Lys Lys Asp Asp Asp Ala Asn Ile Asn Gly Tyr Gln Leu Ser Glu Arg
                325                 330                 335

Asn Val Leu Ser Asn Asn Ser Val Ile Gln Ser Ala Gln Pro Val Met
            340                 345                 350

Leu Ser Thr Trp Tyr Asp Arg Gly Lys Leu Ser Met Thr Arg Pro Pro
        355                 360                 365

Met Gln Thr Thr Phe Ile Asn Asn Leu Val Tyr Gln Leu Asp Val Ala
    370                 375                 380

Pro Ser Thr Ala Asp Trp Val Arg Gly Leu Ala Ile Ser Val Asp Tyr
385                 390                 395                 400

Thr Pro Asp Ser Glu Tyr Gly Asn Asn Tyr Gly Ile Asp Lys Ala Glu
                405                 410                 415

Tyr Val Pro Ser Phe Ala Lys Val Lys Gly Asn Ile Thr Asp Gly Lys
            420                 425                 430

Val Ser Pro Leu Val Ser Lys Gly Thr Lys Ala Glu Ser Lys Lys Glu
        435                 440                 445

Leu Lys Gly Cys Asp Ala Phe Gly Thr Gly Asp Ile Val Tyr Leu Pro
    450                 455                 460

Leu Lys Lys Ala Gly Ala Asp Leu Ser Lys Met Asp Glu Pro Leu Val
465                 470                 475                 480

Trp Thr Asp Thr Val Lys Ser Ala Arg Leu Gly Pro Asp Trp Leu Asn
                485                 490                 495

Ala Asn Trp Gly Gly Glu Lys Lys Ala Tyr Lys Gly Cys
            500                 505

<210> SEQ ID NO 31
<211> LENGTH: 2307
<212> TYPE: DNA
<213> ORGANISM: Microbulbifer degradans 2-40

<400> SEQUENCE: 31
atgagcacaa aactaaccca gtcgatcaag tggttggcac ccatgttaat ggccatgcag      60
gtatcaacgg cgtatgcagc agacccagtt tctgttgaag cgtccaccga tgatggcaat     120
gggcctagca acacattaga taatgattta tccacgcgtt ggtctgccaa tggtagcggc     180
cagtggattc gctacaacct tggcactagc tacaatattg aatctttaga tattgcgttt     240
tacaaaggcg atcagcgcaa cgcgagcttt gacgttttaa catcaggaga tggccaaaac     300
tggaataccg tattcagcgg tacgcagcca agcagtacgg cagatcaaca aactatctcc     360
ctatctgact cgataggtca gtacgtacaa attgttggtt acggcaattc atctaacagc     420

```
tggaacagta tcaccgaagt tgatatagat acttcagtgg ttgatgacgg caataccggt    480
ggcggtagtt taagtgcaag cgccagtgcc gatgatggca atgtggccgg taacgtactt    540
gatggcgacc taaacacccg ttggtccgcc aatggcaatg ccagtggtt gcgcttagat     600 cttggtgcta cgcaagtggt tggcactgta aatattgctt tctttaaagg taatcaacgc    660
agtgctaatt tgatataga agccagtacc gatggttcga actggacccg tgtagtggct     720
ggtgcacaca gttcaggttc ttctgtaagc ttggagcctt tttcattctc acctgttaac    780
gcgcgctaca ttcgctacgt tggttatggc aacagtgcca acagctggaa ctcaatcacc    840
gagatgagtg ttgcagctag tggtggttct agtagttcga gcagttcttc aagcagctca    900
tcgagttcat ctagctcaac cagttcatct agttcaagca gctcttcaag ttcctcgtct    960
agctcttcta gcagttcgtc tagttctagt agctcaagca gttcttcaag ttctagctcg   1020
tcgaatggcg gtgtaccagg taatacttat accgcaacac ccgattcgct aaacgatgta   1080
ttggcgacgg tgtctggtgg cgacgaaatt gtggttactg gctccggtga aatatcgata   1140
aaaaatatta gctttaattc acctgtgtta attcgcgcaa actctattgg cggcaccacg   1200
ttaaccaatg caacccttac taactgtaat aacattagtt tgcagggttt tgtgtttggt   1260
cctaacgacg agagcacgct gttaaagatt gtgaactcca ccaacatcaa atatattgcgc  1320 aacttgtttg atcacaaaaa cgttaccgaa agccaaacgt ctttagtgat gactcaagcc   1380
agccaatata ttgaaattgc ttacaacgag ttccgcgata aaaatttagg tgaccgcagt   1440
ggtaccaaaa ttacgggtag ctacattaaa acccagttcg acgacccgtt gatgagtaaa   1500
aatattcaca tccatcacaa ccactttaaa acattgcgc ataccttgt ggacggtgta     1560 ccagcgggtg attcggatcg tgaagtaatt gcaatgggta ttgccgattc gcaagacgta   1620
gtaaccaaca atattgttga gtacaacctt tcgagaact gcgatggcga aaacgaaatt    1680
gttacagtta aaacctctaa caatattttc cgctacaaca ccttcaaaaa ctccatgggt   1740
tccttgtcgt tccgtttagg ttcgaacaac caagcttatg caactatttt ttacggtgta   1800
ggttctggtg cgtcggttgc taatgataac tatgaaacag gcggtgtgcg cgtgtacggc   1860
gcgggtcata ctattcacaa caactatatg gaaggcctaa cagggcttag ctggagacgc   1920
ccaattttag tggattcggg tgataccttca gaaagctcgg gtaacgatag ccacgaagtg   1980
tctactaatg tgcaggttta cgataacgtt attgttaata gtttaggtgg cggcattcat   2040
gtaggcggcg acaagtacag caaaatgccc accaatatca ccattactaa caacgtagtt   2100
agcggtagtg acggtatatt atttaacaat cacgctaatc aatcttctaa cacttggtcg   2160
ggcaaccagg cttacgcaac aggttctgct gtagcggttg ctggcggttc attaggtgct   2220
tcggaagttg ttgtgttatc tagcgagcca actattaata agccaacacc gcttaccgca   2280
agtgatgtag gcccaagtgc gccttaa                                       2307
```

<210> SEQ ID NO 32
<211> LENGTH: 768
<212> TYPE: PRT
<213> ORGANISM: Microbulbifer degradans 2-40

<400> SEQUENCE: 32

```
Met Ser Thr Lys Leu Thr Gln Ser Ile Lys Trp Leu Ala Pro Met Leu
  1               5                  10                  15

Met Ala Met Gln Val Ser Thr Ala Tyr Ala Ala Asp Pro Val Ser Val
             20                  25                  30
```

-continued

```
Glu Ala Ser Thr Asp Asp Gly Asn Gly Pro Ser Asn Thr Leu Asp Asn
         35                  40                  45

Asp Leu Ser Thr Arg Trp Ser Ala Asn Gly Ser Gly Gln Trp Ile Arg
     50                  55                  60

Tyr Asn Leu Gly Thr Ser Tyr Asn Ile Glu Ser Leu Asp Ile Ala Phe
 65                  70                  75                  80

Tyr Lys Gly Asp Gln Arg Asn Ala Ser Phe Asp Val Leu Thr Ser Gly
                 85                  90                  95

Asp Gly Gln Asn Trp Asn Thr Val Phe Ser Gly Thr Gln Pro Ser Ser
            100                 105                 110

Thr Ala Asp Gln Gln Thr Ile Ser Leu Ser Asp Ser Ile Gly Gln Tyr
        115                 120                 125

Val Gln Ile Val Gly Tyr Gly Asn Ser Ser Asn Ser Trp Asn Ser Ile
    130                 135                 140

Thr Glu Val Asp Ile Asp Thr Ser Val Val Asp Asp Gly Asn Thr Gly
145                 150                 155                 160

Gly Gly Ser Leu Ser Ala Ser Ala Ser Ala Asp Asp Gly Asn Val Ala
                165                 170                 175

Gly Asn Val Leu Asp Gly Asp Leu Asn Thr Arg Trp Ser Ala Asn Gly
            180                 185                 190

Asn Gly Gln Trp Leu Arg Leu Asp Leu Gly Ala Thr Gln Val Val Gly
        195                 200                 205

Thr Val Asn Ile Ala Phe Phe Lys Gly Asn Gln Arg Ser Ala Asn Phe
    210                 215                 220

Asp Ile Glu Ala Ser Thr Asp Gly Ser Asn Trp Thr Arg Val Val Ala
225                 230                 235                 240

Gly Ala His Ser Ser Gly Ser Ser Val Ser Leu Glu Pro Phe Ser Phe
                245                 250                 255

Ser Pro Val Asn Ala Arg Tyr Ile Arg Tyr Val Gly Tyr Gly Asn Ser
            260                 265                 270

Ala Asn Ser Trp Asn Ser Ile Thr Glu Met Ser Val Ala Ala Ser Gly
        275                 280                 285

Gly Ser Ser Ser Ser Ser Ser Ser Ser Ser Ser Ser Ser Ser Ser Ser
    290                 295                 300

Ser Ser Thr Ser Ser Ser Ser Ser Ser Ser Ser Ser Ser Ser Ser Ser
305                 310                 315                 320

Ser Ser Ser Ser Ser Ser Ser Ser Ser Ser Ser Ser Ser Ser Ser Ser
                325                 330                 335

Ser Ser Ser Ser Ser Asn Gly Gly Val Pro Gly Asn Thr Tyr Thr Ala
            340                 345                 350

Thr Pro Asp Ser Leu Asn Asp Val Leu Ala Thr Val Ser Gly Gly Asp
        355                 360                 365

Glu Ile Val Val Thr Gly Ser Gly Glu Ile Ser Ile Lys Asn Ile Ser
    370                 375                 380

Phe Asn Ser Pro Val Leu Ile Arg Ala Asn Ser Ile Gly Gly Thr Thr
385                 390                 395                 400

Leu Thr Asn Ala Thr Leu Thr Asn Cys Asn Asn Ile Ser Leu Gln Gly
                405                 410                 415

Phe Val Phe Gly Pro Asn Asp Glu Ser Thr Leu Leu Lys Ile Val Asn
            420                 425                 430

Ser Thr Asn Ile Lys Ile Leu Arg Asn Leu Phe Asp His Lys Asn Val
        435                 440                 445

Thr Glu Ser Gln Thr Ser Leu Val Met Thr Gln Ala Ser Gln Tyr Ile
```

```
                450                 455                 460
Glu Ile Ala Tyr Asn Glu Phe Arg Asp Lys Asn Leu Gly Asp Arg Ser
465                 470                 475                 480

Gly Thr Lys Ile Thr Gly Ser Tyr Ile Lys Thr Gln Phe Asp Asp Pro
                485                 490                 495

Leu Met Ser Lys Asn Ile His Ile His Asn His Phe Lys Asn Ile
                500                 505                 510

Ala Pro Tyr Leu Val Asp Gly Val Pro Ala Gly Asp Ser Asp Arg Glu
                515                 520                 525

Val Ile Ala Met Gly Ile Ala Asp Ser Gln Asp Val Val Thr Asn Asn
530                 535                 540

Ile Val Glu Tyr Asn Leu Phe Glu Asn Cys Asp Gly Glu Asn Glu Ile
545                 550                 555                 560

Val Thr Val Lys Thr Ser Asn Asn Ile Phe Arg Tyr Asn Thr Phe Lys
                565                 570                 575

Asn Ser Met Gly Ser Leu Ser Phe Arg Leu Gly Ser Asn Asn Gln Ala
                580                 585                 590

Tyr Gly Asn Tyr Phe Tyr Gly Val Gly Ser Gly Ala Ser Val Ala Asn
                595                 600                 605

Asp Asn Tyr Glu Thr Gly Gly Val Arg Val Tyr Gly Ala Gly His Thr
                610                 615                 620

Ile His Asn Asn Tyr Met Glu Gly Leu Thr Gly Leu Ser Trp Arg Arg
625                 630                 635                 640

Pro Ile Leu Val Asp Ser Gly Asp Thr Ser Glu Ser Ser Gly Asn Asp
                645                 650                 655

Ser His Glu Val Ser Thr Asn Val Gln Val Tyr Asp Asn Val Ile Val
                660                 665                 670

Asn Ser Leu Gly Gly Gly Ile His Val Gly Gly Asp Lys Tyr Ser Lys
                675                 680                 685

Met Pro Thr Asn Ile Thr Ile Thr Asn Asn Val Val Ser Gly Ser Asp
                690                 695                 700

Gly Ile Leu Phe Asn Asn His Ala Asn Gln Ser Ser Asn Thr Trp Ser
705                 710                 715                 720

Gly Asn Gln Ala Tyr Ala Thr Gly Ser Ala Val Ala Val Ala Gly Gly
                725                 730                 735

Ser Leu Gly Ala Ser Glu Val Val Leu Ser Ser Glu Pro Thr Ile
                740                 745                 750

Asn Lys Pro Thr Pro Leu Thr Ala Ser Asp Val Gly Pro Ser Ala Pro
                755                 760                 765

<210> SEQ ID NO 33
<211> LENGTH: 1008
<212> TYPE: DNA
<213> ORGANISM: Microbulbifer degradans 2-40

<400> SEQUENCE: 33
atgcaagcag gcgatgttgt actgcccgca atggcatacg atttaagcca ttggaaaatt      60
accgttccgc tagacgacaa caaagatggc aaagttgacg aagtggatac caaggcgctg     120
caaaagtata tgcactcaga ctatttctat gtaaatagcg agggcggatt ggtatttgct     180
actcctaacc aagccaccac taccagcggc tcgtcaaact cacgcagtga attgcgccaa     240
atgattcgcg gcaccaatac tagaattgga actaagtcgc caggcaataa ctttgcattg     300
gcttcgcacc cacaggcaaa agcatttggc gatataggcg caaacttaaa agctacttta     360
```

-continued

```
gcggtaaacc acgttgccct taatgccaaa tatactgata agtttcctgc atactctgtt    420
gtagtggggc aaattcacgc cggcaaagat aaagacctaa tcgccaaagg cgaggggtat    480
ggctggggta acgagcctat caaaatctat tacaaaaaat ggcccgatca taaaacgggg    540
tcagtttttt ggacatacga gcgcaaccta gaaaaagcaa atccagatag aaccgatatt    600
gcttatccag tatggggcaa cacttgggat aattcagaaa acccaggcga caaaggcata    660
gcattagatg aatcttttag ctatgagata aacgtgtaca agacatcat gcacttaacc      720
tttactgcgg cgaataaacc tacagttaaa tacagcatta acctagcaaa caatgtaaat    780
gcttacggca aggtggatga aaagatcat cctaaaggtt atttaggcga ttggttgtac      840
tttaaagccg gcgcttacga tcagtgtagt gtgaaagatg accctggctt ttggtaccca    900
gcctgcgctg taccggcga ttgggaaacc gacaagaaaa acggtgacta cacacgcgta     960
acatttacaa agcttgagct aggtaaaggc tatagcgtaa gcaagtaa                 1008
```

<210> SEQ ID NO 34
<211> LENGTH: 335
<212> TYPE: PRT
<213> ORGANISM: Microbulbifer degradans 2-40

<400> SEQUENCE: 34

```
Met Gln Ala Gly Asp Val Val Leu Pro Ala Met Ala Tyr Asp Leu Ser
  1               5                  10                  15

His Trp Lys Ile Thr Val Pro Leu Asp Asp Asn Lys Asp Gly Lys Val
             20                  25                  30

Asp Glu Val Asp Thr Lys Ala Leu Gln Lys Tyr Met His Ser Asp Tyr
         35                  40                  45

Phe Tyr Val Asn Ser Glu Gly Gly Leu Val Phe Ala Thr Pro Asn Gln
     50                  55                  60

Ala Thr Thr Thr Ser Gly Ser Ser Asn Ser Arg Ser Glu Leu Arg Gln
 65                  70                  75                  80

Met Ile Arg Gly Thr Asn Thr Arg Ile Gly Thr Lys Ser Pro Gly Asn
                 85                  90                  95

Asn Phe Ala Leu Ala Ser His Pro Gln Ala Lys Ala Phe Gly Asp Ile
            100                 105                 110

Gly Gly Asn Leu Lys Ala Thr Leu Ala Val Asn His Val Ala Leu Asn
        115                 120                 125

Ala Lys Tyr Thr Asp Lys Phe Pro Ala Tyr Ser Val Val Val Gly Gln
    130                 135                 140

Ile His Ala Gly Lys Asp Lys Asp Leu Ile Ala Lys Gly Glu Gly Tyr
145                 150                 155                 160

Gly Trp Gly Asn Glu Pro Ile Lys Ile Tyr Tyr Lys Lys Trp Pro Asp
                165                 170                 175

His Lys Thr Gly Ser Val Phe Trp Thr Tyr Glu Arg Asn Leu Glu Lys
            180                 185                 190

Ala Asn Pro Asp Arg Thr Asp Ile Ala Tyr Pro Val Trp Gly Asn Thr
        195                 200                 205

Trp Asp Asn Ser Glu Asn Pro Gly Asp Lys Gly Ile Ala Leu Asp Glu
    210                 215                 220

Ser Phe Ser Tyr Glu Ile Asn Val Tyr Lys Asp Ile Met His Leu Thr
225                 230                 235                 240

Phe Thr Ala Ala Asn Lys Pro Thr Val Lys Tyr Ser Ile Asn Leu Ala
                245                 250                 255
```

```
Asn Asn Val Asn Ala Tyr Gly Lys Val Asp Glu Lys Asp His Pro Lys
                260                 265                 270

Gly Tyr Leu Gly Asp Trp Leu Tyr Phe Lys Ala Gly Ala Tyr Asp Gln
            275                 280                 285

Cys Ser Val Lys Asp Asp Pro Gly Phe Trp Tyr Pro Ala Cys Ala Gly
        290                 295                 300

Thr Gly Asp Trp Glu Thr Asp Lys Lys Asn Gly Asp Tyr Thr Arg Val
305                 310                 315                 320

Thr Phe Thr Lys Leu Glu Leu Gly Lys Gly Tyr Ser Val Ser Lys
                325                 330                 335

<210> SEQ ID NO 35
<211> LENGTH: 1818
<212> TYPE: DNA
<213> ORGANISM: Microbulbifer degradans 2-40

<400> SEQUENCE: 35
atgggcgcag gtgcgttaat agcttctgcg tcgctcgcga atgctgcaac ttttgtttta      60
gaaaaggtaa atacagggtt ttccgtcgac ggtggcaacg gcgctgtgga ggcgcgtcag     120
gtttaccttt gggaaacaaa taccaataac gtcaaccaga actgggttca aattagccat     180
ggtggcggtt actactccta taaaaaacaa aatacgaatt tatgcttaga cggtggcagt     240
ggtggtgccc gccttcagcc tgtcacacta gaggtgtgtg attcgagcaa ttcgaccag      300 cactggaaca agtgaaagt atacacgggc accgaaattt atcgcatgga aaagcgcaat     360
gcaccgggtt tctctataga tggtaacggt ggagcggctg caaggcaggc gatttattta     420
tggaattcaa acagtaataa cgttaaccag cagtgggaat ttattcgcac agatgaagat     480
acaggtgatg gcaagcttgc tattgcaact gcatttgacg acggttcaag tcacagcagc     540
tacccagcat caaaagccat tgacggcaac accgcttggg cttcgcgctg gctgcttct      600 ggctcgccag taaatctaac tattcagctt gaacaaacta gccgcgtaac tgaagtgggc     660
attgcatggg ggcagggcgg ctctcgcgcg tatacgttcg aaatctatgc gcgaccaggc     720
actagcggct cttggacaaa agtgtttgat gatgtgagta gcggttcgac ggcgggtatt     780
gaagtgtttg atattactga tattgatgct cagcaaattc gagtaaaaac ttttgagaat     840
actgctggta ccacttggac gaatattacc gaggttgaaa tttatggggc tgatggcggg     900
tcatctagca gttctagttc atctagctct acgtctagta ctagttctac ttccagcaca     960
agttctagct cgggcgggtt taacctgaac cctaacgcgc tccccttcaag taattttaac    1020 cttttctcagt ggtacctcag cgtgcctacc gatacagatg gtagcggtac ggcagacagc    1080
attaaagaag gtgagttgaa ctcgggctac gagaataaca gttactttta cacgggttct    1140
gatggtggca tggtatttaa gtgtccaatt tctggctata aacatctac tggtaccagc     1200 tatacgcgca ccgaattgcg tgaaatgttg cgtgcgggta atcatcaat tgctaccagt     1260 ggtgtaaata aaaataactg ggtgttttggt tcggcaccta gcagtgcgca ggcagcggct    1320
ggcggtgttg acggcaacat gaaagcaacc ctagcagtga attatgtaac aaccacgggc    1380
gatagctcac aggtggggcg cgtcattatc ggtcagattc acgccgaaaa aaacgagcct    1440
attcgcctgt actatcgcaa gctacccggt aactctaaag gcggtattta ttacgctcac    1500
gaagatgccg atgcggtga ggtttgggta gatatgattg gttcgcgcag cagtagtgct    1560
tctaatcctt cagatggcat tgcattgaac gaggtgttta gctacgagat tgatgtaact    1620
aacaatatgt taactgtgaa aatttaccgt gatggtaaat caacagtaac aagccagtac    1680
```

```
aacatggtta atagtggtta cgacgactcc gacgattgga tgtatttcaa agcgggcgta      1740
tacaatcaga acaatactgg aaatggttca gactatgtgc aagcgacgtt ctactcgctt      1800
acgcatactc acgactag                                                    1818
```

<210> SEQ ID NO 36
<211> LENGTH: 605
<212> TYPE: PRT
<213> ORGANISM: Microbulbifer degradans 2-40

<400> SEQUENCE: 36

```
Met Gly Ala Gly Ala Leu Ile Ala Ser Ala Ser Leu Ala Asn Ala Ala
 1               5                  10                  15

Thr Phe Val Leu Glu Lys Val Asn Thr Gly Phe Ser Val Asp Gly Gly
            20                  25                  30

Asn Gly Ala Val Glu Ala Arg Gln Val Tyr Leu Trp Glu Thr Asn Thr
        35                  40                  45

Asn Asn Val Asn Gln Asn Trp Val Gln Ile Ser His Gly Gly Gly Tyr
    50                  55                  60

Tyr Ser Tyr Lys Lys Gln Asn Thr Asn Leu Cys Leu Asp Gly Gly Ser
65                  70                  75                  80

Gly Gly Ala Arg Leu Gln Pro Val Thr Leu Glu Val Cys Asp Ser Ser
                85                  90                  95

Asn Tyr Asp Gln His Trp Asn Lys Val Lys Val Tyr Thr Gly Thr Glu
           100                 105                 110

Ile Tyr Arg Met Glu Lys Arg Asn Ala Pro Gly Phe Ser Ile Asp Gly
       115                 120                 125

Asn Gly Gly Ala Ala Ala Arg Gln Ala Ile Tyr Leu Trp Asn Ser Asn
   130                 135                 140

Ser Asn Asn Val Asn Gln Gln Trp Glu Phe Ile Arg Thr Asp Glu Asp
145                 150                 155                 160

Thr Gly Asp Gly Lys Leu Ala Ile Ala Thr Ala Phe Asp Asp Gly Ser
                165                 170                 175

Ser His Ser Ser Tyr Pro Ala Ser Lys Ala Ile Asp Gly Asn Thr Ala
           180                 185                 190

Trp Ala Ser Arg Trp Ala Ala Ser Gly Ser Pro Val Asn Leu Thr Ile
       195                 200                 205

Gln Leu Glu Gln Thr Ser Arg Val Thr Glu Val Gly Ile Ala Trp Gly
   210                 215                 220

Gln Gly Gly Ser Arg Ala Tyr Thr Phe Glu Ile Tyr Ala Arg Pro Gly
225                 230                 235                 240

Thr Ser Gly Ser Trp Thr Lys Val Phe Asp Asp Val Ser Ser Gly Ser
                245                 250                 255

Thr Ala Gly Ile Glu Val Phe Asp Ile Thr Asp Ile Asp Ala Gln Gln
           260                 265                 270

Ile Arg Val Lys Thr Phe Glu Asn Thr Ala Gly Thr Thr Trp Thr Asn
       275                 280                 285

Ile Thr Glu Val Glu Ile Tyr Gly Ala Asp Gly Ser Ser Ser Ser
   290                 295                 300

Ser Ser Ser Ser Ser Thr Ser Ser Thr Ser Ser Thr Ser Ser Thr
305                 310                 315                 320

Ser Ser Ser Ser Gly Gly Phe Asn Leu Asn Pro Asn Ala Pro Pro Ser
                325                 330                 335

Ser Asn Phe Asn Leu Ser Gln Trp Tyr Leu Ser Val Pro Thr Asp Thr
           340                 345                 350
```

```
Asp Gly Ser Gly Thr Ala Asp Ser Ile Lys Glu Gly Glu Leu Asn Ser
        355                 360                 365
Gly Tyr Glu Asn Asn Ser Tyr Phe Tyr Thr Gly Ser Asp Gly Gly Met
        370                 375                 380
Val Phe Lys Cys Pro Ile Ser Gly Tyr Lys Thr Ser Thr Gly Thr Ser
385                 390                 395                 400
Tyr Thr Arg Thr Glu Leu Arg Glu Met Leu Arg Ala Gly Asn Thr Ser
                405                 410                 415
Ile Ala Thr Ser Gly Val Asn Lys Asn Asn Trp Val Phe Gly Ser Ala
            420                 425                 430
Pro Ser Ser Ala Gln Ala Ala Gly Gly Val Asp Gly Asn Met Lys
        435                 440                 445
Ala Thr Leu Ala Val Asn Tyr Val Thr Thr Thr Gly Asp Ser Ser Gln
        450                 455                 460
Val Gly Arg Val Ile Ile Gly Gln Ile His Ala Glu Lys Asn Glu Pro
465                 470                 475                 480
Ile Arg Leu Tyr Tyr Arg Lys Leu Pro Gly Asn Ser Lys Gly Gly Ile
                485                 490                 495
Tyr Tyr Ala His Glu Asp Ala Asp Gly Gly Glu Val Trp Val Asp Met
            500                 505                 510
Ile Gly Ser Arg Ser Ser Ala Ser Asn Pro Ser Asp Gly Ile Ala
        515                 520                 525
Leu Asn Glu Val Phe Ser Tyr Glu Ile Asp Val Thr Asn Asn Met Leu
        530                 535                 540
Thr Val Lys Ile Tyr Arg Asp Gly Lys Ser Thr Val Thr Ser Gln Tyr
545                 550                 555                 560
Asn Met Val Asn Ser Gly Tyr Asp Asp Ser Asp Asp Trp Met Tyr Phe
                565                 570                 575
Lys Ala Gly Val Tyr Asn Gln Asn Asn Thr Gly Asn Gly Ser Asp Tyr
            580                 585                 590
Val Gln Ala Thr Phe Tyr Ser Leu Thr His Thr His Asp
        595                 600                 605

<210> SEQ ID NO 37
<211> LENGTH: 1575
<212> TYPE: DNA
<213> ORGANISM: Microbulbifer degradans 2-40

<400> SEQUENCE: 37
atgttaaaag tagttatcaa agcctttgtt gtaaccctgt ctggtttaat tattagtgcg      60
tgtggtggtg gcgatagtaa gtcccctgaa accacgccga caccaacgcc gacgccaacg     120
ccgacaccaa cgccgacacc aacgccgaca ccaacgccaa cgccgacgcc aacgccaacg     180
ccaacaccaa caccaacacc tacaccggta gagtgtacgc cagcgttaag cactataagc     240
tctgccttcg acgatggcag taacgatggc tatgtaccgg caaatacaat agatgacgac     300
ctaaccgatg agtcgcgttg gtcttcgttt ggcgatggca gtggatagt gtttgatctt     360 gctatcgcaa agacgtaag agaaatacac agtgcttggt ataaaggtga tactcgcact     420 agttttacg acatagaaag ttcgctagat gcggtatctt ggagcacctt gcaaactaac     480
cttcagtcac aaggtactac aagcctagag gcggtaacgt tagacagcac cgatgcgcgt     540
tacattcgcg tggttggccc cggcaacacc gacaacacat ggaacagctt gatagaagta     600
gatatttacg attgtggtga aacaggtacg cctaccgaag atcctgttgt agtagagcca     660
```

```
ccagagccgc cagcgccaac agatggtgac atgccagcaa ccacgccaaa tccgccgctc    720
gtaactgacg cgttagaccc agatgccgcg ccatcgagta acttcgattt atggccttgg    780
tatttaagtg tgccaaccga tacagatggc agcggcactg cagatagtat taaagagtcc    840
gacctaaacg cgggctacga aagttcggaa ttttttttaca cagctgcaga tggcggtatg    900
gtatttaaat gcccagttgc gggctttaaa acctctacca atacttctta tacgcgcgtg    960
gagctaagag aaatgttacg cagagggaac agcagtattt ctacccaagg tgtaaatggt   1020
aacaactggg tgtttggttc tgcaccgcaa agcgatttaa acgcagccgg tggaatagac   1080
ggcaacctgc gagccacatt ggccgtaaac aaggtaacca ccacgcacgg cgatggcttt   1140
gaataccaag ttggccgcgt aattattggt caaatacacg cgaacgacga cgagccaatt   1200
cgcttgtact accgcaaatt accttctaat agcaaaggct caatttactt cgcgcacgag   1260
ttgttagatg gtgacgacac ttggcacgaa atgatcggca gccgtggcga caacgctagc   1320
gacccagccg acggtatagc gctagatgaa acgttcagct acgaaataga tgtacgcggc   1380
aacacgctca ctgtaaccat tatgcgtgaa ggcaaacccg acgtaaccaa agtgctagac   1440
atgagcgcca gcggctacga cgaaggcggc cagtacatgt actttaaagc tggcgtgtac   1500
aaccaaaata actcgggcga ccccgatgac tacgtgcaag caactttcta tgcattagag   1560
gccacccaca actag                                                    1575

<210> SEQ ID NO 38
<211> LENGTH: 524
<212> TYPE: PRT
<213> ORGANISM: Microbulbifer degradans 2-40

<400> SEQUENCE: 38

Met Leu Lys Val Val Ile Lys Ala Phe Val Thr Leu Ser Gly Leu
  1               5                  10                  15

Ile Ile Ser Ala Cys Gly Gly Gly Asp Ser Lys Ser Pro Glu Thr Thr
                 20                  25                  30

Pro Thr Pro Thr Pro Thr Pro Thr Pro Thr Pro Thr Pro Thr
             35                  40                  45

Pro Thr Pro Thr Pro Thr Pro Thr Pro Thr Pro Thr Pro Thr
 50                  55                  60

Pro Thr Pro Thr Pro Val Glu Cys Thr Pro Ala Leu Ser Thr Ile Ser
 65                  70                  75                  80

Ser Ala Phe Asp Asp Gly Ser Asn Asp Gly Tyr Val Pro Ala Asn Thr
                 85                  90                  95

Ile Asp Asp Asp Leu Thr Asp Glu Ser Arg Trp Ser Ser Phe Gly Asp
                100                 105                 110

Gly Lys Trp Ile Val Phe Asp Leu Ala Ile Ala Lys Asp Val Arg Glu
            115                 120                 125

Ile His Ser Ala Trp Tyr Lys Gly Asp Thr Arg Thr Ser Phe Tyr Asp
        130                 135                 140

Ile Glu Ser Ser Leu Asp Ala Val Ser Trp Ser Thr Leu Gln Thr Asn
145                 150                 155                 160

Leu Gln Ser Gln Gly Thr Thr Ser Leu Glu Ala Val Thr Leu Asp Ser
                165                 170                 175

Thr Asp Ala Arg Tyr Ile Arg Val Val Gly Arg Gly Asn Thr Asp Asn
            180                 185                 190

Thr Trp Asn Ser Leu Ile Glu Val Asp Ile Tyr Asp Cys Gly Glu Thr
        195                 200                 205
```

-continued

Gly Thr Pro Thr Glu Asp Pro Val Val Glu Pro Pro Glu Pro Pro
           210                 215                 220

Ala Pro Thr Asp Gly Asp Met Pro Ala Thr Thr Pro Asn Pro Pro Leu
225                 230                 235                 240

Val Thr Asp Ala Leu Asp Pro Asp Ala Ala Pro Ser Ser Asn Phe Asp
                245                 250                 255

Leu Trp Pro Trp Tyr Leu Ser Val Pro Thr Asp Thr Asp Gly Ser Gly
            260                 265                 270

Thr Ala Asp Ser Ile Lys Glu Ser Asp Leu Asn Ala Gly Tyr Glu Ser
            275                 280                 285

Ser Glu Phe Phe Tyr Thr Ala Ala Asp Gly Gly Met Val Phe Lys Cys
290                 295                 300

Pro Val Ala Gly Phe Lys Thr Ser Thr Asn Thr Ser Tyr Thr Arg Val
305                 310                 315                 320

Glu Leu Arg Glu Met Leu Arg Arg Gly Asn Ser Ser Ile Ser Thr Gln
                325                 330                 335

Gly Val Asn Gly Asn Asn Trp Val Phe Gly Ser Ala Pro Gln Ser Asp
                340                 345                 350

Leu Asn Ala Ala Gly Gly Ile Asp Gly Asn Leu Arg Ala Thr Leu Ala
            355                 360                 365

Val Asn Lys Val Thr Thr Thr His Gly Asp Gly Phe Glu Tyr Gln Val
370                 375                 380

Gly Arg Val Ile Ile Gly Gln Ile His Ala Asn Asp Asp Glu Pro Ile
385                 390                 395                 400

Arg Leu Tyr Tyr Arg Lys Leu Pro Ser Asn Ser Lys Gly Ser Ile Tyr
                405                 410                 415

Phe Ala His Glu Leu Leu Asp Gly Asp Asp Thr Trp His Glu Met Ile
            420                 425                 430

Gly Ser Arg Gly Asp Asn Ala Ser Asp Pro Ala Asp Gly Ile Ala Leu
            435                 440                 445

Asp Glu Thr Phe Ser Tyr Glu Ile Asp Val Arg Gly Asn Thr Leu Thr
450                 455                 460

Val Thr Ile Met Arg Glu Gly Lys Pro Asp Val Thr Lys Val Leu Asp
465                 470                 475                 480

Met Ser Ala Ser Gly Tyr Asp Glu Gly Gly Gln Tyr Met Tyr Phe Lys
                485                 490                 495

Ala Gly Val Tyr Asn Gln Asn Asn Ser Gly Asp Pro Asp Asp Tyr Val
            500                 505                 510

Gln Ala Thr Phe Tyr Ala Leu Glu Ala Thr His Asn
            515                 520

<210> SEQ ID NO 39
<211> LENGTH: 765
<212> TYPE: DNA
<213> ORGANISM: Microbulbifer degradans 2-40

<400> SEQUENCE: 39
ttgccagacg ccaccgaata cctacctgat tggttaacag cgggcaacga agtggccaac      60 acctttaca catcccctca aaccggcgcc atggtgttta attgcccaac acacggcagc     120
accaccagca gcgcgacaaa atattcacgt acagaattaa gggaaatgtt acgagggctg     180
aatacacgcc cttcaaccaa gggtataggg cggaacaatt gggtgctatc aaccgctcca     240
caccaaaacc aagtcagtgc aggcggcatc gatggcacct agaagcagt tctgagcgtt     300 gattacgtat cccaaactgg gccagcgcat atgataggcc gcgtgatagt ggggcaaatt     360

```
cacggtgaag atgacgagcc tgtgcgaatt tattaccgca aactgccgca caacaccaaa    420
ggctcggtgt attttgcaag cgagcacccc ggcggcgaag atgtgttcta tccaatgata    480
ggcagtagta gcaatagcgc ggccgaccca gaagatggta tagcgctagg cgaaaagtgg    540
gggtatcgca ttcatataga aggcaggcag cttagtgtaa gaattattcg cgaagacggg    600
cgctatgtgg agcaatcact cactatcggc gaagcgtaca ataacgattg gttttacttt    660
aaagcggggg tatataacca aataatgat ggcaacccag atgaatatgc ccaagcctct     720 tttttaaac ttaaagcaac acataaacag tataataaac aataa                    765
```

<210> SEQ ID NO 40
<211> LENGTH: 254
<212> TYPE: PRT
<213> ORGANISM: Microbulbifer degradans 2-40

<400> SEQUENCE: 40

```
Met Pro Asp Ala Thr Glu Tyr Leu Pro Asp Trp Leu Thr Ala Gly Asn
 1               5                  10                  15

Glu Val Ala Asn Thr Phe Tyr Thr Ser Pro Gln Thr Gly Ala Met Val
             20                  25                  30

Phe Asn Cys Pro Thr His Gly Ser Thr Thr Ser Ala Thr Lys Tyr
         35                  40                  45

Ser Arg Thr Glu Leu Arg Glu Met Leu Arg Gly Leu Asn Thr Arg Pro
     50                  55                  60

Ser Thr Lys Gly Ile Gly Arg Asn Asn Trp Val Leu Ser Thr Ala Pro
 65                  70                  75                  80

His Gln Asn Gln Val Ser Ala Gly Gly Ile Asp Gly Thr Leu Glu Ala
                 85                  90                  95

Val Leu Ser Val Asp Tyr Val Ser Gln Thr Gly Pro Ala His Met Ile
            100                 105                 110

Gly Arg Val Ile Val Gly Gln Ile His Gly Glu Asp Asp Glu Pro Val
        115                 120                 125

Arg Ile Tyr Tyr Arg Lys Leu Pro His Asn Thr Lys Gly Ser Val Tyr
    130                 135                 140

Phe Ala Ser Glu His Pro Gly Gly Glu Asp Val Phe Tyr Pro Met Ile
145                 150                 155                 160

Gly Ser Ser Ser Asn Ser Ala Ala Asp Pro Glu Asp Gly Ile Ala Leu
                165                 170                 175

Gly Glu Lys Trp Gly Tyr Arg Ile His Ile Glu Gly Arg Gln Leu Ser
            180                 185                 190

Val Arg Ile Ile Arg Glu Asp Gly Arg Tyr Val Glu Gln Ser Leu Thr
        195                 200                 205

Ile Gly Glu Ala Tyr Asn Asn Asp Trp Phe Tyr Phe Lys Ala Gly Val
    210                 215                 220

Tyr Asn Gln Asn Asn Asp Gly Asn Pro Asp Glu Tyr Ala Gln Ala Ser
225                 230                 235                 240

Phe Phe Lys Leu Lys Ala Thr His Lys Gln Tyr Asn Lys Gln
                245                 250
```

<210> SEQ ID NO 41
<211> LENGTH: 1230
<212> TYPE: DNA
<213> ORGANISM: Microbulbifer degradans 2-40

<400> SEQUENCE: 41

-continued

```
atgaaaaagg ccaaactcat aaggctaaac ctactctacc cgctagtggc taccctaggg      60
ctagcaacct tctctgcaca agcagaggta atttattcca acggttttga cggcttgccg     120
cttggtaacg ccagcgacag agatataaaa aacacctgga gcacccgcta tgcaaaaggc     180
ccagacgagg gcagggtaac caccgttacc gattcacata caggcaaagc catacgcatt     240
aaatacccag ccaatgccaa tcaatcgtcg ccaagtggcg ccacctggga accgacata      300
ggccatagcg gcgaagagct gtatatgtct tactgggtga aatttgatta cgatttcgat     360
tttgtgaaag gcggtaaaat gcctggctta gcaggcgcca ccgagttccc ctacggcgac     420
aacggcttta ccaccgctt aatgtggcgc gaagacggga acttgagtt ttacttgcac       480
gggtacgaaa taacaatag ccaaggcgcc gaaccctacc gtgtattttg aattacgcc       540
ggttaccacg cacgtgttat acccggccag tggcaccata ttgaaattcg ccaaaaacta    600
aacaccccag ggcagcgcaa tggcgtattg cagggttggt tagatggtgt attggtatgt    660
aacgatagcg acaactctgg tgtgcgtggc gctggccacg gcagcaccaa gctaaaccac    720
ctttactttt ctacctttt tggcgggtcg agcgcgccgg taagccagtg caacctaaa     780
actgatgtgt acgcaaacta cgatgactt atcgtatcca ccacgcgtat ggtatgaat     840
ggcaacccgg gcactggttc ttctagttca tcttcaagtt caagcagttc tacttcgagc    900
tcgtcgtcca gctcttcatc cagctccagc agttcatcgg gcggcagctc taattgtacg    960
gtggttccca gtggctcggc taagcacgaa ataaacctca acaattccag ctgcttgcag  1020
tttaacgaaa acttacgcgg taaaaccttt gcggtgtggg atagcgacag caacccttct  1080
tgcgacttta gaggcaccgt aacctccact aatggtactg ggtcgctaaa cgtgcccgac  1140
aactacgaag ccaccgattc gctcaccggc accaaagtaa gtattcaacc cagtaatggc  1200
tgtaaatacc taaaagtaag agcgctataa                                   1230
```

<210> SEQ ID NO 42
<211> LENGTH: 409
<212> TYPE: PRT
<213> ORGANISM: Microbulbifer degradans 2-40

<400> SEQUENCE: 42

```
Met Lys Lys Ala Lys Leu Ile Arg Leu Asn Leu Leu Tyr Pro Leu Val
  1               5                  10                  15

Ala Thr Leu Gly Leu Ala Thr Phe Ser Ala Gln Ala Glu Val Ile Tyr
             20                  25                  30

Ser Asn Gly Phe Asp Gly Leu Pro Leu Gly Asn Ala Ser Asp Arg Asp
         35                  40                  45

Ile Lys Asn Thr Trp Ser Thr Arg Tyr Ala Lys Gly Pro Asp Glu Gly
     50                  55                  60

Arg Val Thr Thr Val Thr Asp Ser His Thr Gly Lys Ala Ile Arg Ile
 65                  70                  75                  80

Lys Tyr Pro Ala Asn Ala Asn Gln Ser Ser Pro Ser Gly Ala Thr Trp
                 85                  90                  95

Glu Thr Asp Ile Gly His Ser Gly Glu Glu Leu Tyr Met Ser Tyr Trp
            100                 105                 110

Val Lys Phe Asp Tyr Asp Phe Asp Phe Val Lys Gly Lys Met Pro
        115                 120                 125

Gly Leu Ala Gly Ala Thr Glu Phe Pro Tyr Gly Asp Asn Gly Phe Thr
    130                 135                 140

Thr Arg Leu Met Trp Arg Glu Asp Gly Lys Leu Glu Phe Tyr Leu His
145                 150                 155                 160
```

Gly Tyr Glu Ile Asn Asn Ser Gln Gly Ala Glu Pro Tyr Arg Val Phe
            165                 170                 175

Trp Asn Tyr Ala Gly Tyr His Ala Arg Val Ile Pro Gly Gln Trp His
        180                 185                 190

His Ile Glu Ile Arg Gln Lys Leu Asn Thr Pro Gly Gln Arg Asn Gly
    195                 200                 205

Val Leu Gln Gly Trp Leu Asp Gly Val Leu Val Cys Asn Asp Ser Asp
    210                 215                 220

Asn Ser Gly Val Arg Gly Ala Gly His Gly Ser Thr Lys Leu Asn His
225                 230                 235                 240

Leu Tyr Phe Ser Thr Phe Phe Gly Gly Ser Ser Ala Pro Val Ser Gln
            245                 250                 255

Trp Gln Pro Lys Thr Asp Val Tyr Ala Asn Tyr Asp Asp Phe Ile Val
            260                 265                 270

Ser Thr Thr Arg Ile Gly Met Asn Gly Asn Pro Gly Thr Gly Ser Ser
        275                 280                 285

Ser Ser Ser Ser Ser Ser Ser Ser Thr Ser Ser Ser Ser Ser Ser Ser
    290                 295                 300

Ser Ser Ser Ser Ser Ser Ser Ser Gly Gly Ser Ser Asn Cys Thr
305                 310                 315                 320

Val Val Pro Ser Gly Ser Ala Lys His Glu Ile Asn Leu Asn Asn Ser
            325                 330                 335

Ser Cys Leu Gln Phe Asn Glu Asn Leu Arg Gly Lys Thr Phe Ala Val
        340                 345                 350

Trp Asp Ser Asp Ser Asn Pro Ser Cys Asp Phe Arg Gly Thr Val Thr
        355                 360                 365

Ser Thr Asn Gly Thr Gly Ser Leu Asn Val Pro Asp Asn Tyr Glu Ala
    370                 375                 380

Thr Asp Ser Leu Thr Gly Thr Lys Val Ser Ile Gln Pro Ser Asn Gly
385                 390                 395                 400

Cys Lys Tyr Leu Lys Val Arg Ala Leu
            405

<210> SEQ ID NO 43
<211> LENGTH: 4665
<212> TYPE: DNA
<213> ORGANISM: Microbulbifer degradans 2-40

<400> SEQUENCE: 43

| | | | | | |
|---|---|---|---|---|---|
| atgagaagtg | tattgcttcc | agtaatgctt | ctgtcttcgg | gggtagctct | agctactaat | 60 |
| gctgaagata | cgaacagttc | aaataattat | gtttcttata | gtaataacgg | ttatggcgat | 120 |
| catgctagcg | cattaacatt | cgctgccgaa | aaccgttgtt | cgcaagtgct | taccatttgg | 180 |
| cggcctgccc | atcctcgagc | gtgcccttca | acagtaacct | ggggtgaagt | tctgcctggt | 240 |
| ctgtcaattg | gtgtagcaac | tcaagcattc | gatcgaccta | atcgcgtaat | gtatagcgat | 300 |
| atttcagtta | aaaacgaaac | gggtttatct | attgctgcag | gctctaagtt | aattttgcc | 360 |
| aatagttctt | taccactttt | aaatgccgaa | gggcaaacag | aagctgggca | gccatacctt | 420 |
| ataaccacgc | aagatttacc | ctctgggcaa | accgttacgc | tgcgcgcaga | atttaagccg | 480 |
| cgccttcgtc | cgcttagctt | tgatgcaggc | tttgatatac | tgcaagtaag | cgacggtgta | 540 |
| gtaagtatcg | ctggtgaagc | tagggtagtg | cgtaccttaa | ctgcaaatgt | gagtgaccct | 600 |
| gcaggcgtga | gttctgccgt | tagctatcaa | tggcaggcca | atggggtgga | tattgctggt | 660 |

```
gcaacttctg caacctataa gcttacccca gaagacgaaa gcaaagttat tactgtcacg    720
gcatcttata tagatgacgc gggctttgcg gaaaatatcc aatccaatgc aactacggca    780
gtggccgccc gcaatgaaaa taccgaaggc aacttgcaaa tacagggcga acgcttagct    840
ggtgcaactt tgcgagccgt gctgggcgac aataacggta tagccggtaa cgctacttat    900
cattggtatg tagagggcca agctatagag ggtgcgacgg aatctatttt gtaccttggc    960
agcgagttgg tgggtaaaac cattacagct acggcaagct ataccgacta cgatgaatat   1020
tcagagtcgc cttccgccac tacttcacat attgcaactt caatagtaag tagtgaacaa   1080
gagttggttg cggccttagc gtctgctagt aacggcgaat ggatagcgct cgcgagtggc   1140
gagtatgcca atatggcaga aattgccatt gccaatggcg ttacattaac tgcgggccaa   1200
gatggcgatg cggttattag cggtgcgaca tgtatcgaat taagcggcaa tcagtctggg   1260
ctggttggct taacatttga taacttaagt ccattatttg gctccgcatg tgacgacaat   1320
aacaagttaa acagtgtatg ggtgtctggt gataacgtta ccgttagcca taaccgtttt   1380
cttggtcatg ctgaagacct cggtagtgta gccgagtaca actacgttta tttgcgtggc   1440
tcttataatg ttattgagcg caatgtattt agcggtaaga atctagatat aaaaggcgca   1500
gcagtttctg tctataacaa aggcgacggc agtgaaggtg gtcatgttgt tcagtacaac   1560
ctgttcaaag atatgcctgg cacgagcgtg caatctagcg cttacgcgtt acaggttggc   1620
cgctctacgg gtagcgacgg cttaggtgaa ggtcagcacg ttgtgcgctt taaccgtttc   1680
gataatgtaa tggcagaccg ccgcattatt aaggttcaag ctagccgcag cagcgtatat   1740
ggcaatacca ttgttaattc aaccggtggt atttcgttgg aagacggtta tgaaaatacc   1800
gttagcaata acgttatact ttctgcgggc gataatagcg acgatagcgg cattatgttc   1860
agcccgtttg gtcacactgt tactggcaat tatatcgcag gattaaaaac cacctcttcg   1920
caacgcgcag cgttattgtt aaatacagaa acggttgcca attctggtaa tagtgcacta   1980
agcgttagcc gagtaactgt tgctaacaac actgtaataa acagtaataa tgcaattgct   2040
acttataccg gcagtaagtg tgtggcagat acttttgttg ctagtttcga aaataactta   2100
gttgctaacg gcgttgctgg tcaaggggct aatggtgccg acagctatgc gtttgataac   2160
ggttgtgcaa taaactccct agaaagtaac tttagcaacg aaacctatt tgcttcaggt   2220
gcagatcttg tgccgctagc gggcagtgct ggtgaagcaa ccttagtggc aacggctaat   2280
ggcttattga acgatgctaa ttcactggcg ggcgcaaatg ccagcgcgtt aatagtactt   2340
agcgaattag atgtggggcc tgggtcgagt tttgtgcaac ctgtagcggg tgcttacaac   2400
ggtgctttaa atcttgattt tactcattgg tacatcactt ccctagtgg cgatgcacag   2460
tacaaccctc agtggttact cgatggctat accagtgaaa cgagttta ctacgacgcc   2520
gatggcgcag ctgtatttaa aacaccaaat atagcgggca ctacatctgc caatacaaaa   2580
tactcgcgta ccgagttgcg tgaaatgatg cgcgggccag agcaaagccc taagccagca   2640
gattggccaa gtacgcaagg cataaacaaa acaactggg tgtttctaa ctcgtatcag   2700
cgagtgcaat atgaggccgg tggtgtggat ggcgtgatgg aagccacact caaggttgat   2760
catgtgtcta ccactgttac cgaagggtac gagtacatga tggggcgggt tattgttggc   2820
caaattcatg cgtccgacga tgagccattc cgtttgtact atcgcaaatt accgggcaac   2880
agtttggggt ctgtgtattt tgctaccgag gtgccaggct taggcgataa ccgctacgac   2940
atgattggtg atagcaaaga agactcgcca aacccttag atggcattgc gctgggcgaa   3000
gtttggagtt accgcgtaga agctaagggt gatgatttaa ccgttaccat tatgcgtgaa   3060
```

-continued

```
ggtaaaccag atgttacgcg cacagtaaaa actgctgccg cttacgccaa cgactggatg    3120
tattttaaag cggggtgta caaccaaaat aatggtggtg atccatcgga ttacgcgcaa     3180
gcaacctttt attccattgt tgtaagtcac gatgcgcccc cagtagaacc gggtaacggt    3240
gaagatgaag gtaatggtgg aacaaccaca gaagttaccg atggcccatc tttgcaaact    3300
gcaattcttg ctgcttctgc aggcgatact atcgagattg gcgcaggtga ctacgccaat    3360
atgggcacag ttgtggttac cgacggggtg accattacac gcgccgaagg cagtaacgct    3420 gttattctg gcgagttttg tttgcaggtt agtggtgatg gtgcgcgtat tacagggttg     3480
gaatttgcgg atttaattgt acccgcagat agcgctaatc actgccgcag caatggtgat    3540
ggcaatattg taattaccgg tgatgacgta gtgtttgatc acaaccttct gtcgggtgat    3600
gccgaattcc caacacctgt ggacgacgac gaccacaact ggctagtact aaaaggcagt    3660
aacgcactgg ttgagcgcaa cacttttcaa aaccgtcgcg gtatagccgc agatggcgta    3720
agccaagtgc gaggtggttt tatttctatc tacgtaaatg gttctgcaac gggtaatact    3780
gtgcaataca acctgtttaa agacatgttg ttgaatgatc agtctactgc gtatgccatt    3840
atgcttggcc gaaccactgg tttagattca atgttagacg ggtttaatac tattcagtac    3900
aaccgtttcg ataatattga ttccaaaacc cgcgtaattc gagtgcaggg tagtagcaat    3960
actattagcc acaacactgt agtcaattcg caaggtatgc tcgcgttaga aagcggtcaa    4020
aataatgttg ttagctacaa cgttattta ccttctggta ccgacagtaa tgatggcggt     4080
atttctgcag cgccatacgg ccataccatt gtgggtaact atattgcagg ctccaacacc    4140
acttccagtg agcgcggtgc catctaccta ataacgacg tggatgagcc aggtaacctc     4200
gccgctacgc catcggcagt ggaaatagct ggcaacacga ttattaactc taagcaaccc    4260
attcatattg gtgctaaggg ctgcgaagtg ggcccggcgt ttatagcaaa tttcagtaac    4320
aacctaatag cgaacggtgt tagcggtgta tctgaatttt atgaaggtgc gccagtttca    4380
ggtcgagcgg ctattcgtta cagctgtgag ctagaccctg cacactcgtt taccggcgaa    4440
gcctacttta gcgatttgct ttacaacact tcgggtgcgt atggcggtgg cctatggttc    4500
gatgctgcca gcacctttgg ttacgacggc gaggctacgc taatagcagg cgagaatggc    4560
ttaatagaag ctactggttc tctcgctggt aaaggagcgc caagtaattc attagtagtg    4620
gtagaagaga ccgatgtagg tgtgggctct gccaccaatt tttaa                    4665
```

<210> SEQ ID NO 44
<211> LENGTH: 1554
<212> TYPE: PRT
<213> ORGANISM: Microbulbifer degradans 2-40

<400> SEQUENCE: 44

```
Met Arg Ser Val Leu Leu Pro Val Met Leu Leu Ser Ser Gly Val Ala
 1               5                  10                  15

Leu Ala Thr Asn Ala Glu Asp Thr Asn Ser Ser Asn Asn Tyr Val Ser
            20                  25                  30

Tyr Ser Asn Asn Gly Tyr Gly Asp His Ala Ser Ala Leu Thr Phe Ala
        35                  40                  45

Ala Glu Asn Arg Cys Ser Gln Val Leu Thr Ile Trp Arg Pro Ala His
    50                  55                  60

Pro Arg Ala Cys Pro Ser Thr Val Thr Trp Gly Glu Val Leu Pro Gly
65                  70                  75                  80

Leu Ser Ile Gly Val Ala Thr Gln Ala Phe Asp Arg Pro Asn Arg Val
```

```
                    85                  90                  95
Met Tyr Ser Asp Ile Ser Val Lys Asn Glu Thr Gly Leu Ser Ile Ala
                100                 105                 110

Ala Gly Ser Lys Leu Ile Phe Ala Asn Ser Ser Leu Pro Leu Leu Asn
                115                 120                 125

Ala Glu Gly Gln Thr Glu Ala Gly Gln Pro Tyr Leu Ile Thr Thr Gln
            130                 135                 140

Asp Leu Pro Ser Gly Gln Thr Val Thr Leu Arg Ala Glu Phe Lys Pro
145                 150                 155                 160

Arg Leu Arg Pro Leu Ser Phe Asp Ala Gly Phe Asp Ile Leu Gln Val
                165                 170                 175

Ser Asp Gly Val Val Ser Ile Ala Gly Glu Ala Arg Val Arg Thr
                180                 185                 190

Leu Thr Ala Asn Val Ser Asp Pro Ala Gly Val Ser Ser Ala Val Ser
            195                 200                 205

Tyr Gln Trp Gln Ala Asn Gly Val Asp Ile Ala Gly Ala Thr Ser Ala
            210                 215                 220

Thr Tyr Lys Leu Thr Pro Glu Asp Glu Ser Lys Val Ile Thr Val Thr
225                 230                 235                 240

Ala Ser Tyr Ile Asp Asp Ala Gly Phe Ala Glu Asn Ile Gln Ser Asn
                245                 250                 255

Ala Thr Thr Ala Val Ala Ala Arg Asn Glu Asn Thr Glu Gly Asn Leu
                260                 265                 270

Gln Ile Gln Gly Glu Arg Leu Ala Gly Ala Thr Leu Arg Ala Val Leu
            275                 280                 285

Gly Asp Asn Asn Gly Ile Ala Gly Asn Ala Thr Tyr His Trp Tyr Val
290                 295                 300

Glu Gly Gln Ala Ile Glu Gly Ala Thr Glu Ser Ile Leu Tyr Leu Gly
305                 310                 315                 320

Ser Glu Leu Val Gly Lys Thr Ile Thr Ala Thr Ala Ser Tyr Thr Asp
                325                 330                 335

Tyr Asp Glu Tyr Ser Glu Ser Pro Ser Ala Thr Thr Ser His Ile Ala
            340                 345                 350

Thr Ser Ile Val Ser Ser Glu Gln Glu Leu Val Ala Ala Leu Ala Ser
            355                 360                 365

Ala Ser Asn Gly Glu Trp Ile Ala Leu Ala Ser Gly Glu Tyr Ala Asn
            370                 375                 380

Met Ala Glu Ile Ala Ile Ala Asn Gly Val Thr Leu Thr Ala Gly Gln
385                 390                 395                 400

Asp Gly Asp Ala Val Ile Ser Gly Ala Thr Cys Ile Glu Leu Ser Gly
                405                 410                 415

Asn Gln Ser Gly Leu Val Gly Leu Thr Phe Asp Asn Leu Ser Pro Leu
            420                 425                 430

Phe Gly Ser Ala Cys Asp Asp Asn Asn Lys Leu Asn Ser Val Trp Val
            435                 440                 445

Ser Gly Asp Asn Val Thr Val Ser His Asn Arg Phe Leu Gly His Ala
            450                 455                 460

Glu Asp Leu Gly Ser Val Ala Glu Tyr Asn Tyr Val Tyr Leu Arg Gly
465                 470                 475                 480

Ser Tyr Asn Val Ile Glu Arg Asn Val Phe Ser Gly Lys Asn Leu Asp
                485                 490                 495

Ile Lys Gly Ala Ala Val Ser Val Tyr Asn Lys Gly Asp Gly Ser Glu
            500                 505                 510
```

```
Gly Gly His Val Val Gln Tyr Asn Leu Phe Lys Asp Met Pro Gly Thr
            515                 520                 525

Ser Val Gln Ser Ser Ala Tyr Ala Leu Gln Val Gly Arg Ser Thr Gly
        530                 535                 540

Ser Asp Gly Leu Gly Glu Gly Gln His Val Val Arg Phe Asn Arg Phe
545                 550                 555                 560

Asp Asn Val Met Ala Asp Arg Arg Ile Ile Lys Val Gln Ala Ser Arg
                565                 570                 575

Ser Ser Val Tyr Gly Asn Thr Ile Val Asn Ser Thr Gly Gly Ile Ser
            580                 585                 590

Leu Glu Asp Gly Tyr Glu Asn Thr Val Ser Asn Val Ile Leu Ser
        595                 600                 605

Ala Gly Asp Asn Ser Asp Asp Ser Gly Ile Met Phe Ser Pro Phe Gly
        610                 615                 620

His Thr Val Thr Gly Asn Tyr Ile Ala Gly Leu Lys Thr Thr Ser Ser
625                 630                 635                 640

Gln Arg Ala Ala Leu Leu Leu Asn Thr Glu Thr Val Ala Asn Ser Gly
                645                 650                 655

Asn Ser Ala Leu Ser Val Ser Arg Val Thr Val Ala Asn Asn Thr Val
            660                 665                 670

Ile Asn Ser Asn Asn Ala Ile Ala Thr Tyr Thr Gly Ser Lys Cys Val
        675                 680                 685

Ala Asp Thr Phe Val Ala Ser Phe Glu Asn Asn Leu Val Ala Asn Gly
        690                 695                 700

Val Ala Gly Gln Gly Ala Asn Gly Ala Asp Ser Tyr Ala Phe Asp Asn
705                 710                 715                 720

Gly Cys Ala Ile Asn Ser Leu Glu Ser Asn Phe Ser Asn Glu Thr Tyr
                725                 730                 735

Phe Ala Ser Gly Ala Asp Leu Val Pro Leu Ala Gly Ser Ala Gly Glu
            740                 745                 750

Ala Thr Leu Val Ala Thr Ala Asn Gly Leu Leu Asn Asp Ala Asn Ser
        755                 760                 765

Leu Ala Gly Ala Asn Ala Ser Ala Leu Ile Val Leu Ser Glu Leu Asp
        770                 775                 780

Val Gly Pro Gly Ser Ser Phe Val Gln Pro Val Ala Gly Ala Tyr Asn
785                 790                 795                 800

Gly Ala Leu Asn Leu Asp Phe Thr His Trp Tyr Ile Thr Phe Pro Ser
                805                 810                 815

Gly Asp Ala Gln Tyr Asn Pro Gln Trp Leu Leu Asp Gly Tyr Thr Ser
            820                 825                 830

Glu Asn Glu Phe Tyr Tyr Asp Ala Asp Gly Ala Ala Val Phe Lys Thr
        835                 840                 845

Pro Asn Ile Ala Gly Thr Thr Ser Ala Asn Thr Lys Tyr Ser Arg Thr
        850                 855                 860

Glu Leu Arg Glu Met Met Arg Gly Pro Glu Gln Ser Pro Lys Pro Ala
865                 870                 875                 880

Asp Trp Pro Ser Thr Gln Gly Ile Asn Lys Asn Asn Trp Val Phe Ser
                885                 890                 895

Asn Ser Tyr Gln Arg Val Gln Tyr Glu Ala Gly Gly Val Asp Gly Val
            900                 905                 910

Met Glu Ala Thr Leu Lys Val Asp His Val Ser Thr Thr Val Thr Glu
        915                 920                 925
```

```
                                    -continued

Gly Tyr Glu Tyr Met Met Gly Arg Val Ile Val Gly Gln Ile His Ala
            930                 935                 940

Ser Asp Asp Glu Pro Phe Arg Leu Tyr Tyr Arg Lys Leu Pro Gly Asn
945                 950                 955                 960

Ser Leu Gly Ser Val Tyr Phe Ala Thr Glu Val Pro Gly Leu Gly Asp
                965                 970                 975

Asn Arg Tyr Asp Met Ile Gly Asp Ser Lys Glu Asp Ser Pro Asn Pro
            980                 985                 990

Leu Asp Gly Ile Ala Leu Gly Glu Val Trp Ser Tyr Arg Val Glu Ala
        995                 1000                1005

Lys Gly Asp Asp Leu Thr Val Thr Ile Met Arg Glu Gly Lys Pro Asp
    1010                1015                1020

Val Thr Arg Thr Val Lys Thr Ala Ala Ala Tyr Ala Asn Asp Trp Met
1025                1030                1035                1040

Tyr Phe Lys Ala Gly Val Tyr Asn Gln Asn Asn Gly Gly Asp Pro Ser
                1045                1050                1055

Asp Tyr Ala Gln Ala Thr Phe Tyr Ser Ile Val Val Ser His Asp Ala
            1060                1065                1070

Pro Pro Val Glu Pro Gly Asn Gly Glu Asp Glu Gly Asn Gly Gly Thr
        1075                1080                1085

Thr Thr Glu Val Thr Asp Gly Pro Ser Leu Gln Thr Ala Ile Leu Ala
    1090                1095                1100

Ala Ser Ala Gly Asp Thr Ile Glu Ile Gly Ala Gly Asp Tyr Ala Asn
1105                1110                1115                1120

Met Gly Thr Val Val Val Thr Asp Gly Val Thr Ile Thr Arg Ala Glu
                1125                1130                1135

Gly Ser Asn Ala Val Ile Ser Gly Glu Phe Cys Leu Gln Val Ser Gly
            1140                1145                1150

Asp Gly Ala Arg Ile Thr Gly Leu Glu Phe Ala Asp Leu Ile Val Pro
        1155                1160                1165

Ala Asp Ser Ala Asn His Cys Arg Ser Asn Gly Asp Gly Asn Ile Val
    1170                1175                1180

Ile Thr Gly Asp Asp Val Val Phe Asp His Asn Leu Leu Ser Gly Asp
1185                1190                1195                1200

Ala Glu Phe Pro Thr Pro Val Asp Asp Asp His Asn Trp Leu Val
                1205                1210                1215

Leu Lys Gly Ser Asn Ala Leu Val Glu Arg Asn Thr Phe Gln Asn Arg
            1220                1225                1230

Arg Gly Ile Ala Ala Asp Gly Val Ser Gln Val Arg Gly Gly Phe Ile
        1235                1240                1245

Ser Ile Tyr Val Asn Gly Ser Ala Thr Gly Asn Thr Val Gln Tyr Asn
    1250                1255                1260

Leu Phe Lys Asp Met Leu Leu Asn Asp Gln Ser Thr Ala Tyr Ala Ile
1265                1270                1275                1280

Met Leu Gly Arg Thr Thr Gly Leu Asp Ser Met Leu Asp Gly Phe Asn
                1285                1290                1295

Thr Ile Gln Tyr Asn Arg Phe Asp Asn Ile Asp Ser Lys Thr Arg Val
            1300                1305                1310

Ile Arg Val Gln Gly Ser Ser Asn Thr Ile Ser His Asn Thr Val Val
        1315                1320                1325

Asn Ser Gln Gly Met Leu Ala Leu Glu Ser Gly Gln Asn Asn Val Val
    1330                1335                1340

Ser Tyr Asn Val Ile Leu Pro Ser Gly Thr Asp Ser Asn Asp Gly Gly
```

```
                1345            1350            1355            1360
Ile Ser Ala Ala Pro Tyr Gly His Thr Ile Val Gly Asn Tyr Ile Ala
            1365            1370            1375
Gly Ser Asn Thr Thr Ser Ser Glu Arg Gly Ala Ile Tyr Leu Asn Asn
            1380            1385            1390
Asp Val Asp Glu Pro Gly Asn Leu Ala Ala Thr Pro Ser Ala Val Glu
            1395            1400            1405
Ile Ala Gly Asn Thr Ile Ile Asn Ser Lys Gln Pro Ile His Ile Gly
            1410            1415            1420
Ala Lys Gly Cys Glu Val Gly Pro Ala Phe Ile Ala Asn Phe Ser Asn
1425            1430            1435            1440
Asn Leu Ile Ala Asn Gly Val Ser Gly Val Ser Glu Phe Tyr Glu Gly
            1445            1450            1455
Ala Pro Val Ser Gly Arg Ala Ala Ile Arg Tyr Ser Cys Glu Leu Asp
            1460            1465            1470
Pro Ala His Ser Phe Thr Gly Glu Ala Tyr Phe Ser Asp Leu Leu Tyr
            1475            1480            1485
Asn Thr Ser Gly Ala Tyr Gly Gly Gly Leu Trp Phe Asp Ala Ala Ser
            1490            1495            1500
Thr Phe Gly Tyr Asp Gly Glu Ala Thr Leu Ile Ala Gly Glu Asn Gly
1505            1510            1515            1520
Leu Ile Glu Ala Thr Gly Ser Leu Ala Gly Lys Gly Ala Pro Ser Asn
            1525            1530            1535
Ser Leu Val Val Val Glu Glu Thr Asp Val Gly Val Gly Ser Ala Thr
            1540            1545            1550
Asn Phe

<210> SEQ ID NO 45
<211> LENGTH: 1008
<212> TYPE: DNA
<213> ORGANISM: Microbulbifer degradans 2-40

<400> SEQUENCE: 45
atgcaagcag gcgatgttgt actgcccgca atggcatacg atttaagcca ttggaaaatt      60
accgttccgc tagacgacaa caaagatggc aaagttgacg aagtggatac caaggcgctg     120
caaaagtata tgcactcaga ctatttctat gtaaatagcg agggcggatt ggtatttgct     180
actcctaacc aagccaccac taccagcggc tcgtcaaact cacgcagtga attgcgccaa     240
atgattcgcg gcaccaatac tagaattgga actaagtcgc caggcaataa cttttgcattg    300 gcttcgcacc cacaggcaaa agcatttggc gatataggcg gcaacttaaa agctacttta     360 gcggtaaaacc acgttgccct taatgccaaa tatactgata agtttcctgc atactctgtt    420
gtagtggggc aaattcacgc cggcaaagat aaagacctaa tcgccaaagg cgagggtat      480 ggctgggta cgagcctat caaatctat acaaaaaat ggcccgatca taaacgggg         540 tcagtttttt ggacatacga gcgcaaccta gaaaaagcaa atccagatag aaccgatatt     600
gcttatccag tatggggcaa cacttgggat aattcagaaa acccaggcga caaggcata     660 gcattagatg aatctttag ctatgagata acgtgtaca aagacatcat gcacttaacc      720
tttactgcgg cgaataaacc tacagttaaa tacagcatta acctagcaaa caatgtaaat     780
gcttacggca aggtggatga aaaagatcat cctaaaggtt atttaggcga ttggttgtac    840
tttaaagccg gcgcttacga tcagtgtagt gtgaaagatg accctggctt ttggtaccca    900
gcctgcgctg gtaccggcga ttgggaaacc gacaagaaaa acggtgacta cacacgcgta    960
```
acatttacaa agcttgagct aggtaaaggc tatagcgtaa gcaagtaa 1008

<210> SEQ ID NO 46
<211> LENGTH: 335
<212> TYPE: PRT
<213> ORGANISM: Microbulbifer degradans 2-40

<400> SEQUENCE: 46

```
Met Gln Ala Gly Asp Val Val Leu Pro Ala Met Ala Tyr Asp Leu Ser
 1               5                  10                  15

His Trp Lys Ile Thr Val Pro Leu Asp Asp Asn Lys Asp Gly Lys Val
             20                  25                  30

Asp Glu Val Asp Thr Lys Ala Leu Gln Lys Tyr Met His Ser Asp Tyr
         35                  40                  45

Phe Tyr Val Asn Ser Glu Gly Leu Val Phe Ala Thr Pro Asn Gln
     50                  55                  60

Ala Thr Thr Thr Ser Gly Ser Ser Asn Ser Arg Ser Glu Leu Arg Gln
 65                  70                  75                  80

Met Ile Arg Gly Thr Asn Thr Arg Ile Gly Thr Lys Ser Pro Gly Asn
                 85                  90                  95

Asn Phe Ala Leu Ala Ser His Pro Gln Ala Lys Ala Phe Gly Asp Ile
            100                 105                 110

Gly Gly Asn Leu Lys Ala Thr Leu Ala Val Asn His Val Ala Leu Asn
        115                 120                 125

Ala Lys Tyr Thr Asp Lys Phe Pro Ala Tyr Ser Val Val Val Gly Gln
130                 135                 140

Ile His Ala Gly Lys Asp Lys Asp Leu Ile Ala Lys Gly Glu Gly Tyr
145                 150                 155                 160

Gly Trp Gly Asn Glu Pro Ile Lys Ile Tyr Tyr Lys Lys Trp Pro Asp
                165                 170                 175

His Lys Thr Gly Ser Val Phe Trp Thr Tyr Glu Arg Asn Leu Glu Lys
            180                 185                 190

Ala Asn Pro Asp Arg Thr Asp Ile Ala Tyr Pro Val Trp Gly Asn Thr
        195                 200                 205

Trp Asp Asn Ser Glu Asn Pro Gly Asp Lys Gly Ile Ala Leu Asp Glu
    210                 215                 220

Ser Phe Ser Tyr Glu Ile Asn Val Tyr Lys Asp Ile Met His Leu Thr
225                 230                 235                 240

Phe Thr Ala Ala Asn Lys Pro Thr Val Lys Tyr Ser Ile Asn Leu Ala
                245                 250                 255

Asn Asn Val Asn Ala Tyr Gly Lys Val Asp Glu Lys Asp His Pro Lys
            260                 265                 270

Gly Tyr Leu Gly Asp Trp Leu Tyr Phe Lys Ala Gly Ala Tyr Asp Gln
        275                 280                 285

Cys Ser Val Lys Asp Pro Gly Phe Trp Tyr Pro Ala Cys Ala Gly
    290                 295                 300

Thr Gly Asp Trp Glu Thr Asp Lys Lys Asn Gly Asp Tyr Thr Arg Val
305                 310                 315                 320

Thr Phe Thr Lys Leu Glu Leu Gly Lys Gly Tyr Ser Val Ser Lys
                325                 330                 335
```

<210> SEQ ID NO 47
<211> LENGTH: 343
<212> TYPE: PRT
<213> ORGANISM: Microbulbifer degradans 2-40

```
<400> SEQUENCE: 47

Met Ser His Pro Ala Gln His Leu Val Arg Arg Gly Ile Cys Ser Leu
 1               5                  10                  15

Thr Thr Gly Leu Ile Ile Ser Leu Val Thr Ile Ser Gly Cys Gly Val
            20                  25                  30

Lys Thr Glu Lys Ile Gly Thr Gln Thr Ser Asn Lys Pro Leu Thr Ile
        35                  40                  45

Ser Ala Asp Ser Ala Asn Thr Pro Ile Thr Ser Arg Gly Ile Gly Pro
 50                  55                  60

Ala Leu Thr His Ala Thr Leu Asp Pro Gln Lys Pro Pro Ala Ile Asn
 65                  70                  75                  80

Phe Ala Leu Thr Asn Trp Lys Ile Thr Leu Pro Asp Ala Thr Glu Tyr
                85                  90                  95

Leu Pro Asp Trp Leu Thr Ala Gly Asn Glu Val Ala Asn Thr Phe Tyr
            100                 105                 110

Thr Ser Pro Gln Thr Gly Ala Met Val Phe Asn Cys Pro Thr His Gly
        115                 120                 125

Ser Thr Thr Ser Ser Ala Thr Lys Tyr Ser Arg Thr Glu Leu Arg Glu
130                 135                 140

Met Leu Arg Gly Leu Asn Thr Arg Pro Ser Thr Lys Gly Ile Gly Arg
145                 150                 155                 160

Asn Asn Trp Val Leu Ser Thr Ala Pro His Gln Asn Gln Val Ser Ala
                165                 170                 175

Gly Gly Ile Asp Gly Thr Leu Glu Ala Val Leu Ser Val Asp Tyr Val
            180                 185                 190

Ser Gln Thr Gly Pro Ala His Met Ile Gly Arg Val Ile Val Gly Gln
        195                 200                 205

Ile His Gly Glu Asp Asp Glu Pro Val Arg Ile Tyr Tyr Arg Lys Leu
210                 215                 220

Pro His Asn Thr Lys Gly Ser Val Tyr Phe Ala Ser Glu His Pro Gly
225                 230                 235                 240

Gly Glu Asp Val Phe Tyr Pro Met Ile Gly Ser Ser Asn Ser Ala
                245                 250                 255

Ala Asp Pro Glu Asp Gly Ile Ala Leu Gly Glu Lys Trp Gly Tyr Arg
            260                 265                 270

Ile His Ile Glu Gly Arg Gln Leu Ser Val Arg Ile Ile Arg Glu Asp
        275                 280                 285

Gly Arg Tyr Val Glu Gln Ser Leu Thr Ile Gly Glu Ala Tyr Asn Asn
290                 295                 300

Asp Trp Phe Tyr Phe Lys Ala Gly Val Tyr Asn Gln Asn Asn Asp Gly
305                 310                 315                 320

Asn Pro Asp Glu Tyr Ala Gln Ala Ser Phe Phe Lys Leu Lys Ala Thr
                325                 330                 335

His Lys Gln Tyr Asn Lys Gln
            340

<210> SEQ ID NO 48
<211> LENGTH: 307
<212> TYPE: PRT
<213> ORGANISM: Klebsiella pneumoniae

<400> SEQUENCE: 48

Met Leu Lys Ser Gly Val Met Val Ala Ser Leu Cys Leu Phe Ser Val
 1               5                  10                  15
```

```
Pro Ser Arg Ala Ala Val Pro Ala Pro Gly Asp Lys Phe Glu Leu Ser
            20                  25                  30

Gly Trp Ser Leu Ser Val Pro Val Asp Ser Asp Asn Asp Gly Lys Ala
        35                  40                  45

Asp Gln Ile Lys Glu Lys Thr Leu Ala Ala Gly Tyr Arg Asn Ser Asp
    50                  55                  60

Phe Phe Thr Leu Ser Asp Ala Gly Gly Met Val Phe Lys Ala Pro Ile
65                  70                  75                  80

Ser Gly Ala Lys Thr Ser Lys Asn Thr Thr Tyr Thr Arg Ser Glu Leu
                85                  90                  95

Arg Glu Met Leu Arg Lys Gly Asp Thr Ser Ile Ala Thr Gln Gly Val
            100                 105                 110

Ser Arg Asn Asn Trp Val Leu Ser Ala Pro Leu Ser Glu Gln Lys
        115                 120                 125

Lys Ala Gly Gly Val Asp Gly Thr Leu Glu Ala Thr Leu Ser Val Asp
    130                 135                 140

His Val Thr Thr Thr Gly Val Asn Trp Gln Val Gly Arg Val Ile Ile
145                 150                 155                 160

Gly Gln Ile His Ala Asn Asn Asp Glu Pro Ile Arg Leu Tyr Tyr Arg
                165                 170                 175

Lys Leu Pro His His Gln Lys Gly Ser Val Tyr Phe Ala His Glu Pro
            180                 185                 190

Arg Lys Gly Phe Gly Asp Glu Gln Trp Tyr Glu Met Ile Gly Thr Leu
        195                 200                 205

Gln Pro Ser His Gly Asn Gln Thr Ala Ala Pro Thr Glu Pro Glu Ala
    210                 215                 220

Gly Ile Ala Leu Gly Glu Thr Phe Ser Tyr Arg Ile Asp Ala Thr Gly
225                 230                 235                 240

Asn Lys Leu Thr Val Thr Leu Met Arg Glu Gly Arg Pro Asp Val Val
                245                 250                 255

Lys Thr Val Asp Met Ser Lys Ser Gly Tyr Ser Glu Ala Gly Gln Tyr
            260                 265                 270

Leu Tyr Phe Lys Ala Gly Val Tyr Asn Gln Asn Lys Thr Gly Lys Pro
        275                 280                 285

Asp Asp Tyr Val Gln Ala Thr Phe Tyr Arg Leu Lys Ala Thr His Gly
    290                 295                 300

Ala Gln Arg
305

<210> SEQ ID NO 49
<211> LENGTH: 760
<212> TYPE: PRT
<213> ORGANISM: Microbulbifer degradans 2-40

<400> SEQUENCE: 49

Met Lys Lys Glu Asn Val Asn Ile Ala Lys Gln Gly Leu Leu Val Val
1               5                   10                  15

Leu Val Ser Phe Phe Met Ser Phe Ser Leu Met Gly Cys Ala Lys Glu
            20                  25                  30

Ile Leu Val Asn Ser Gln Glu Gln Tyr Ala Glu Ala Leu Ser Ser Val
        35                  40                  45

Lys Pro Gly Asp Thr Ile Val Leu Ala Asn Gly Glu Trp Lys Asp Phe
    50                  55                  60

Glu Ile Val Phe Thr Gly Lys Gly Thr Glu Lys Ala Pro Ile Thr Leu
```

```
            65                  70                  75                  80
Thr Ala Gln Thr Lys Gly Lys Val Leu Ile Thr Gly Glu Ser Asn Leu
                 85                  90                  95
Ala Leu Ala Gly Glu His Leu Val Val Ser Gly Leu Val Phe Thr Asn
                100                 105                 110
Gly Tyr Thr Pro Ser Asp Ala Val Ile Ser Phe Arg Ala Ala Lys Pro
                115                 120                 125
Val Ala Glu Asp Asp Tyr Ser Thr Val Ala Met His Ser Arg Val Thr
            130                 135                 140
Glu Val Val Ile Asp Asn Phe Ser Asn Pro Glu Arg Phe Glu Thr Asp
145                 150                 155                 160
Ser Trp Val Leu Ile Tyr Gly Lys His Asn Arg Val Asp His Ser Asn
                165                 170                 175
Phe Thr Gly Lys Arg Asn Lys Gly Val Leu Met Ala Val Arg Leu Asp
                180                 185                 190
Thr Thr His Ser Arg Glu Asn His His Glu Ile Asp His Asn Tyr Phe
                195                 200                 205
Gly Pro Arg Asp Ile Leu Gly Ser Asn Gly Glu Thr Leu Arg Ile
210                 215                 220
Gly Thr Ser His Phe Ser Leu Ser Asp Ser Phe Thr Leu Val Glu Asn
225                 230                 235                 240
Asn Tyr Phe Asp Arg Cys Asn Gly Glu Leu Glu Ile Ile Ser Asn Lys
                245                 250                 255
Ser Gly Ser Asn Lys Phe Ile Gly Asn Thr Phe Glu Ser Arg Gly
                260                 265                 270
Thr Leu Thr Met Arg His Gly His Gly Asn Val Ile Glu Asn Asn Val
                275                 280                 285
Phe Phe Gly Asn Gly Lys Asp His Thr Gly Gly Ile Arg Val Ile Asn
            290                 295                 300
Glu Arg Gln Thr Val Arg Asn Asn Tyr Met Ser Asp Leu Ala Gly Tyr
305                 310                 315                 320
Arg Phe Gly Gly Gly Leu Val Val Met Asn Gly Val Pro Asn Ser Ala
                325                 330                 335
Ile Asn Arg Tyr His Gln Val Lys Asn Ala Val Ile Glu Asn Asn Thr
                340                 345                 350
Leu Val Asn Val Asp His Ile Gln Leu Ala Ala Gly Ser Asp Lys Glu
            355                 360                 365
Arg Thr Ala Thr Pro Val Asp Ser Lys Phe Ser Asn Asn Leu Ile Val
            370                 375                 380
Asn Asp Asp Lys Arg Asn Pro Phe Thr Val Tyr Asp Asp Val Ser Gly
385                 390                 395                 400
Ile Thr Phe Ser Asn Asn Ser Ile Ser Ala Ala Ser Lys Glu Leu Lys
                405                 410                 415
Lys Gly Phe Glu Val Asp Ala Ala Lys Ile Ala Lys Asn Asp Gln Gly
                420                 425                 430
Met Val Phe Asp Ala Ser Gly Thr Tyr Gly Ala Ser Lys Ser Leu Lys
            435                 440                 445
Pro Val Arg Lys Gln Asp Val Gly Ala Ser Trp Phe Val Lys Ser Glu
            450                 455                 460
Asp Arg Lys Ala Phe Gln Ser Gly Lys Thr Val Lys Ala Gly Ala Gly
465                 470                 475                 480
Gln Asn Ser Ile Tyr Asp Ala Val Glu Gln Val Glu Asp Gly Gly Val
                485                 490                 495
```

Val Glu Leu Ala Ala Gly Asp Tyr Val Glu Ala Lys Thr Ile Thr Ile
            500                 505                 510
Asn Lys Thr Val Thr Val Lys Ala Ala Gly Glu Lys Val Asn Ile
        515                 520                 525
Glu Phe Tyr Lys Lys Ser Leu Phe Glu Val Val Asp Gly Gly Ser Leu
    530                 535                 540
Gln Leu Glu Gly Leu Ala Ile Ser Gly Ala Ser Ser Pro Asp Asp Val
545                 550                 555                 560
Gly Asn Ala Val Val Arg Thr Ser Arg Tyr Ser Met Leu Lys Asn Tyr
                565                 570                 575
Arg Leu Glu Leu Lys Asn Cys Glu Phe Thr Asp Leu Asp Val Asn Arg
            580                 585                 590
Phe Phe Asn Val Val Ser Val Ser Lys Ser Thr Leu Ala Asp Asn Ile
        595                 600                 605
Leu Leu Glu Asn Val Ser Val Lys Lys Val Thr Gly Ser Val Leu Lys
    610                 615                 620
Leu Asp Leu Glu Ser Asp Asp Tyr Gly Ile Tyr Asn Ala Glu Tyr Val
625                 630                 635                 640
Thr Ile Lys Asn Ser Gln Phe Glu Asp Val Asp Gly Pro Leu Ile Thr
                645                 650                 655
Tyr Tyr Arg Gly Gly Thr Asp Glu Ser Thr Phe Gly Pro His Phe Glu
            660                 665                 670
Met Thr Gly Ser Thr Leu Lys Asn Val Gly Asn Gly Ser Lys Asn Lys
        675                 680                 685
Leu Asn Ala Ser Leu Tyr Leu His Gly Val Gln Val Thr Ala Ile Ser
    690                 695                 700
Asn Asn Lys Trp Leu Asp Ser Lys Pro Val Ile Glu His Thr Val
705                 710                 715                 720
Gly Glu Pro Val Thr Ser Val Val Asp Asn Thr Phe Val Asn Thr Ala
                725                 730                 735
Lys Leu Asp Leu Gln Glu Leu Tyr Ser Lys Lys Thr Thr Thr Ala Val
            740                 745                 750
Ile Lys Asn Asn Thr Tyr Lys Lys
        755                 760

<210> SEQ ID NO 50
<211> LENGTH: 713
<212> TYPE: PRT
<213> ORGANISM: Pseudomonas sp.

<400> SEQUENCE: 50

Met Asn Tyr Leu Lys Lys Val Val Leu Val Ser Phe Cys Ala Phe Phe
1               5                   10                  15
Ser Leu Ser Leu Met Ala Gln Thr His Pro Ser Ile Met Leu Thr Lys
            20                  25                  30
Ala Asn Val Ala Ala Val Lys Lys Gly Val Asn Thr Tyr Pro Leu Leu
        35                  40                  45
Arg Gln Ser Tyr Gln Ala Val Lys Asn Ala Ala Asp Lys Ala Leu Ala
    50                  55                  60
Gln Pro Ile Val Val Pro Val Pro Lys Asp Gly Gly Gly Tyr Thr
65                  70                  75                  80
His Glu Gln His Lys Lys Asn Tyr Ser Asn Met Leu Asn Cys Gly Val
                85                  90                  95
Ala Tyr Gln Ile Ser Gly Glu Lys Lys Tyr Ala Asp Tyr Val Lys Asn

-continued

```
            100                 105                 110
Val Met Leu Asn Tyr Ala Ser Gln Tyr Gly Lys Trp Pro Leu His Pro
        115                 120                 125
Lys Arg Lys Ser Glu Glu Asp Gly Gly Arg Ile Phe Trp Gln Ser Leu
    130                 135                 140
Asn Asp Phe Val Trp Gln Leu Tyr Thr Ile Gln Ala Tyr Asp Leu Val
145                 150                 155                 160
Tyr Asp Gly Ile Pro Ala Thr Asp Arg Lys Thr Ile Glu Glu Lys Leu
                165                 170                 175
Phe Val Pro Ile Leu Lys Phe Phe Thr Glu Asp Arg Tyr Asp Val Phe
            180                 185                 190
Asn Lys Ile His Asn His Gly Thr Trp Asn Leu Ala Ala Val Gly Ile
        195                 200                 205
Thr Gly Tyr Val Leu Asn Lys Arg Glu Tyr Val Glu Met Ala Ile Lys
    210                 215                 220
Gly Ser Lys Lys Asp Gly Lys Thr Gly Tyr Leu Ala Gln Ile Asp Gln
225                 230                 235                 240
Leu Phe Ser Pro Asp Gly Tyr Tyr Met Glu Gly Pro Tyr Tyr Gln Arg
                245                 250                 255
Tyr Ala Leu Leu Pro Phe Val Leu Phe Ala Lys Ala Ile Asn Asn Tyr
            260                 265                 270
Glu Pro Ser Arg Lys Ile Phe Glu Tyr Arg Asp Lys Leu Leu Ser Lys
        275                 280                 285
Ala Ile His Thr Ser Leu Gln Thr Ser Tyr Thr Asp Lys Thr Phe Phe
    290                 295                 300
Pro Leu Asn Asp Ala Ile Lys Asp Lys Thr Tyr Glu Ser Val Glu Leu
305                 310                 315                 320
Val Tyr Gly Val Asp Leu Ala Tyr Ala Asp Ile Lys Ala Glu Val Asp
                325                 330                 335
Leu Leu Asp Ile Ala Arg Gln Gln Asn Arg Val Ile Val Ser Asp Ala
            340                 345                 350
Gly Leu Lys Val Ala Ala Asp Leu Ala Ala Gly Lys Ala Val Pro Phe
        355                 360                 365
Lys Tyr Gln Thr Leu Trp Ile Arg Asp Gly Gly Lys Gly Asp Glu Gly
    370                 375                 380
Gly Leu Gly Ile Leu Arg Asn Gly Pro Asn Thr Asp Gln Gln Cys Val
385                 390                 395                 400
Val Leu Lys Ala Ala Ser Gln Gly Met Gly His Gly His Phe Asp Arg
                405                 410                 415
Leu Asn Leu Leu Phe Tyr Asp Asn Thr Thr Glu Ile Phe Pro Asp Tyr
            420                 425                 430
Gly Ala Ala Arg Phe Leu Asn Ile Asp Thr Lys Asn Gly Gly Gly Tyr
        435                 440                 445
Leu Pro Glu Asn Asn Thr Trp Ala Lys Gln Thr Val Ala His Asn Ala
    450                 455                 460
Leu Val Val Asp Gln Thr Ser His Phe Asn Ala Lys Leu Gly Pro Ala
465                 470                 475                 480
Asp Lys Ala Ser Pro Thr Leu Leu Tyr Phe Ser Asn Gln Pro Asn Leu
                485                 490                 495
Lys Val Val Ser Ala Lys Glu Asp Lys Ala Tyr Thr Asp Val Thr Met
            500                 505                 510
Leu Arg Thr Ser Ala Leu Val Lys Val Glu Gly Leu Asp Lys Pro Leu
        515                 520                 525
```

-continued

Leu Ile Asp Val Met Gln Ala Gln Ser Ala Lys Ser His Gln Tyr Asp
        530                 535                 540

Leu Pro Phe Trp Tyr Lys Gly Gln Leu Val Asn Thr Ser Phe Pro Val
545                 550                 555                 560

Thr Ala Lys Ala Asn Gln Leu Thr Ala Leu Gly Asp Lys Asn Gly Tyr
                565                 570                 575

Gln His Ile Trp Leu Asn Ala Ser Asn Pro Leu Glu Gly Lys Ser Gly
                580                 585                 590

Met Val Gly Leu Leu Asn Lys Asn Arg Phe Tyr Thr Thr His Phe Val
        595                 600                 605

Ser Asp Asn Pro Leu Glu Val Lys Leu Leu Ser Ile Gly Ala Asn Asp
        610                 615                 620

Pro Glu Met Asn Leu Val Asp Gly Lys Ala Phe Met Leu Ser Ser Ser
625                 630                 635                 640

Gly Gln Asn Gln Thr Phe Val Ser Ile Thr Glu Thr His Gly Gly Thr
                645                 650                 655

Asp Pro Ile Asn Glu Thr Val Ser Ser Ala Leu Pro Thr Val Ser Gly
                660                 665                 670

Leu Lys Leu Ile Lys Ser Asp Ala Gln Gln Thr Ile Ile Ser Phe Lys
                675                 680                 685

Val Asn Glu Arg Thr Tyr Thr Tyr Gln Ile Asn Tyr Thr Glu Lys Gln
        690                 695                 700

Gln Leu Tyr Ile Ile Lys Ile Lys Glu
705                 710

<210> SEQ ID NO 51
<211> LENGTH: 736
<212> TYPE: PRT
<213> ORGANISM: Microbulbifer degradans 2-40

<400> SEQUENCE: 51

Met Leu Ser Val Asn Thr Ile Lys Asn Thr Leu Leu Ala Ala Val Leu
1               5                   10                  15

Val Ser Val Pro Ala Thr Ala Gln Val Ser Gly Asn Gly His Pro Asn
                20                  25                  30

Leu Ile Val Thr Glu Gln Asp Val Ala Asn Ile Ala Ala Ser Trp Glu
        35                  40                  45

Ser Tyr Asp Ala Tyr Ala Glu Gln Leu Asn Ala Asp Lys Thr Asn Leu
    50                  55                  60

Asp Ala Phe Met Ala Glu Gly Val Val Pro Met Pro Lys Asp Ala
65                  70                  75                  80

Gly Gly Gly Tyr Thr His Glu Gln His Lys Arg Asn Tyr Lys Ala Ile
                85                  90                  95

Arg Asn Ala Gly Phe Leu Tyr Gln Val Thr Gly Asp Glu Lys Tyr Leu
                100                 105                 110

Thr Phe Ala Lys Asp Leu Leu Leu Ala Tyr Ala Lys Met Tyr Pro Ser
        115                 120                 125

Leu Gly Glu His Pro Asn Arg Lys Glu Gln Ser Pro Gly Arg Leu Phe
    130                 135                 140

Trp Gln Ser Leu Asn Glu Ala Val Trp Leu Val Tyr Ser Ile Gln Gly
145                 150                 155                 160

Tyr Asp Ala Ile Ile Asp Gly Leu Ala Ala Glu Glu Lys Gln Glu Ile
                165                 170                 175

Glu Ser Gly Val Phe Leu Pro Met Ala Lys Phe Leu Ser Val Glu Ser

-continued

```
            180                 185                 190
Pro Glu Thr Phe Asn Lys Ile His Asn His Gly Thr Trp Ala Val Ala
        195                 200                 205
Ala Val Gly Met Thr Gly Tyr Val Leu Gly Asn Asp Glu Leu Val Glu
        210                 215                 220
Ile Ser Leu Met Gly Leu Asp Lys Thr Gly Lys Ala Gly Phe Met Lys
225                 230                 235                 240
Gln Leu Asp Lys Leu Phe Ser Pro Asp Gly Tyr Tyr Thr Glu Gly Pro
                245                 250                 255
Tyr Tyr Gln Arg Tyr Ala Leu Met Pro Phe Ile Trp Phe Ala Lys Ala
            260                 265                 270
Ile Glu Thr Asn Glu Pro Glu Arg Lys Ile Phe Glu Tyr Arg Asn Asn
            275                 280                 285
Ile Leu Leu Lys Ala Val Tyr Thr Thr Ile Asp Leu Ser Tyr Ala Gly
        290                 295                 300
Tyr Phe Phe Pro Ile Asn Asp Ala Leu Lys Asp Lys Gly Ile Asp Thr
305                 310                 315                 320
Val Glu Leu Val His Ala Leu Ala Ile Val Tyr Ser Ile Thr Gly Asp
                325                 330                 335
Asn Thr Leu Leu Asp Ile Ala Gln Glu Gln Gly Arg Ile Ser Leu Thr
                340                 345                 350
Gly Asp Gly Leu Lys Val Ala Lys Ala Val Gly Glu Gly Leu Thr Gln
            355                 360                 365
Pro Tyr Asn Tyr Arg Ser Ile Leu Leu Gly Asp Gly Ala Asp Gly Asp
        370                 375                 380
Gln Gly Ala Leu Ser Ile His Arg Leu Gly Glu Gly His Asn His Met
385                 390                 395                 400
Ala Leu Val Ala Lys Asn Thr Ser Gln Gly Met Gly His Gly His Phe
                405                 410                 415
Asp Lys Leu Asn Trp Leu Leu Tyr Asp Asn Gly Asn Glu Ile Val Thr
                420                 425                 430
Asp Tyr Gly Ala Ala Arg Tyr Leu Asn Val Glu Ala Lys Tyr Gly Gly
            435                 440                 445
His Tyr Leu Ala Glu Asn Asn Thr Trp Ala Lys Gln Thr Ile Ala His
        450                 455                 460
Asn Thr Leu Val Val Asn Glu Gln Ser His Phe Tyr Gly Asp Val Thr
465                 470                 475                 480
Thr Ala Asp Leu His His Pro Glu Val Leu Ser Phe Tyr Ser Gly Glu
                485                 490                 495
Asp Tyr Gln Leu Ser Ser Ala Lys Glu Ala Asn Ala Tyr Asp Gly Val
                500                 505                 510
Glu Phe Val Arg Ser Met Leu Leu Val Asn Val Pro Ser Leu Glu His
            515                 520                 525
Pro Ile Val Val Asp Val Leu Asn Val Ser Ala Asp Lys Ala Ser Thr
        530                 535                 540
Phe Asp Leu Pro Leu Tyr Phe Asn Gly Gln Ile Ile Asp Phe Ser Phe
545                 550                 555                 560
Lys Val Lys Asp Asn Lys Asn Val Met Lys Met Leu Gly Lys Arg Asn
                565                 570                 575
Gly Tyr Gln His Leu Trp Leu Arg Asn Thr Ala Pro Val Gly Asp Ala
                580                 585                 590
Ser Glu Arg Ala Thr Trp Ile Leu Asp Asp Arg Phe Tyr Ser Tyr Ala
            595                 600                 605
```

```
Phe Val Thr Ser Thr Pro Ser Lys Lys Gln Asn Val Leu Ile Ala Glu
            610                 615                 620

Leu Gly Ala Asn Asp Pro Asn Tyr Asn Leu Arg Gln Gln Gln Val Leu
625                 630                 635                 640

Ile Arg Arg Val Glu Lys Ala Lys Gln Ala Ser Phe Val Ser Val Leu
                    645                 650                 655

Glu Pro His Gly Lys Tyr Asp Gly Ser Leu Glu Thr Thr Ser Gly Ala
                660                 665                 670

Tyr Ser Asn Val Lys Ser Val Lys His Val Ser Glu Asn Gly Lys Asp
                675                 680                 685

Val Val Val Asp Leu Lys Asp Gly Ser Asn Val Val Ala Leu
690                 695                 700

Ser Tyr Asn Ala Asn Ser Glu Gln Val His Lys Val Asn Ala Gly Glu
705                 710                 715                 720

Glu Ala Ile Glu Trp Lys Gly Phe Ser Ser Val Val Arg Arg Lys
                    725                 730                 735

<210> SEQ ID NO 52
<211> LENGTH: 713
<212> TYPE: PRT
<213> ORGANISM: Pseudomonas sp.

<400> SEQUENCE: 52

Met Asn Tyr Leu Lys Lys Val Leu Val Ser Phe Cys Ala Phe Phe
1               5                   10                  15

Ser Leu Ser Leu Met Ala Gln Thr His Pro Ser Ile Met Leu Thr Lys
                20                  25                  30

Ala Asn Val Ala Ala Val Lys Lys Gly Val Asn Thr Tyr Pro Leu Leu
            35                  40                  45

Arg Gln Ser Tyr Gln Ala Val Lys Asn Ala Ala Asp Lys Ala Leu Ala
        50                  55                  60

Gln Pro Ile Val Val Pro Val Pro Lys Asp Gly Gly Gly Tyr Thr
65                  70                  75                  80

His Glu Gln His Lys Lys Asn Tyr Ser Asn Met Leu Asn Cys Gly Val
                85                  90                  95

Ala Tyr Gln Ile Ser Gly Glu Lys Lys Tyr Ala Asp Tyr Val Lys Asn
            100                 105                 110

Val Met Leu Asn Tyr Ala Ser Gln Tyr Gly Lys Trp Pro Leu His Pro
        115                 120                 125

Lys Arg Lys Ser Glu Glu Asp Gly Gly Arg Ile Phe Trp Gln Ser Leu
130                 135                 140

Asn Asp Phe Val Trp Gln Leu Tyr Thr Ile Gln Ala Tyr Asp Leu Val
145                 150                 155                 160

Tyr Asp Gly Ile Pro Ala Thr Asp Arg Lys Thr Ile Glu Glu Lys Leu
                165                 170                 175

Phe Val Pro Ile Leu Lys Phe Thr Glu Asp Arg Tyr Asp Val Phe
            180                 185                 190

Asn Lys Ile His Asn His Gly Thr Trp Asn Leu Ala Ala Val Gly Ile
        195                 200                 205

Thr Gly Tyr Val Leu Asn Lys Arg Glu Tyr Val Glu Met Ala Ile Lys
210                 215                 220

Gly Ser Lys Lys Asp Gly Lys Thr Gly Tyr Leu Ala Gln Ile Asp Gln
225                 230                 235                 240

Leu Phe Ser Pro Asp Gly Tyr Tyr Met Glu Gly Pro Tyr Tyr Gln Arg
```

-continued

```
            245                 250                 255
Tyr Ala Leu Leu Pro Phe Val Leu Phe Ala Lys Ala Ile Asn Asn Tyr
                260                 265                 270
Glu Pro Ser Arg Lys Ile Phe Glu Tyr Arg Asp Lys Leu Leu Ser Lys
                275                 280                 285
Ala Ile His Thr Ser Leu Gln Thr Ser Tyr Thr Asp Lys Thr Phe Phe
                290                 295                 300
Pro Leu Asn Asp Ala Ile Lys Asp Lys Thr Tyr Glu Ser Val Glu Leu
305                 310                 315                 320
Val Tyr Gly Val Asp Leu Ala Tyr Ala Asp Ile Lys Ala Glu Val Asp
                325                 330                 335
Leu Leu Asp Ile Ala Arg Gln Gln Asn Arg Val Ile Val Ser Asp Ala
                340                 345                 350
Gly Leu Lys Val Ala Ala Asp Leu Ala Ala Gly Lys Ala Val Pro Phe
                355                 360                 365
Lys Tyr Gln Thr Leu Trp Ile Arg Asp Gly Lys Gly Asp Glu Gly
                370                 375                 380
Gly Leu Gly Ile Leu Arg Asn Gly Pro Asn Thr Asp Gln Gln Cys Val
385                 390                 395                 400
Val Leu Lys Ala Ala Ser Gln Gly Met Gly His Gly His Phe Asp Arg
                405                 410                 415
Leu Asn Leu Leu Phe Tyr Asp Asn Thr Thr Glu Ile Phe Pro Asp Tyr
                420                 425                 430
Gly Ala Ala Arg Phe Leu Asn Ile Asp Thr Lys Asn Gly Gly Gly Tyr
                435                 440                 445
Leu Pro Glu Asn Asn Thr Trp Ala Lys Gln Thr Val Ala His Asn Ala
450                 455                 460
Leu Val Val Asp Gln Thr Ser His Phe Asn Ala Lys Leu Gly Pro Ala
465                 470                 475                 480
Asp Lys Ala Ser Pro Thr Leu Leu Tyr Phe Ser Asn Gln Pro Asn Leu
                485                 490                 495
Lys Val Val Ser Ala Lys Glu Asp Lys Ala Tyr Thr Asp Val Thr Met
                500                 505                 510
Leu Arg Thr Ser Ala Leu Val Lys Val Glu Gly Leu Asp Lys Pro Leu
                515                 520                 525
Leu Ile Asp Val Met Gln Ala Gln Ser Ala Lys Ser His Gln Tyr Asp
                530                 535                 540
Leu Pro Phe Trp Tyr Lys Gly Gln Leu Val Asn Thr Ser Phe Pro Val
545                 550                 555                 560
Thr Ala Lys Ala Asn Gln Leu Thr Ala Leu Gly Asp Lys Asn Gly Tyr
                565                 570                 575
Gln His Ile Trp Leu Asn Ala Ser Asn Pro Leu Glu Gly Lys Ser Gly
                580                 585                 590
Met Val Gly Leu Leu Asn Lys Asn Arg Phe Tyr Thr His Phe Val
                595                 600                 605
Ser Asp Asn Pro Leu Glu Val Lys Leu Leu Ser Ile Gly Ala Asn Asp
                610                 615                 620
Pro Glu Met Asn Leu Val Asp Gly Lys Ala Phe Met Leu Ser Ser Ser
625                 630                 635                 640
Gly Gln Asn Gln Thr Phe Val Ser Ile Thr Glu Thr His Gly Gly Thr
                645                 650                 655
Asp Pro Ile Asn Glu Thr Val Ser Ser Ala Leu Pro Thr Val Ser Gly
                660                 665                 670
```

Leu Lys Leu Ile Lys Ser Asp Ala Gln Gln Thr Ile Ile Ser Phe Lys
        675                 680                 685

Val Asn Glu Arg Thr Tyr Thr Tyr Gln Ile Asn Tyr Thr Glu Lys Gln
        690                 695                 700

Gln Leu Tyr Ile Ile Lys Ile Lys Glu
705                 710

<210> SEQ ID NO 53
<211> LENGTH: 311
<212> TYPE: PRT
<213> ORGANISM: Microbulbifer degradans 2-40

<400> SEQUENCE: 53

Tyr Gly Ala Asp Gly Gly Ser Ser Ser Ser Ser Ser Ser Ser Ser Ser
 1               5                  10                  15

Thr Ser Ser Thr Ser Ser Thr Ser Ser Thr Ser Ser Ser Ser Gly Gly
            20                  25                  30

Phe Asn Leu Asn Pro Asn Ala Pro Pro Ser Ser Asn Phe Asn Leu Ser
        35                  40                  45

Gln Trp Tyr Leu Ser Val Pro Thr Asp Thr Asp Gly Ser Gly Thr Ala
    50                  55                  60

Asp Ser Ile Lys Glu Gly Glu Leu Asn Ser Gly Tyr Glu Asn Asn Ser
65                  70                  75                  80

Tyr Phe Tyr Thr Gly Ser Asp Gly Gly Met Val Phe Lys Cys Pro Ile
                85                  90                  95

Ser Gly Tyr Lys Thr Ser Thr Gly Thr Ser Tyr Thr Arg Thr Glu Leu
            100                 105                 110

Arg Glu Met Leu Arg Ala Gly Asn Thr Ser Ile Ala Thr Ser Gly Val
        115                 120                 125

Asn Lys Asn Asn Trp Val Phe Gly Ser Ala Pro Ser Ser Ala Gln Ala
130                 135                 140

Ala Ala Gly Gly Val Asp Gly Asn Met Lys Ala Thr Leu Ala Val Asn
145                 150                 155                 160

Tyr Val Thr Thr Thr Gly Asp Ser Ser Gln Val Gly Arg Val Ile Ile
                165                 170                 175

Gly Gln Ile His Ala Glu Lys Asn Glu Pro Ile Arg Leu Tyr Tyr Arg
            180                 185                 190

Lys Leu Pro Gly Asn Ser Lys Gly Gly Ile Tyr Tyr Ala His Glu Asp
        195                 200                 205

Ala Asp Gly Gly Glu Val Trp Val Asp Met Ile Gly Ser Arg Ser Ser
    210                 215                 220

Ser Ala Ser Asn Pro Ser Asp Gly Ile Ala Leu Asn Glu Val Phe Ser
225                 230                 235                 240

Tyr Glu Ile Asp Val Thr Asn Asn Met Leu Thr Val Lys Ile Tyr Arg
                245                 250                 255

Asp Gly Lys Ser Thr Val Thr Ser Gln Tyr Asn Met Val Asn Ser Gly
            260                 265                 270

Tyr Asp Asp Ser Asp Asp Trp Met Tyr Phe Lys Ala Gly Val Tyr Asn
        275                 280                 285

Gln Asn Asn Thr Gly Asn Gly Ser Asp Tyr Val Gln Ala Thr Phe Tyr
    290                 295                 300

Ser Leu Thr His Thr His Asp
305                 310

<210> SEQ ID NO 54
<211> LENGTH: 307
<212> TYPE: PRT
<213> ORGANISM: Klebsiella pneumoniae

<400> SEQUENCE: 54

Met Leu Lys Ser Gly Val Met Val Ala Ser Leu Cys Leu Phe Ser Val
1               5                   10                  15

Pro Ser Arg Ala Ala Val Pro Ala Pro Gly Asp Lys Phe Glu Leu Ser
            20                  25                  30

Gly Trp Ser Leu Ser Val Pro Val Asp Ser Asp Asn Asp Gly Lys Ala
        35                  40                  45

Asp Gln Ile Lys Glu Lys Thr Leu Ala Ala Gly Tyr Arg Asn Ser Asp
    50                  55                  60

Phe Phe Thr Leu Ser Asp Ala Gly Gly Met Val Phe Lys Ala Pro Ile
65                  70                  75                  80

Ser Gly Ala Lys Thr Ser Lys Asn Thr Thr Tyr Thr Arg Ser Glu Leu
                85                  90                  95

Arg Glu Met Leu Arg Lys Gly Asp Thr Ser Ile Ala Thr Gln Gly Val
            100                 105                 110

Ser Arg Asn Asn Trp Val Leu Ser Ser Ala Pro Leu Ser Glu Gln Lys
        115                 120                 125

Lys Ala Gly Gly Val Asp Gly Thr Leu Glu Ala Thr Leu Ser Val Asp
    130                 135                 140

His Val Thr Thr Thr Gly Val Asn Trp Gln Val Gly Arg Val Ile Ile
145                 150                 155                 160

Gly Gln Ile His Ala Asn Asn Asp Glu Pro Ile Arg Leu Tyr Tyr Arg
                165                 170                 175

Lys Leu Pro His His Gln Lys Gly Ser Val Tyr Phe Ala His Glu Pro
            180                 185                 190

Arg Lys Gly Phe Gly Asp Glu Gln Trp Tyr Glu Met Ile Gly Thr Leu
        195                 200                 205

Gln Pro Ser His Gly Asn Gln Thr Ala Ala Pro Thr Glu Pro Glu Ala
    210                 215                 220

Gly Ile Ala Leu Gly Glu Thr Phe Ser Tyr Arg Ile Asp Ala Thr Gly
225                 230                 235                 240

Asn Lys Leu Thr Val Thr Leu Met Arg Glu Gly Arg Pro Asp Val Val
                245                 250                 255

Lys Thr Val Asp Met Ser Lys Ser Gly Tyr Ser Glu Ala Gly Gln Tyr
            260                 265                 270

Leu Tyr Phe Lys Ala Gly Val Tyr Asn Gln Asn Lys Thr Gly Lys Pro
        275                 280                 285

Asp Asp Tyr Val Gln Ala Thr Phe Tyr Arg Leu Lys Ala Thr His Gly
    290                 295                 300

Ala Gln Arg
305

<210> SEQ ID NO 55
<211> LENGTH: 524
<212> TYPE: PRT
<213> ORGANISM: Microbulbifer degradans 2-40

<400> SEQUENCE: 55

Met Leu Lys Val Val Ile Lys Ala Phe Val Val Thr Leu Ser Gly Leu
1               5                   10                  15

Ile Ile Ser Ala Cys Gly Gly Gly Asp Ser Lys Ser Pro Glu Thr Thr

-continued

```
                20                  25                  30
Pro Thr Pro Thr Pro Thr Pro Thr Pro Thr Pro Thr Pro Thr
            35                  40                  45

Pro Thr Pro Thr Pro Thr Pro Thr Pro Thr Pro Thr Pro Thr
        50                  55                  60

Pro Thr Pro Thr Pro Val Glu Cys Thr Pro Ala Leu Ser Thr Ile Ser
    65                  70                  75                  80

Ser Ala Phe Asp Asp Gly Ser Asn Asp Gly Tyr Val Pro Ala Asn Thr
                85                  90                  95

Ile Asp Asp Asp Leu Thr Asp Glu Ser Arg Trp Ser Ser Phe Gly Asp
            100                 105                 110

Gly Lys Trp Ile Val Phe Asp Leu Ala Ile Ala Lys Asp Val Arg Glu
        115                 120                 125

Ile His Ser Ala Trp Tyr Lys Gly Asp Thr Arg Thr Ser Phe Tyr Asp
    130                 135                 140

Ile Glu Ser Ser Leu Asp Ala Val Ser Trp Ser Thr Leu Gln Thr Asn
145                 150                 155                 160

Leu Gln Ser Gln Gly Thr Thr Ser Leu Glu Ala Val Thr Leu Asp Ser
                165                 170                 175

Thr Asp Ala Arg Tyr Ile Arg Val Val Gly Arg Gly Asn Thr Asp Asn
            180                 185                 190

Thr Trp Asn Ser Leu Ile Glu Val Asp Ile Tyr Asp Cys Gly Glu Thr
        195                 200                 205

Gly Thr Pro Thr Glu Asp Pro Val Val Glu Pro Pro Glu Pro Pro
    210                 215                 220

Ala Pro Thr Asp Gly Asp Met Pro Ala Thr Thr Pro Asn Pro Pro Leu
225                 230                 235                 240

Val Thr Asp Ala Leu Asp Pro Asp Ala Ala Pro Ser Ser Asn Phe Asp
                245                 250                 255

Leu Trp Pro Trp Tyr Leu Ser Val Pro Thr Asp Thr Asp Gly Ser Gly
            260                 265                 270

Thr Ala Asp Ser Ile Lys Glu Ser Asp Leu Asn Ala Gly Tyr Glu Ser
        275                 280                 285

Ser Glu Phe Phe Tyr Thr Ala Ala Asp Gly Gly Met Val Phe Lys Cys
    290                 295                 300

Pro Val Ala Gly Phe Lys Thr Ser Thr Asn Thr Ser Tyr Thr Arg Val
305                 310                 315                 320

Glu Leu Arg Glu Met Leu Arg Arg Gly Asn Ser Ser Ile Ser Thr Gln
                325                 330                 335

Gly Val Asn Gly Asn Asn Trp Val Phe Gly Ser Ala Pro Gln Ser Asp
            340                 345                 350

Leu Asn Ala Ala Gly Gly Ile Asp Gly Asn Leu Arg Ala Thr Leu Ala
        355                 360                 365

Val Asn Lys Val Thr Thr Thr His Gly Asp Gly Phe Glu Tyr Gln Val
    370                 375                 380

Gly Arg Val Ile Ile Gly Gln Ile His Ala Asn Asp Asp Glu Pro Ile
385                 390                 395                 400

Arg Leu Tyr Tyr Arg Lys Leu Pro Ser Asn Ser Lys Gly Ser Ile Tyr
                405                 410                 415

Phe Ala His Glu Leu Leu Asp Gly Asp Asp Thr Trp His Glu Met Ile
            420                 425                 430

Gly Ser Arg Gly Asp Asn Ala Ser Asp Pro Ala Asp Gly Ile Ala Leu
        435                 440                 445
```

```
Asp Glu Thr Phe Ser Tyr Glu Ile Asp Val Arg Gly Asn Thr Leu Thr
            450                 455                 460

Val Thr Ile Met Arg Glu Gly Lys Pro Asp Val Thr Lys Val Leu Asp
465                 470                 475                 480

Met Ser Ala Ser Gly Tyr Asp Glu Gly Gln Tyr Met Tyr Phe Lys
            485                 490                 495

Ala Gly Val Tyr Asn Gln Asn Asn Ser Gly Asp Pro Asp Tyr Val
            500                 505                 510

Gln Ala Thr Phe Tyr Ala Leu Glu Ala Thr His Asn
            515                 520
```

<210> SEQ ID NO 56
<211> LENGTH: 307
<212> TYPE: PRT
<213> ORGANISM: Klebsiella pneumoniae

<400> SEQUENCE: 56

```
Met Leu Lys Ser Gly Val Met Val Ala Ser Leu Cys Leu Phe Ser Val
  1               5                  10                  15

Pro Ser Arg Ala Ala Val Pro Ala Gly Asp Lys Phe Glu Leu Ser
            20                  25                  30

Gly Trp Ser Leu Ser Val Pro Val Asp Ser Asp Asn Asp Gly Lys Ala
            35                  40                  45

Asp Gln Ile Lys Glu Lys Thr Leu Ala Ala Gly Tyr Arg Asn Ser Asp
        50                  55                  60

Phe Phe Thr Leu Ser Asp Ala Gly Gly Met Val Phe Lys Ala Pro Ile
 65                  70                  75                  80

Ser Gly Ala Lys Thr Ser Lys Asn Thr Thr Tyr Thr Arg Ser Glu Leu
                85                  90                  95

Arg Glu Met Leu Arg Lys Gly Asp Thr Ser Ile Ala Thr Gln Gly Val
            100                 105                 110

Ser Arg Asn Asn Trp Val Leu Ser Ser Ala Pro Leu Ser Glu Gln Lys
            115                 120                 125

Lys Ala Gly Gly Val Asp Gly Thr Leu Glu Ala Thr Leu Ser Val Asp
        130                 135                 140

His Val Thr Thr Thr Gly Val Asn Trp Gln Val Gly Arg Val Ile Ile
145                 150                 155                 160

Gly Gln Ile His Ala Asn Asn Asp Glu Pro Ile Arg Leu Tyr Tyr Arg
                165                 170                 175

Lys Leu Pro His His Gln Lys Gly Ser Val Tyr Phe Ala His Glu Pro
            180                 185                 190

Arg Lys Gly Phe Gly Asp Glu Gln Trp Tyr Glu Met Ile Gly Thr Leu
            195                 200                 205

Gln Pro Ser His Gly Asn Gln Thr Ala Ala Pro Thr Glu Pro Glu Ala
        210                 215                 220

Gly Ile Ala Leu Gly Glu Thr Phe Ser Tyr Arg Ile Asp Ala Thr Gly
225                 230                 235                 240

Asn Lys Leu Thr Val Thr Leu Met Arg Glu Gly Arg Pro Asp Val Val
                245                 250                 255

Lys Thr Val Asp Met Ser Lys Ser Gly Tyr Ser Glu Ala Gly Gln Tyr
            260                 265                 270

Leu Tyr Phe Lys Ala Gly Val Tyr Asn Gln Asn Lys Thr Gly Lys Pro
            275                 280                 285

Asp Asp Tyr Val Gln Ala Thr Phe Tyr Arg Leu Lys Ala Thr His Gly
```

Ala Gln Arg
    305

<210> SEQ ID NO 57
<211> LENGTH: 387
<212> TYPE: PRT
<213> ORGANISM: Microbulbifer degradans 2-40

<400> SEQUENCE: 57

Gly Glu Ala Thr Leu Val Ala Thr Ala Asn Gly Leu Leu Asn Asp Ala
 1               5                  10                  15

Asn Ser Leu Ala Gly Ala Asn Ala Ser Ala Leu Ile Val Leu Ser Glu
            20                  25                  30

Leu Asp Val Gly Pro Gly Ser Ser Phe Val Gln Pro Val Ala Gly Ala
        35                  40                  45

Tyr Asn Gly Ala Leu Asn Leu Asp Phe Thr His Trp Tyr Ile Thr Phe
    50                  55                  60

Pro Ser Gly Asp Ala Gln Tyr Asn Pro Gln Trp Leu Leu Asp Gly Tyr
65                  70                  75                  80

Thr Ser Glu Asn Glu Phe Tyr Tyr Asp Ala Asp Gly Ala Ala Val Phe
                85                  90                  95

Lys Thr Pro Asn Ile Ala Gly Thr Thr Ser Ala Asn Thr Lys Tyr Ser
            100                 105                 110

Arg Thr Glu Leu Arg Glu Met Met Arg Gly Pro Glu Gln Ser Pro Lys
        115                 120                 125

Pro Ala Asp Trp Pro Ser Thr Gln Gly Ile Asn Lys Asn Asn Trp Val
    130                 135                 140

Phe Ser Asn Ser Tyr Gln Arg Val Gln Tyr Glu Ala Gly Gly Val Asp
145                 150                 155                 160

Gly Val Met Glu Ala Thr Leu Lys Val Asp His Val Ser Thr Thr Val
                165                 170                 175

Thr Glu Gly Tyr Glu Tyr Met Met Gly Arg Val Ile Val Gly Gln Ile
            180                 185                 190

His Ala Ser Asp Asp Glu Pro Phe Arg Leu Tyr Tyr Arg Lys Leu Pro
        195                 200                 205

Gly Asn Ser Leu Gly Ser Val Tyr Phe Ala Thr Glu Val Pro Gly Leu
    210                 215                 220

Gly Asp Asn Arg Tyr Asp Met Ile Gly Asp Ser Lys Glu Asp Ser Pro
225                 230                 235                 240

Asn Pro Leu Asp Gly Ile Ala Leu Gly Glu Val Trp Ser Tyr Arg Val
                245                 250                 255

Glu Ala Lys Gly Asp Asp Leu Thr Val Thr Ile Met Arg Glu Gly Lys
            260                 265                 270

Pro Asp Val Thr Arg Thr Val Lys Thr Ala Ala Tyr Ala Asn Asp
        275                 280                 285

Trp Met Tyr Phe Lys Ala Gly Val Tyr Asn Gln Asn Asn Gly Gly Asp
    290                 295                 300

Pro Ser Asp Tyr Ala Gln Ala Thr Phe Tyr Ser Ile Val Val Ser His
305                 310                 315                 320

Asp Ala Pro Pro Val Glu Pro Gly Asn Gly Glu Asp Glu Gly Asn Gly
                325                 330                 335

Gly Thr Thr Thr Glu Val Thr Asp Gly Pro Ser Leu Gln Thr Ala Ile
            340                 345                 350

```
Leu Ala Ala Ser Ala Gly Asp Thr Ile Glu Ile Gly Ala Gly Asp Tyr
        355                 360                 365
Ala Asn Met Gly Thr Val Val Val Thr Asp Gly Val Thr Ile Thr Arg
        370                 375                 380
Ala Glu Gly
385

<210> SEQ ID NO 58
<211> LENGTH: 307
<212> TYPE: PRT
<213> ORGANISM: Klebsiella pneumoniae

<400> SEQUENCE: 58

Met Leu Lys Ser Gly Val Met Val Ala Ser Leu Cys Leu Phe Ser Val
  1               5                  10                  15
Pro Ser Arg Ala Ala Val Pro Ala Pro Gly Asp Lys Phe Glu Leu Ser
                 20                  25                  30
Gly Trp Ser Leu Ser Val Pro Val Asp Ser Asp Asn Asp Gly Lys Ala
             35                  40                  45
Asp Gln Ile Lys Glu Lys Thr Leu Ala Ala Gly Tyr Arg Asn Ser Asp
         50                  55                  60
Phe Phe Thr Leu Ser Asp Ala Gly Gly Met Val Phe Lys Ala Pro Ile
 65                  70                  75                  80
Ser Gly Ala Lys Thr Ser Lys Asn Thr Thr Tyr Thr Arg Ser Glu Leu
                 85                  90                  95
Arg Glu Met Leu Arg Lys Gly Asp Thr Ser Ile Ala Thr Gln Gly Val
                100                 105                 110
Ser Arg Asn Asn Trp Val Leu Ser Ser Ala Pro Leu Ser Glu Gln Lys
            115                 120                 125
Lys Ala Gly Gly Val Asp Gly Thr Leu Glu Ala Thr Leu Ser Val Asp
        130                 135                 140
His Val Thr Thr Thr Gly Val Asn Trp Gln Val Gly Arg Val Ile Ile
145                 150                 155                 160
Gly Gln Ile His Ala Asn Asn Asp Glu Pro Ile Arg Leu Tyr Tyr Arg
                165                 170                 175
Lys Leu Pro His His Gln Lys Gly Ser Val Tyr Phe Ala His Glu Pro
            180                 185                 190
Arg Lys Gly Phe Gly Asp Glu Gln Trp Tyr Glu Met Ile Gly Thr Leu
        195                 200                 205
Gln Pro Ser His Gly Asn Gln Thr Ala Ala Pro Thr Glu Pro Glu Ala
    210                 215                 220
Gly Ile Ala Leu Gly Glu Thr Phe Ser Tyr Arg Ile Asp Ala Thr Gly
225                 230                 235                 240
Asn Lys Leu Thr Val Thr Leu Met Arg Glu Gly Arg Pro Asp Val Val
                245                 250                 255
Lys Thr Val Asp Met Ser Lys Ser Gly Tyr Ser Glu Ala Gly Gln Tyr
            260                 265                 270
Leu Tyr Phe Lys Ala Gly Val Tyr Asn Gln Asn Lys Thr Gly Lys Pro
        275                 280                 285
Asp Asp Tyr Val Gln Ala Thr Phe Tyr Arg Leu Lys Ala Thr His Gly
    290                 295                 300
Ala Gln Arg
305

<210> SEQ ID NO 59
```

-continued

```
<211> LENGTH: 373
<212> TYPE: PRT
<213> ORGANISM: Microbulbifer degradans 2-40

<400> SEQUENCE: 59
```

| | | | | | | | | | | | | | | | |
|---|---|---|---|---|---|---|---|---|---|---|---|---|---|---|---|
| Asn | Val | Val | Ser | Met | Asn | Gly | Thr | Ser | Asn | Pro | Gln | Pro | Glu | Gly | |
| 1 | | | | 5 | | | | | 10 | | | | | 15 | |
| Gly | Arg | Leu | Leu | Val | Ile | Asp | Gly | Asp | Gly | Ile | Ile | Lys | Gln | Ala | |
| | | | 20 | | | | | 25 | | | | | 30 | | |
| Ile | Tyr | Lys | Pro | Ile | Ala | Gly | His | Val | Tyr | Glu | Ile | Thr | Ala | Tyr | Val |
| | | 35 | | | | | 40 | | | | | 45 | | | |
| Tyr | Gly | His | Gly | Thr | Ile | Gly | Ile | Gln | Asp | Leu | Gly | Ser | Asp | Asn | Val |
| | 50 | | | | | 55 | | | | | 60 | | | | |
| Tyr | Glu | Thr | Ser | Thr | Ala | His | Gly | Asn | Ser | Trp | Gln | Gln | Ile | Ser | Val |
| 65 | | | | | 70 | | | | | 75 | | | | | 80 |
| Thr | Tyr | Val | Ser | Thr | Gly | Ser | Pro | Ala | Met | Leu | Tyr | Ala | Lys | Tyr | Gly |
| | | | | 85 | | | | | 90 | | | | | 95 | |
| Pro | Gly | Ser | Gly | Asp | Ser | Tyr | Phe | Asp | Val | Phe | Asp | Ala | Lys | Asp | Ile |
| | | | 100 | | | | | 105 | | | | | 110 | | |
| Ser | Thr | Ala | Glu | Asp | Leu | Ser | Lys | Gln | Pro | Pro | Ala | Pro | Ile | Met | Arg |
| | | | 115 | | | | | 120 | | | | | 125 | | |
| Tyr | Ala | Ser | Gln | Val | Ile | Asp | Leu | Ser | Trp | Trp | Lys | Ile | Thr | Leu | Pro |
| | | 130 | | | | | 135 | | | | | 140 | | | |
| Ile | Asn | Asn | Ala | Met | Glu | Ile | Tyr | Thr | Pro | Glu | Leu | Leu | Thr | Tyr | Glu |
| 145 | | | | | 150 | | | | | 155 | | | | | 160 |
| Ile | Asp | Pro | Trp | Phe | Lys | Leu | Val | Glu | Asp | Glu | Gly | Tyr | Ala | Val | |
| | | | | 165 | | | | | 170 | | | | | 175 | |
| Gln | Phe | Arg | Ala | Asn | His | Gly | Gly | Ser | Thr | Thr | Gly | Gly | Ser | Ser | Asn |
| | | | 180 | | | | | 185 | | | | | 190 | | |
| Pro | Arg | Ser | Glu | Leu | Arg | Glu | Leu | Thr | Gln | Asn | Tyr | His | Tyr | Arg | Asn |
| | | 195 | | | | | 200 | | | | | 205 | | | |
| Ser | Lys | Ser | Ala | Ala | Ala | Trp | Ser | Asn | Thr | Ser | Gly | Thr | His | Glu | Met |
| | 210 | | | | | 215 | | | | | 220 | | | | |
| Trp | Ile | Lys | Gln | Lys | Val | Thr | His | Leu | Thr | Tyr | Val | Lys | Pro | His | Val |
| 225 | | | | | 230 | | | | | 235 | | | | | 240 |
| Val | Val | Gly | Gln | Ile | His | Asp | Ser | Gly | Asp | Asp | Val | Thr | Val | Phe | Arg |
| | | | | 245 | | | | | 250 | | | | | 255 | |
| Val | Glu | Gly | His | Leu | Gly | Gln | Gly | Gly | Asp | Trp | Asp | Asn | Asn | Gly | Thr |
| | | | 260 | | | | | 265 | | | | | 270 | | |
| Val | Gly | Val | Met | Asp | Thr | His | Ala | Asn | Ile | Trp | Ile | Thr | Asn | Gly | Asn |
| | | 275 | | | | | 280 | | | | | 285 | | | |
| Asp | Arg | His | Gly | Tyr | Leu | Val | Asp | Asp | Asn | Tyr | Glu | Leu | Gly | Thr | Val |
| | 290 | | | | | 295 | | | | | 300 | | | | |
| Phe | Thr | Val | Lys | Phe | Ile | Ala | Arg | Asp | Gly | Lys | Val | Glu | Tyr | Glu | Tyr |
| 305 | | | | | 310 | | | | | 315 | | | | | 320 |
| Asn | Gly | Arg | Lys | Leu | Asp | Tyr | Val | His | Glu | Glu | Ser | Phe | Ser | Gly | Ala |
| | | | | 325 | | | | | 330 | | | | | 335 | |
| Tyr | Phe | Lys | Leu | Gly | Asn | Tyr | Thr | Gln | Ser | His | Asn | Gly | Thr | Ala | Pro |
| | | | 340 | | | | | 345 | | | | | 350 | | |
| Gly | Glu | Thr | Asp | Asp | Ala | Tyr | Ala | Glu | Thr | Tyr | Val | Tyr | Asp | Tyr | Tyr |
| | | 355 | | | | | 360 | | | | | 365 | | | |
| Ile | Lys | His | Thr | Glu | | | | | | | | | | | |
| | | | | 370 | | | | | | | | | | | |

<210> SEQ ID NO 60
<211> LENGTH: 256
<212> TYPE: PRT
<213> ORGANISM: Corynebacterium sp.

<400> SEQUENCE: 60

Met Thr Leu Thr Arg Lys Arg Gly Leu Thr Ala Ala Leu Thr Ala Thr
1               5                   10                  15

Ala Leu Leu Val Gly Ser Met Val Val Gly Ser Gly Ala Ala Ala
            20                  25                  30

Ala Glu Pro Cys Asp Tyr Pro Ala Gln Gln Leu Asp Leu Thr Asp Trp
        35                  40                  45

Lys Val Thr Leu Pro Ile Gly Ser Ser Gly Lys Pro Ser Glu Ile Glu
    50                  55                  60

Gln Pro Ala Leu Asp Thr Phe Ala Thr Ala Pro Trp Phe Gln Val Asn
65                  70                  75                  80

Ala Lys Cys Thr Gly Val Gln Phe Arg Ala Ala Val Asn Gly Val Thr
                85                  90                  95

Thr Ser Gly Ser Gly Tyr Pro Arg Ser Glu Leu Arg Glu Met Thr Asp
            100                 105                 110

Gly Gly Glu Glu Lys Ala Ser Trp Ser Ala Thr Ser Gly Thr His Thr
        115                 120                 125

Met Val Phe Arg Glu Ala Phe Asn His Leu Pro Glu Val Lys Pro His
    130                 135                 140

Leu Val Gly Ala Gln Ile His Asp Gly Asp Asp Val Thr Val Phe
145                 150                 155                 160

Arg Leu Glu Gly Thr Ser Leu Tyr Ile Thr Lys Gly Asp Asp Thr His
                165                 170                 175

His Lys Leu Val Thr Ser Asp Tyr Lys Leu Asn Thr Val Phe Glu Gly
            180                 185                 190

Lys Phe Val Val Ser Gly Gly Lys Ile Lys Val Tyr Tyr Asn Gly Val
        195                 200                 205

Leu Gln Thr Thr Ile Ser His Thr Ser Ser Gly Asn Tyr Phe Lys Ala
    210                 215                 220

Gly Ala Tyr Thr Gln Ala Asn Cys Ser Asn Ser Ser Pro Cys Ser Ser
225                 230                 235                 240

Ser Asn Tyr Gly Gln Val Ser Leu Tyr Lys Leu Gln Val Thr His Ser
                245                 250                 255

<210> SEQ ID NO 61
<211> LENGTH: 892
<212> TYPE: PRT
<213> ORGANISM: Microbulbifer degradans 2-40

<400> SEQUENCE: 61

Met Lys Phe Lys Ser Leu Val Ala Leu Phe Leu Leu Gly Leu Leu Thr
1               5                   10                  15

Ala Cys Gly Gly Gly Ser Ser Asn Pro Asp Pro Asp Pro Asp Pro Ile
            20                  25                  30

Glu Glu Pro Glu Gly Glu Pro Glu Gly Glu Pro Glu Gly Glu Pro Glu
        35                  40                  45

Gly Glu Pro Glu Gly Glu Pro Glu Gly Glu Pro Glu Gly Glu Pro Glu
    50                  55                  60

Gly Glu Pro Glu Gly Glu Pro Gln Glu Ser Asn Phe Pro Arg Gly Ser
65                  70                  75                  80

Leu Gly Asp Asn Asp Thr Val Pro Asp Val Val Cys Thr Gln Thr Val

-continued

```
                 85                  90                  95
Asn Ser Thr Ser Glu Leu Glu Asp Ala Val Ser Tyr Glu Met Thr Pro
            100                 105                 110
Gly Thr Thr Leu Cys Leu Ala Asp Gly Asn Tyr Thr Asn Leu Glu Ile
            115                 120                 125
Gln Phe Gly Gly Ile Gly Thr Glu Ala Asn Pro Ile Thr Val Ala Ala
            130                 135                 140
Ala Asn Pro Gly Met Val Thr Ile Gly Gly Glu Val Gly Ile Arg Met
145                 150                 155                 160
Ser Gly Glu Tyr Val Leu Gln Gly Leu Ile Phe Lys Asp Gly Glu
            165                 170                 175
Ser Ala Ser Ser Asp Leu Ile Gln Thr Arg Gly Asn Ser Asn Ala Pro
            180                 185                 190
Cys Asn Asn Cys Arg Ile Thr Glu Ile Ala Ile Ile Asp Phe Asp Gln
            195                 200                 205
Asn Ser Asp Ser Ser Gly Lys Trp Val His Ile Tyr Gly Ala His Asn
            210                 215                 220
Arg Val Asp His Ser Trp Phe Ser Gly Lys Thr Thr Arg Gly Ala Leu
225                 230                 235                 240
Leu Val Val Asp Arg Tyr Ile Glu Asp Gly Val Asp Pro Leu Asp Ala
                    245                 250                 255
Glu Ile Asp Tyr Ala Gln Ile Asp His Asn Tyr Phe Gly Asp Arg Pro
            260                 265                 270
Pro Val Asp Gly Lys Ala Tyr Ala Ser Ser Gly Asp Asn Glu Tyr Glu
            275                 280                 285
Gly Ile Arg Ile Gly Thr Ser Asp Ser His Thr Gly Asp Ser Phe Ser
            290                 295                 300
Val Ile Glu His Asn Tyr Phe Glu Arg Ile Gln Gly Glu Ala Glu Val
305                 310                 315                 320
Ile Ser Asn Lys Ser Gly Asn Asn Arg Ile Glu His Asn Thr Val Arg
                    325                 330                 335
Asn Ser Tyr Gly Ser Ile Thr Thr Arg His Gly Ser Ser Ala Thr Ile
            340                 345                 350
Thr Asn Asn Phe Ile Ile Gly Asp Gly His Pro Tyr Ala Gly Gly Leu
            355                 360                 365
Arg Ile Ile Asp Asp Gly His Thr Val Thr Asn Asn Tyr Ile Gln Gly
            370                 375                 380
Ala Arg Tyr Leu Ala Thr Thr His His Gly Gly Ile Val Leu Met Gly
385                 390                 395                 400
Ser Asp Gly Ser Thr Thr Asn Gly Tyr Gln Gln Leu Thr Asn Val Leu
            405                 410                 415
Val Ala His Asn Thr Val Asp Ser Val Asn Ser Leu Asn Val Asp
            420                 425                 430
Gly Gly Gln Lys Ser Thr Asn Pro Asn Asn Val Tyr Leu Val Asn Asn
            435                 440                 445
Ile Ile Ala Asn Gly Ile Gly Pro Val Ile Thr Glu Ala Ala Asp Gly
            450                 455                 460
Met Pro Gly Ser Ser Val Ile Ala Gly Asn Ile Phe Tyr Gly Gln Ser
465                 470                 475                 480
Phe Ser Asp Ser Ser Ser Leu Thr Ser Val Asp Gly Ile Thr Trp Leu
            485                 490                 495
Asp Val Ala Phe Ala Ala Asp Met Gln Gly Val Met Arg Ala Thr Gly
            500                 505                 510
```

```
Ser Ser Pro Asp Leu Thr Ala Ala Ala Asp Thr Gly Asp Phe Ala
        515                 520                 525

Ala Val Thr Leu Asp Met Asp Gly Leu Ala Arg Ala Ala Thr Thr Gln
530                 535                 540

Ala Gly Ala Asp Asp Ile Gly Gly Asn Pro Val Arg Gly Ile Leu
545                 550                 555                 560

Asn Ser Tyr Asp Val Gly Pro Ile Ser Tyr Arg Pro Pro Met Thr Thr
                565                 570                 575

Pro His Val Ala Glu Val Asp Val Ala Asn Tyr Ala Phe Asp Glu Gly
                580                 585                 590

Ala Ala Gly Trp Thr Leu Val Asp Ala Val Val Asn Thr Asn Ala Ala
        595                 600                 605

Glu Val Phe Ala Arg Gly Ala Ser Val Glu Val Thr Gly Ala Asn Gly
    610                 615                 620

Arg Ala Ser Gln Val Val Ser Leu Thr Ala Asn Thr Asn Tyr Thr Leu
625                 630                 635                 640

Thr Ala Phe Val Lys Gly Thr Ala Thr Leu Ala Ala Asp Val Gly Gly
                645                 650                 655

Thr Val Tyr Arg Ser Asp Val Asn Ser Ser Leu Glu Tyr Lys Leu Ala
                660                 665                 670

Thr Val Ser Phe Asn Ser Gly Asp Ala Thr Ser Ala Thr Ile Tyr Gly
            675                 680                 685

Glu Val Asp Asp Phe Val Leu Asn Tyr Ala Pro Ile Gly Glu Ala Ser
    690                 695                 700

Leu Asp Gly Phe Pro Gly Ala Asp Thr Thr Phe Trp Ser Val Tyr Glu
705                 710                 715                 720

Gly Ala Gly Ile Gly Gln Val Gln Gly Ser Asp Asn Ser Ala Ala Gly
                725                 730                 735

Ala Asp Gly Ser Val Lys Phe Lys Leu Glu Asp Ala Thr Glu Val Gly
                740                 745                 750

Thr Pro Arg Ile Ser Gln Val Leu Thr Gly Leu Glu Leu Asn Thr Asp
        755                 760                 765

Tyr Thr Leu Ser Met Tyr Ala Leu Tyr Lys Lys Ser Ala Asp Val Thr
770                 775                 780

Val Thr Met Gly Ala Phe Val Gly Glu Thr Asp Thr Val Leu Ala Ser
785                 790                 795                 800

Lys Val Val Asp Phe Glu Asp Leu Val Ala Ala Asn Ala Pro Lys Gly
                805                 810                 815

Asp Asp Ser Phe Arg Gln Asp Thr Leu Thr Phe Asn Thr Gly Ser Asn
                820                 825                 830

Ser Thr Ile Thr Ile Phe Ala Glu Tyr Asn Ala Asn Thr Ile Ile Ala
        835                 840                 845

Asp Gly Gly Asp Ala Gly Asp Thr Glu Phe Arg Val Asp Glu Phe Ala
        850                 855                 860

Leu Thr Tyr Glu Gly Ala Pro Ala Ala Asp Ala Lys Ala Tyr Phe Asp
865                 870                 875                 880

Glu Phe Arg Leu Val Ser His Ala Ser Leu Ala Asp
                885                 890

<210> SEQ ID NO 62
<211> LENGTH: 398
<212> TYPE: PRT
<213> ORGANISM: Pseudomonas sp.
```

<400> SEQUENCE: 62

| | | | | | | | | | | | |
|---|---|---|---|---|---|---|---|---|---|---|---|
|Met|Pro|Gly|Asp|Lys|Val|Ile|Met|Lys|Ser|Gly|Glu|Trp|Lys|Ser|Gln|
|1| | | |5| | | | |10| | | | |15| |

Phe Ile His Phe Lys Gly Lys Gly Thr Ala Glu Lys Pro Ile Thr Leu
            20                  25                  30

Thr Ala Glu Thr Lys Gly Ser Val Leu Leu Thr Gly Asn Ser Asn Leu
        35                  40                  45

Lys Ile Asp Gly Glu Trp Leu Val Asp Gly Leu Ser Phe Lys Asn
 50                  55                  60

Gly Phe Ser Leu Lys Asp Asp Val Val Phe Thr Lys Thr Thr Thr
 65                  70                  75                  80

Asn Ser Arg Leu Thr Asn Thr Ser Ile Glu Asn Tyr Asn Pro Val Asp
                85                  90                  95

Lys Thr Leu Asp Tyr Lys Trp Val Ser Leu Tyr Gly His His Asn Arg
            100                 105                 110

Val Asp His Cys Ser Ile Thr Gly Lys Asn His Gln Gly Thr Thr Leu
            115                 120                 125

Val Val Trp Leu Asp Asp Lys Pro Asn Tyr His Gln Ile Asp His Asn
130                 135                 140

Tyr Phe Gly Pro Arg Pro Glu Leu Gly Ala Asn Gly Gly Glu Thr Ile
145                 150                 155                 160

Arg Ile Gly Thr Ser Ala Phe Ser Met Asn Asp Ser Tyr Arg Thr Val
                165                 170                 175

Gln Asn Asn Ile Phe Asp Lys Cys Asp Gly Glu Val Glu Ile Ile Ser
            180                 185                 190

Ile Lys Ser Gly Phe Asn Lys Ile Leu Asn Asn Leu Phe Tyr Glu Cys
            195                 200                 205

Ala Gly Thr Val Thr Phe Arg His Gly Asn Asn Ser Glu Val Ser Asn
210                 215                 220

Asn Tyr Phe Ile Ala Asn Asn Val Thr Asn Ser Gly Gly Val Arg Ile
225                 230                 235                 240

Ile Gly Glu Asn Gln Lys Val Tyr Gly Asn Tyr Leu Tyr Lys Val Ala
                245                 250                 255

Gly Arg Thr Leu Arg Ser Ala Ile Ser Val Met Asn Ala Tyr Glu Lys
            260                 265                 270

Pro Ala Leu Asn Asp Tyr Trp Gln Val Lys Asn Ala Asp Ile Gln Asn
            275                 280                 285

Asn Ile Ile Val Gly Ala Arg Glu Ala Phe Val Leu Gly Ser Gly Lys
            290                 295                 300

Asp Asn Asp Arg Thr Leu Ala Pro Asp Gly Val Asn Ile Ser Asn Asn
305                 310                 315                 320

Tyr Ile Ile Asn Pro Thr Thr Leu Leu Val Thr Gln Asp Glu Pro Lys
                325                 330                 335

Asn Leu Lys Met Gln Asn Asn Gln Val Glu Gly Ala Ser Ile Val Thr
            340                 345                 350

Gly Phe Val Lys Met Gly Asn Asp Leu Gln Met Ser Asp Gly Ile Trp
            355                 360                 365

Gln Lys Lys Thr Glu Ile Lys Lys Pro Phe Trp Leu Ala Thr Ala Ile
            370                 375                 380

Gly Pro Glu Trp Lys Lys Asp His Arg Ser Phe Ile Phe Lys
385                 390                 395

<210> SEQ ID NO 63

```
<211> LENGTH: 525
<212> TYPE: PRT
<213> ORGANISM: Microbulbifer degradans 2-40

<400> SEQUENCE: 63

Met Lys Lys Ile Val Ala Ser Leu Leu Ile Gly Leu Cys Ser Leu Ala
  1               5                  10                  15

Val Cys Ala Glu Thr His Ile Tyr Asp Gly Lys Gly Lys Glu Thr Trp
             20                  25                  30

Thr Lys Thr Asp Leu Lys Pro Gly Asp Val Val Ile Pro Asn Gly
         35                  40                  45

Thr Tyr Ala Asp Leu Lys Ile Asn Val Gln Gly Lys Gly Glu Gln Ala
     50                  55                  60

Lys Pro Ile Val Leu Lys Ala Glu Thr Pro Gly Gly Val Val Leu Thr
 65                  70                  75                  80

Gly Ala Ser Trp Leu Arg Tyr Trp Gly Tyr Phe Ile Val Val Asp Gly
                 85                  90                  95

Phe Asp Phe Asn Asp Val Thr Tyr Ser Met Tyr Lys Asn Lys Val Arg
                100                 105                 110

Ala Ile Ile Ala Asn Arg Arg Ala Gly Ser Ser Glu Ser Ser Lys
            115                 120                 125

Asp Met Cys Gln Ala Cys Val Leu Gln Arg Val Arg Ile Asp Asn Glu
    130                 135                 140

Asn Asp Lys Ala Ile Asp Thr Glu Tyr Lys Trp Ile Glu Leu Tyr Gly
145                 150                 155                 160

Tyr Asn Asn Val Val Arg Tyr Asn Tyr Phe Gly Ala Lys Lys Ser Gly
                165                 170                 175

Ser Arg Val Leu Gln Val Gln Leu Lys His Ala Asn Ala Gln Lys Leu
            180                 185                 190

Pro Val Ser His Val Ile Gln Tyr Asn Tyr Phe Ala Ser Arg Asn Ala
        195                 200                 205

Gly Lys Ala Val Gly Asn Gly Gly Glu Ala Leu Leu Val Gly Asp Ser
    210                 215                 220

Asn Met Gln His Val Asp Ala Lys Val Thr Val Ala Asn Asn Leu Phe
225                 230                 235                 240

Tyr Asp Ala Ser Ile Leu Gly Glu Pro Glu Val Ile Ser Asn Lys Ser
                245                 250                 255

Ser Ser Asn Ile Tyr Arg Ser Asn Thr Val Arg Asn Thr Thr Ala Ser
            260                 265                 270

Leu Thr Leu Arg His Gly Asn Arg Asn Thr Val Glu Asn Asn Trp Phe
        275                 280                 285

Leu Gln Asp Gln Thr Glu Gly Ser Gly Gly Ile Arg Val Ile Gly Asp
    290                 295                 300

Asp Asn Ile Ile His Asn Asn Tyr Ile Ala Gly Ser Ala Gly Gly
305                 310                 315                 320

Lys Ser Ala Ala Tyr Arg Pro Ala Leu Gly Ile Ala Ala Gly Tyr Ser
                325                 330                 335

Lys Lys Asp Asp Asp Ala Asn Ile Asn Gly Tyr Gln Leu Ser Glu Arg
            340                 345                 350

Asn Val Leu Ser Asn Asn Ser Val Ile Gln Ser Ala Gln Pro Val Met
        355                 360                 365

Leu Ser Thr Trp Tyr Asp Arg Gly Lys Leu Ser Met Thr Arg Pro Pro
    370                 375                 380

Met Gln Thr Thr Phe Ile Asn Asn Leu Val Tyr Gln Leu Asp Val Ala
```

```
                385                 390                 395                 400

Pro Ser Thr Ala Asp Trp Val Arg Gly Leu Ala Ile Ser Val Asp Tyr
            405                 410                 415

Thr Pro Asp Ser Glu Tyr Gly Asn Asn Tyr Gly Ile Asp Lys Ala Glu
            420                 425                 430

Tyr Val Pro Ser Phe Ala Lys Val Lys Gly Asn Ile Thr Asp Gly Lys
            435                 440                 445

Val Ser Pro Leu Val Ser Lys Gly Thr Lys Ala Glu Ser Lys Lys Glu
    450                 455                 460

Leu Lys Gly Cys Asp Ala Phe Gly Thr Gly Asp Ile Val Tyr Leu Pro
465                 470                 475                 480

Leu Lys Lys Ala Gly Ala Asp Leu Ser Lys Met Asp Glu Pro Leu Val
            485                 490                 495

Trp Thr Asp Thr Val Lys Ser Ala Arg Leu Gly Pro Asp Trp Leu Asn
            500                 505                 510

Ala Asn Trp Gly Gly Glu Lys Lys Ala Tyr Lys Gly Cys
            515                 520                 525

<210> SEQ ID NO 64
<211> LENGTH: 398
<212> TYPE: PRT
<213> ORGANISM: Pseudomonas sp.

<400> SEQUENCE: 64

Met Pro Gly Asp Lys Val Ile Met Lys Ser Gly Glu Trp Lys Ser Gln
1               5                   10                  15

Phe Ile His Phe Lys Gly Lys Gly Thr Ala Glu Lys Pro Ile Thr Leu
            20                  25                  30

Thr Ala Glu Thr Lys Gly Ser Val Leu Leu Thr Gly Asn Ser Asn Leu
        35                  40                  45

Lys Ile Asp Gly Glu Trp Leu Val Val Asp Gly Leu Ser Phe Lys Asn
    50                  55                  60

Gly Phe Ser Leu Lys Asp Asp Val Val Phe Thr Lys Thr Thr Thr
65                  70                  75                  80

Asn Ser Arg Leu Thr Asn Thr Ser Ile Glu Asn Tyr Asn Pro Val Asp
                85                  90                  95

Lys Thr Leu Asp Tyr Lys Trp Val Ser Leu Tyr Gly His His Asn Arg
            100                 105                 110

Val Asp His Cys Ser Ile Thr Gly Lys Asn His Gln Gly Thr Thr Leu
            115                 120                 125

Val Val Trp Leu Asp Asp Lys Pro Asn Tyr His Gln Ile Asp His Asn
    130                 135                 140

Tyr Phe Gly Pro Arg Pro Glu Leu Gly Ala Asn Gly Glu Thr Ile
145                 150                 155                 160

Arg Ile Gly Thr Ser Ala Phe Ser Met Asn Asp Ser Tyr Arg Thr Val
                165                 170                 175

Gln Asn Asn Ile Phe Asp Lys Cys Asp Gly Glu Val Glu Ile Ile Ser
            180                 185                 190

Ile Lys Ser Gly Phe Asn Lys Ile Leu Asn Asn Leu Phe Tyr Glu Cys
        195                 200                 205

Ala Gly Thr Val Thr Phe Arg His Gly Asn Asn Ser Glu Val Ser Asn
    210                 215                 220

Asn Tyr Phe Ile Ala Asn Asn Val Thr Asn Ser Gly Gly Val Arg Ile
225                 230                 235                 240
```

```
Ile Gly Glu Asn Gln Lys Val Tyr Gly Asn Tyr Leu Tyr Lys Val Ala
                245                 250                 255

Gly Arg Thr Leu Arg Ser Ala Ile Ser Val Met Asn Ala Tyr Glu Lys
            260                 265                 270

Pro Ala Leu Asn Asp Tyr Trp Gln Val Lys Asn Ala Asp Ile Gln Asn
        275                 280                 285

Asn Ile Ile Val Gly Ala Arg Glu Ala Phe Val Leu Gly Ser Gly Lys
    290                 295                 300

Asp Asn Asp Arg Thr Leu Ala Pro Asp Gly Val Asn Ile Ser Asn Asn
305                 310                 315                 320

Tyr Ile Ile Asn Pro Thr Thr Leu Leu Val Thr Gln Asp Glu Pro Lys
                325                 330                 335

Asn Leu Lys Met Gln Asn Asn Gln Val Glu Gly Ala Ser Ile Val Thr
            340                 345                 350

Gly Phe Val Lys Met Gly Asn Asp Leu Gln Met Ser Asp Gly Ile Trp
        355                 360                 365

Gln Lys Lys Thr Glu Ile Lys Lys Pro Phe Trp Leu Ala Thr Ala Ile
    370                 375                 380

Gly Pro Glu Trp Lys Lys Asp His Arg Ser Phe Ile Phe Lys
385                 390                 395

<210> SEQ ID NO 65
<211> LENGTH: 542
<212> TYPE: PRT
<213> ORGANISM: Microbulbifer degradans 2-40

<400> SEQUENCE: 65

Met Leu Ala Leu Ser Ala Ser Leu Thr Gln Ala Ala Thr Ile Ser Asn
1               5                   10                  15

Ser Gly Phe Glu Ser Gly Phe Asp Gly Trp Thr Asp Thr Asp Pro Ser
                20                  25                  30

Ala Leu Ser Ser Asp Ala Asn Asn Gly Ser Arg Ser Ala Lys Ile Thr
            35                  40                  45

Gly Ser Ala Gly Arg Val Asp Gln Asp Val Ala Val Thr Pro Asn Thr
        50                  55                  60

Asn Tyr Gln Leu Thr Ala Tyr Val Leu Gly Ser Gly Arg Val Gly Val
65                  70                  75                  80

Asn Thr Gly Thr Ala Val Tyr Asp Glu Ala Val Asn Thr Ser Ser Trp
                85                  90                  95

Ser Lys Val Thr Val Asn Phe Asn Ser Gly Ser Ala Asn Ser Val Glu
            100                 105                 110

Val Phe Gly Lys Tyr Asn Ser Gly Thr Gly Arg Phe Asp Asp Phe Ser
        115                 120                 125

Leu Val Glu Thr Gly Thr Pro Thr Pro Thr Pro Thr Pro Thr Pro Thr
    130                 135                 140

Pro Thr Pro Thr Pro Ala Gly Cys Asn Ser Leu Asn Thr Ile Asp Ile
145                 150                 155                 160

Ser Ser Ala Thr Asp Asp Gly Ser His Asp Gly His Gly Pro His Leu
                165                 170                 175

Ala Val Asp Gly Asp Leu Ser Ala Asp Ser Arg Trp Ser Ser Lys Gly
            180                 185                 190

Asp Gly Lys Ala Ile Thr Leu Asp Leu Gly Ala Glu Ala Thr Val Arg
        195                 200                 205

Gln Leu Lys Thr Ala Trp Tyr Lys Gly Asp Ser Arg Thr Ala Tyr Phe
    210                 215                 220
```

```
Asp Val Glu Thr Ser Thr Asp Lys Ser Asn Trp Ser Thr Ala Leu Ser
225                 230                 235                 240

Asn Val Gln Ser Gln Gly Ser Thr Gly Leu Lys Ser Asn Ser Ile Asp
            245                 250                 255

Asp Val Thr Ala Arg Tyr Val Arg Ile Val Gly His Gly Asn Ser Ser
                260                 265                 270

Asn Thr Trp Asn Ser Leu Ile Glu Ala Gln Val Leu Gly Cys Ala Gly
        275                 280                 285

Thr Val Thr Pro Thr Pro Thr Pro Thr Pro Thr Pro Thr Pro Thr Pro
290                 295                 300

Thr Pro Thr Pro Thr Pro Thr Pro Ser Gly Ser Lys Ile Pro Glu Ser
305                 310                 315                 320

Ile Thr Asn Ser Asp Val Trp Asp Leu Glu Gly Glu Asn Pro His Pro
                325                 330                 335

Leu Val Asp Pro Tyr Thr Leu Glu Phe Val Pro Leu Glu Ala Arg Val
            340                 345                 350

Thr Thr Pro Asn Gly Asn Gly Trp Arg His Glu Tyr Lys Ile Ala Ser
                355                 360                 365

Ser Glu Arg Thr Ala Met Thr Ala Thr Tyr Glu Asp Phe Ser Ala Thr
370                 375                 380

Ile Lys Val Asp Leu Ser Thr Gly Gly Lys Thr Ile Val Ala Gln His
385                 390                 395                 400

His Ala Gly Asp Thr Gly Thr Ile Met Lys Leu Tyr Val Ser Asp Thr
                405                 410                 415

Ser Glu Ser Gly Phe Phe Asp Ser Val Ala Ala Asn Gly Ile Phe Asp
            420                 425                 430

Val Tyr Val Arg Ile Arg Asn Thr Ser Gly Val Glu Glu Lys Lys Pro
                435                 440                 445

Leu Gly Thr Ile Arg Ser Gly Asp Ser Phe Ser Phe His Val Leu Asn
            450                 455                 460

Asn Tyr Gly Val Val Lys Val Ser Ala Phe Gly Lys Asn Leu Glu Thr
465                 470                 475                 480

Glu Val Glu Asp Asp Ser Ala Ser Tyr Leu Lys Phe Gly Asn Tyr Leu
                485                 490                 495

Gln Ser Gln Tyr Pro Gln Gly Ser Lys Asp Cys Gly Ser His Gly Asp
            500                 505                 510

Ser Asp Ser Phe Arg Ala Cys Tyr Glu Asp Ile Gly Ile Thr Glu Ala
            515                 520                 525

Lys Ile Thr Met Thr Asn Val Ser Tyr Thr Arg Ile Thr Lys
530                 535                 540
```

<210> SEQ ID NO 66
<211> LENGTH: 398
<212> TYPE: PRT
<213> ORGANISM: Pseudoalteromonas sp.

<400> SEQUENCE: 66

```
Met Tyr Arg Phe Gly Glu Ile Lys Ile Met Ile Asn Gln Lys Ser Leu
 1               5                  10                  15

Phe Met Leu Ala Ala Met Thr Ala Ser Ser Phe Val Gln Ala Ala
            20                  25                  30

Thr Ile Asn Asn Ala Gly Phe Glu Asp Gly Trp Ser Asn Trp Asn Glu
        35                  40                  45

Thr Glu Pro Ala Ala Ile Ser Gly Ser Ala Tyr Lys Gly Ser Lys Ser
```

```
            50                  55                  60
Leu Lys Ile Gln Gly Ser Pro Gly Arg Val Tyr Gln Asn Val Asp Val
 65                  70                  75                  80

Asp Arg Asn Thr Gln Tyr Thr Leu Ser Ala Tyr Val Leu Gly Lys Gly
                 85                  90                  95

Gln Ile Gly Ile Asn Asp Leu Asn Gly Leu Phe Lys Asn Glu Lys Phe
                100                 105                 110

Asn Val Ser Ser Trp Thr Lys Val Ser Arg Thr Phe Thr Thr Ala Asn
                115                 120                 125

Thr Gly Thr Leu Gln Val Phe Ala Lys His Asp Lys Ser Ser Asn Asp
                130                 135                 140

Val Arg Phe Asp Asn Phe Ser Leu Thr Lys Gly Thr Ser Gly Gly Gly
145                 150                 155                 160

Asp Thr Gly Gly Gly Asp Thr Gly Ser Gly Ser Gly Ile Ala Ser Asn
                165                 170                 175

Ile Thr Asn Gly Ser Ile Phe Asp Leu Glu Gly Asn Asn Pro His Pro
                180                 185                 190

Leu Val Asn Ser Asn Thr Leu Glu Phe Val Pro Leu Glu Ala Arg His
                195                 200                 205

Ile Thr Pro Asn Gly Asn Gly Trp Arg His Glu Tyr Lys Val Lys Glu
                210                 215                 220

Ser Ala Arg Ala Ala Met Thr Glu Thr Tyr Glu Val Phe Glu Ala Thr
225                 230                 235                 240

Val Lys Val Glu Met Ser Asp Gly Gly Lys Thr Ile Ile Ser Gln His
                245                 250                 255

His Ala Ser Asp Thr Gly Thr Ile Ser Lys Val Tyr Val Ser Asp Thr
                260                 265                 270

Asp Glu Ser Gly Phe Asp Asp Ser Val Ala Gly Asn Gly Ile Phe Asp
                275                 280                 285

Val Tyr Val Arg Leu Arg Asn Thr Ser Gly Lys Glu Lys His Ala
                290                 295                 300

Leu Gly Thr Ile Arg Ser Gly Gly Ser Phe Asn Leu Lys Val Val Asn
305                 310                 315                 320

Asn Tyr Gly Asp Val Asp Val Thr Ala Leu Gly Thr Thr Phe Gly Ile
                325                 330                 335

Pro Val Glu Asp Asp Ser Glu Ser Tyr Phe Lys Phe Gly Asn Tyr Leu
                340                 345                 350

Gln Ser Gln Asp Pro Tyr Thr Leu Asp Glu Cys Gly Glu Ser Gly Asn
                355                 360                 365

Ser Asp Ser Phe Lys Glu Cys Phe Lys Asp Leu Gly Ile Thr Lys Ala
370                 375                 380

Lys Val Thr Met Thr Asp Val Ser Tyr Thr Arg Arg Thr Asn
385                 390                 395

<210> SEQ ID NO 67
<211> LENGTH: 335
<212> TYPE: PRT
<213> ORGANISM: Microbulbifer degradans 2-40

<400> SEQUENCE: 67

Met Gln Ala Gly Asp Val Val Leu Pro Ala Met Ala Tyr Asp Leu Ser
 1               5                  10                  15

His Trp Lys Ile Thr Val Pro Leu Asp Asp Asn Lys Asp Gly Lys Val
                20                  25                  30
```

```
Asp Glu Val Asp Thr Lys Ala Leu Gln Lys Tyr Met His Ser Asp Tyr
         35                  40                  45

Phe Tyr Val Asn Ser Glu Gly Gly Leu Val Phe Ala Thr Pro Asn Gln
         50                  55                  60

Ala Thr Thr Thr Ser Gly Ser Ser Asn Ser Arg Ser Glu Leu Arg Gln
 65                  70                  75                  80

Met Ile Arg Gly Thr Asn Thr Arg Ile Gly Thr Lys Ser Pro Gly Asn
                 85                  90                  95

Asn Phe Ala Leu Ala Ser His Pro Gln Ala Lys Ala Phe Gly Asp Ile
             100                 105                 110

Gly Gly Asn Leu Lys Ala Thr Leu Ala Val Asn His Val Ala Leu Asn
         115                 120                 125

Ala Lys Tyr Thr Asp Lys Phe Pro Ala Tyr Ser Val Val Gly Gln
130                 135                 140

Ile His Ala Gly Lys Asp Lys Asp Leu Ile Ala Lys Gly Glu Gly Tyr
145                 150                 155                 160

Gly Trp Gly Asn Glu Pro Ile Lys Ile Tyr Tyr Lys Lys Trp Pro Asp
                 165                 170                 175

His Lys Thr Gly Ser Val Phe Trp Thr Tyr Glu Arg Asn Leu Glu Lys
             180                 185                 190

Ala Asn Pro Asp Arg Thr Asp Ile Ala Tyr Pro Val Trp Gly Asn Thr
         195                 200                 205

Trp Asp Asn Ser Glu Asn Pro Gly Asp Lys Gly Ile Ala Leu Asp Glu
     210                 215                 220

Ser Phe Ser Tyr Glu Ile Asn Val Tyr Lys Asp Ile Met His Leu Thr
225                 230                 235                 240

Phe Thr Ala Ala Asn Lys Pro Thr Val Lys Tyr Ser Ile Asn Leu Ala
                 245                 250                 255

Asn Asn Val Asn Ala Tyr Gly Lys Val Asp Glu Lys Asp His Pro Lys
             260                 265                 270

Gly Tyr Leu Gly Asp Trp Leu Tyr Phe Lys Ala Gly Ala Tyr Asp Gln
         275                 280                 285

Cys Ser Val Lys Asp Asp Pro Gly Phe Trp Tyr Pro Ala Cys Ala Gly
     290                 295                 300

Thr Gly Asp Trp Glu Thr Asp Lys Lys Asn Gly Asp Tyr Thr Arg Val
305                 310                 315                 320

Thr Phe Thr Lys Leu Glu Leu Gly Lys Gly Tyr Ser Val Ser Lys
                 325                 330                 335

<210> SEQ ID NO 68
<211> LENGTH: 235
<212> TYPE: PRT
<213> ORGANISM: Vibrio halioticoli

<400> SEQUENCE: 68

Met Ile Lys Lys His Gln Ile Thr Leu Phe Ile Val Ala Thr Val Val
  1               5                  10                  15

Ala Val Ser Ala Asn Ala Ala Ser Val Asp Tyr Arg Gln Glu Tyr Lys
                 20                  25                  30

His Asn Asp Lys Ser Tyr Ala Ser Arg Val Lys Val Gly Ser Ser Val
             35                  40                  45

Gly His His Phe Phe Ser Leu Glu Ala Lys Gln Thr Gly Lys Pro Ile
         50                  55                  60

Ser Asp Trp Gln Ala Ala Asp Asn Glu Phe Val Tyr Gly Tyr Asn Phe
 65                  70                  75                  80
```

```
                -continued

Lys Val Asn Lys Lys Trp Arg Ile Thr Pro Ser Met Pro Ile Thr Phe
                85                  90                  95

Gly Asn Asp Arg Val Thr Tyr Lys Pro Gln Val Arg Val Gln Tyr Lys
                100                 105                 110

Phe Asp Ser Gly Leu Thr Ser Lys Leu Arg Tyr Arg His Glu Phe Arg
                115                 120                 125

Asn Tyr Thr Gly Asp Lys Ser Asp Lys Asp Ser Ile Asp Arg Ser Lys
                130                 135                 140

Ile Thr Gly Asn Leu Asp Tyr Lys Val Gly Ala Leu Gln Leu Gly Phe
145                 150                 155                 160

Glu Ala Asn Tyr Ala Glu Asp Phe Phe His Asp Asn Glu Trp Phe Gly
                165                 170                 175

Gly Lys Ser Ala Lys Arg His Asn Glu Trp Asp Tyr Asn Val Lys Ile
                180                 185                 190

Gly Tyr Lys Glu Thr Asp Trp Asp Trp Arg Pro Tyr Ile Glu Leu Gly
                195                 200                 205

Asn Val Gln Tyr Ser Asn Gly Pro Ser Val Thr Asn Ser Asn Arg Gln
                210                 215                 220

Leu Arg Thr Arg Val Gly Leu Thr Tyr Ser Phe
225                 230                 235

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Gly Glu Pro
  1

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Val Val Val Val Asp
  1               5
```

ALGINASES, SYSTEMS CONTAINING ALGINASES AND METHODS OF CLONING, PURIFYING AND/OR UTILIZING ALGINASES

CROSS-REFERENCE TO RELATED APPLICATIONS

This claims priority to U.S. Provisional Application No. 60/576,000, filed Jun. 1, 2004, the contents of which are incorporated herein, in their entirety, by reference.

This invention was made with government support under Contract Number SA7528051E awarded by the National Oceanic and Atmospheric Administration and Contract Number DEB 0109869 awarded by the National Science Foundation. The government has certain rights in the invention.

BACKGROUND OF THE INVENTION

1. Field of the Invention

The invention is generally directed to alginases. In particular, the present invention is directed to alginases found in *Microbulbifer degradans* and systems containing such alginases and methods of cloning, purifying and/or utilizing such alginases.

2. Background of the Invention

*Saccharophagus degradans* strain 2-40 (herein referred to as "*S. degradans* 2-40" or "2-40") is a representative of an emerging group of marine bacteria that degrade complex polysaccharides (CP). *S. degradans* has been deposited at the American Type Culture Collection and bears accession number ATCC 43961. *S. degradans* 2-40, formerly known and referred to synonomously herein as *Microbulbifer degradans* strain 2-40 ("*M. degradans* 2-40"), is a marine γ-proteobacterium that was isolated from decaying *Sparina alterniflora*, a salt marsh cord grass in the Chesapeake Bay watershed. Consistent with its isolation from decaying plant matter, *S. degradans* strain 2-40 is able to degrade many complex polysaccharides, including cellulose, pectin, xylan, and chitin, which are common components of the cell walls of higher plants. *S. degradans* strain 2-40 is also able to depolymerize algal cell wall components, such as agar, agarose, and laminarin, as well as protein, starch, pullulan, and alginic acid. In addition to degrading this plethora of polymers, *S. degradans* strain 2-40 can utilize each of the polysaccharides as the sole carbon source. Therefore, *S. degradans* strain 2-40 is not only an excellent model of microbial degradation of insoluble complex polysaccharides (ICPs) but can also be used as a paradigm for complete metabolism of these ICPs. ICPs are polymerized saccharides that are used for form and structure in animals and plants. They are insoluble in water and therefore are difficult to break down.

*Microbulbifer degradans* strain 2-40 requires at least 1% sea salts for growth and will tolerate salt concentrations as high as 10%. It is a highly pleomorphic, Gram-negative bacterium that is aerobic, generally rod-shaped, and motile by means of a single polar flagellum. Previous work has determined that 2-40 can degrade at least 10 different carbohydrate polymers (CP), including agar, chitin, alginic acid, carboxymethylcellulose (CMC), β-glucan, laminarin, pectin, pullulan, starch and xylan (Ensor, Stotz et al. 1999). In addition, it has been shown to synthesize a true tyrosinase (Kelley, Coyne et al. 1990). 16S rDNA analysis shows that 2-40 is a member of the gamma-subclass of the phylum *Proteobacteria*, related to *Microbulbifer hydrolyticus* (Gonzalez and Weiner 2000) and to *Teridinibacter* sp., (Distel, Morrill et al. 2002) cellulolytic nitrogen-fixing bacteria that are symbionts of shipworms.

These exo- and extra-cellular structures (ES) include small protuberances, larger bleb-like structures that appear to be released from the cell, fine fimbrae or pili, and a network of fibril-like appendages which may be tubules of some kind. Immunoelectron microscopy has shown that agarases, alginases and/or chitinases are localized in at least some types of 2-40 ES. The surface topology and pattern of immunolocalization of 2-40 enzymes to surface protuberances are very similar to what is seen with cellulolytic members of the genus *Clostridium*.

2-40 is a gram negative, pleomorphic, motile with a means of a single polar flagellum (see FIG. 1). Cells average 0.5 μm in width and 1.5-3.0 μm in length (Andrykovich and Marx 1988). During late logarithmic-stationary phases of growth, a black pigment, identified as true melanin (Stosz 1994), is produced and cells become elongated (Marx 1986).

The G+C content of 2-40 is 45.66%, as determined by the ATCC (Stosz 1994). 2-40 is catalase- and peroxidase-positive (González and Weiner 2000). It is a strict aerobe capable of respiratory, but not fermentative, metabolism, and requires both sea salts and carbohydrates for growth (Marx 1986, Stosz 1994). It does not form spores or accumulate β-hydroxybutyrate. As an estuarine bacterium, 2-40 is capable of reproduction in a wide range of temperatures (5° C. to 40° C.) and can tolerate 2-10% sea salt. 2-40 can also grow in pH range of 4.5-10, with optimum pH of 7.5 (Gonzalez and Weiner 2000).

2-40 is unique in its capability to degrade numerous insoluble complex polysaccharides (ICP) including alginic acid, agar, cellulose, chitin, glucan, pectin, pullulan, starch and xylan (Whitehead 1997). In addition to its ability to degrade these carbohydrates, 2-40 is also capable of producing lipases, proteases, and tyrosinase (Marx 1986, and Stosz 1994).

Previous studies showed that the cell surface morphology of 2-40 changed when the organism was grown on different insoluble complex polysaccharides (Whitehead 1997). When 2-40 was cultivated on either chitin or agarose, scanning and transmission electron microscopy revealed that the presence of cell surface protuberances, hydrolysomes, correlated to the degradation of these two complex polysaccharides. Other changes in the cell topology and morphology were detected during late growth stages. These changes included production of membranous tubules containing agarases and chitinases. These morphological changes may correlate with the ability of 2-40 to survive dynamic changes in the estuarine ecosystem (Chakravorty 1998 and Whitehead 1997).

Preliminary studies suggested that 2-40 be assigned to genus Alteromonas (Andrykovich and Marx 1988). However, a recent search in the MIDI database revealed that *Marinobacterium georgiense* is the closest relative to 2-40 based on fatty acid profile. It also revealed a comparatively low level of similarity with that of *Microbulbifer hydrolyticus* IRE 31, the closest strain to 240 according to its 16S rDNA (Gonzalez and Weiner 2000). Moreover, the GenBank search showed that 2-40 has 93% similarity with *Microbulbifer hydrolyticus*, and 91.2% similarity with a cellulytic nitrogen-fixing bacterium, isolated from the gland of Deshayes in three different species of shipworm (González and Weiner 2000). While the taxonomy is not yet fully settled, based upon the 16S rDNA analysis, strain 2-40 was placed in genus *Microbulbifer* as a new species, *Microbulbifer degradans*. It is a member of the γ-subclass of the phylum *Proteobacteria* (González and Weiner 2000 and Weiner et al., 2000).

Marsh grass *Spartina alterniflora* is found to be the most common species in the salt marshes of the east coast of North America (Ford 1993). In addition to *S. alterniflora*, which is a dominant species at mid level of elevations, *Spartina patens* and *Distichlis spicata* dominate at high elevation while *Zostera marina* and brown algae are common in low marsh elevation (Chakravorty 1998). Salt marsh grass supports a wide range of algal population, including green, brown, blue-green, and red algae, in addition to a diverse bacterial, fungal, protozoan, and invertebrate populations (Stosz 1994). 2-40 was shown to have capabilities to produce different degradative enzyme systems and to utilize a variety of substrates, all of which increase the organism's ability to survive in this environment. It can also naturally recycle several ICPs, thus may be employed in bioremediation (Chakravorty 1998).

In natural environments, numerous amounts and various kinds of ICPs are formed and accumulate leading to the requirement for efficient mechanisms for their degradation. As part of the carbon cycle, they are recycled to their primary elements (Whitehead 1997 and Chakravorty 1998). These ICP, composed of homo- and heteropolysaccharides, account for substantial agriculture, aquaculture and algalculture wastes. With the exception of starch, these compounds compose the cell wall structure in plants and fungi (Whitehead 1997). Because of their binding, branching sugar composition, and complexed formation with other polymers, the degradation of ICPs is not a trivial process. However, these ICPs can be hydrolyzed by microorganisms to produce monosaccharide feedstock. For example, in the marine environment, around $10^{11}$ tons of chitin wastes are produced annually, yet, apart from living or recently living biota, only traces of it are found in marine sediments. This is explained by the presence of microorganisms that degrade chitin and recycle the carbon and nitrogen (Salyers et al., 1996). For economical and environmental considerations, biomeredation, using prokaryotes is an efficient way to recycle ICP. Bacteria and fungi degrade ICP to provide saccharide feedstock (Salyers et al., 1996).

In addition to feedstock, degradation of alginic acid yields 4-deoxy-L-erythro-hex-4-ene-pyranosylurinate containing oligosaccharides, which are thought to be active biological molecules. These oligosaccharides can elicit plant germination, shoot elongation and root growth promoting activities (Natsume et al., 1994). They also stimulate the growth of *Bifidobacteria*, a useful food industry organism (Akiyama et al., 1992).

Alginic acid is a high molecular weight linear polysaccharide polymer produced mainly by seaweed, as well as many species of marine algae and certain bacteria (Linhardt et al., 1986 and Chakravorty 1998). It is comprised of (1-4)-linked β-D-mannuronic acid (M) and α-L-guluronic acid (G), (See FIG. 2), (Gacesa 1992). The salts of alginic acid are commonly referred to as alginate, which include: ammonium alginate, calcium alginate, potassium alginate, and sodium alginate (Chakravorty 1998). The primary structure of alginic acid is highly variable based on the monomer ratios and distribution of monomers into homopolymeric blocks (GG or MM) or heteropolymeric blocks (MG) (Doubet and Quatrano 1982).

The composition of alginate greatly depends on the producing organism and its physiology. Algal alginates are unbranched (1-4) linked glycuronans containing residues of β-D-mannosyluronic acid and the C5 epimer α-L-gulosyluronic acid, whereas bacteria normally produce their alginate being invariably O-acetylated, where O-acetyl groups are found on the 2 and/or 3 positions of D-mannuronate residues (Gacesa 1988). This acetylation often affects water-binding properties and ion-binding selectivity of the polymer (Wong et al., 2000). The level of alginate's susceptibility to degradation is normally influenced by both the block structure and degree of O-acetylation within the macromolecule (Wong et al., 2000).

Algal and bacterial alginates also differ in their molecular weight. Alginate produced by *A. vinelandii* has a molecular weight of $2 \times 10^6$ Da, whereas algal alginates have a range of 48000 to 186000 Da; in general, bacterial alginates usually have higher molecular mass than algal polymer (Peña et al., 2002).

Alginate, a viscous polysaccharide, is found in the cell wall of the brown seaweeds (Phaeophyceae) and produced by several species of bacteria. Like its structure, the function of alginate varies depending on its source. In brown algae, alginate comprises about 60% of the cell wall mass of *Fucus distichus* (Doubet and Quatrano 1982). Approximately 22,000 tons/annum of alginate are extracted from numerous brown algal genera to be used in a variety of applications by the food, pharmaceutical and other industries. Most of the commercial alginate is extracted mainly from genera *Macrocystis, Laminaria*, and *Ascophyllum* (Wong et al., 2000). The brown algae alginate is believed to function as an intercellular skeletal matrix (Ertesvåg et al., 1995).

In addition to the brown algae, alginate is also produced by two bacterial families, Azotobacteriaceae and Pseudomodaceae (Wong et al., 2000). *Azotobacter vinelandii, A. chroococcum, Pseudomonas aeruginosa* and other Pseudomonads synthesize alginate as an extracellular polysaccharide (Gacesa 1992), and as a major component of many biofilms (Weiner et al., 1998). It has its ability to form viscous solutions at relatively low concentrations and to form gels with $Ca^{+2}$ (Davidson et al., 1976).

Alginate is enzymatically degraded by a group of enzymes that catalyze the β-elimination of the 4-O— linked glycosidic bond forming unsaturated uronic acid-containing oligosaccharides (Preiss and Ashwell 1962a, Kiss 1974, Caswell et al., 1986, Gacesa 1992, and Wong et al., 2000).

Alginases, typically lyases, are members of the class polysaccharide lyases, or eliminases, (EC 4.2.2.-). They normally act in a wide range of naturally acidic polysaccharides. Enzymes of this class have low or intermediate molecular weight (20-110 kDa) and are characteristically, usually, monomeric, having the same molecular weight when determined under reducing or non-reducing conditions. They act through a β-elimination mechanism (Haugen et al., 1990), rather than hydrolysis, to cleave certain glycosidic linkage in the acidic polysaccharides. This reaction results in unsaturated oligosaccharide products (uronic acid residues) at the new non-reducing end (Haugen et al., 1990, Linhardt et al., 1986). Polysaccharides cleaved by elimination generally contain a carboxylate group on the carbon adjacent to the glycosidic linkage (Haugen et al., 1990, Gacesa 1992). However, one group reported that alginases are hydrolyases (Schaumann and Weide, 1990), where the enzyme was isolated from marine fungi, *Dendryphiella salina* and *Asteromyces cruciatus*. The mechanism of action of this enzyme, though, is not fully understood (Gacesa 1992).

Alginate lyase (EC 4.2.2.3) catalyzes the reaction of alginate degradation by elimination mechanism (Romeo and Preston 1986b, Linhardt et al, 1986, Gacesa 1992, Wong et al., 2000). This reaction targets the glycosidic 1→4 O-linkage between alginate monomers. The results are: a) formation of double bond between the C4 and C5 of the six-carbon ring, from which the 4-O-glycosidic bond is eliminated; b) depolymerization of alginate; and finally c) a product containing 4-deoxy-L-erythro-hex-4-enopyranosyluronic acid as the non-reducing terminal (Gacesa 1992 and Wong et al., 2000).

Alginases are normally utilized to degrade alginate as a carbon source; however, interestingly alginate-producing organisms are not usually capable of growing on alginate as the sole source of carbon. On the other hand, organisms capable of utilizing alginic acid as a sole source of carbon produce both exo- and endolytic alginases, unless they exhibit commensalisms with another organisms to degrade the complex polysaccharide to monomeric subunits (Gacesa 1992).

Alginate lyases have been isolated from different organisms including marine algae, marine bacteria, marine mollusk, fungi, and a wide variety of microorganisms (Hansen et al., 1984, Gacesa 1992, Wong et al., 2000).

TABLE 1.1

Alginase producing organisms.

| Organism | Source | Enzyme | Reference |
|---|---|---|---|
| 2-40 (Microbulbifur degradans) | salt marsh grass bacterial isolates | alginic acid lyase | Marx 1986, Stosz 1994, Whitehead 1997, this study |
| *Agrobacterium tumefaciens* str. C58 | Genome sequence[1] | alginic acid lyase | Goodne et al., 2001 |
| *Alginovibrio aqualiticus* | marine bacterium | alginic acid lyase | Stevens & Levin 1977 |
| *Alteromonas* sr. strain KLIA | marine bacterium | alginic acid lyase | Sawabe et al., 1997 |
| *Alteromonas* spp. | soil bacterium | alginic acid lyase | Vilter 1986 |
| *Aplysia* spp. | Mollusks | alginic acid lyase | Kloareg et al., 1989 |
| *Asteromyces cruciatus* | marine bacterium | alginic acid hydrolyase | Schaumann & Weide 1990 |
| *Azotobacter chroococcum* | soil bacterium | alginic acid lyase | Kennedy et al., 1992 |
| *Azotobacter vinelandii* | soil bacterium | alginic acid lyase | Kennedy et al., 1992 |
| *Bacillus circulans* | soil bacterium | alginic acid lyase | Hansen et al., 1984 |
| *Bacillus halodurans* | Genome sequence[1] | alginic acid lyase | Takami et al., 1999 |
| Bacteriophage that infects *A. vinelandii* | Phage | alginic acid lyase | Davidson et al., 1977 |
| *Beneckea pelagia* | marine bacterium | alginic acid lyase | Pitt & Raisbeck 1978 |
| *Chlorella* virus | virus | alginic acid lyase | Suda et al., 1999 |
| *Choromylitis meridonalis* | Mollusk | alginic acid lyase | Seiderer et al., 1982 |
| *Clostridium grantii* | soil bacterium | alginic acid lyase | Mountfort et al., 1994 |
| *Corynebacterium* spp. | soil/marine bacterium | alginic acid lyase | Matsubara et al., 1998 |
| *Dollabella auricular* | Mollusk | alginic acid lyase | Nishizawa et al., 1968 |
| *Enterobacter cloacae* | soil/marine bacterium | alginic acid lyase | Shimokawa et al., 1997 |
| Fucus zygotes | brown algae | alginic acid lyase | Vreeland & Laetsch 1990 |
| *Haliotis corrugate* | Mollusk | alginic acid lyase | Linhardt et al., 1986 |
| *Haliotis rufescens* | Mollusk | alginic acid lyase | Linhardt et al., 1986 |
| *Haliotis tuberculata* | Mollusk | alginic acid lyase | Kloareg & Quatrano 1987 |
| *Katherina tunicate* | Mollusk | alginic acid lyase | Kloareg & Quattrano 1987 |
| *Klebsiella pneumoniae* | soil/marine bacterium | alginic acid lyase | Boyd & Turvey 1977, Lange et al., 1989 |
| *Laminaria digitata* | brown algae | alginic acid lyase | Madgwick et al., 1978 |
| *Littorina* spp. | brown algae | alginic acid lyase | Elaykova & Favorov 1974 |
| *Mesorhizobium loti* | Genome sequence[1] | alginic acid lyase | Kaneko et al., 2000 |
| *Pelvetia canalitulata* | brown algae | alginic acid lyase | Madgwick et al., 1978 |
| *Perna perna* | Mollusk | alginic acid lyase | Seiderer et al., 1982 |
| *Photobacterium* spp. | marine bacterium | alginic acid lyase | Romeo & Preston 1986a |
| *Pseudoalteromonas elyakovii* | | alginic acid lyase | Sawabe et al., 2001 |
| *Pseudomonas alginovora* | marine bacterium | alginic acid lyase | Chavagnat et al., 1996 |
| *Pseudomonas aeruginosa* | marine bacterium | alginic acid lyase | Linker et al., 1984 |
| *Pseudomonas maltophilia* | marine bacterium | alginic acid lyase | Sutherland & Keen 1981 |
| *Pseudomonas putida* | marine bacterium | alginic acid lyase | Conti et al., 1994 |
| *Pseudomonas syringae* pv. *phaseolicola* | Plant pathogen | alginic acid lyase | Ott et al., 2001 |
| *Pseudomonas syringae* pv. *syringae* | Plant pathogen | alginic acid lyase | Preston et a., 2000 |
| *Salmonella enterica* subsp. *enterica serovar typhi* | Genome sequence[1] | alginic acid lyase | Parkhill et al., 2001 |
| *Sphingomonas* species Al | | alginic acid lyase | Yoon et al., 2000 |
| *Spinula solidissima* | Mollusk | alginic acid lyase | Jacober et al., 1980 |
| *Staphylococcus aureus* subsp. *aureus* MW2 | Genome sequence[1] | alginic acid lyase | Baba, et al., 2002 |
| *Turbo corrutus* | Mollusk | alginic acid lyase | Muramatsu et al., 1977 |
| *Undaria pinnatifida* | brown algae | alginic acid lyase | Watanabe & Nishizawa 1982 |
| *Vibrio alginolyticus* | marine bacterium | alginic acid lyase | Kitamikado et al., 1992 |
| *Vibrio harveyi* | marine bacterium | alginic acid lyase | Kitamikado et al., 1992 |
| *Xanthomonas axonopodis* pv. *citri* str. 306 | Genome sequence[1] | alginic acid lyase | Da Silva et al., 2002 |
| *Yersinia pestis* KIM | Genome sequence[1] | alginic acid lyase | Deng, et al., 2002 |

[1]Genome sequence obtained from National Center for Biotechnology Information (NCBI) data base, (www.ncbi.nlm.nih.gov). Table partially adapted from Chakravorty 1998.

Table 1.2 illustrates alginase properties from some marine and other gram-negative bacteria. The table shows that optimum pH for most alginases ranges around neutral; specifically it falls in between 6-8.5, while optimum temperature for alginases from different sources has a broad range.

Alginate monomers are linked by 4-O-glycosidic bonds. These bonds can be chemically degraded either by lyase activity (Haug et al., 1967, Doubet and Quatrano 1982) or reportedly by alkali-catalyzed β-elimination (Kiss 1974). The alkali may actually disrupt all polysaccharide linkages being non specific for alginate linkages.

Alginase, and well as other degradative enzymes produced by 2-40 could be useful bioremediation tools. As human population increases and more food is required, agricultural, aquacultural, and algalcultural wastes also increase and can become a serious problem. The wastes are mostly recalcitrant complex carbohydrates, namely cellulose, chitin and agar. The complex carbohydrates from natural and human practices are composed of monosaccharide, many of which can provide valuable feedstock when hydrolyzed. The degradative protuberances of 2-40 could be used as bioremediation tools when used as concentrated, organized, protective enzyme packets.

TABLE 1.2

Alginate lyases from marine and gram-negative bacteria: localization and properties.

| Source | Localization[a] | Endo/Exolytic | Molecular weight (kDa) | pI | Opt pH | Opt T | Ref. |
|---|---|---|---|---|---|---|---|
| Marine bacteria | | | | | | | |
| *Alginovibrio aquatilis* | Extracellular | Endolytic | 110 | — | 8 | — | Stevens and Levin 1977. |
| *Alteromonas* sp. Strain H-4 | Extracellular | Endolytic | 32 | 4.7 | 7.5 | 30 | Sawabe et al., 1992, Sawabe et al., 1997. |
| *Beneckae pelagia* | Intracellular | — | — | — | 8 | 25 | Sutherland and Keen 1981 |
|  | Extracellular | — | | | | | Pitt and Raisbeck 1978 |
| *Halomonas marina* | Intracellular | — | 39 | 7.78 | — | — | Kraiwattanapon et al., 1999 |
| *Photobacterium* sp (ATCC 433367) | Periplasm (R) | Endolytic | 30 | 6 | — | — | Malissard et al., 1995. Malissard et al., 1993. |
| *Pseudomonas* sp. (marine) | Intracellular/Extracellular | Endolytic | 94 / 32 | — | 7.5 / 7.5 | — | Muramatsu and Sogi, 1990 |
| *Pseudomonas alginovora* (strain X017) | Extracellular | Endolytic | 32 | 5.5 | 7.5 | — | Boyen et al., 1990 |
| *Vibrio* sp. (marine bacterium) | Extracellular | — | — | — | 8.5 | 45 | Chavagnat F, et al. 1996. Takeshita and Muramatsu 1995 Takeshita et al., 1993 |
| *Vibrio alginolyticus* ATCC 17749 | Extracellular | Endolytic | 47 | 4.6 | 8.2 | — | Kitamikado et al., 1992, Kitamikado et al., 1990. |
| *Vibrio halioticoli* | NA | NA | 252aa | NA | NA | NA | Wong et al., 2000. |
| *Vibrio harveyi* AL-128 | Extracellular | Endolytic | 57 | 4.3 | 7.8 | — | Kitamikado 1992, Kitamikado et al., 1990, Tseng et al., 1992 |
| Gram-negative bacterial | | | | | | | |
| *A. chroococcum* | Periplasm | Endolytic | 43 | — | — | 30 | Peciña and Paneque 1994, Peciña et al., 1999 |
| *A. vinelandii* | Intracellular | — | ~50 | — | 7.5 | — | Davidson et al., 1977 |
| *Enterobacter cloacae* M-1 | Extracellular | Endolytic | 32-38 | 8.9 | 7.8 | 30 | Nibu et al., 1995 | pI: isoelectric point, the pH at which a molecule carriers no net electric charge.
Opt pH: optimum pH,
Opt T: Optimum temperature.

TABLE 1.2

Alginate lyases from marine and gram-negative bacteria: localization and properties (cont'd).

| Source | Localization[a] | Endo/Exolytic | Molecular weight (kDa) | pI | Opt pH | Opt T | Ref. |
|---|---|---|---|---|---|---|---|
| K. aerogenes type 25 | Intracellular | Endolytic | 28-31.6 | — | 7 | 37 | Lange et al., 1989. |
| | Extracellular | Endolytic | — | — | 7 | — | Boyd and Turvey 1977, Haugen et al., 1990 |
| K. pneumoniae subsp. aerogenes | Extra/intracellular (R) | — | 28 | 8.9 | — | — | Caswell et al., 1989 |
| P. syringae pv. syringae | Periplasmic | Endolytic | 40 | 8.2 | 7 | 42 | Wong et al., 2000 |
| Pseudomonas sp. OS-ALG-9 | Intracellular | — | 90, 72, 60, 54 | — | — | — | Kraiwattanapong et al., 1997 |
| Sphingomonas sp. | Cytoplasm | Endolytic | 60 | 9.03 | 7.5-8.5 | 70 | Yonemoto et al., 1991, Yonemoto et al., 1993, Yonemoto et al., 1992. |
| Streptomyces coelicolor | NA | NA | 259aa | NA | NA | NA | Redenbach et al., 1996 |

—: Not determined,
NA: not available,
[a]Localization in native culture, except R,
R = recombinant expression in E. coli.
N/A: not available,
Opt: optimum,
T: temperature ° C.,
aa: amino acid residues.
Adapted from Wong et al., 2000.

Alginase has potential medical importance. The alginate glycocalyx abundantly produced by mucoid strains of Pseudomonas aeruginosa is considered a major virulence factor in endocarditis (Bayer et. al., 1992). It also contributes to the morbidity and mortality associated with pseudomonal infections in patients with cystic fibrosis (Dinwiddie 1990, Gacesa, P. 1988) where alginate promotes attachment to the host cell and inhibits the phagocytosis (Bayer et al., 1992, Gacesa 1992, Monday and Schiller 1996).

Pseudomonas aeruginosa is one of the most important opportunistic human pathogens, causing septicemia and severe or even lethal infection to the respiratory tract, urinary tract, intestines and many other sites (Cross et al., 1983). This organism exhibits inherent resistance to a wide range of antibiotics, which makes infection with this pathogen common and hard to treat (Monday and Schiller 1996).

In a recent study, the effect of alginase on the polymorphonuclear leukocyte (PMN)-directed and antibiotic-mediated phagocytosis and killing of mucoid P. aeruginosa was investigated both in vitro and in vivo. The study showed that pretreating of mucoid P. aeruginosa strain 144MR with alginase significantly enhanced PMN phagocytosis, rendering the bacteria more susceptible to PMN-mediated killing than 144MR cells not treated with alginase (P<0.05), approximating the levels of that of non-mucoid strain, 144NM. More importantly, the study also showed that treating the mucoid strain 144MR with alginase caused a significant removal of bacterial cell surface alginate as determined by immunofluroscence staining with a murine monoclonal anti-alginate antibody (Bayer et. al., 1992).

SUMMARY OF THE INVENTION

One aspect of the present invention is directed to systems of alginases and related proteins.

A further aspect of the invention is directed to a method for the degradation of substances comprising alginate. The method involves contacting the alginate containing substances with one or more compounds obtained from Saccharophagus degradans strain 2-40.

Another aspect of the present invention is directed to groups of enzymes that catalyze reactions involving alginate.

Another aspect of the present invention is directed to polynucleotides that encode alginase polypeptides.

A further aspect of the invention is directed to chimeric genes and vectors comprising genes that encode alginase polypeptides.

A further aspect of the invention is directed to a method for the identification of a nucleotide sequence encoding an alginase polypeptide from S. degradans. An S. degradans genomic library can be constructed in E. coli and screened for the desired activity. Transformed E. coli cells with specific activity are created and isolated.

Further aspects of the invention are directed to utilization of the alginase substances in food, beer, wine, animal feeds, textile production and laundering, pulp and paper industry, agricultural and other industries.

Other aspects, features, and advantages of the invention will become apparent from the following detailed description, which when taken in conjunction with the accompanying figures, which are part of this disclosure, and which illustrate by way of example the principles of this invention.

BRIEF DESCRIPTION OF THE FIGURES

FIGS. 9a and 9b show an alignment of alginase proteins (9A: SEQ ID NOS 1-7; 9B: SEQ ID NOS 8-10);

FIG. 17 shows separation of S. degradans 2-40 alginases and a zymogram gel;

DETAILED DESCRIPTION

Figure 1:
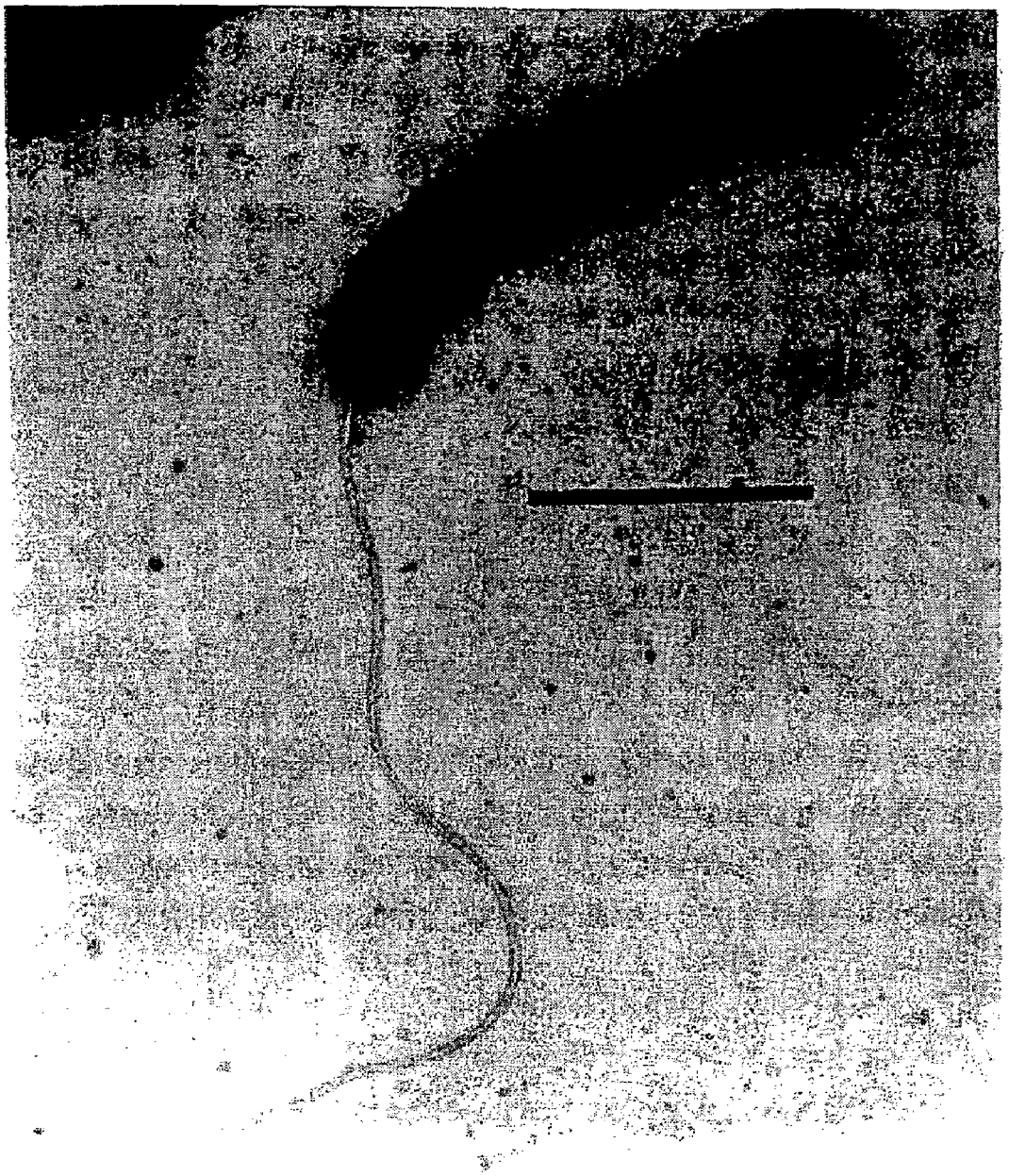
FIG. 1 shows a transmission electron micrograph of 2-40 strain.
Figure 2:
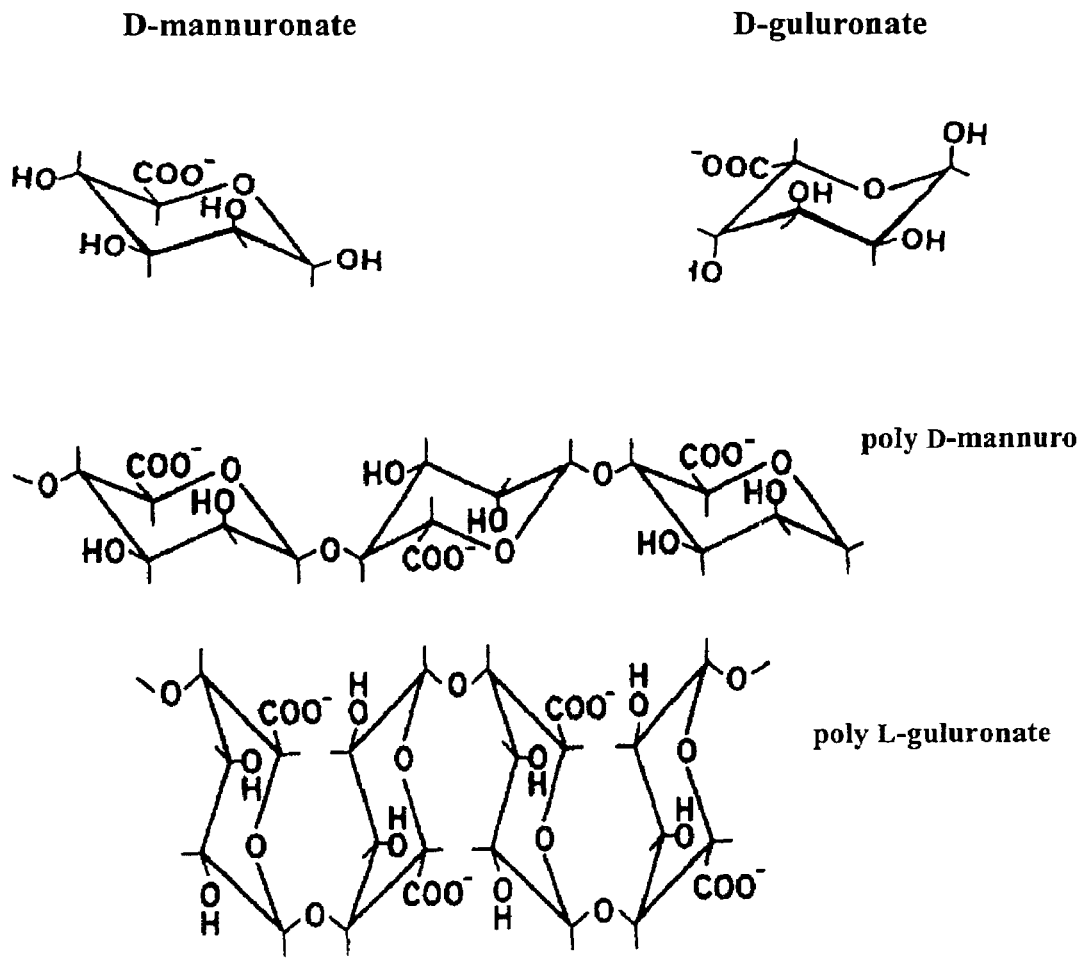
FIG. 2 illustrates the structure of alginic acid.

Analysis of the genome sequence of S. degradans 2-40 reveals an abundance of genes coding for enzymes that are predicted to degrade plant-derived carbohydrates. To date, 2-40 is the only sequenced marine bacterium with apparently complete cellulase and xylanase systems, as well as a number of other systems containing plant-wall active carbohydrases.

In addition to cellulase, mannase, agarase, pectate lyases, arabinosidase, β-galacosidase, chitinase, and endogluconase, eleven alginate lyases were identified. Alginase genes were determined using [tblastn][1], in which protein query sequences of alginases of other sources were compared against 2-40 nucleotide genomic sequence, which has been translated in all six reading frames. Protein sequences of alginases from other microorganisms were obtained from the National Center for Biotechnology Information (NCBI) database.[2]

[1] tblastn compares the protein "Sequence 1" against the nucleotide "Sequence 2" which has been translated in all six readings frames.
[2] Established in 1988 as a national resource for molecular biology information, NCBI creates public databases, conducts research in computational biology, develops software tools for analyzing genome data, and disseminates biomedical information.

Gene models were figured using three gene modeling programs on the all contigs. These programs were: (1) Generation (ORNL)[3] uses predominantly 6-mer statistics to recognize coding regions; it uses a proximity rule-based start call with ATG and GTG as potential starts. (2) Glimmer uses interpolated Markov models (IMMs) to identify the coding regions; it uses ATG, GTG, and TTG as potential starts. (3) Critica (v1.05) uses blastn to produce alignments from the entire dataset and derives dicodon statistics to recognize coding sequences. It uses ATG, GTG, and TTG as potential starts. The Generation and Glimmer training set selected consisted of non-overlapping open reading frames (ORFs) greater than 900 bp in length, Doe Joint Genome Institute.]

[3] Oak Ridge National Laboratory: conducts genetics research and system development in genomic sequencing.

A number of bacteria and fungi synthesize alginases. However, 2-40 is prodigiously degrading alginic acid, and therefore deemed a promising vehicle for producing alginate degrading enzymes. Additionally, since 2-40 also synthesizes at least 10 additional carbohydrase systems, alginase production could serve a paradigm for the efficient production of other degradative enzyme systems.

Improving and increasing the efficiency of microbial digestion, i.e. bioremediation, of alginate, for the present study, and cellulose, chitin, and other biomass of complex polysaccharides, in general, could not only result in reducing the accumulation of wastes, but could also help in production of alternative feedstock, fuels and/or chemicals. For this reason, 2-40 may be exploited for bioremediation of multiple complex polysaccharides, in general, and of alginate in specific that are environmentally and medically important.

So far, few alginases are commercially available. Alginases that can be employed clinically, in turning kelp harvest waste into feedstock, and in bioremediating indigenous biofilms are still required (Weiner et al., 1998). Purification of more effective and readily available alginase would be of great significance in both of these applications.

Alginases from marine bacterium, 2-40, can be produced, concentrated and purified in large quantities to potentially bioremediate alginic acid-containing biofilm.

The genome sequence of 2-40 was recently obtained in conjunction with the Department of Energy's Joint Genome Initiative (JGI). The finished draft sequence dated Jan. 19, 2005 comprises 5.1 Mbp contained in a single contiguous sequence. Automated annotation of open reading frames (ORFs) was performed by the computational genomics division of the Oak Ridge National Laboratory (ORNL), and the annotated sequence is available on the World Wide Web Experimental Approach: Previous studies showed that 2-40 degradative systems were induced by the corresponding homologous carbon source (Stosz 1994 and Whitehead 1997). 2-40 alginase was repressed by glucose and maximally induced by alginic acid and xylose (Whitehead 1997).

In order to maximize the yield of alginases, the composition of the growth medium was modified from the minimal medium used in the previous work on 2-40 (Chakravorty 1998). Unless otherwise noted, in the following experiments all concentrations are weight/volume. For the following experiments, 2-40 inocula were always exponentially grown at 25° C. in minimal medium (Table 2.1), supplemented with 0.2% glucose, pH 7.6 to a concentration of $10^4$ cells/ml.

The initial experiments were batch fermentations carried out in 250 ml Erlenmeyer flasks, agitated at 200 rpm with rotary shaker, and incubated at 25° C. During the course of growth 2-40, cell number was determined by Total Viable Count (TVC). Alginase activity was assayed in the spent media (supernatant) fractions by DNSA (3,5-Dinitrosalicylic acid) standard procedures, described later. The chemicals and buffers, with their cost, are listed in Table 2.2.

Growth conditions were optimized to increase the enzyme yield. 2-40 was grown in minimal media containing a final concentration (wt/v) of 0.2% of one of 7 different carbon sources, alginate, fructose, glucose, sorbitol, xylose (Sigma), galactose (Fisher), and lactose (Difco), Table 2.1. Cultures were incubated at 25° C., in 250 ml baffled flasks filled with 100 ml of medium, with agitation at 200 rpm on a rotary shaker for 32 hr. This generally corresponded to the start of the decline phase. Every four hours, a sample was withdrawn to assess growth and alginase activity (Procedure details described later).

TABLE 2.1

Composition of Minimal Growth Media

| Name | Composition | Concentration | Source | Cost (USD) |
|---|---|---|---|---|
| Minimal medium | Instant Ocean (sea salts) | 2.3% | Aquarium Systems, France | $2.5/kg |
| | Yeast Extract (YE) | 0.1% | Difco, US | $185/kg |
| | Polysaccharide | 0.2% | (see text) | See table 3.1a, p. 52 |
| | 1M Tris-HCL, pH 7.6[a] | 50 mM | Sigma, USA | $82/kg |
| | NH$_4$Cl | 0.05% | Fisher Scientific, USA | $42/kg |
| Plate medium | Minimal medium + 1.5% agar[b] | | | $0.75/Liter |

[a]Tris-HCl and NH$_4$Cl were separately filter-sterilized then added after autoclaving and sufficient cooling since Tris-HCl acts a nitrogen-chelating factor at high temperature, making nitrogen unavailable for the organism growth.
[b]Plate media did not require the addition of polysaccharide, since 2-40 is capable of utilizing agar as the sole carbon source
Cost: all are costs are calculated in US dollars.

TABLE 2.2

Chemicals, buffers, and reagents[a]

| Name of chemical, buffer, or reagent | Description | Source | Cost (USD) |
|---|---|---|---|
| Alginic acid | Sodium Salt, from *Macrocystis pyrifera* (Kelp) | Sigma | $126/kg |
| Casein hydrolysate | Enzymatic digest of casein | Gibco laboratories | $115/kg |
| DNSA | 3,5-Dinitrosalicylic acid | Sigma | $212/kg |
| DNSA reagent | 0.63% DNSA, 2.14% NaOH, 0.5% phenol | Prepared in the lab | ND |
| Native-PAGE Tank buffer | 10x Tris/Glycine Buffer, pH 8.3 | BIO-RAD | ND |
| Native-PAGE sample loading buffer | 0.125 M Tris, pH 6.8, 20% glycerol, 0.1% brome phenol blue | Prepared in the lab | ND |
| Peptone | Bacto-Peptone | Difco | $37/kg |
| PIPES buffer | 20 mM, pH 6.8 (adjusted with NaOH) | Sigma | ND |

TABLE 2.2-continued

Chemicals, buffers, and reagents[a]

| Name of chemical, buffer, or reagent | Description | Source | Cost (USD) |
|---|---|---|---|
| SDS-PAGE Tank buffer | 0.1% SDS added to native buffer | BIO-RAD | ND |
| SDS-PAGE sample loading buffer | native-PAGE loading buffer + 4% SDS | Prepared in the lab | ND |

[a]listed alphabetically
Cost: all costs are calculated in US dollars.
ND: determined.

Results of the initial experiment confirmed that alginic acid induced the highest 2-40 alginase productivity (see Results section for detailed description), hence, it was expected that when the inducer's concentration, i.e. alginic acid, increases, the yield of alginase, in turn, would also increase. This was shown by using minimal growth medium supplemented with alginic acid (Sodium salt from *Macrocystis pyrifera* [Kelp] Sigma) at various concentrations (wt/v), ranging from 0.1 to 0.6% for 48 hrs n order, to obtain the highest enzyme yield. All cultures were incubated at 25° C., pH 7.6. Samples were withdrawn every 4 hrs to monitor biomass growth and measure the alginase activity.

Previous work has shown that yeast extract was stimulatory for growth and/or alginase synthesis. To determine the requirements of 2-40 for vitamins and/or amino acids for alginase synthesis, minimal medium, with (wt/v) 0.5% alginate and 2.3% IO,was supplemented with either yeast extract (YE), casein hydrolysate (C), as a rich source of amino acids, or peptone (P) at a range of concentrations between 0.0 and 2.0%. These media were inoculated with 2-40 which was cultures as described above.

Marine bacterium 2-40 requires sea salt. Thus, the effect of the sea salt (Instant Ocean) concentration on growth and alginase production of 2-40 was investigated by the following procedure: 0.5% alginate/0.2% YE (wt/v) minimal medium was supplemented with different concentrations of Instant Ocean (IO): 1, 2.3, 3.5, 5, and 7% (wt/v) inoculated with $10^4$ cells/ml 2-40 inoculum and at 25° C., agitated by rotary shaker at 200 rpm and grown for 48 hrs. Samples were withdrawn every 4 hrs to monitor growth and alginase activity.

When present in growth media, glucose supported a high yield of biomass, at the same time it repressed alginase activity. To increase biomass, glucose, at different concentrations (wt/v) ranging from 0.0 to 0.2%, was included with alginate minimal medium in concentration (wt/v) from 0.5 to 0.3%, to make the final concentration (wt/v) of carbon 0.5%. The purpose of this strategy was to build biomass as 2-40 used glucose and then turn on enzyme activity as the glucose was consumed and 2-40 switch to alginate. During the incubation time period, growth was determined, and both alginase activity and glucose consumption were measured.

In preliminary experiments, it was found that a medium composed of 0.05% glucose, 0.45% alginate, 3.5% sea salts, and 0.2% Yeast extract (wt/v), (pH 7.6) enhanced alginase productions compared with similar semi-defined medium without glucose. To confirm these results, 2-40 was grown in a 250 ml Erlenmeyer flask containing 100 ml of the alginase production medium (APM), described above, for 48 hrs at 25° C. with 200 rpm shaking speed. Throughout the incubation time, growth was determined using OD change and alginase activity was assayed using the DNSA procedure.

2-40 was grown in a 14-L stirred fermentor (Microferm Fermentor, New Brunswick Scientific, N.J.) filled with 8L of the APM, that was used in the flask experiment. The conditions used were 25° C., agitation at 400 rpm, aeration at 6000 cc/min, no pH control and a 2% 2-40 inoculum. Under these conditions, the organism was grown for 52 hrs. During the incubation period, samples were withdrawn to monitor growth calorimetrically and to detect alginase activity by the DNSA method.

To prevent excessive foam build-up, oil-based antifoam was added to the fermentor medium prior autoclaving. In fermentation, the fermentor reactor can be divided into two zones, the first is liquid zone where fermentation processes happen and diffused air occurs as bubbles and as an oxygen source. The second zone is the foam phases which is relatively inert, has a high volume portion of air and contain a large amount of long-living lamellae, the thin film separating two bubbles. Formation of foam takes two stages; (1) drainage, which is water flow from the foam phase, driven by gravity and curvature, and (2) bubble rupture which occurs when the lamellae, separating two bubbles, rupture. The antifoam mechanism works by enhancing the rate of lamellae rupture. First, emulsion droplets collide with air bubbles resulting in the deposition of the antifoam particles onto the air bubble surfaces, followed by the deform of emulsion droplets to produce lenses on the water/air interface (Pelton 2002).

Data of alginase activity of the above fermentation experiments were statistically analyzed by a linear model (Glantz 2002) using the SAS system program for Windows, version 8, 1999.

Total Viable and Biomass Count. At each time point, samples were taken and the total viable count and optical densities (600 nm) were determined in triplicate. For total viable counts, minimal media agar plates were used. In this case agar was the sole source of carbon. The Ultroscopec 2000 (Pharmacia Biotech) was used for all photometric measurements (Optical density).

Determination of alginase activity by DNSA reducing sugar assay. This method was developed by Sumner and Sisler (Sumner and Sisler. 1944). At each time point, one ml culture sample was centrifuged at 10,000×g/10 min at 4° C. (using Biofuge A centrifuge, American Scientific Products) and the supernatant was stored at −20° C. until assayed. In this procedure, 0.3 ml of the supernatant fraction or enzyme preparation was incubated with 0.7 ml of substrate (0.5% sodium alginate in phosphate buffer, pH 7.0) for 30 min at 25° C. After incubation, 1 ml of DNSA (Dinitrosalicyclic acid) reagent (2.14% NaOH, 0.63% DNSA, 0.5% phenol) was added to the reaction mixture and samples were boiled for 5 min., cooled under tap water and measured for absorbency at 575 nm. Buffer was used as blank. Negative control contained 0.3 ml sterile medium and 0.7 ml buffer. The amount of reduced sugar produced by the reaction was determined by comparing each OD measurement to a linear regression (100 to 500 µg/ml) of galactose concentrations. For each new preparation of DNSA reagent, a galactose standard curve was plotted. One unit of alginase enzyme was defined as the amount of enzyme that produces 1.0 µg of reducing sugar (measured as D-galactose) from alginic acid per 30 min at pH 7.0 and 25° C.

Proteins concentration (BCA Assay). The protein content of each sample was determined according to PIERCE BCA protein Assay (Pierce Rockford, Ill.) as outlined by the manufacturer. The BCA assay is a sensitive, stable and highly specific reagent. In this reaction, protein reacts with $Cu^{2+}$ in an alkaline medium, producing $Cu^{1+}$. A detectable purple color product, formed by the reaction of two molecules of BCA with one cuprous ion ($Cu^{1+}$), is measured at 540 nm.

Procedurally, 10 µl of the enzyme preparation (supernatant fraction) was incubated with 200 µl of working reagent (composed of 1:50 dilution of reagent A:B) for 30 min at 37° C. in 96-well ELISA plate. The color was then measured at 540 nm. For calculating the protein concentration, a standard curve was constructed using a serial dilution of 20 to 200 µg/ml of Bovine serum albumin (BSA) with each newly prepared batch of BCA reagent.

In order to obtain the maximum yield of alginase, 8 L of optimized growth medium, defined by the results of the previous experiments, were inoculated with 24 hr 2-40 culture. Culture was incubated for 32 hr, where alginase production reaches its peak. At the end of the incubation period (32 hr), alginase was separated from cells by centrifuging the culture at 10000×g for 20 min/4° C. Cells were harvested and the cell-free supernatant, containing alginase, were concentrated using the procedure described in the next section, for the purpose of purifying the enzyme.

Concentration of cell-free extract. After harvesting cells from the fermentor, the cell-free supernatant, containing alginase, was first concentrated at 4° C. by running it through Pellicon XL concentration device (Millipore) supplied with 10 kDa MW cut-off PGCLC10 membranes (Millipore, Piscatway, N.J.), then immediately exchanged with 20 mM PIPES buffer, pH 6.8. It is important to note that only de-ionized water (DI $H_2O$) was utilized during the process of concentration.

Ammonium sulfate precipitation. Previous experiments on precipitating alginase with ammonium sulfate determined that maximum alginase activity was detected at 70% fraction (Chakravorty 1998). Therefore, alginase preparation was precipitated with 70% saturated ammonium sulfate at 4° C. with constant stirring. The solution was allowed to equilibrate for 1 hr at 4° C. before centrifugation. The precipitate was then collected by centrifugation at 10000×g for 45 min at 4° C. and re-suspended in 20 mM PIPES buffer, pH 6.8.

Dialysis. The enzyme preparation was transferred into Spectrapor membrane with Mw cut-off 6000-8000 (Spectrum Laboratories, Inc.) and dialyzed against 20 mM PIPES buffer, pH 6.8, at 4° C. for 12 hrs with constant stirring to remove the ammonium sulfate from the enzyme preparation.

Ultra-filtration/Final concentration. The dialyzed enzyme solution was ultra-filtered and concentrated using Centriplus YM-10 Centrifugal filter; a device containing 10 kDa cut off regenerated cellulose membrane (Amicon Bioseparation, Millipore Corp, Bedford, Mass.). In this process, the sample was placed in the concentrator's reservoir, and then the device was centrifuged for 2 hrs at 3000×g and 4° C. The Centriplus YM-10 retentate (concentrate) was the final alginase concentrate used for the experiments in the next section.

At each step of purification or concentration, a sample was taken and frozen for later determining alginase activity, total protein, specific activity and percentage yield, to assess the effectiveness of the purification process.

The next sets of experiments were all carried out using the last preparation of concentrated alginase enzyme, the Centriplus YM-10 alginase concentrate.

Alginase concentrate was analyzed by discontinuous 12% (wt/v) sodium dodecyl sulfate polyacrylamide get electrophoresis (SDS-PAGE), according to standard procedures (Laemmli 1970). For molecular weight determination, 12% (wt/v) SDS-PAGE mini-gel was loaded with the following: 20 µl of broad-range unstained protein marker (6.5 to 200 KDa, Bio-Rad 161-0314), and 200 µl of Centriplus retentate. Gel was run for 5 hrs 200 volts, at room temperature. SDS—gel was stained with silver stain according to Bio-Rad protocol at current of 0.1 Amp. Alginase bands were identified by comparing SDS bands to the ones that showed activity in zymogram gel (described below).

To detect the activity of the alginase preparation, proteins of the alginase concentrate were separated by 12% native-PAGE, run for 5 hrs at 200 volts and constant current of 0.1 Amp. The alginase-containing native-PAGE were overlaid on zymogram gels, 8% native polyacrylamide containing 0.1% alginic acid, and incubated for 16 hrs in 20 mM Pipes buffer at room temperature. After incubation, the zymogram gels were stained with 0.08% (wt/v) toluidine blue-O in 7% (v/v) glacial acetic for 30 min. After decanting the stain, gels were de-stained in D.I. $H_2O$ for 30 min and observing the activity bands. Toluidine blue non-specifically binds the non-degraded alginic acid (Langille 1996). Thus, the activity bands were unstained.

Activity of the purified alginase was assayed by the DNSA method at 5, 10, 20, 25, 37, and 55° C. Aliquots of 0.3 ml of the alginase concentrate were mixed with 0.7 ml of 0.5% alginate, pH 7.0, and incubated at the above mentioned temperatures for 30 min. Alginase activity was then determined by the DNSA method described previously.

Aliquots of alginase concentrate were incubated with 0.5% alginate, pH 7.0, in test tubes at 25° C. At 5 minute interval, reaction was stopped by boiling the reaction mixture with DNSA reagent for 5 minutes. The reaction mixtures were then cooled in cold water. Absorption was then measured at 575 nm.

Aliquots of the alginase concentrate in 20 mM PIPES buffer, pH 6.8, were equilibrated to 40, 50 and 60° C. in a water bath for 12 hrs. At certain time points, the heat-treated alginase samples were transferred to a chilled water bath. The residual activity was immediately determined using the DNSA procedure as previously described.

Alginase concentrate was dispensed in 0.5 ml aliquots and divided into three sets for determination of the enzyme shelf life at room temperature (25° C.), 4° C., and −20° C. The duration of the experiment was 60 days. Alginase activity was determined during the storage time using the DNSA method.

To determine the relative affinity if the alginase for its substrate, Michaelis-Menten constant was determined using the alginase concentrate, the Centriplus YM-10 concentrate. Aliquots 100 µl of alginase concentrate, contains approximately 86 □g protein, were mixed with alginic acid at concentration from 0.1 to 1.0% and incubated at 25° C. and alginase activity was monitored over a period of 2 hrs. Reaction initial rate, $K_m$ and $V_{max}$ were calculated.

To identify the alginase-encoding genes, 2-40's genomic sequence was surveyed for alginase genes using the protein sequence of alginases determined in other alginase-producing organisms. This was accomplished by utilizing the data base from the NCBI, National Center for Biotechnology Information[4], using protein query-translated database, tblastn, of the BLAST[5] algorithm, Basic Local Alignment Search Tool, (Altschul et al., 1990, 1994 and 1997, Karlin and Altschul 1990 and 1993,) at the NCBI.

[5] BLAST® (Basic Local Alignment Search Tool) is a set of similarity search programs, developed at NCBI, designed to explore all of the available sequence databases regardless of weather the query is protein or DNA.

After finding alginases in the 2-40 genome, the protein sequence of each alginase was analyzed using SMART[6] (Simple Modular Architecture Research Tool) for the identification and annotation of genetically mobile domains and the analysis of domain architectures (Letunic et al., 2002, Schultz et al., 2000). These domains were annotated with respect to the functional class, tertiary structures and functionally important residues. Finally, using The Expert Protein Analysis System, ExPASy[7], the molecular weight and pl of each alginase were determined.

[7] The ExPASy (Expert Protein Analysis System) proteomics server of the Swiss Institute of Bioinformatics (SIB) is dedicated to the analysis of protein sequences and structures as well as 2-D PAGE.

Results 2-40 was grown in minimal media supplemented with 0.2% of alginate, fructose, galactose, glucose, lactose, sorbitol, or xylose. The cultures were incubated for 32 hrs at 25° C. with aeration. Growth was monitored by measuring the optical density (OD) at 600 nm, and enzyme activity (µg reducing sugar/ml) was determined by the DNSA protocol.

Figure 10:
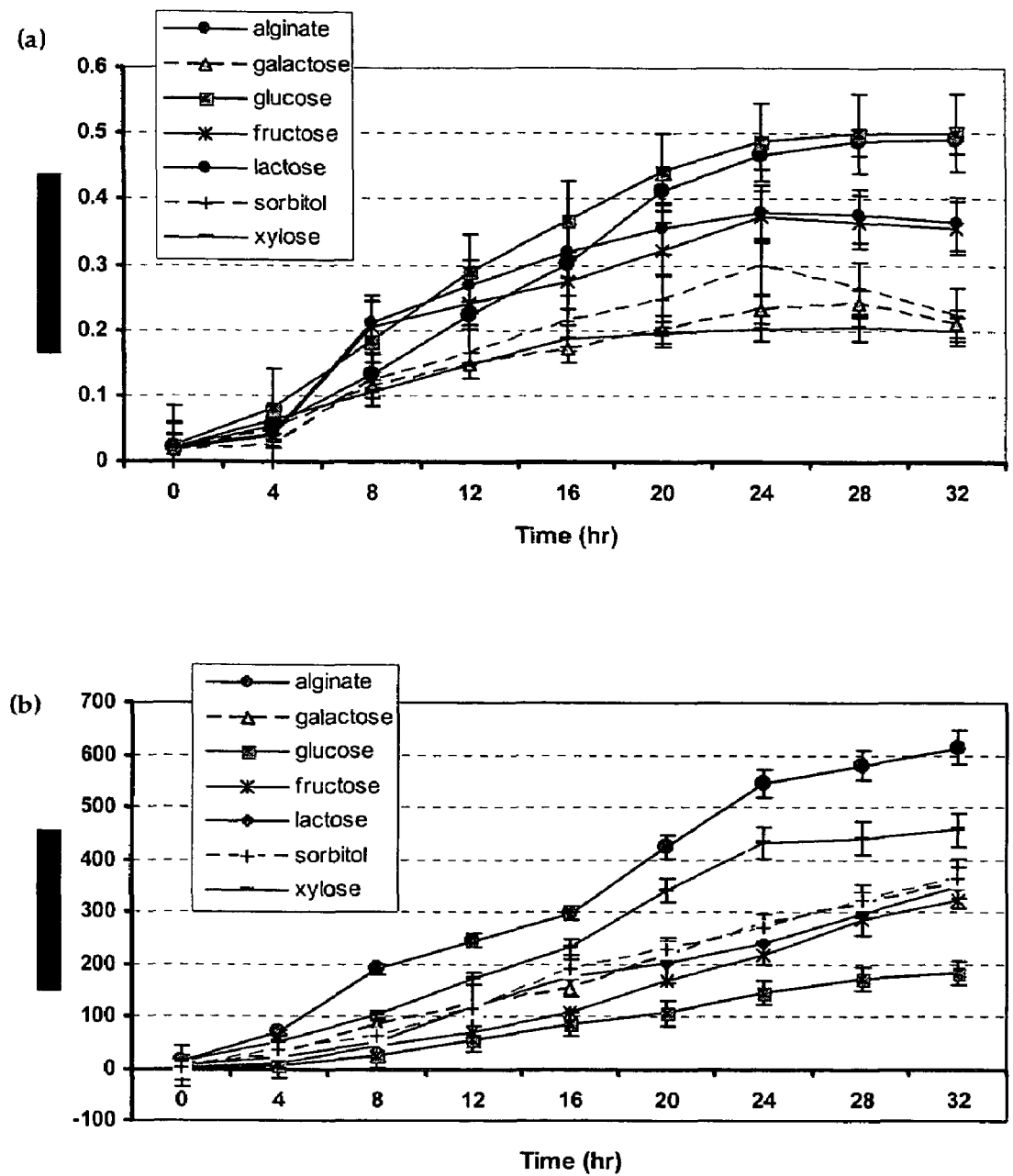
FIG. 10 are plots of the growth and alginase production of S. degradans 2-40 as functions of carbon source in the growth medium.

The lag phase lasted 4 hours for all cultures growing in each of the seven carbon sources. The log phase lasted 9 hrs in fructose, galactose, lactose, sorbitol and xylose, and 13 hrs in both alginate and glucose (FIG. 10). Decline phase did not start before 32 hrs when cultures were grown with alginate, glucose, fructose, lactose, or xylose as the main carbon source, while it started at the $28^{th}$ hr in case of galactose and as early as the $24^{th}$ hr in case of sorbitol. The decline phase in sorbitol was also steeper than the other carbon sources.

Alginase activity was detected in the spent media after 4 hrs in all the carbon sources. Alginate induced the production of 615 units of alginase activity while xylose induced 457 units at 32 hrs in the spent media.

Figure 26:
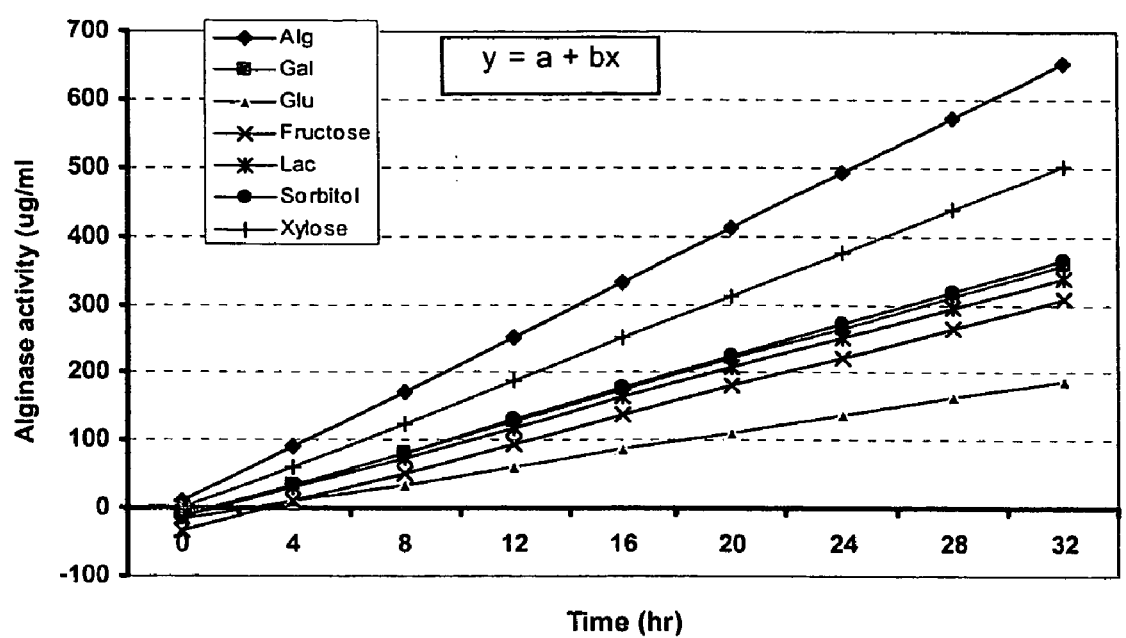
FIG. 26 is a plot of alginase production as a function of carbon source.
Figure 27:
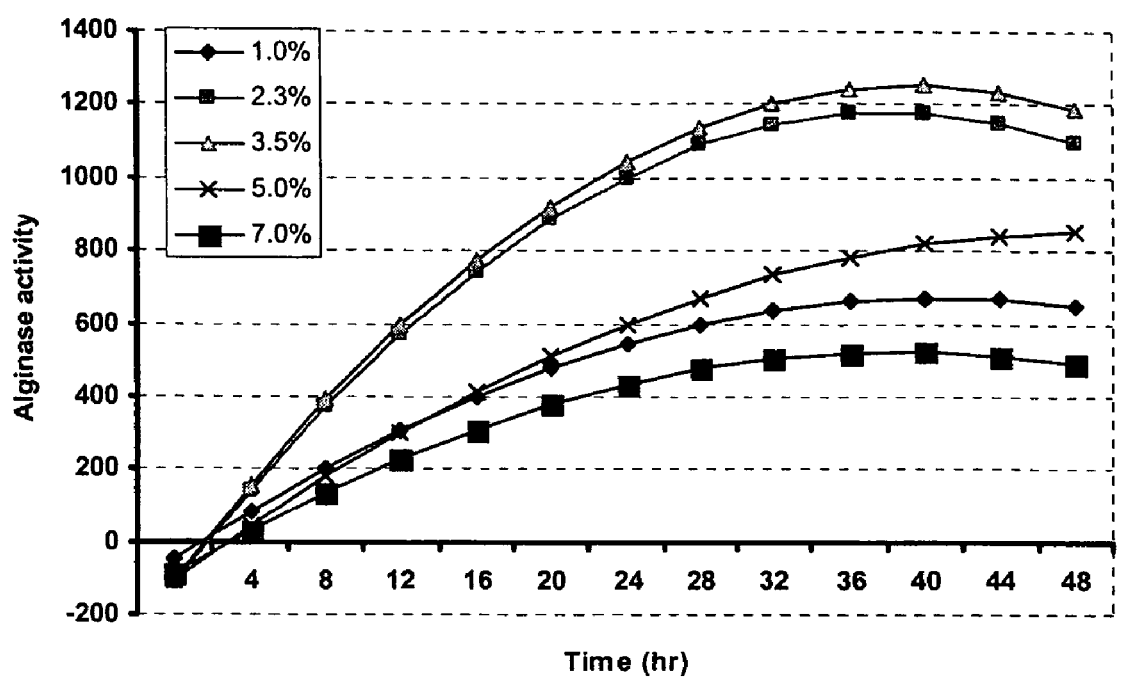
FIG. 27 is a plot of alginase production as a function of Instant Ocean concentration.

To analyze alginase activity as a function of carbon source, alginase activity was fitted to the following equation: y=a+bx, where, y: is alginase activity, a: is intercept, b: is slop and x: is time (FIG. 26 and Table 3.1a). Analysis showed that time (T) explained 69% of the variations, while carbon source (S) and the interaction of carbon source with time (S*T) explained 23% and 8% of the variations, respectively (Table 3.1b). Statistics were not applied to sort out the time variable, however, since it was fully expected that alginases would accumulate with time. There was some enzyme activity loss which becomes apparent during the late stationary and decline phases of growth. One possibility is that enzymes are slowly degraded over time, initially more slowly than production. In fact, some protease actively was reported in 2-40 previously (Chakravorty 1998). The "F" values determine the variation significance according to the F distribution critical values table (Moore 1995). The overall means for alginase activity, regardless of time, for each carbon source were also calculated (Table 5.1)

TABLE 5.1

Overall means (±SE) of alginase activity as function of carbon source in 2-40 growth medium.

| Carbon source | Alginate | Galactose | Glucose | Fructose | Lactose | Sorbitol | Xylose |
|---|---|---|---|---|---|---|---|
| Mean* | 332.52[A] | 173.89[D] | 86.70[G] | 137.04[F] | 162.89[E] | 176.78[C] | 250[B] |

*Means with the same letter are not significantly different at Pr < 0.05, with Tukey Test.
SE (Standard Error) = 0.421

Figure 11:
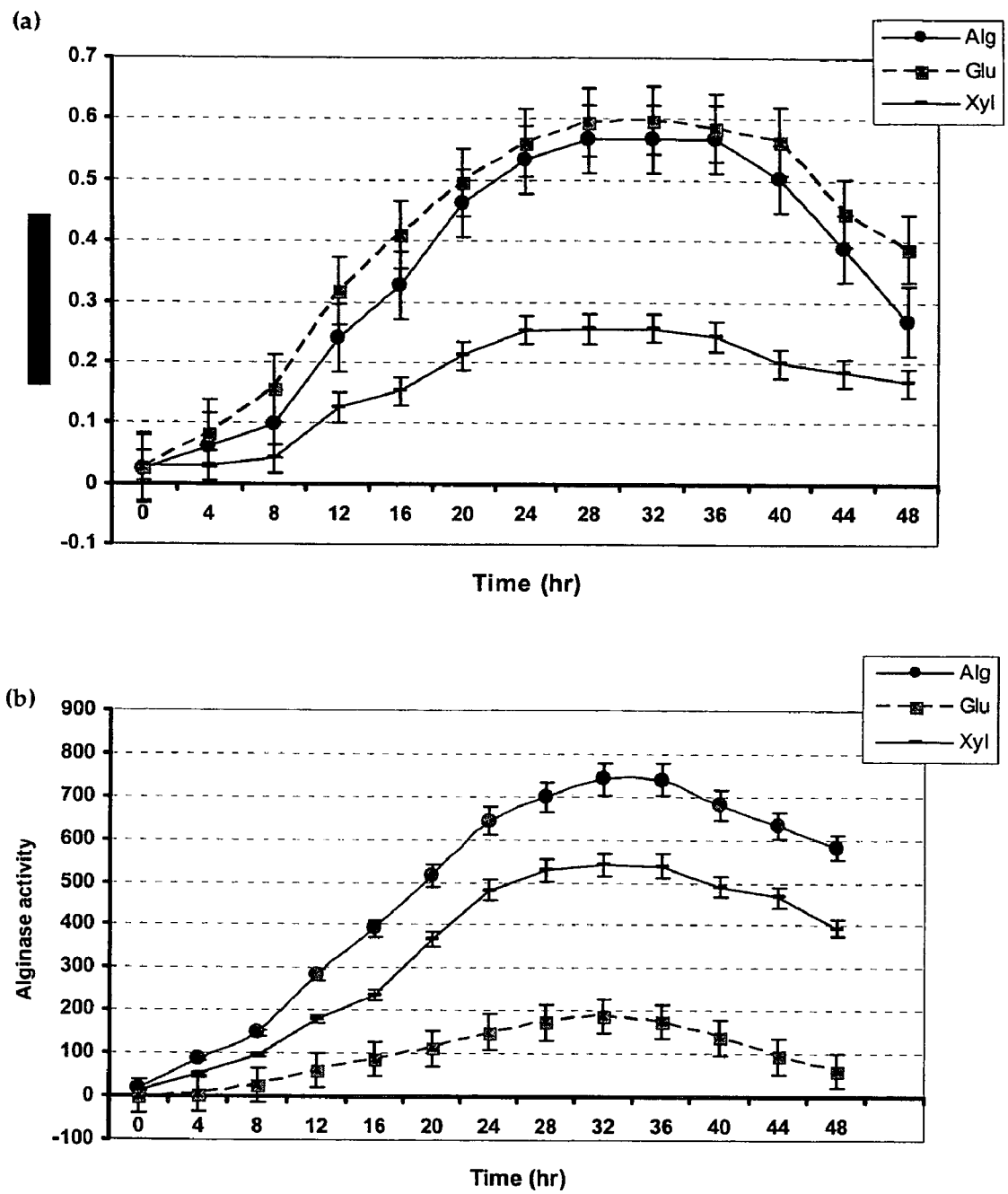
FIGS. 11 and 11a are plots of the growth and alginase production of S. degradans 2-40 as functions of alginate, glucose, or xylose as the main carbon source in the growth medium.

To identify the best carbon source for alginase production, alginate, glucose and xylose were tested for their effect on alginase yield by growing 2-40 in minimal media supplemented with (wt/v) 0.2% of either of alginate, glucose, or xylose for 48 hrs at the same growth conditions described above. Growth measurements showed that decline phase began after 36 hrs in all the three carbon sources. Alginase activities in the supernatant neither increased nor decreased between 32 and 36 hrs of growth, however (unexpectedly) started to significantly decrease after 36 hrs. Results also showed that 36 hrs was the peak harvest time for alginase activity for 2-40 grown in alginate and xylose and 29 hrs when 2-40 was grown in glucose. The yield was also very different: alginate, 693 units of activity; xylose, 506 units; glucose 151 units (FIG. 11).

Figure 11A:
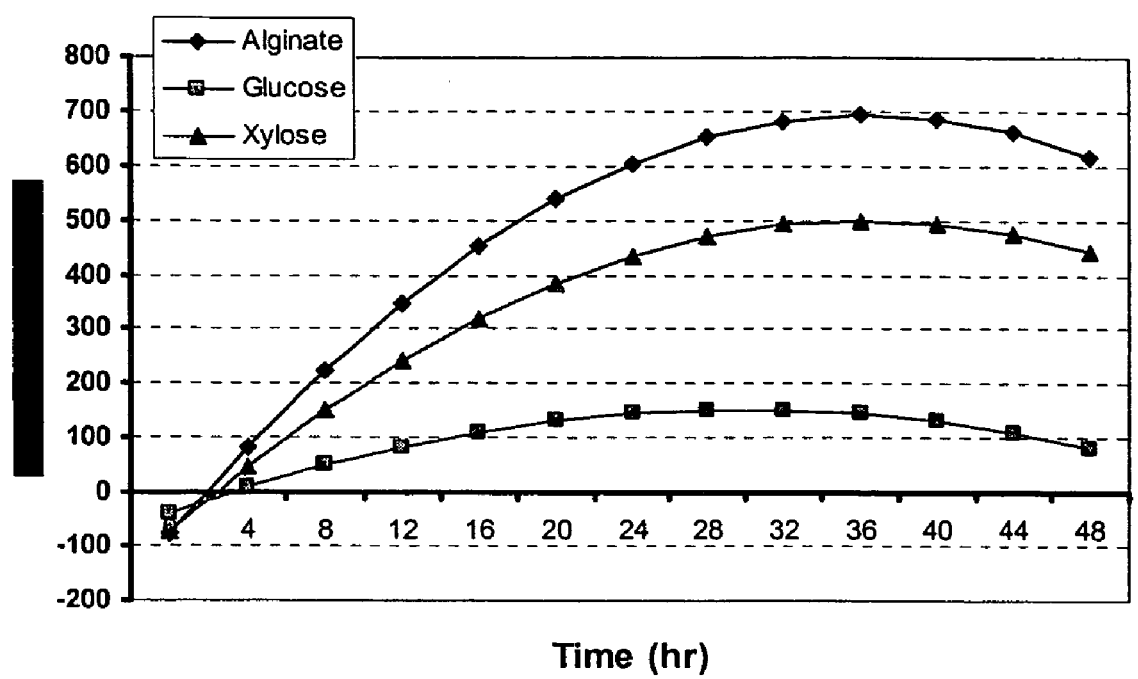

These results were subject to statistical analysis. A curve linear relationship was suggested to fit the relation between alginase activity and time as follows: $y = a + b_1 x + b_2 x^2$, where, y is alginase activity, a is intercept, $b_1$ and $b_2$ are partial regression coefficients and x is time. Briefly, these results showed that alginase yields were statistically different depending on the substrate, and that time of harvest was the most important variable. FIG. 11a shows the effect of growing 2-40 in alginate, glucose or xylose, as the main carbon source, on alginase activity over a period of 48 hrs. The maximum alginase activities obtained in the three carbon sources were significantly different, and that the highest alginase activity was in the alginate medium at 36 hrs, and this was statistically valid (Table 3.2) as was the finding that carbon source (S), time (T), and the interaction between the two variables (S*T) explained 42%, 47% and 11% of the variations, respectively (Table 5.2a). The overall means for alginase activity for each of the three carbon sources were also calculated (Table 5.2b).

Analysis of the effect of Alginate, Glucose and Xylose as the main carbon source in the growth medium on alginase activity.

TABLE 5.2a

ANOVA table for alginase activity as a function of carbon source (S), time (T), and their interaction (T * S) in 2-40 growth medium.

| Source | DF | SS | SS %[a] | Mean Square | F Value[b] |
|---|---|---|---|---|---|
| S | 2 | 2832675 | 42 | 1416337 | 79592 |
| Error I | 6 | 107 | 0.001 | 17.795 | |
| T | 12 | 3213645 | 47 | 267803 | 91557 |
| Linear T | 1 | 2242200 | (32) | 2242200 | 766564 |
| Quadratic T | 1 | 773372 | (11) | 773372 | 264401 |
| S * T | 24 | 772705 | 11 | 32196 | 11007 |
| Error II | 72 | 210.564 | 0.003 | 2.925 | |
| Corrected Total | 116 | 6819344 | 100 | | |

Source: source of variations,
DF: Degrees of freedom,
SS: Sum of Squares,
Coefficient of variation = 0.664054,
$R^2$ = 0.999969
[a]Sum Square % = (SS Variable/SS Total) * 100
[b]F values are significant at P < 0.0001

TABLE 5.2b

Overall means (±SE) of alginase activity of alginate, glucose and xylose as the main source of carbon in the 2-40 growth medium.

| Carbon source | Alginate | Glucose | Xylose |
|---|---|---|---|
| Mean* | 475.15[A] | 98.54[C] | 337.54[B] |

*Population mean, means with the same letter are not significantly different at Pr < 0.05, with Tukey Test. SE (Standard Error) = 0.1043

TABLE 3.2

Intercept (a), partial regression coefficients ($b_1$ and $b_2$), maximum alginase activity as a function of carbon source in 2-40 growth medium.

| | Carbon Sources | | |
|---|---|---|---|
| | Alginate | Glucose | Xylose |
| A | -75.43 | -39.62 | -72.08 |
| $b_1$ | 42.22 | 12.96 | 31.53 |
| $b_2$ | -0.58 | -0.22 | -0.43 |
| Max alginase activity* | 693[A] | 151[C] | 506[B] |
| Time of max. activity | 36.39 | 29.45 | 36.66 |
| $R^2$ | 0.9585 | 0.8630 | 0.9258 |
| Cost: $/Liter | 1.013 | 2.07 | 0.999 |
| Cost: $/1000 units | 1.46 | 13.7 | 1.97 |

*Maximum activities were analyzed with t-test, activities with the same letters are not significantly different at DF = 74 and P < 0.05
Cost: all costs are in USD.

Figure 12:
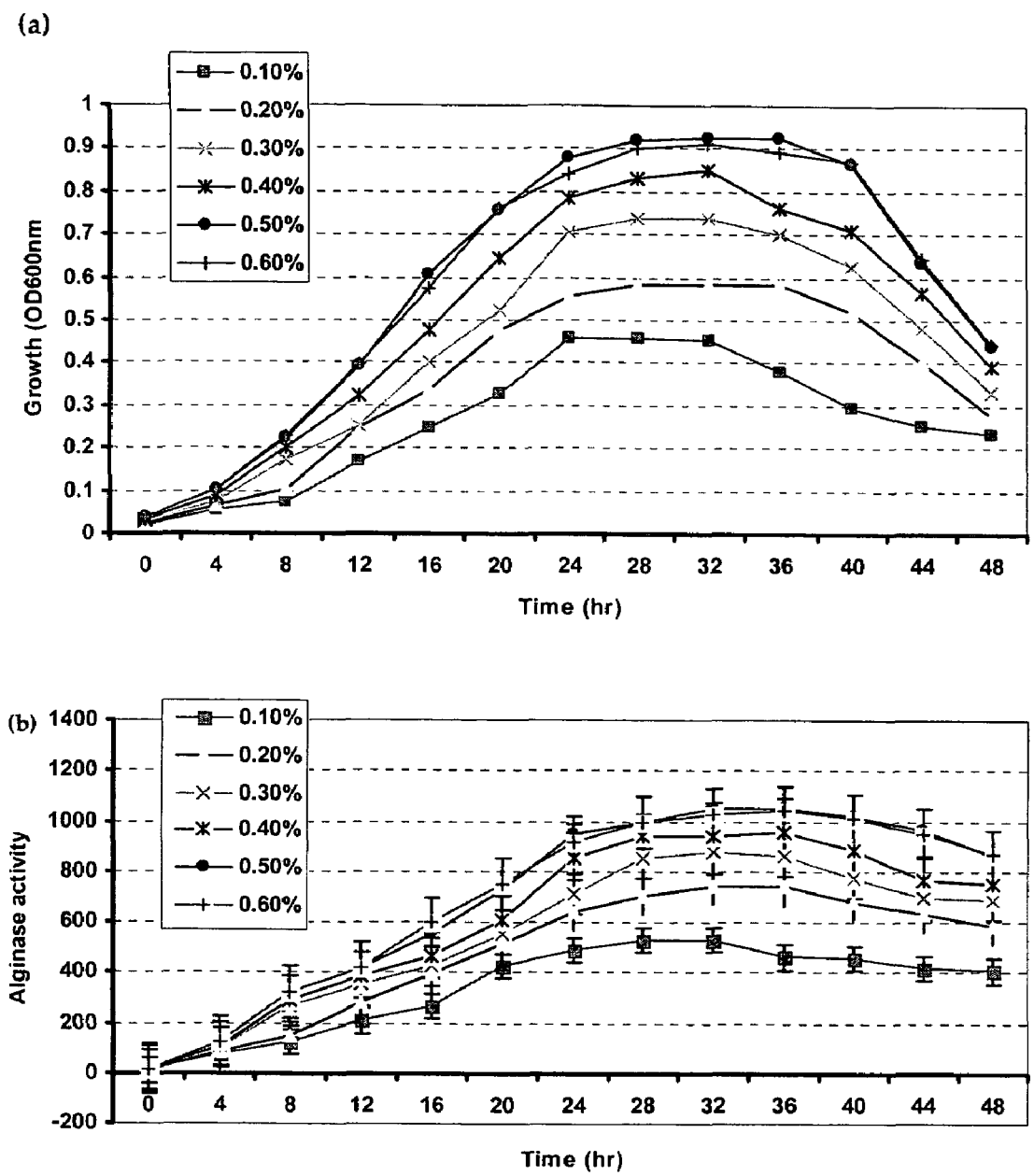
FIG. 12 are plots of the growth and alginase production of S. degradans 2-40 as functions of alginate concentration in the minimum medium.

The effect of alginate concentration, as the main source of carbon, on growth and enzyme production was investigated by growing 2-40 in the minimum medium supplemented with alginate at concentrations (wt/v) of 0.1-0.6% and determining the enzyme activity at each concentration. Maximum activity was observed at 36.8 hrs in alginate concentrations of 0.5% and 37 hrs at concentration 0.6% with no significant increase in the activity at 0.6% (difference was analyzed with t-test). In fact, alginase production reached 1019 units at 0.5% and 1012 units at 0.6% (concentrations of more than 0.5% increased viscosity leading to reduced aeration). Moreover, the alginase production curves at both 0.5% and 0.6% were very similar. Since both growth and alginase activity increased with increasing alginate concentration up to 0.5%, this concentration was deemed to be the optimal as was 32 h of incubation, 25° C. and 200 rpm agitation, (FIG. 12).

Figure 24:
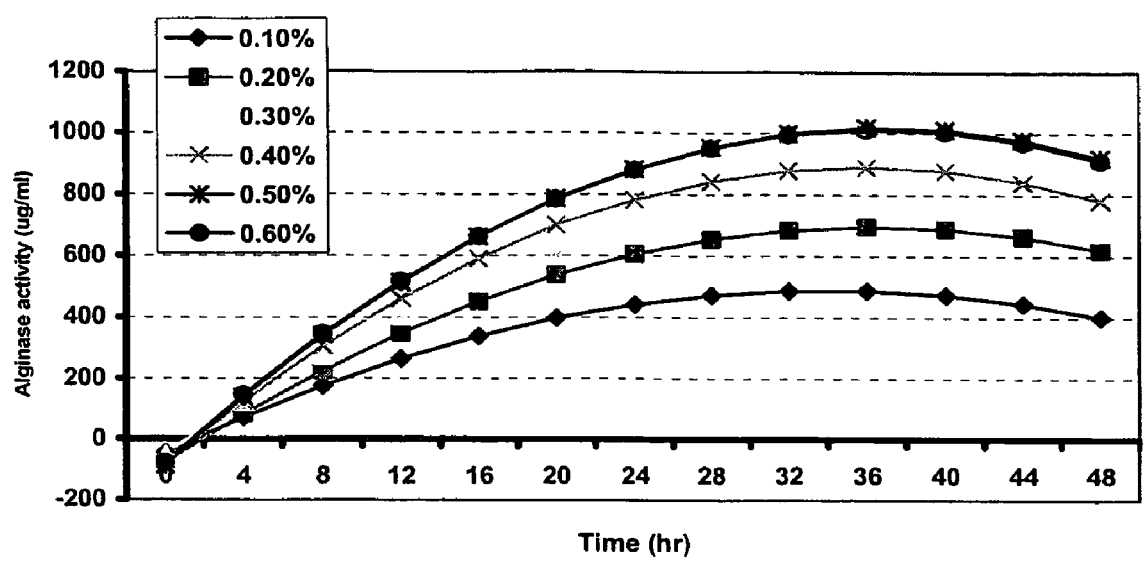
FIG. 24 shows a plot of alginase production as a function of alginate concentration.

For prediction of alginase production of 2-40 as a function of alginate concentration over the period of 48 hr the following quadratic equation was used:

$$y = a + b_1 x + b_2 x^2,$$

where y: alginase activity, a: intercept, $b_1$ and $b_2$ are the graph partial regression coefficients for each concentration curve, and x: time. Alginase production was fitted to the above formula, with $R^2$ value of 0.94, indicating the appropriateness of the chosen formula. FIG. 24 and Table 3.3 depict the effect of alginate concentration on alginase production over the incubation period. Table 3.3 shows that alginate concentrations varied in intercept, ranging from −87.42 (at 0.5% alginate) up to −47.02 (at 0.1% alginate). This resulted in reaching maximum alginase activity at different time points for each alginate concentration. Analysis of variance illustrated that 79% of the variations were attributed to time, while 16% were attributed to alginate concentration, underscoring the importance of time as a significant factor in alginase production. "F" values confirm the significance of variations attributed to both time and alginate concentration (Table 5.3a). The overall means for alginase activity, regardless of time, for each concentration were also calculated (Table 5.3b).

Tables 5.3a and b—Analysis of the effect of alginate concentration on alginase activity.

TABLE 5.3a

ANOVA table for alginase activity as a function of alginate concentration (C), incubation time (T), and their interaction (C * T) in 2-40 growth medium.

| Source | DF | SS | SS %[a] | Mean Square | F Value[b] |
|---|---|---|---|---|---|
| C | 5 | 3859829 | 16 | 771966 | 36760 |
| Error I | 12 | 249 | 0.001 | 21 | |
| T | 12 | 19381397 | 79 | 1615116 | 209755 |
| Linear T | 1 | 14450075 | (59) | 14450075 | 1876633 |
| Quadratic T | 1 | 4231089 | (17) | 4231089 | 546492 |
| C * T | 60 | 1089846 | 4.5 | 18164 | 2359 |
| Error II | 144 | 1108 | 0.004 | 7.7 | |
| Corrected Total | 233 | 24332430 | 100 | | |

Source: source of variations,
DF: Degrees of freedom,
SS: Sum of Squares,
Coefficient of variation = 9.176513,
$R^2$ = 0.999954
[a]Sum Square % = (SS variable/SS Total) * 100
[b]F value is significant at P < 0.0001

TABLE 5.3b

Overall means (±SE) of alginase activity as function of alginate concentration in 2-40 growth medium.

| | Alginate concentration (%) | | | | | |
|---|---|---|---|---|---|---|
| | 0.1 | 0.2 | 0.3 | 0.4 | 0.5 | 0.6 |
| Mean* | 338.67[E] | 474.90[D] | 532.31[C] | 615.21[B] | 701.72[A] | 700.13[A] |

*Population Mean, means with the same letter are not significantly different at Pr < 0.05, with Tukey Test.
SE (Standard Error) = 0.0711

Figure 13:
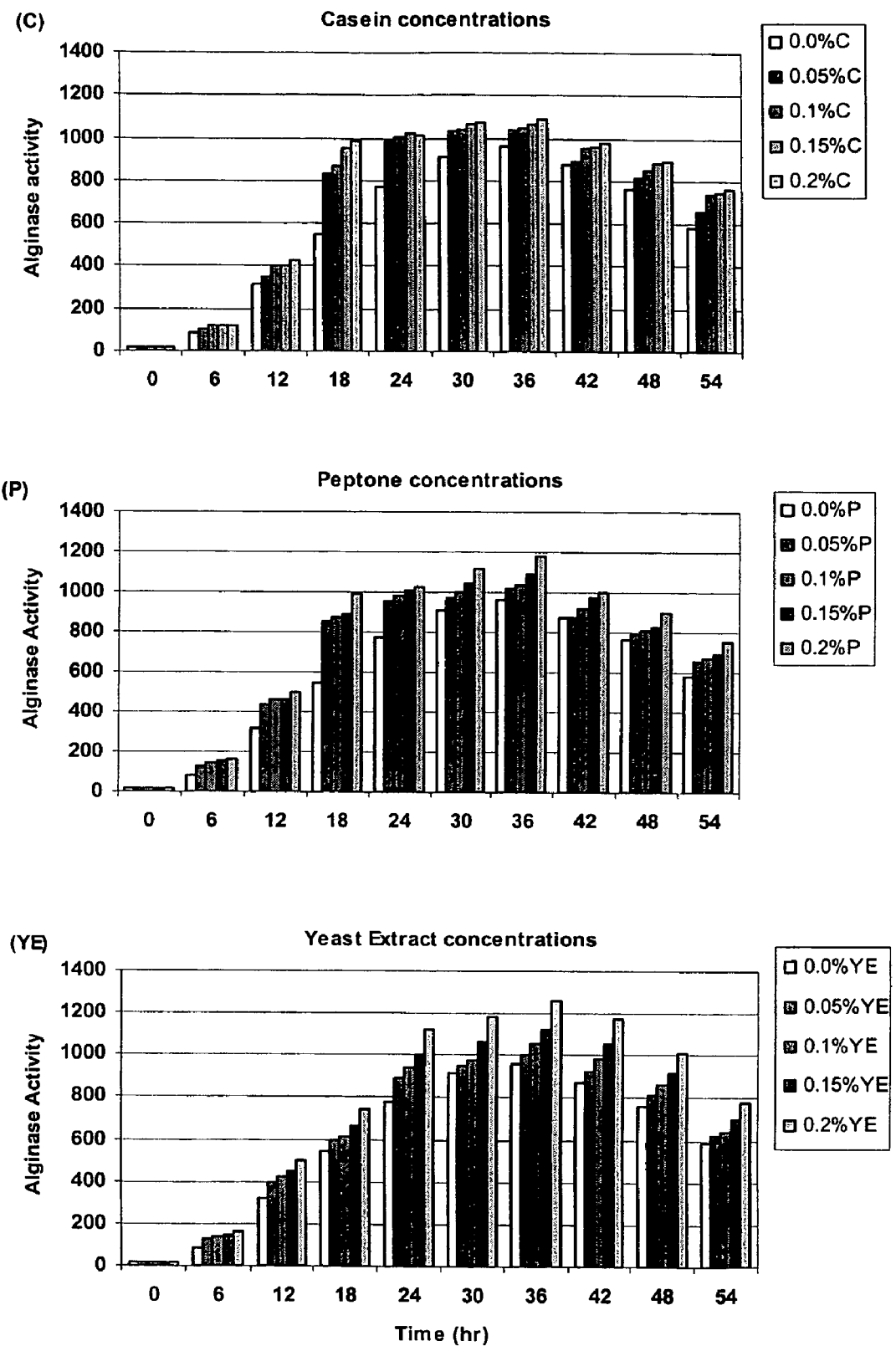
FIG. 13 are plots of S. degradans 2-40 alginase production as a function of growth factors requirement.

The 0.5% alginate minimal medium was supplemented with casein, yeast extract, or peptone at concentrations from 0.0 to 2 g/l. Activity was monitored every 6 hours during 54 hours of incubation. Alginase activity (in the supernatant) was maximum between 24 to 36 hrs, during stationary phase, after which enzyme activity declined slightly in the casein medium, and dramatically in YE and peptone media. In 0.2% YE, alginase activity peaked at 34 hrs with 1162 units. In 0.2% peptone, alginase activity was 1149 units at 34.36 hrs. In 0.2% casein, maximum alginase activity reached 1064 units at 34.98 hrs (FIG. 13). Without any supplement to the alginate minimal medium, alginase activity was 965 units at 34 hrs. For prediction of alginase production of 2-40 as a function of casein, peptone or yeast extract concentration, the following quadratic equation was used:

$$y = a + b_1 c + b_{11} c^2 + b_2 t + b_{22} t^2,$$

where y is alginase activity, a is the intercept, c is growth factor concentration, t is time, $b_1$, $b_{11}$, $b_2$ and $b_{22}$ are partial regression coefficients.

Figure 25A:
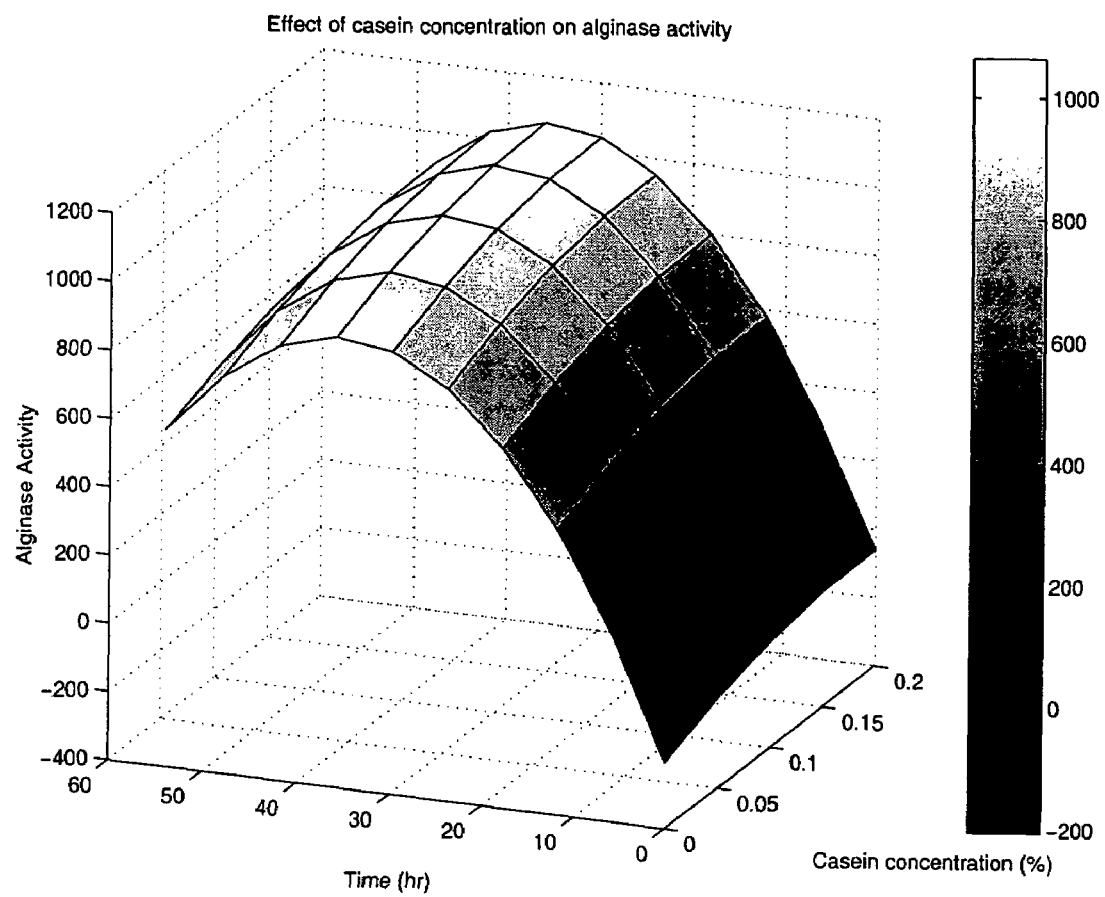
FIGS. 25a-c are plots of alginase production as a function of casein concentration, peptone concentration and yeast extract, respectively.
Figure 25B:
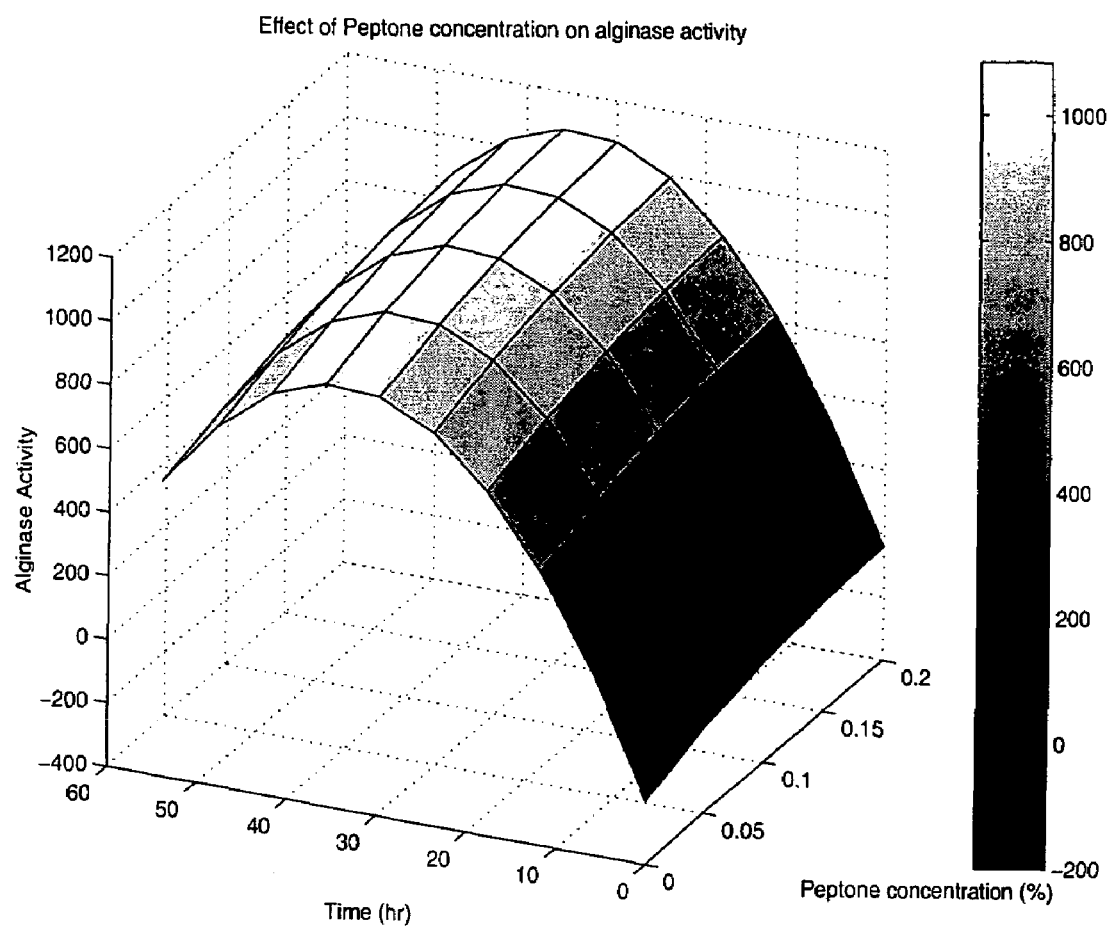
Figure 25C:
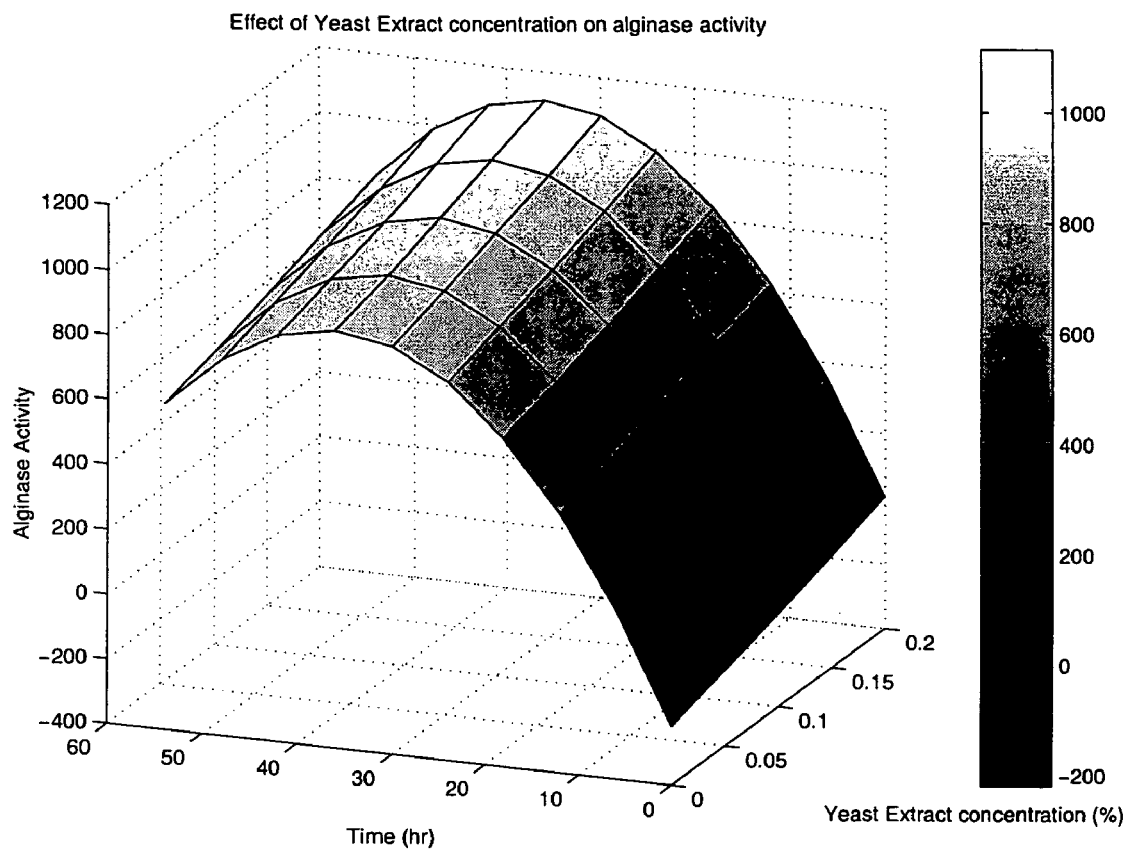

The above mentioned quadratic equation was used to analyze the observations of alginase production as a function growth factor type and concentration over the period of 54 hrs. These analysis validated alginase production as a variable of casein concentration (FIG. 25a, and table 5.4a), peptone concentration (FIG. 25b, Table 5.4b), and yeast extract concentration (FIG. 25c, Table 5.4c) with time. Analysis of variance (Table 3.4) showed that, again, 93% of the variations were attributed to time (T), 0.05% to the growth factor type (S), and 3% to the growth factor concentration (C). However, the "F" values illustrated that each of these variables are indeed significant. Moreover, analysis showed that maximum alginase activity was induced in a concentration of 0.2% for all three substrates. In fact, analysis showed that further increase in the casein and yeast extract concentrations over 0.2% decreased the alginase activity, and in the case of peptone, increase in the concentration over 2% did slightly increase alginase activity; however according to t-test analysis this increase is statistically insignificant. The maxima of alginase activity as variable of the three substrate concentrations were analyzed using t-test. These showed that alginase activity was significantly higher in 0.2% yeast extract than in the same concentration of casein or peptone (Table 3.5).

5.4 Analysis of the effect of growth factor in the growth medium on alginase activity.

TABLE 5.4a

Maximum alginase activity of 2-40 when grown in casein as a growth factor in the growth medium.

| | Casein Concentration (%) | | | | |
|---|---|---|---|---|---|
| | 0 | 0.05 | 0.1 | 0.15 | 0.2 |
| Max activity* | 919 | 989 | 1037 | 1062 | 1064 |
| Time at max activity | 34.98 | 34.98 | 34.98 | 34.98 | 34.98 |

$R^2 = 0.9335$
*Maximum alginase activities at 0.15 and 0.2 were analyzed wit t-test and the difference was found significant at DF = 56, and P < 0.05

TABLE 5.4b

Maximum alginase activity of 2-40 when grown in peptone as a growth factor in the growth medium.

| | Peptone Concentration (%) | | | | |
|---|---|---|---|---|---|
| | 0 | 0.05 | 0.1 | 0.15 | 0.2 |
| Max activity* | 973 | 1035 | 1085 | 1123 | 1149 |
| Time at max activity | 34.36 | 34.36 | 34.36 | 34.36 | 34.36 |

$R^2 = 0.9140$
*Maximum alginase activities at 0.15 and 0.2 were analyzed wit t-test and the difference was found significant at DF = 56, and P < 0.05

TABLE 5.4c

Maximum alginase activity of 2-40 when grown in yeast extract as a growth factor in the growth medium.

| | Yeast Extract Concentration (%) | | | | |
|---|---|---|---|---|---|
| | 0 | 0.05 | 0.1 | 0.15 | 0.2 |
| Max activity* | 1003 | 1071 | 1119 | 1150 | 1162 |
| Time at max activity | 33.94 | 33.94 | 33.94 | 33.94 | 33.94 |

$R^2 = 0.9217$
*Maximum alginase activities at 0.15 and 0.2 were analyzed wit t-test and the difference was found significant at DF = 56, and P < 0.05

TABLE 3.4

ANOVA table for alginase activity as a function of growth factor (S), growth factor concentration (C), time (T), and their interactions (S * C, S * T, and T * C)

| Source | DF | SS | SS %* | Mean Square | F Value[a] |
|---|---|---|---|---|---|
| S | 2 | 29048 | 0.05 | 14523.896 | 7.69[b] |
| C | 4 | 1972561 | 3.22 | 493140 | 261 |
| Linear C | 1 | 1876352 | (3.06) | 1876352 | 731 |
| Quadratic C | 1 | 35669 | (0.05) | 35669 | 14 |
| S * C | 8 | 100051 | 0.16 | 12506 | 6.62 |
| Error I | 30 | 56669 | 0.09 | 1889 | 0.74[c] |
| T | 9 | 56986991 | 93 | 6331888 | 2466 |
| Linear T | 1 | 29174527 | (47) | 29174526.63 | 11364 |
| Quadratic T | 1 | 25544774 | (42) | 25544774 | 9950 |
| S * T | 18 | 512786 | 0.8 | 28488 | 11 |

TABLE 3.4-continued

ANOVA table for alginase activity as a function of growth factor (S), growth factor concentration (C), time (T), and their interactions (S * C, S * T, and T * C)

| Source | DF | SS | SS %* | Mean Square | F Value[a] |
|---|---|---|---|---|---|
| T * C | 36 | 637381 | 1 | 17705 | 6.9 |
| Error II | 342 | 877992 | 1.4 | 2567 | |
| Corrected Total | 449 | 61173480 | 100 | | |

Source: source of variations,
DF: Degrees of freedom,
SS: Sum of Squares,
Coefficient of variation = 7.314432,
$R^2 = 985648$
* SS % = (SS variable/SS Total) * 100
[a]All F values are significant at P < 0.0002, unless otherwise noted.
[b]F value is significant is significant at P = 0.002
[c]F value is significant is significant at P = 0.8446

TABLE 3.5

T-test of maximum alginase activities obtained when casein, peptone, or yeast extract was added to 2-40 medium as growth factor.

| | Casein | Peptone | Yeast Extract |
|---|---|---|---|
| Max alginase activity | 1064 | 1149 | 1162 |
| Time at max activity | 34.98 | 34.36 | 33.94 |
| Concentration at max activity (%) | 0.2% | 0.2% | 0.2% |
| $R^2$ | 0.9335 | 0.914 | 0.9217 |
| Cost: $/Liter | 1.44 | 1.28 | 1.58 |
| Cost: $/1000 units | 1.35 | 1.11 | 1.35 |

Maximum alginase activities of casein, peptone and yeast extract were compared with t-test and the differences in alginase activity were found significant at DF = 56, and P < 0.05
Cost: all costs are in USD.

Figure 14:
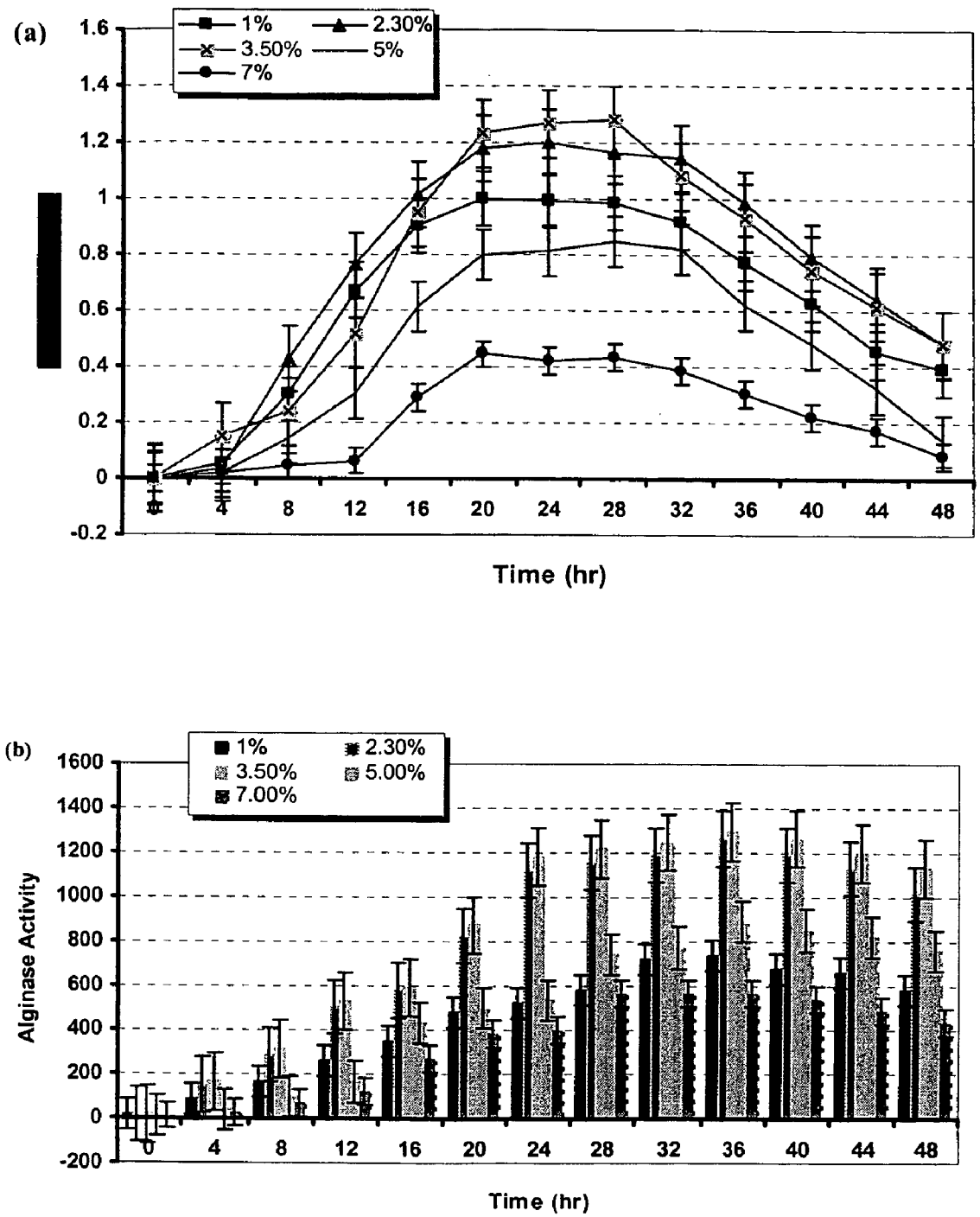
FIG. 14 are plots of the growth and alginase production of S. degradans 2-40 as a function of concentration of sea salt.

2-40 is a marine bacterium requiring sea salts. Instant Ocean (IO), a mixture of sea salts, was applied in the minimal medium at concentrations of 0.1, 2.3, 3.5, 5, and 7%. 2-40 grew in a wide range of salt from 1-5%, with slower growth at 7% (FIG. 14). Maximum alginase activities were detected between 38-39 hours in 2.3-3.5% IO, 1180-1252 units. Alginase yields at 2.3% and 3.5% IO were analyzed by t-test and difference found to be significant. Additionally, since growing 2-40 in 3.5% IO would inhibit the growth of some contaminant microorganisms (e.g. *Bacillus* sp.), this concentration was applied in subsequent experiments. For prediction of alginase activity as a function of instant ocean concentration, alginase activity was fitted to a quadratic equation over time and represented by the formula: $y=a+b_1 x+b_2 x^2$, where y is alginase activity, a is intercept, $b_1$ and $b_2$ are the graph partial regression coefficients, and x is time.

To analyze the effect of Instant Ocean (IO) concentration on alginase production by 2-40, alginase activity was fitted to a quadratic relationship, with $R^2$ ranging from 0.9151 to 0.9631 (Table 3.6). Analysis showed that the IO concentration affected alginase activity, with alginase activity reaching a maximum concentration at different time points (FIG. 24 and Table 3.6). A T-test was used to compare the two highest alginase activity maxima which were obtained in 2.3% and 3.5% IO. T-test showed that 3.5% IO supported significantly higher alginase yield than 2.3% IO did and so the statistical analysis was particularly revealing in this case. Table 5.5a, shows the analysis of variance of alginase activity as affected by IO concentration and incubation time. This analysis reveals that 25% of variations can be attributed to IO concentration (C), 67% to incubation time (T) and 7% to the interaction of IO concentration with time (C*T). Moreover, "F" values showed the significance of variations attributed to IO concentration and time. The overall means for alginase activity, regardless of time, for each instant ocean concentration were also calculated (Table 5.5b).

5.5 Analysis of the effect of Instant ocean concentration on alginase activity.

TABLE 5.5a

ANOVA table for alginase activity as a function of Instant Ocean concentration (C), time (T), and their interaction (C * T) in 2-40 growth medium.

| Source | DF | SS | SS %[a] | Mean Square | F Value[b] |
|---|---|---|---|---|---|
| C | 4 | 7773734 | 25.5 | 1943433 | 95033 |
| Error I | 10 | 204 | 0 | 20.45 | |
| T | 12 | 20569370 | 67.5 | 1714114 | 480144 |
| Linear T | 1 | 17085204 | 56 | 17085204 | 4785771 |
| Quadratic T | 1 | 2721886 | 9 | 2721886 | 762433 |
| C * T | 48 | 2130499 | 7 | 44385 | 12433 |
| Error II | 120 | 429 | 0.002 | 3.57 | |
| Corrected Total | 194 | 30474236 | 100 | | |

Source: source of variations,
DF: Degrees of freedom,
SS: Sum of Squares,
Coefficient of variation = 9.176513,
$R^2 = 0.999986$
[a]SS % = (SS variable/SS Total) * 100
[b]F values are significant at $P < 0.0001$ TABLE 5.5b Means (±SE) of alginase activity as function of instant ocean concentration.

| | IO concentration (%) | | | | |
|---|---|---|---|---|---|
| | 1 | 2.3 | 3.5 | 5 | 7 |
| Mean* | 450.46[D] | 803.15[B] | 848.64[A] | 510.82[C] | 342.48[E] |

Means with the same letter are not significantly different at $Pr < 0.05$, with Tukey Test.
SE (Standard Error) = 0.0485

TABLE 3.6

Intercept (a), partial regression coefficients ($b_1$ and $b_2$) for alginase activity as a function of Instant Ocean concentration in 2-40 growth medium.

| | Instant Ocean (%) | | | | |
|---|---|---|---|---|---|
| | 1% | 2.3% | 3.5% | 5% | 7% |
| a | −51.30 | −112.48 | −105.47 | −104.56 | −91.17 |
| $b_1$ | 35.19 | 67.56 | 68.82 | 38.59 | 31.53 |
| $b_2$ | −0.43 | −0.88 | −0.87 | −0.39 | −0.40 |
| Maximum activity* | 671.23 | 1180.89 | 1252.41 | 853.72 | 524.29 |
| Time at max Y | 41.07 | 38.29 | 39.46 | 49.66 | 39.04 |
| $R^2$ | 0.959 | 0.9584 | 0.9631 | 0.9444 | 0.9152 |
| Cost: $/liter | 1.53 | 1.575 | 1.61 | 1.64 | 1.69 |

TABLE 3.6-continued

Intercept (a), partial regression coefficients ($b_1$ and $b_2$) for alginase activity as a function of Instant Ocean concentration in 2-40 growth medium.

| | Instant Ocean (%) | | | | |
|---|---|---|---|---|---|
| | 1% | 2.3% | 3.5% | 5% | 7% |
| Cost: $/1000 units | 2.28 | 1.33 | 1.28 | 1.92 | 3.22 |

Maximum alginase activity at both 2.3% and 3.5% were analyzed by t-test, and difference between the two values was found significant at DF = 74 and $P < 0.05$
Cost: all costs are in USD.

Figure 15:
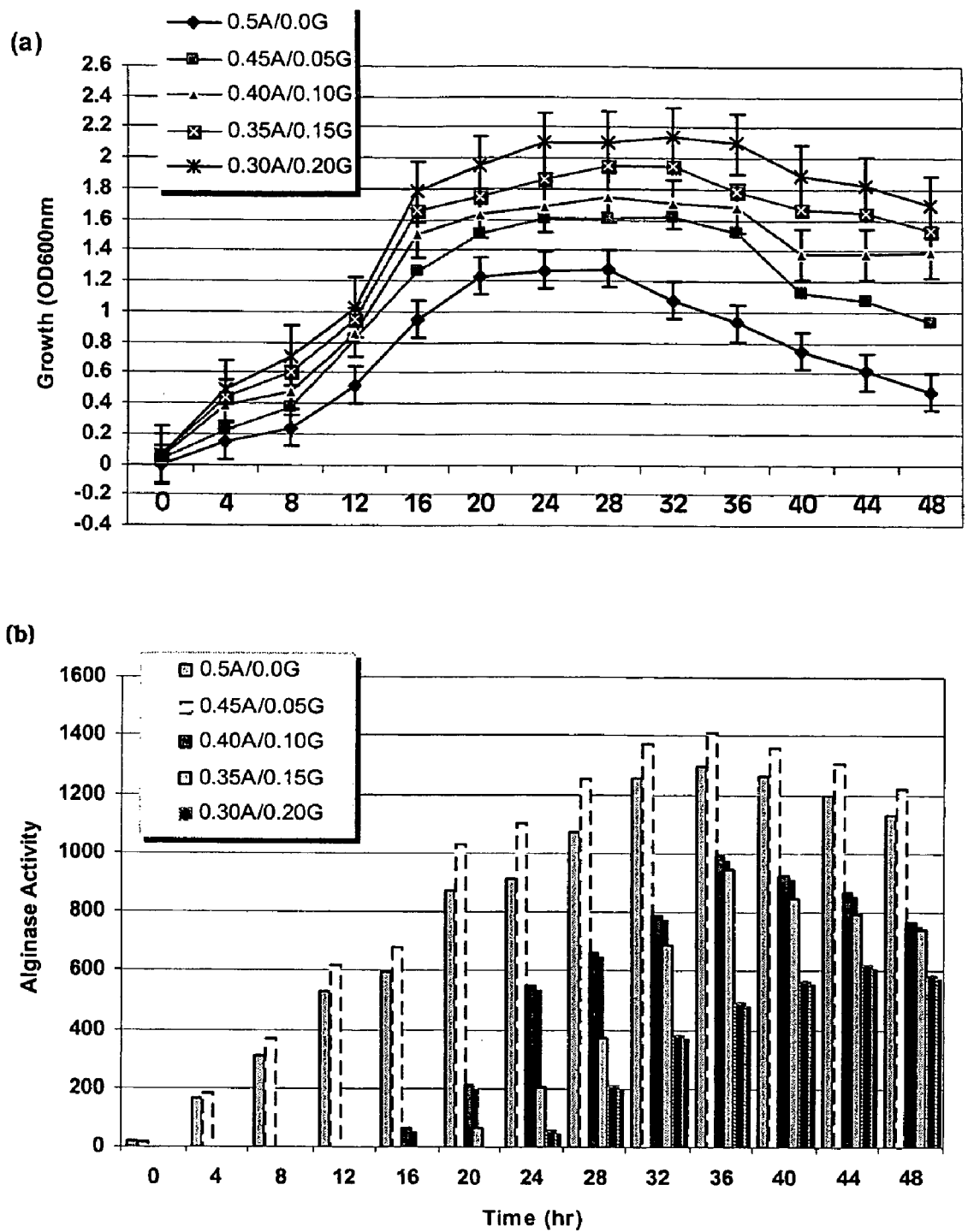
FIGS. 15 and 15a are plots of the growth and alginase production in combinations of alginate and glucose.

In the previous experiments, glucose (G) induced rapid biomass increase, while alginate (A) was the best alginase inducer. Therefore, a combination of these two carbon sources was tested as a way to achieve highest alginase yield. The tested % A: G % (wt/v) ratios were: 0.5A:0.0G, 0.45A:0.05G, 0.40A:0.10G, 0.35A:0.15G, and 0.30A:0.20G (plus 3.5% IO and 0.2% YE). A combination of 0.45% alginate and 0.05% glucose supported 1348 units of alginase at 40 hrs, which is 119 units more than the medium containing 0.5% alginate alone without glucose (FIG. 15). Increasing the glucose concentration, while decreasing alginate concentration delayed alginase production. With a combination of 0.4% A:0.1% G, alginase activity was not detected until 16 hrs and by further increasing glucose concentration to 0.15% (decreasing alginate concentration to 0.35%) detectable alginase production was delayed until 20 hrs. At 0.2% glucose (0.3% alginate), alginase activity was not detected for 24 hrs.

For prediction of alginase activity as a function of alginate/glucose combination, alginase activity was fitted to a quadratic equation over time and represented by the formula: $y = a + b_1 x + b_2 x^2$, where y is alginase activity, a is intercept, $b_1$ and $b_2$ are the graph partial regression coefficients, and x is time.

Figure 15A:
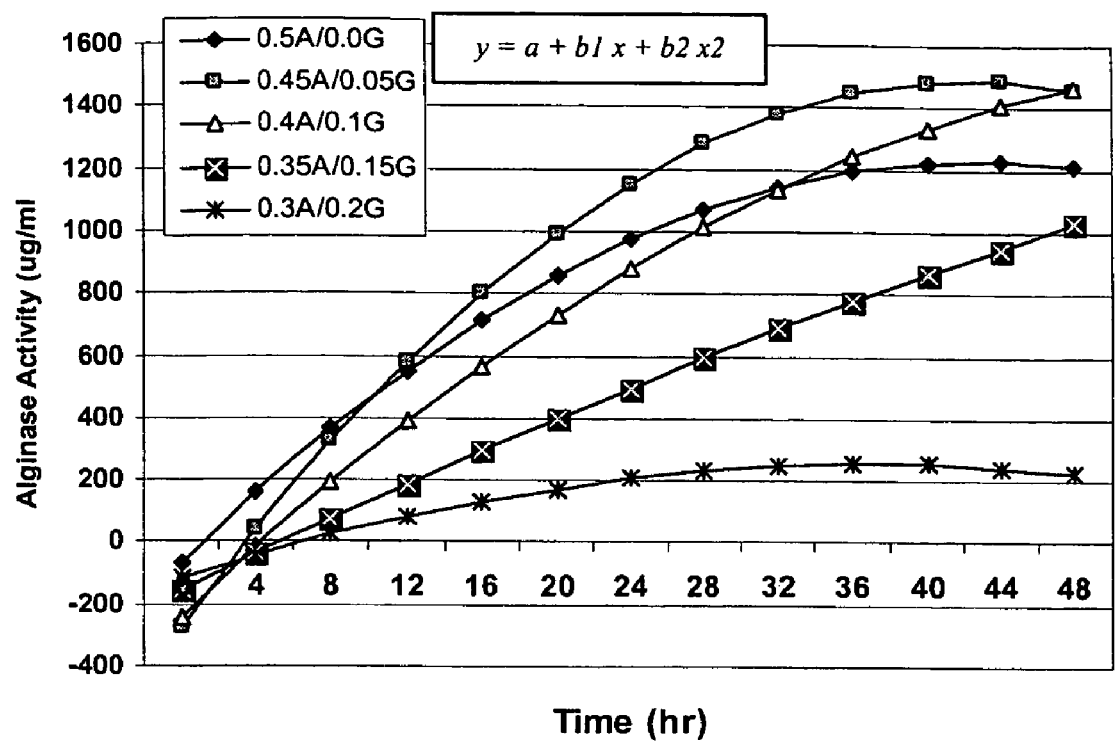
Figure 16:
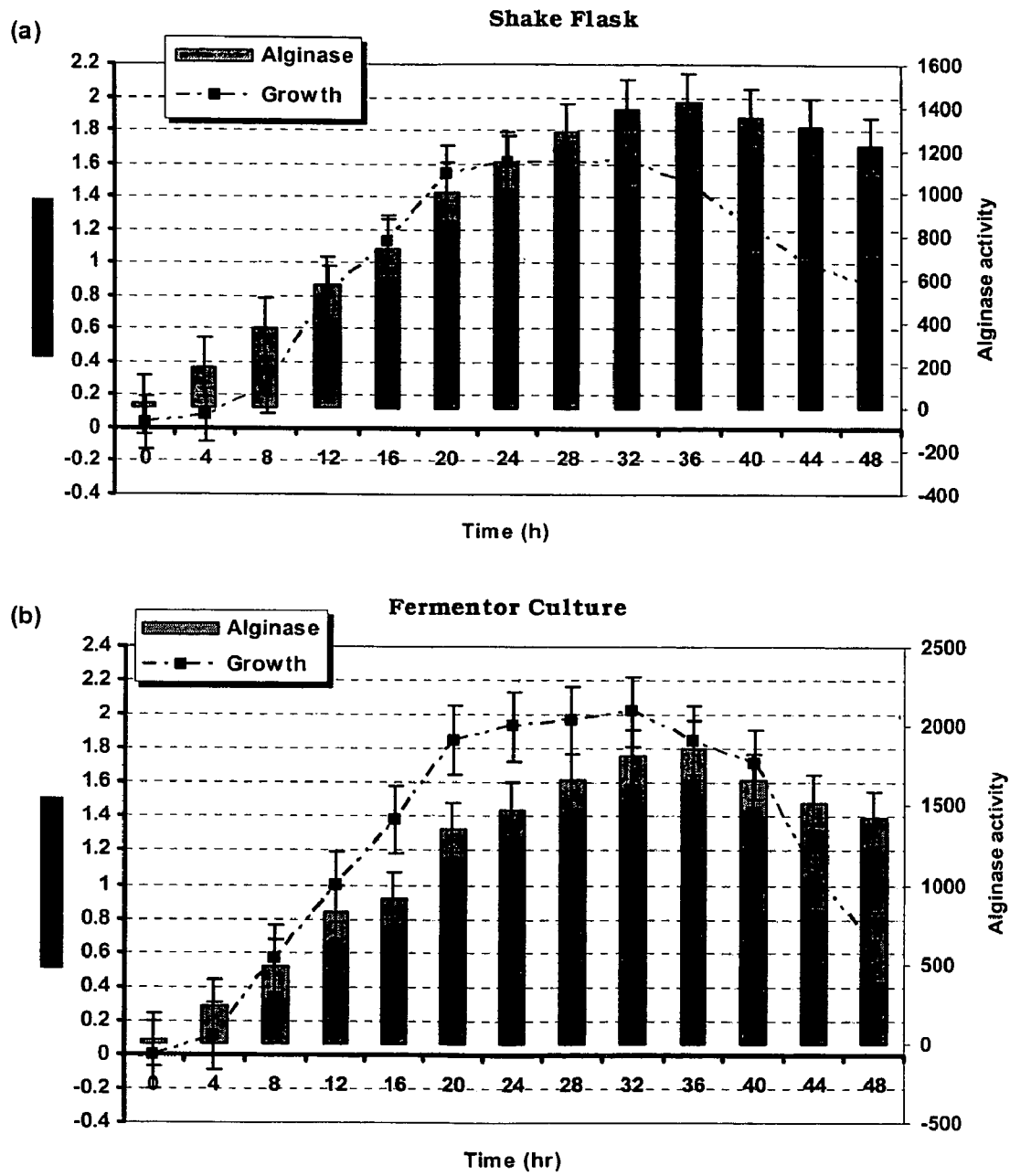
FIG. 16 are plots of the scale-up production of alginase by S. degradans 2-40.
Figure 18:
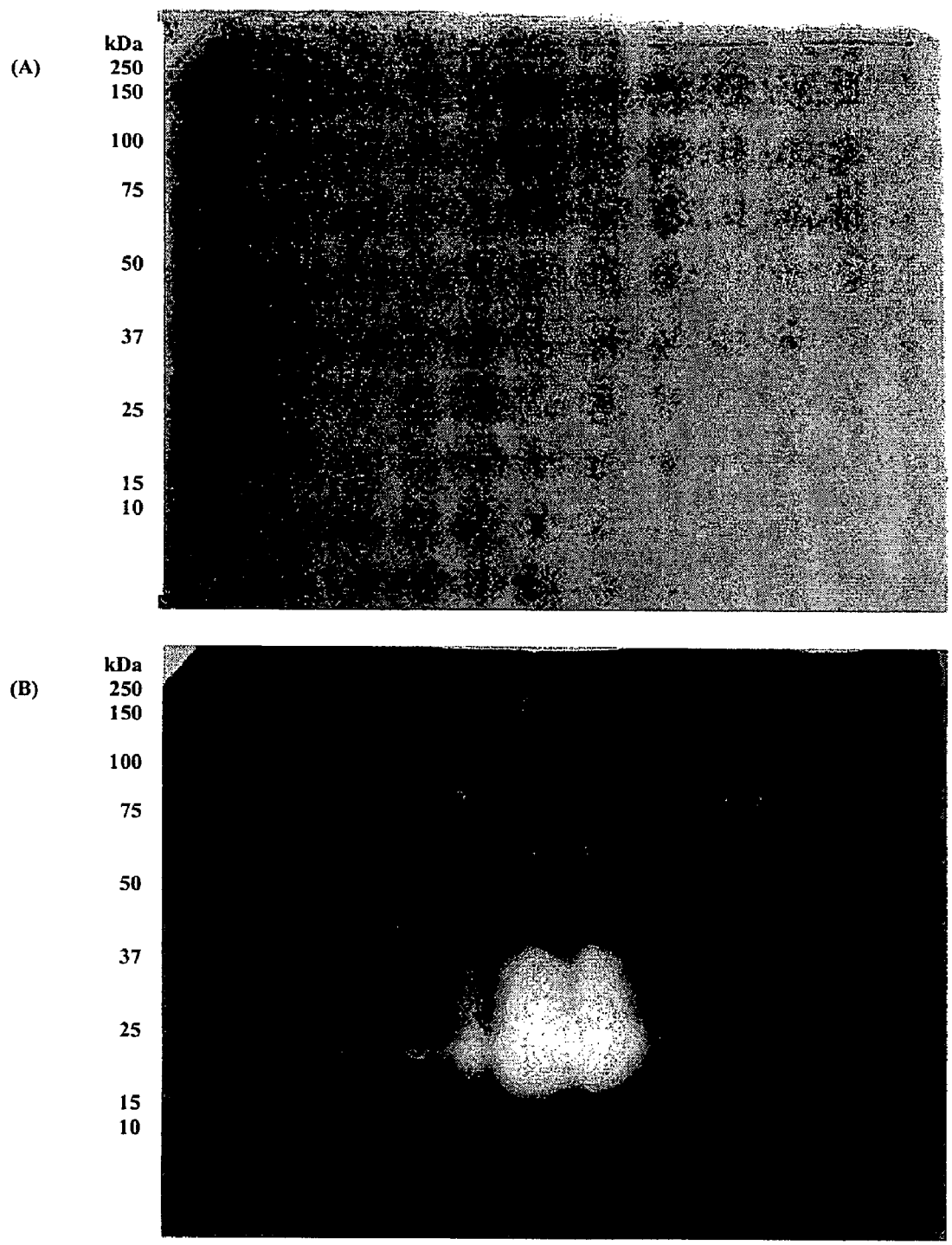
FIG. 18 shows electrophoresis of S. degradans 2-40 alginase and a zymogram gel.

The effect of growing 2-40 in varying Alginate/Glucose combinations (% A/% G) on alginase activity was fitted to a linear relationship over time (FIG. 15a), with $R^2$ ranging between 0.9072 and 0.9736 (also see Table 5.6a). Analysis of these data supported the initial observation that different percentage combinations were significant with respect to alginase production (Table 5.6a). Within the studied incubation period, the combination of 0.45% A/0.05% G induced 1476 alginase units at 42 hrs, which was higher than that induced by 0.5% A/0% G which was 1229 units at 43 hrs. Other A/G combinations induced even higher alginase activities, however beyond the studied incubation period. For instance, 0.4% A/0.1% G induced 1563 alginase units at 62 hrs of incubation, and 0.35% A/0.15% G required 140 hrs to induced 1936 alginase units. Alginase production in both 0.5% A/0% G and 0.45% A/0.05% G were compared with t-test and the difference was found significant. "F" values showed that variations caused by A/G combinations and time were significant (see Table 5.6b).

TABLE 5.6a

Intercept (a), partial regression coefficients ($b_1$ and $b_2$) for alginase activity as a function of alginate/glucose mix ratio (A/G)

| | A %/G % Combinations | | | | |
|---|---|---|---|---|---|
| | 0.5A/ 0.0G | 0.45A/ 0.05G | 0.4A/ 0.1G | 0.35A/ 0.15G | 0.3A/ 0.2G |
| a | −69.84 | −275.45 | −239.31 | −154.32 | −115.55 |
| b1 | 60.1302 | 82.5299 | 57.8239 | 29.6615 | 19.6454 |

TABLE 5.6a-continued

Intercept (a), partial regression coefficients ($b_1$ and $b_2$) for alginase activity as a function of alginate/glucose mix ratio (A/G)

| | A %/G % Combinations | | | | |
|---|---|---|---|---|---|
| | 0.5A/ 0.0G | 0.45A/ 0.05G | 0.4A/ 0.1G | 0.35A/ 0.15G | 0.3A/ 0.2G |
| b2 | −0.6956 | −0.9724 | −0.4638 | −0.1052 | −0.2610 |
| Maximum activity (y) | 1229 | 1476 | 1563 | 1936 | 254 |
| Time of max activity (x) | 43 | 42 | 62 | 140 | 38 |
| $R^2$ | 0.9736 | 0.9072 | 0.9157 | 0.9424 | 0.9578 |

Maximum alginase activities obtained in 0.5A/0.0G and 0.45A/0.05G were analyzed with t-test and the difference between the two combinations was found significant at DF = 74 and P < 0.05.

TABLE 5.6b

ANOVA table for alginase activity as a function of alginate/glucose mix ratio (A/G) in 2-40 growth medium.

| Source | DF | SS | SS %[a] | Mean Square | F Value[b] |
|---|---|---|---|---|---|
| (A/G) | 4 | 3221196 | 5.6 | 805299 | 55538 |
| Error I | 10 | 145 | 0 | 14.5 | |
| T | 12 | 51507752 | 89 | 4292313 | 255.57 |
| Linear T | 1 | 47594980 | (82.7) | 47594980 | 2834 |
| Quadratic T | 1 | 958480 | (1.67) | 958480 | 57 |
| Error II | 168 | 2821596 | 5 | 16795 | |
| Corrected Total | 194 | 57550689 | 100 | | |

Source: source of variations,
DF: Degrees of freedom,
SS: Sum of Squares,
Coefficient of variation = 17.38089,
$R^2$ = 0.950972
[a]SS % = (SS variable/SS Total) * 100
[b]F values are significant at P < 0.0001, except where otherwise mentioned
[c]F value is significant at P = 1.0

Scale-up of alginase production of 2-40

Figure 28:
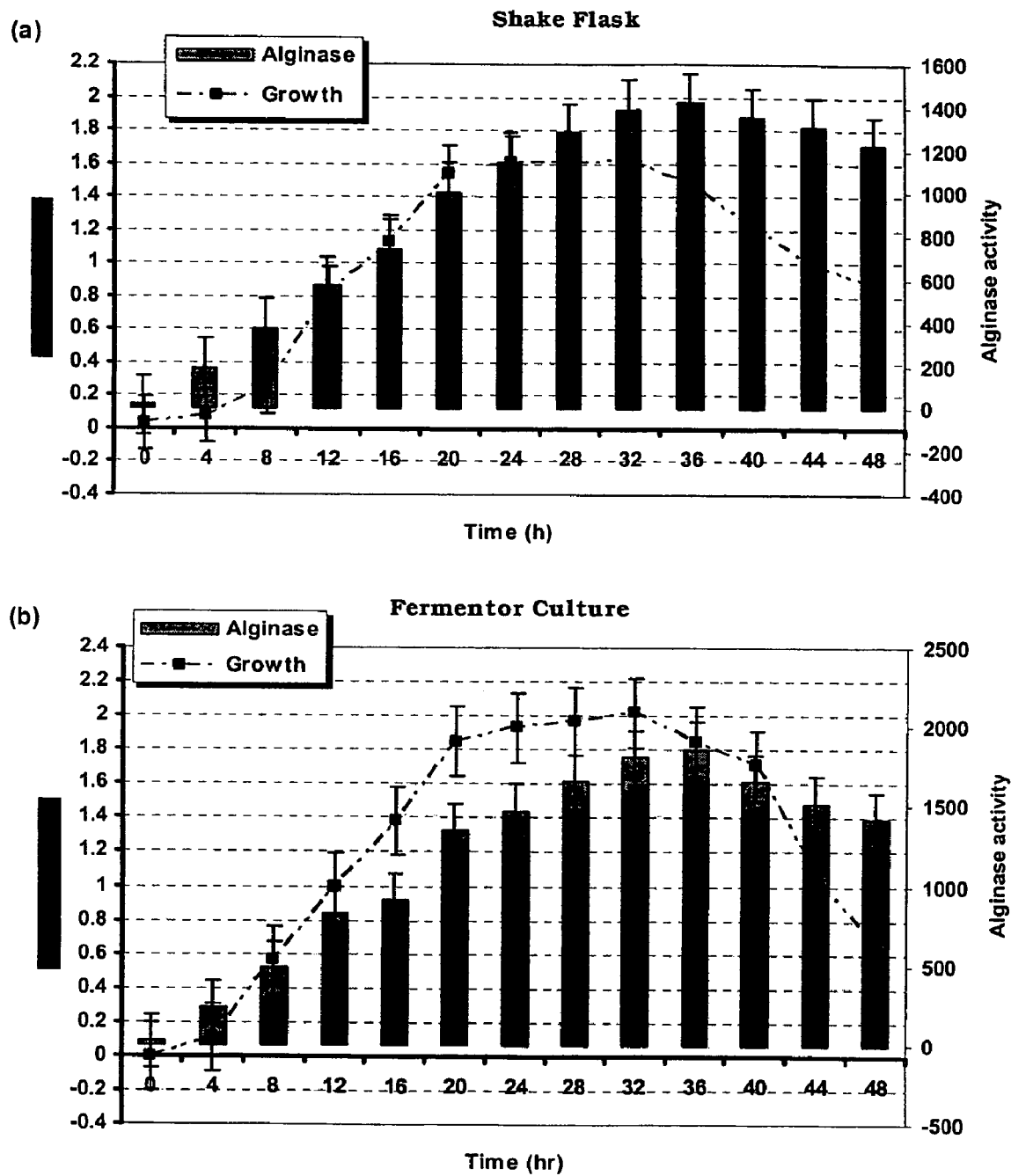
FIGS. 28 (a and b) and 28b are plots of related to shake flask and fermenter cultures.

An optimum medium composition, shown in Table 3.1, was used for the remainder of the experiments because experiments showed that a medium (Alginase Production Medium, APM) composed of: 0.05% glucose, 0.45% alginate, 3.5% sea salts, and 0.2% Yeast extract, pH 7.6 enhanced alginase production nearly two fold (1354 units vs. 693 units, a 95% increase, Table 3.8) more than the preliminary minimal medium. In APM, the lag phase was 8 hrs, the log phase lasted 12 hrs with generation time of 3.68 hr. Stationary phase was reached after 20 hrs, and lasted for 12 hrs after which the decline phase began. The most productive time for alginase harvest was, in fact, at 39 hr, 1355 alginase units at the beginning of the decline phase (FIG. 28 and Table 3.7). This experiment served as a preparatory step for the scale-up experiment of alginase production.

It was postulated that the oxygen limitations of the shake flask would be minimized using a stirred fermentor, with stirring at 400 rpm, and aeration at 6000 cc/min and temperature at 25° C. In APM, the lag phase was 4 hrs, the log phase lasted 16 hrs with generation time of 2.3 hr. Stationary phase was reached after 20 hrs, lasting for 12 hrs after which the decline phase began. The most productive time for alginase harvest was, in fact, at 36 hr, which yielded 1690 alginase units at the beginning of the decline phase. Under these conditions, and after 36 hrs, 2-40 total cells registered an OD of 1.85. I. Growth and alginase production of this experiment are shown in FIG. 28 and Table 3.7. There was no pH control. The initial pH of the un-inoculated medium was 7.6 and the pH of the spent culture was 8.2.

Figure 28B:
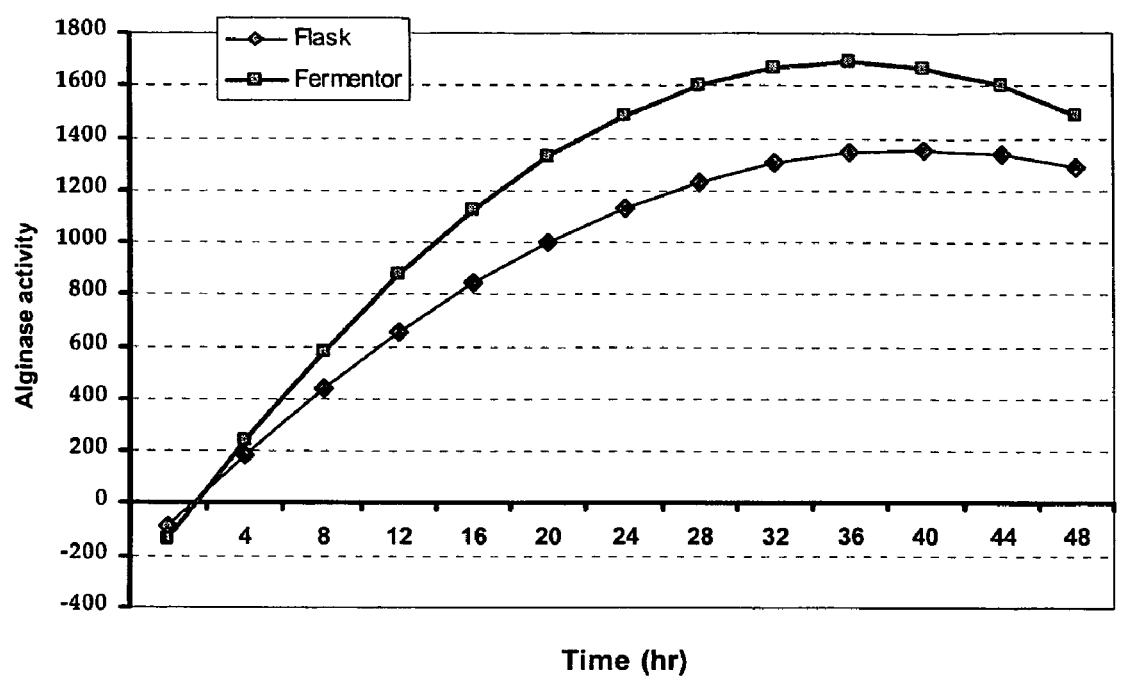

FIG. 28b compares the growth of 2-40 in the optimized alginase production medium (APM) in flask batch culture and in a fermentor. Alginase activity was fitted to a linear relationship with time with $R^2$ value of 0.9811 for the flask and 0.9560 for the Fermentor (Table 5.7). Data analysis showed the maximum alginase activity was reached in shorter time in the case of Fermentor (1690 alginase units at 36 hrs) than in the case of the flask (1355 alginase units at 39 hrs). Analysis of variance of alginase activity showed that 89% of variations were attributed to time, while 3.6% of the variations were attributed to type of incubation vessel. "F" values showed that variations attributed to difference in the incubation vessel type were significant.

5.7 Analysis of the effect of growing 2-40 in flask or fermentor on alginase activity.

TABLE 5.7

ANOVA table for alginase activity as a function of incubation vessel (V), Flask vs. Fermentor, and their interaction (V * T)

| Source | DF | SS | SS %[a] | Mean Square | F Value[b] |
|---|---|---|---|---|---|
| V | 1 | 873865.85 | 3.6 | 873865.85 | 40.45 |
| T | 12 | 21468786 | 89 | 1789065.52 | 82.81 |
| Linear T | 1 | 17129566 | (71) | 17129566 | 792.88 |
| Quadratic T | 1 | 3545159 | (14.8) | 3545159 | 164 |
| V * T | 12 | 502316 | 2 | 41859.71 | 1.94[c] |
| Error | 52 | 1123423 | 4.7 | 21604 | |
| Corrected Total | 77 | 23968391 | 100 | | |

Source: source of variations,
DF: Degrees of freedom,
SS: Sum of Squares,
Coefficient of variation = 14.24759,
$R^2$ = 0.953129
[a]SS % = (SS variable/SS Total) * 100
[b]F values are significant at P < 0.0001, except where otherwise mentioned is significant at P = 0.0508

TABLE 3.8

Optimization of 2-40 growth medium for alginase production.

| # | Medium composition[a,b] | Type of experiment | Alginase peak time (hr)[c] | Alginase activity at peak time (μg reducing sugar/ml/30 min)[d] | % increase[e] | Cost/liter (per 1000 alginase units)[f] |
|---|---|---|---|---|---|---|
| 1 | 0.2% Alg 0.1% YE 2.3% IO | Shake Flask | 36 | 693 | 0 | $1.01/L ($1.548) |
| 2 | 0.5% Alg | Shake | 37 | 1019 | 47 | $1.39/L |

TABLE 3.8-continued

Optimization of 2-40 growth medium for alginase production.

| # | Medium composition[a,b] | Type of experiment | Alginase peak time (hr)[c] | Alginase activity at peak time (μg reducing sugar/ml/30 min)[d] | % increase[e] | Cost/liter (per 1000 alginase units)[f] |
|---|---|---|---|---|---|---|
|   | 0.1% YE 2.3% IO | Flask |  |  |  | ($1.364) |
| 3 | 0.5% Alg 0.2% YE 2.3% IO | Shake Flask | 34 | 1162 | 68 | $1.576/L ($1.356) |
| 4 | 0.5% Alg 0.2% YE 3.5% IO | Shake Flask | 39 | 1252 | 81 | $1.606/L ($1.283) |
| 5 | 0.45% Alg + 0.05% Glu 0.2% YE 3.5% IO | Shake Flask | 39 | 1476 | 113 | $1.87/L ($1.381) |
| 6 | 0.45% Alg + 0.05% Glu (APM)[g] 0.2% YE 3.5% IO | Fermentor (Scale-up) | 36 | 1690 | 143 | $1.87/L ($1.107) |

[a]medium ingredients are referred to as:
Alg: Alginate, YE: Yeast Extract, IO: Instant Ocean, Glu: Glucose.
[b]Ingredient shown in Bold indicates final modifications in medium composition.
[c]peak time (time of maximum alginase activity) was calculated using the proper statistical analysis (discussed later).
[d]Alginase activity compared with medium # 1, Alginase activity at peak time was calculated using statistical analysis.
[e]percentage increase in alginase activity compared to that obtained from 0.2% alginate minimal medium.
[f]cost per liter of medium included the cost of Tris-HCl and $NH_4Cl$. Cost was then divided by the alginase units produced to give the cost per 1000 units of alginase activity. All cost are in USD.
[g]Alginase Production Medium (APM).

The alginase slurry purification criteria are shown in table 3.2. The fermentor's cell-free supernatant was concentrated, using the Pellicon XL concentration device (Millipore) fitted with 10 kDa MW cut-off PGCLC10 membrane (Millipore, Piscatway, N.J.), to 200 ml. This step increased the specific activity (μg reducing sugar/mg protein/ml) 10 fold. Ammonium sulfate precipitation, dialysis, and then ultra-filtration (10 kDa cut-off Mw), each further increased the alginase activity to a final total of 21× the alginase activity in the starting cell-free extract (Table 3.9).

TABLE 3.9

Purification of alginase and its specific activity.

| Purification step | Vol. (ml) | μgRS/ ml[1] | Total units (×1000) | mg protein/ ml[2] | Total protein | SA[3] μgRS/mg protein/ml | Yield (%) | x-fold |
|---|---|---|---|---|---|---|---|---|
| Cell-free extract | 7300 | 1687 | 12315 | 0.78 | 5721 | 2153 | 100 | 1 |
| Pellicon XL[4]-Filtrate | 7100 | 12 | 85 | 0.75 | 5335 | 16 | 0.69 | 0 |
| Retentate | 200 | 31200 | 6240 | 1.44 | 288 | 21667 | 51 | 10 |
| Ammonium Sulfate precipitate | 160 | 30125 | 4820 | 0.98 | 156 | 30897 | 39 | 14 |
| Dialysis | 112 | 36852 | 4127 | 1.04 | 117 | 35273 | 34 | 16 |
| Ultra-filtration[5] | 45 | 38650 | 1739 | 0.86 | 39 | 44590 | 14 | 21 |

[1]μg reducing sugar (RS)/ml, determined by DNSA standard method (see materials and methods).
[2]protein concentration was determined by BCA method (see materials and methods).
[3]Specific activity (SA) units calculated as μg/ml RS per mg/ml protein.
[4]cut-off Mw is 10k Da for pellicon XI membrane
[5]cut-off Mw is 10k Da for Ultra-filtration membrane.

Previous results showed that the most abundant alginate depolymerase has MW of 66 kDa (Chakravorty 1998). However, the present work showed that out of six different active alginases, the 58 kDa alginase (later to be identified in the genome annotation as AlgE) had the highest activity as demonstrated by the zymograms. The aim was to purify, concentrate, and study this alginase and the total alginase concentrate (ultra-filtrate, Table 3.9).

Figure 19:
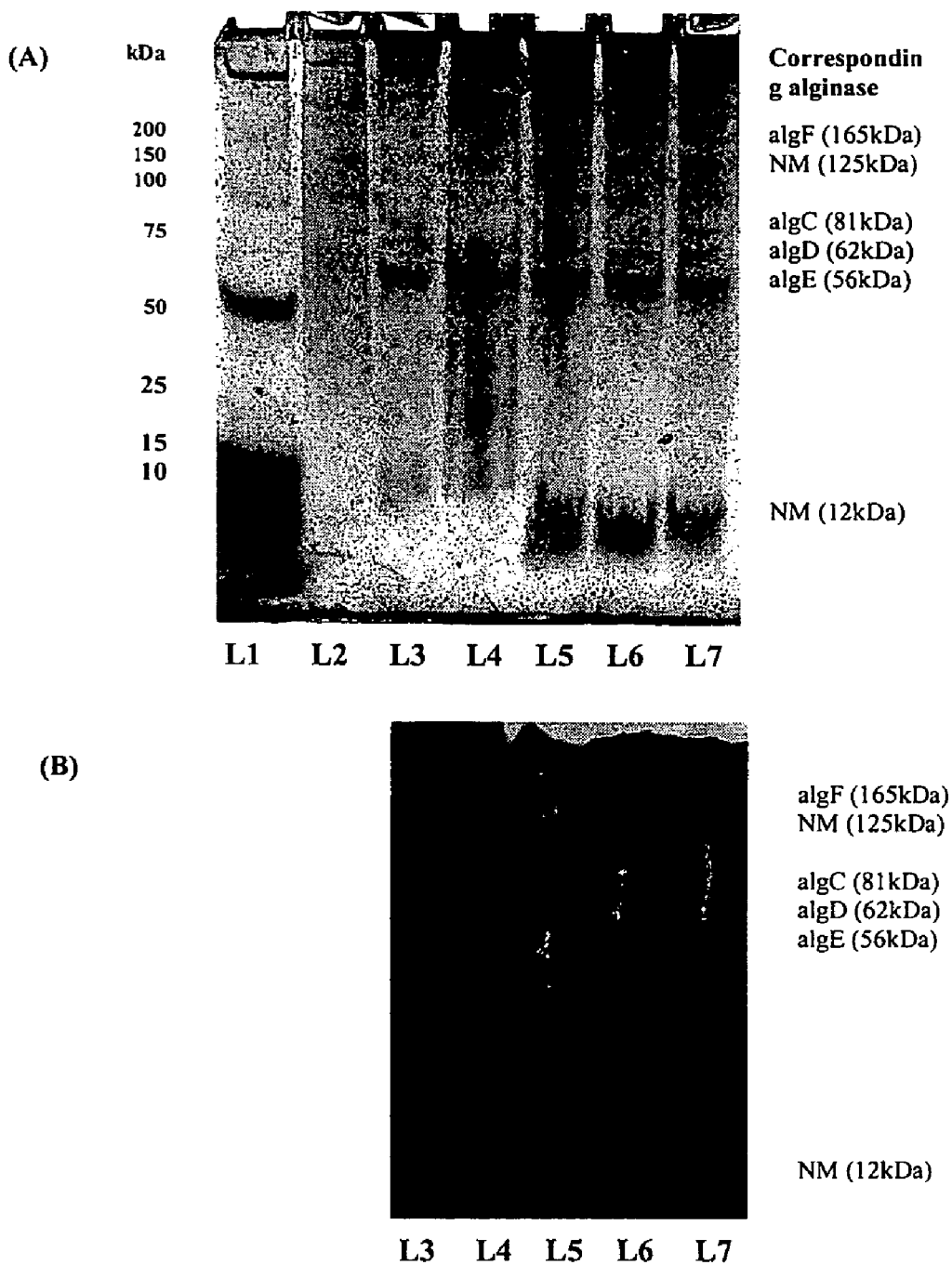
FIG. 19 shows separation of S. degradans 2-40 alginases and a zymogram gel.

To identify and determine the molecular weights of the alginases, proteins in the alginase concentrate were first separated by 12% sodium dodecyl sulfate polyacrylamide get electrophoresis (SDS-PAGE), according to standard procedure (Laemmli 1970), and 12% native-PAGE. The native-PAGE was then overlaid on an 8% polyacrylamide gel containing 0.1% alginic acid and incubated for 16 hrs in 6.8pH PIPES buffer (see Materials and Methods). A comparison of the active bands revealed by the zymogram with those of the SDS-PAGE gel allowed the identification of six alginases. The molecular weights of these alginases, as determined by the SDS-PAGE, were 12, 56, 62, 81, 125 and 165 kDa (FIG. 19). The most active alginase was the 56 kDa, based on the loss of staining from the protein band in the zymogram.

Figure 20:
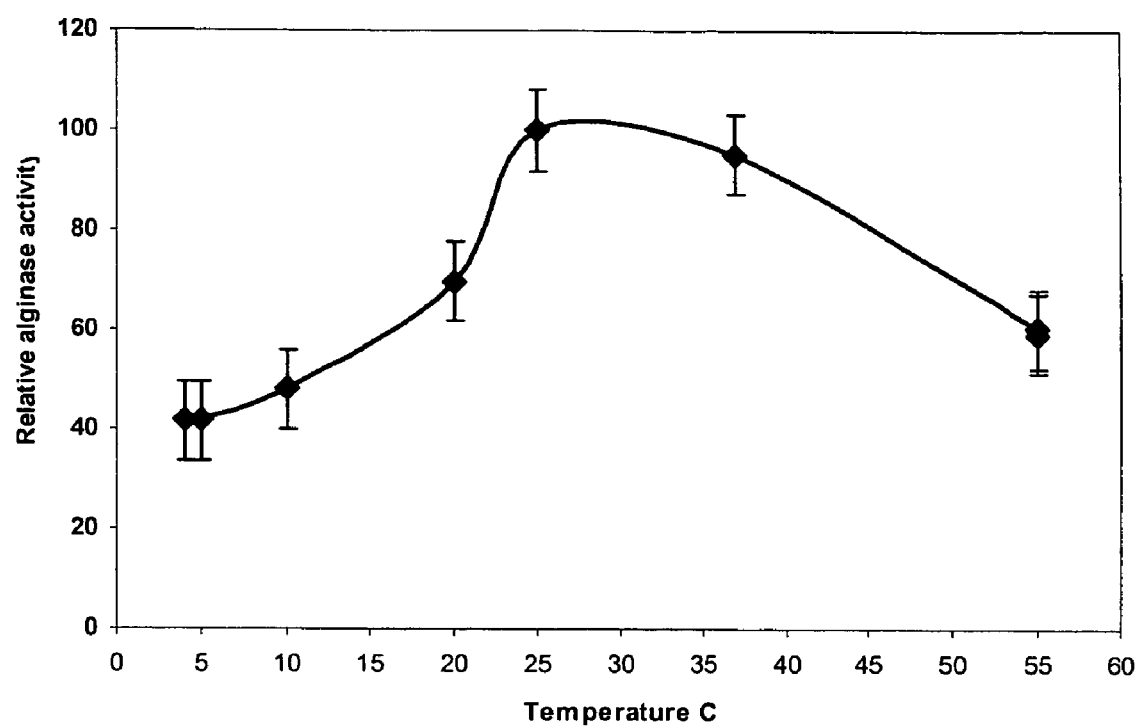
FIG. 20 shows alginase activities as a function of incubation temperature.
Figure 21:
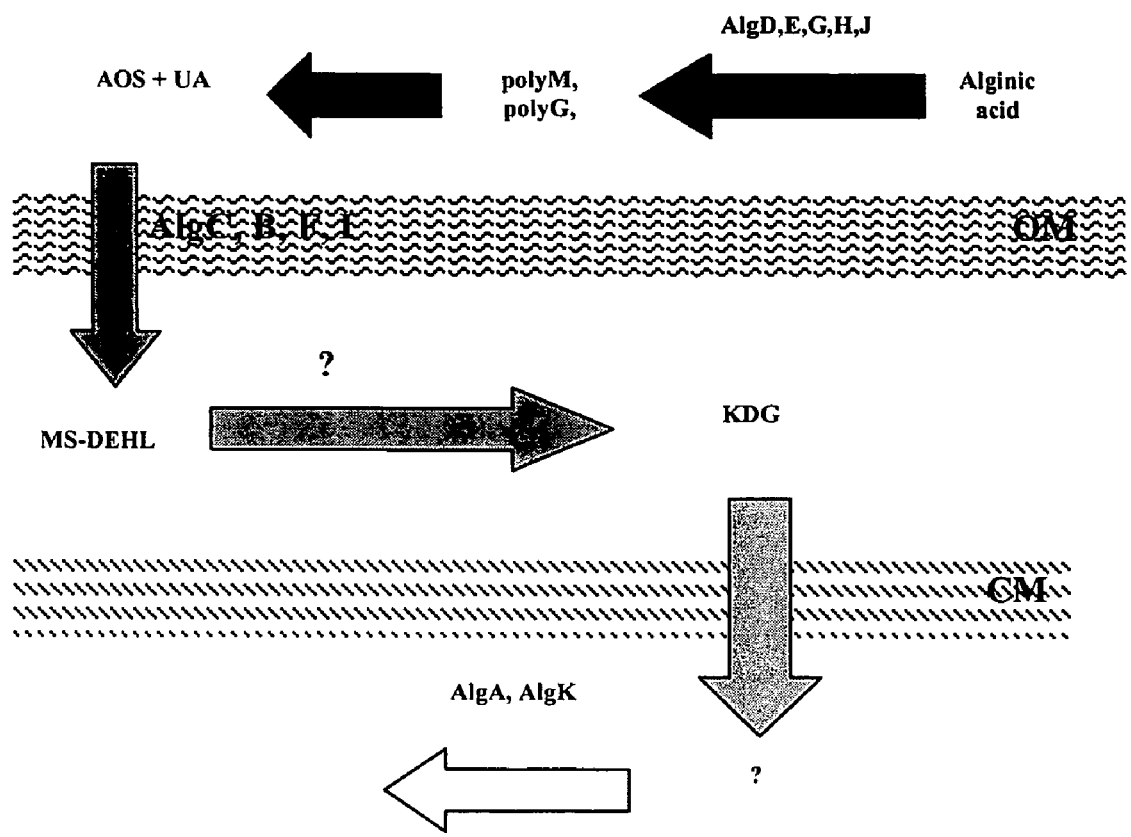
FIG. 21 shows a predicted pathway for alginic acid degradation and transport.
Figure 22:
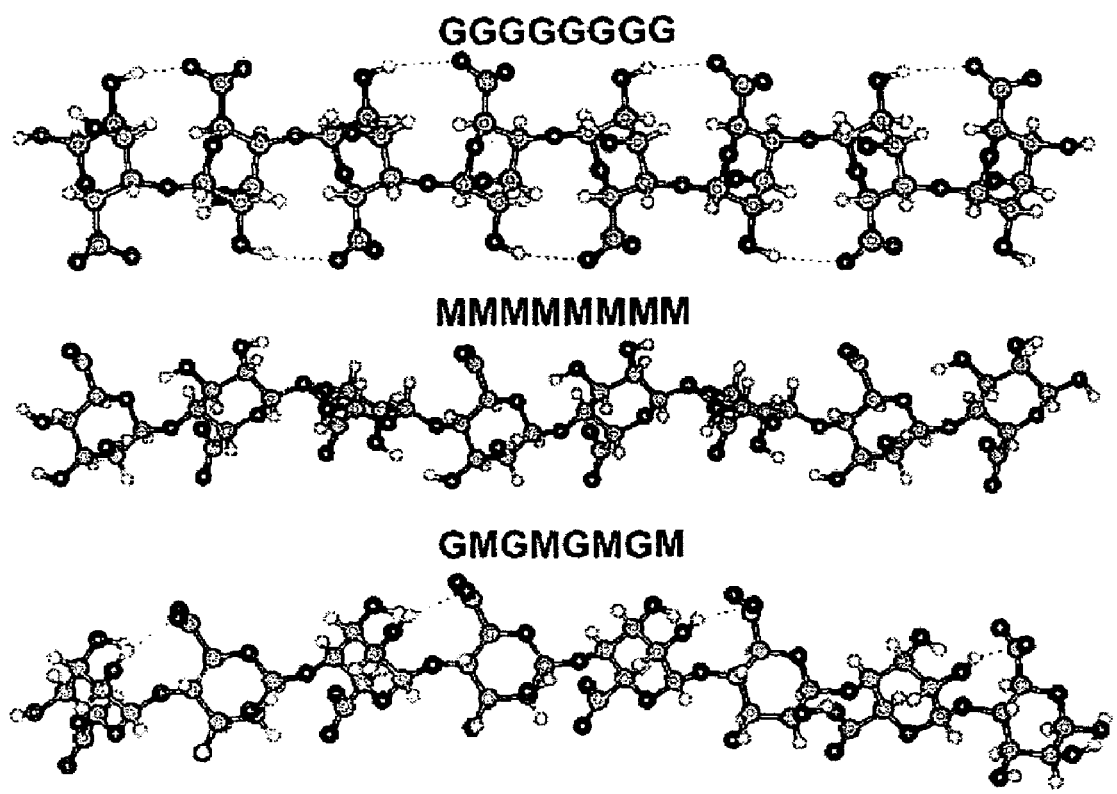
FIG. 22 shows the alginate backbone structure.
Figure 23:
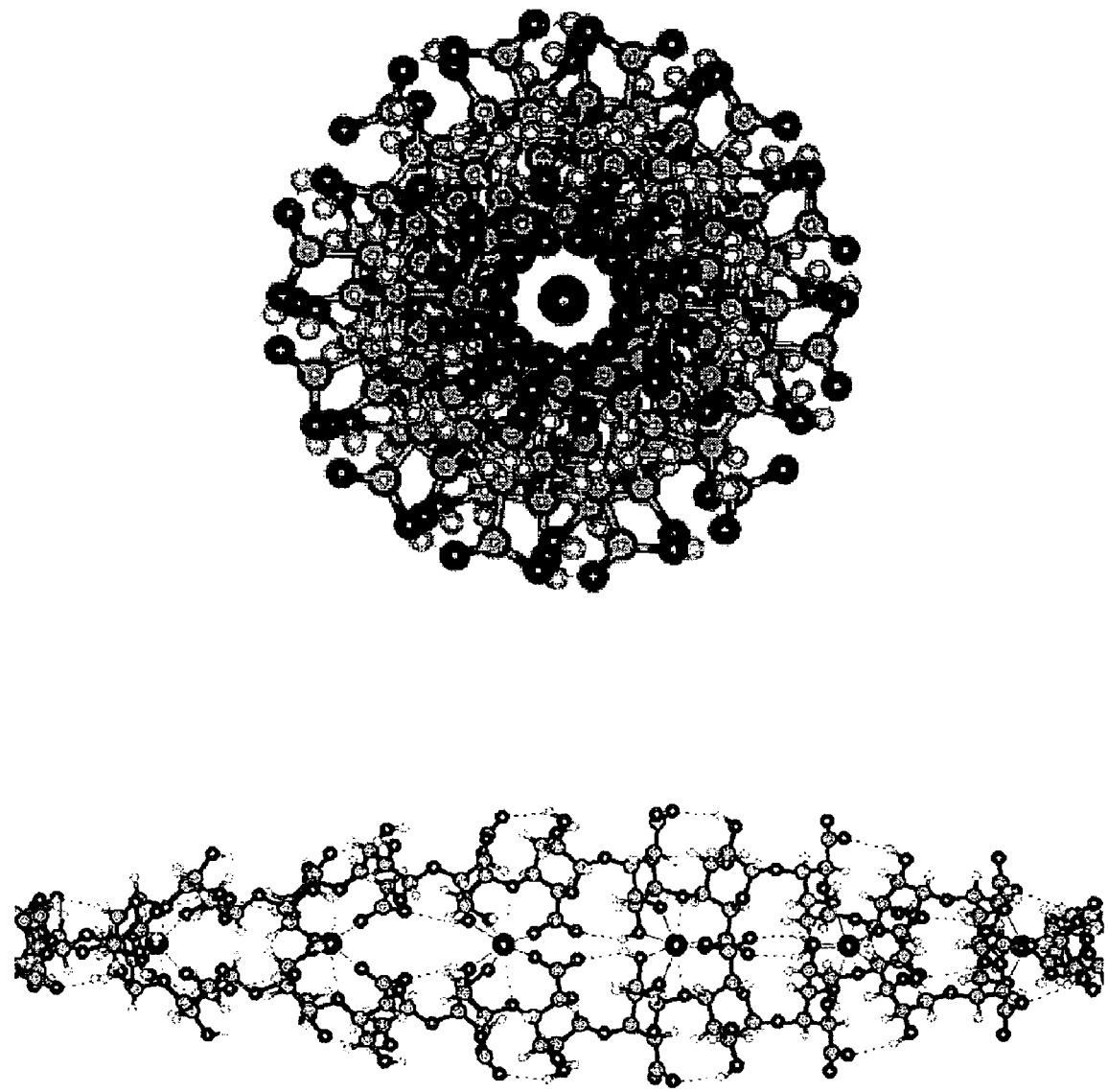
FIG. 23 shows the backbone structure of calcium poly-a-L-guluronate left-handed helix.

To determine the optimum temperature for total alginase activity, aliquots of the alginase concentrate were incubated with 0.5% alginic acid for 30 min at 5, 10, 20, 25, 37, and 55° C. and alginase activity was assayed by the DNSA method. Alginase activity was optimum at a temperature range between 20 and 37° C., with maximum activity at 25° C. (FIG. 20). At elevated temperatures, alginase activity was reduced to 60% of the activity detected at 25° C. after 30 min. At temperature below 20° C., alginase activity dropped to 48% relative to the activity detected at 25° C.

Figure 3:
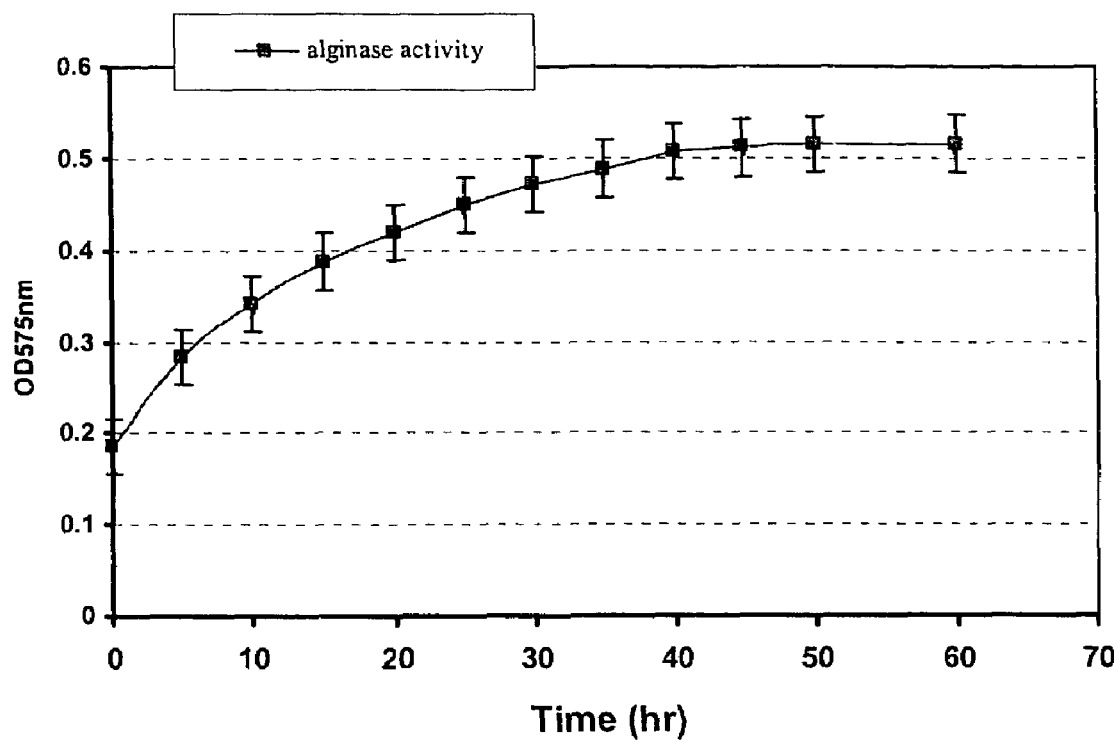
FIG. 3 shows alginase activities as a function of time.
Figure 4:
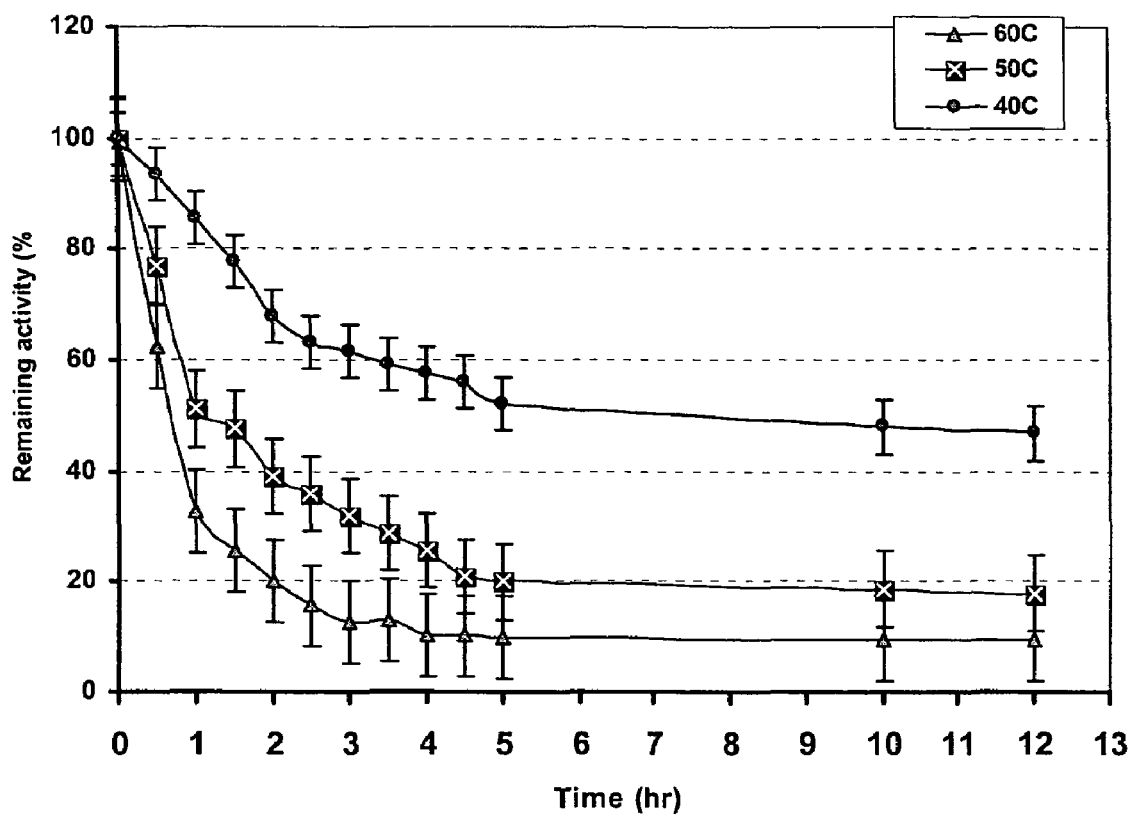
FIG. 4 shows thermostability of alginase.

Aliquots of alginase concentrate were incubated with 0.5% alginate, pH 7.0, at 25° C. First order kinetics for the first 30 min indicated that the DNSA was not substrate-limited over that interval. This is why the DNSA was determined after 30 min, (FIG. 3).

Aliquots of the alginase concentrate in 20 mM PIPES buffer, pH 6.8, were equilibrated to 40, 50 and 60° C. in water baths for 12 hrs. At intervals, alginase samples were withdrawn and cooled in ice and alginase remaining activity was assayed by the DNSA method. At 40° C., the mixed alginase slurry was more stable than at 50° C. which was more stable than 60° C. After one hour (FIG. 13), the alginase preparation lost approximately 15% of its activity at 40° C., 50% at 50° C. and 70% at 60° C. The hyperbolic denaturation curves suggest that one or more of the enzymes in the slurry were heat resistant.

Figure 5:
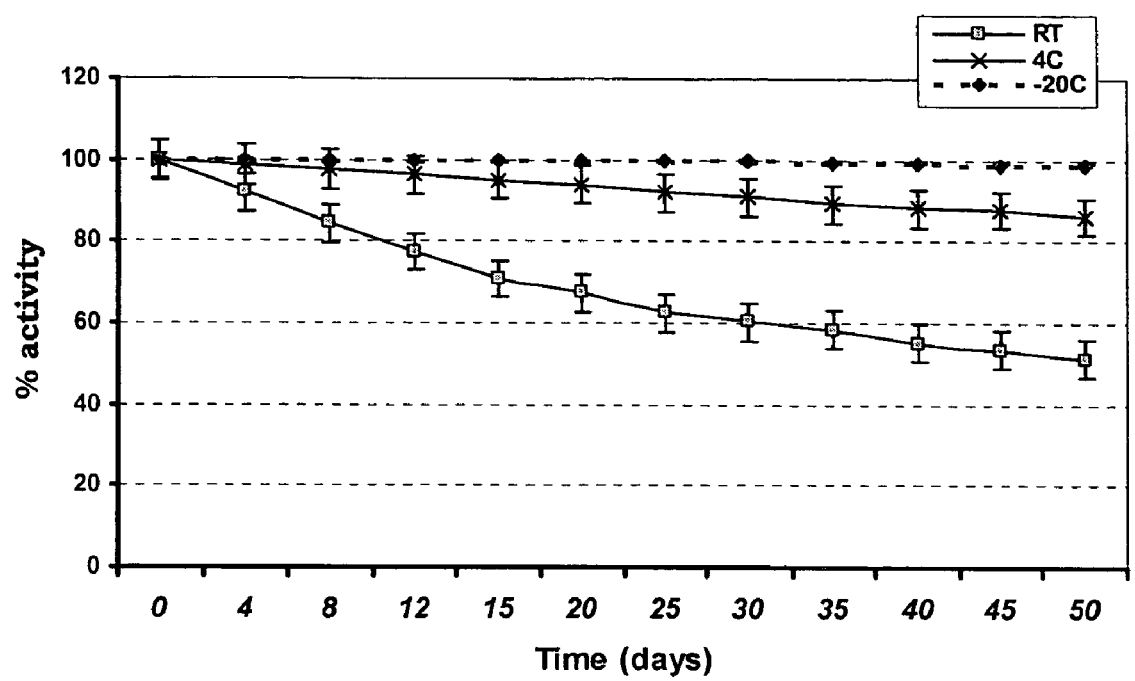
FIG. 5 shows alginase shelf-life.

To determine the shelf-life of the alginase concentrate, 0.5 ml aliquots were dispensed and divided into three sets of tubes. One set was stored at room temperature (25° C.), the second at 4° C., and the third at −20° C. All preparations were stored for up to 60 days. Several tubes were removed from each set at intervals and alginase activity was determined. Alginase was stable at −20° C. (FIG. 5). At 4° C., alginase retained 84% of its activity at the end of 60 days, while at room temperature; it retained less than 50% of its activity.

Figure 6:
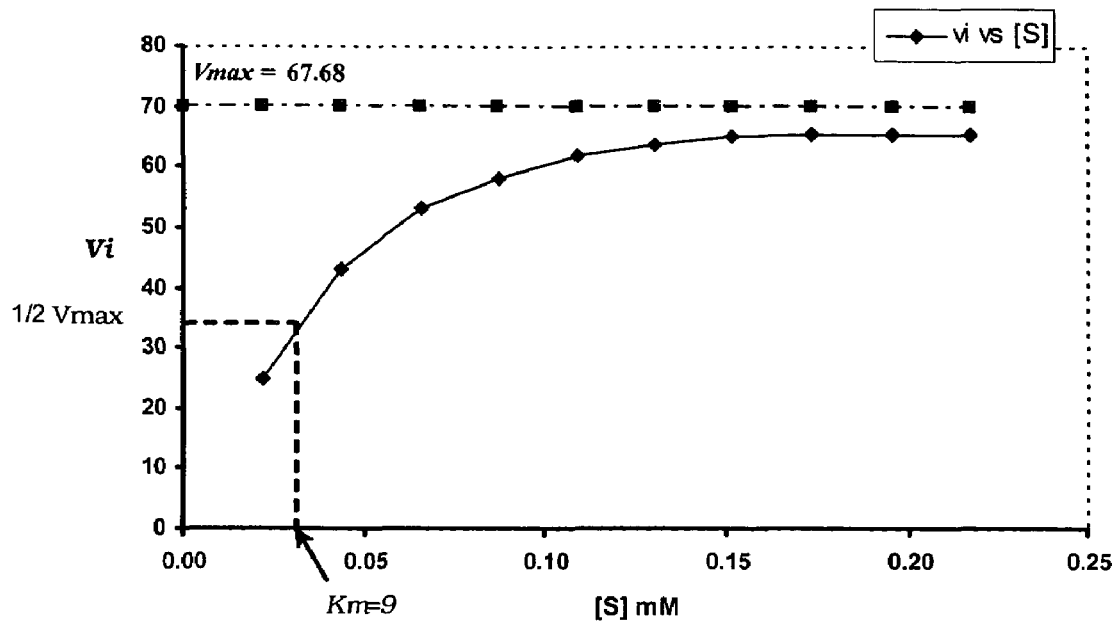
FIG. 6 is a plot of alginase activity rate as a function of alginic acid concentration.

3.3.6 Alginase kinetics. The success of enzyme analysis depends to a great extent on the purity of the enzyme. Additionally, using too little; or too much; enzyme can also lead to analysis failure. However, appropriate amounts, of the partially purified enzymes, can also be analyzed (Lowry and Passonneau 1972). To determine the relative affinity of alginase for its substrate, the Michaelis-Menten constant was determined using the alginase concentrate. 100 μl, containing approximately 86 μg protein, were mixed with alginic acid at concentration from 0.1 to 1.0% and incubated at 25° C. Alginase activity was monitored over a period of 2 hrs. The reaction's initial rate, $K_m$ and $V_{max}$ were calculated. The relationship between the initial velocity, (v), of alginase and the concentration of alginic acid [S], the substrate, was determined by Michaelis-Menten plot, (FIG. 6). The data revealed that the maximum velocity, ($V_{max}$), was approximately 67.68 □g reducing sugar/min and the $K_m$ was 0.0253 mM, suggesting that alginase has a high affinity for its substrate, alginate[1] Molecular weight of sodium alginate was obtained from Sigma, ranging from 12 kDa to 80 kDa. Hence the average, 48 kDa, was used in the calculation of $K_m$ and $V_{max}$.[8]

[8]Molecular weight of sodium alginate was obtained from Sigma, ranging from 12 kDa to 80 kDa. Hence the average, 48 kDa, was used in the calculation of $K_m$ and $V_{max}$.

Figure 7:
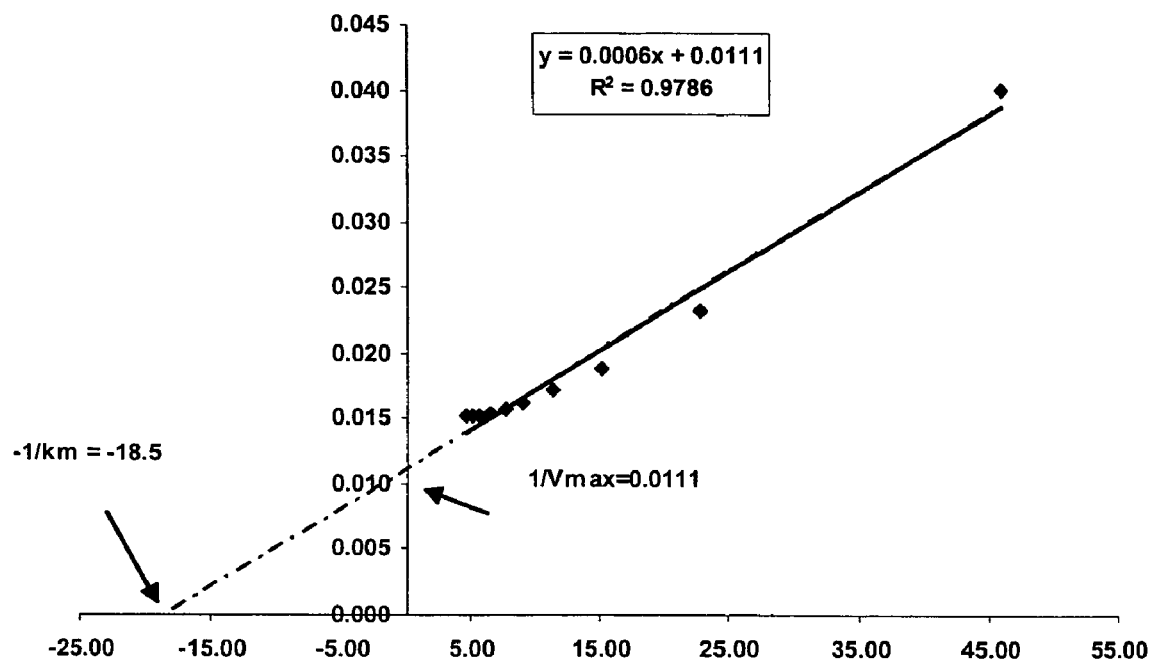
FIG. 7 is a plot of alginase initial velocity as a function of the reciprocal of the alginate concentration.
Figure 8:
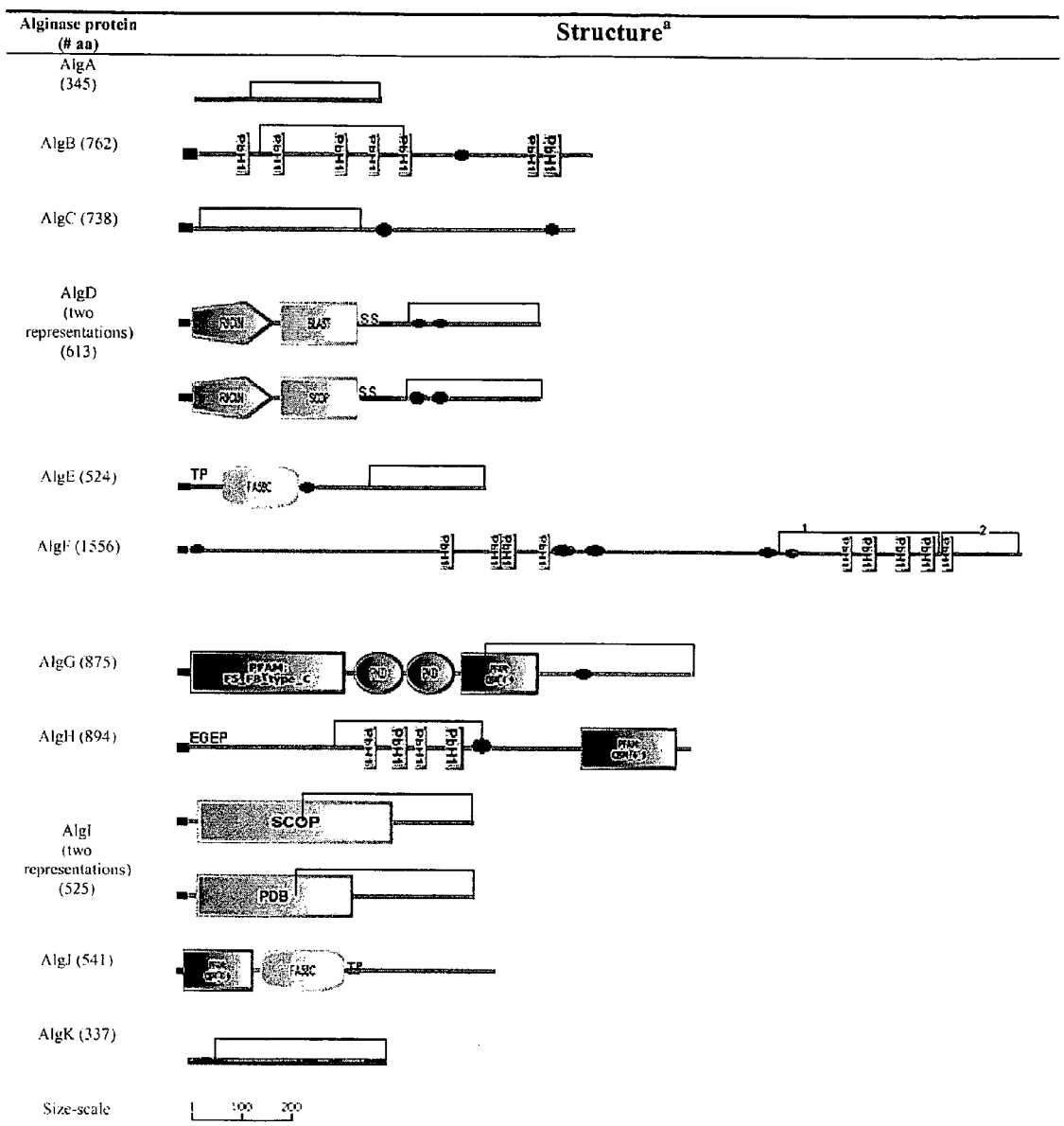
FIG. 8 shows domain structure of the S. degradans 2-40 alginases.

However, because of the hyperbolic shape, Michaelis-Menten plot made it difficult to extrapolate accurately to infinite substrate concentration in order to accurately calculate $V_{max}$, and thus $K_m$. Therefore, Lineweaver-Burk plot was constructed by converting the hyperbolic relationship of Michaelis-Menten equation into a linear function (Lineweaver and Burk. 1937). This was done by plotting the reciprocal of the initial velocity, 1/v, against the reciprocal of alginate concentration, 1/[S]. Hence, $V_{max}$ and $K_m$ were more precisely computed to be 90.09 μgRS/min and 0.054 mM, respectively (FIG. 7). These values are comparable to those determined for purified alginate lyases from other microorganisms (Table 3.10).

TABLE 3.10

$K_m$ values for bacterial alginase compared to 2-40 aglinase

| | Alginate (source) | $K_m$ | $V_{max}$ | Ref |
|---|---|---|---|---|
| 2-40 | *Macrocysts pyrifera* | 2592 mg/ml (0.054 mM) | 90.09 □gRS/min | This work |
| *Azotobacter vinelandii* | M-alginate from *P. aeruginosa*. | 0.46 mM | NR | Ertesvåg et al., 1998 |
| *Pseudomonas* sp. | I - *A. vinelandii* | 1500 mg/ml | NR | Davidson et al., 1976 |
| Pseudomonas sp. | VIII - *A. vinelandii* | 1850 mg/ml | NR | Davidson et al., 1976 |
| *Pseudomonas* sp. | IV - *A. vinelandii* | 2460 mg/ml | NR | Davidson et al., 1976 |
| *Pseudomonas* sp. | V - *A. vinelandii* | 2180 mg/ml | NR | Davidson et al., 1976 |
| *Pseudomonas* sp. | VII - *A. vinelandii* | 4400 mg/ml | NR | Davidson et al., 1976 |

TABLE 3.10-continued

K$_m$ values for bacterial alginase compared to 2-40 aglinase

| | Alginate (source) | K$_m$ | V$_{max}$ | Ref |
|---|---|---|---|---|
| A. chroococcum | Macrocysts pyrifera | 0.08 mM | 183 □g/min | Peciña et al., 1999 |
| AlxM$_B$ from recombinant E. coli | M. pyrifera alginate | 0.011 mM | 141 □mol/min | Chavagnat et al., 1998 |
| AlxM$_B$ from recombinant E. coli | M-blocks[1] | 0.60 mM | 139 □mol/min | Chavagnat et al., 1998 |
| AlxM$_B$ from recombinant E. coli | pentamannuronate | 0.180 mM | 103 □mol/min | Chavagnat et al., 1998 |
| Klebsiella aerogenes | Poly-mannuronate (in 0.05M Tris buffer) | 0.059 mg/ml | 0.019 AU/min[2] | Haugen et al., 1990 |
| Haliotis sp. | Poly-mannuronate (in 0.05M Tris buffer) | 0.052 mg/ml | 0.026 AU/min[2] | Haugen et al., 1990 |

NR: Not reported
[1]M-blocks: mannuronate blocks were prepared from bacteria alginates as reported by Heyraud et al., 1998.
[2]Enzymatic activity was reported as absorbance units (AU) per min A draft of sequence of the 2-40 genome was obtained in conjugation with the United States Department of Energy Joint Genome Institute. To identify the genes encoding 2-40 alginases, the newly released 2-40 genomic sequence was compared to the sequences of 73 previously characterized alginase-producing microorganisms in the NCBI database. The program on choice was Basic Local Alignment Search Tool (BLAST). Eleven open reading frames were detected, namely AlgA, AlgB, AlgC, AlgD, AlgE, AlgF, AlgG, AlgH, AlgI, AlgJ and AlgK (Table 3.11). Amino acid sequences of each the 2-40 alginases were aligned with their best hit alginase from other bacteria and further annotated using the ClustalW alignment program (Thompson, et al., 1994).

The amino acid sequences of the alginases were analyzed by Simple Modular Architecture Research Tool (SMART) to determine the signal peptides, binding domains, repeats, motifs and other features (Tables 3.12 and 3.16 and FIG. 7).

AlgA is a 345 amino acid protein with a calculated Mw of 37 kDa (Table 3.11). It contains a 114 amino acid helicase superfamily c-terminal domain, termed HELICc. In general, this domain family is found in a wide variety of helicases and helicase related proteins. Such proteins normally function as a helicase, in ATP binding or nucleic acid binding. The following describes the domains shown in FIG. 7.

AlgB is a 762 amino acid with a calculated Mw of 83 kDa (Table 3.11). It contains a very interesting stretch of seven Parallel beta-helix (PbH1) repeats. These repeats are found in pectate lyases and rhamno-galacturonase A. Its conformation includes a stack of parallel beta strands that are coiled into a large helix. Each coil of the helix is a structural repeat. Proteins containing these repeats are, mostly, carbohydrases. No carbohydrate binding modules (CBM) were identified, pos-

TABLE 3.11

Alginases[a] produced by 2-40: Mw, pI, and best sequence match using E values.

| Alginase gene | AA | MW (kDa)[b] | pI[b] | Best Hit[c] | E Value[d] | Percent Identity[c] |
|---|---|---|---|---|---|---|
| AlgA | 345 | 37 | 6.83 | Klebsiella pneumoniae | 3e−62 | 47 |
| AlgB | 762 | 83 | 6.15 | Pseudomonas sp. | 5e−85 | 44 |
| AlgC | 738 | 81 | 5.53 | Pseudomonas sp. | 1e−171 | 44 |
| AlgD | 613 | 65 | [0001] | Klebsiella pneumoniae | 1e−84 | 57 |
| AlgE | 524 | 56 | [0002] | Klebsiella pneumoniae | 1e−96 | 63 |
| AlgF | 1554 | 163 | 4.39 | Klebsiella pneumoniae | 4e−60 | 49 |
| AlgG | 875 | 94 | 4.26 | Corynebacterium sp. ALY-1 | 2e−38 | 39 |
| AlgH | 894 | 93 | 4.13 | Pseudomonas sp. | 2e−46 | 30 |
| AlgI | 525 | 57 | 8.92 | Pseudomonas sp. | 6e−36 | 30 |
| AlgJ | 541 | 57 | 4.78 | Pseudoalteromonas sp. IAM14594 | 2e−86 | 67 |
| AlgK | 337 | 37 | 6.46 | Vibrio halioticoli | 3e−47 | 38 |

[a]signal peptides were detected by SMART, Simple Modular Architecture Research Tool. All alginases, except AlgA and AlgK, were determined to have signal peptide.
[b]Molecular weight and pI are determined using the ExPASY program,
[c]2-40 putative alginases were run against the database of the Computational Biology Program of the Life Sciences Division of Oak Ridge National Laboratory, results showed Best hit with its E value and percent identity.
[d]E values: each value represents the number of sequences with a score greater-than, or equal to, X, expected absolutely by chance. E values are calculated using Hidden Markov Models.

sibly because: a) there aren't any, b) there were not found by annotation programs, possibly representing a previously unidentified CBM.

AlgC is a 738 amino acids protein with a calculated Mw of 81 kDa with a low compositional complexity region with sequence of LLGDGADGDQGAL (SEQ ID NO: 14). Perhaps importantly no CBM were detected. In carbohydrases that are part of a multi-array complex, the CBMs are found on the scaffolds and not in the catalytic proteins.

AlgD contains a 140 amino acid carbohydrate binding domain, RICIN, which is a beta-trefoil domain formed from presumed gene triplication. AlgD also contains an FA58C domain, a cell surface-attached carbohydrate-binding domain, and a 24 amino acid stretch of serine between positions 307 and 330 with sequence of [SSSSSSSSSTSSTSSTSSTSSSS](SEQ ID NO: 15). The serine rich sequence is 146 amino acids removed from RICIN and 51 amino acids removed from a predicted active site region (discussed later).

AlgE contains a 39 amino acid domain, between positions 31 and 69 and composed of alternate threonine and proline with sequence of [TTPTPTPTPTPTPTPTPTPTPTPTPTPTPTPTPTP] (SEQ ID NO: 16). This depolymerase also contains a 135 amino acid FA58C domain between positions 71 and 205. A region of low compositional complexity was also found between positions 207 and 230 with sequence of ETGTPT-EDPVVVEPPEPPAPTDGD (SEQ ID NO: 17).

AlgF, the biggest of all eleven 2-40 alginate depolymerases, is composed of 1554 amino acids and has a calculated molecular weight of 163 kDa. It contains 9 repeats of PbH1 (Parallel beta-helix), described above. Three regions of low compositional complexity were detected, the first between positions 759 and 777 with sequence ANGLLN-DANSLAGANASAL (SEQ ID NO: 18), the second between positions 1074 and 1095 with sequence PVEPGNGEDEG-NGGTTTEVTDG (SEQ ID NO: 19), and the third between NO: 19), and the third between positions 1122 and 1133 with sequence GTVVVTDGVTIT(SEQ ID NO: 20).

AlgG, the second largest alginate depolymerases of 2-40, contains a 264 amino acid FA58C domain (described above). This putative depolymerase also contains two repeats of the Polycystic Kidney disease (PDK) domain. These domains contain 14 repeats and are present in microbial collagenases. A 133 amino acid domain, belonging to the CBM-4-9 carbohydrate binding family, was detected between positions 480 and 612 of the protein. The CBM-4-9 family includes diverse binding domains, attaching to several different polysaccharide conformations.

AlgH contains a 47 amino acid region of low compositional complexity starting from position 25 and ending at position 71. This region is rich in proline, glycine and glutamic acid (EGEP). The sequence of this region is PDP-DPD-PIEEPEGEPEGEPEGEPEGEPEGEPEGEPEGEPE GEP (SEQ ID NO: 21) AlgH also contains 4 Parallel beta-helix repeats (described above) ranging between 22 and 32 amino acid long. A low compositional complexity region is located between positions 516 and 531 with sequence of DLTAAAADTGDFMVT(SEQ ID NO: 22). AlgH also contains a 168 amino acid domain of the CBM-4-9 protein family.

AlgI contains a domain of the pectin lyase-like protein superfamily, with two representations, due to overlapping domains. In the first representation, this domain is 345 amino acid-long and located between positions 38 and 382. It has a single-stranded right-handed beta-helix with each turn made by 3 strands with short links duplication and the turns of the helix are structural repeats. In the second, the domain is 276 amino acid-long and located between positions 36 and 312.

AlgJ contains a 122 amino acid CBM-4-9 domain starting at position 10 and ending at position 131 (described above). It also contains a 142 amino acid FA58C domain starting at position 144 and ending at position 285 (described above). AlgJ also contains a 22 amino acid region of low compositional complexity with a repeating sequence of Threonine-Proline (TP), starts from position 290 and ends at position 311. The sequence of this region is: TPTPTPTPTPTPTPTPTPTPTP (SEQ ID NO: 23).

AlgA and AlgK were the smallest of the eleven alginases. No CBM were identified by the SMART analysis.

3.6. Alginases: Unusual domains

AlgD has a Ricin domain. RICIN is a legume lectin from the seeds of the castor bean plant *Ricinus communis* (Rutenber et al., 1987). Primary structure analysis has shown the presence of a similar domain in many carbohydrate-recognizing proteins like plant and bacterial AB-toxins and glycosidases. This domain, known as the ricin B lectin domain, can be present in one or more copies and has been shown in some instance to bind simple sugars, such as galactose or lactose. The ricin B lectin domain is composed of three homologous subdomains of 40 amino acids (alpha, beta and gamma) and a linker peptide of around 15 residues (lambda). It has been proposed that the ricin B lectin domain emerged from gene triplication from a primitive 40 residue galactoside-binding peptide (Hazes 1996). The most distinct sequence feature is the presence of a Q–W pattern. Moreover, ricin B lectin domain has been referred to as $(Q \times W)_3$ (SEQ ID NO: 24) domain since it contains three homologous QxW repeats, some of which contain a conserved disulfide bond. In the 2-40 alginases, this domain is believed to be a CBD, binding alginate to put another domain, the catalytic site, in proximity to the substrate.

FA58C is found in AlgD, E, G and L. It is also present in eukaryotes and assumed to have horizontally transferred to eubacterial genomes. This domain is found as a C terminal of Blood coagulation factors V and VIII (also called F5/8 type C, FA58C, or C1/C2-like domain), where it is composed of 150 amino acids and repeated twice. In these coagulation factors, the repeated domains compose part of a larger functional domain which promotes binding to anionic phospholipids on the surface of platelets and endothelial cells. The C-terminal domain of the second FA58C repeat (C2) of coagulation factor VIII has been shown to be responsible for phosphatidylserine-binding and essential for activity. It forms an amphipathic alpha-helix, which binds to the membrane. FA58C contains two conserved cysteine in most proteins, which link the outermost points of the domain by a disulfide bond. A related domain, named discoidin I-like domain, was found in slime mold, which shares a common C-terminal region of about 110 amino acids with the FA58C domain, but whose N-terminal 40 amino acids are much less conserved. Similar domains have also been detected in other extracellular and membrane proteins. In 2-40, it may be involved in protein-protein interactions.

PKD domains are present in AlgG. They were first identified in the Polycystic Kidney Disease protein 1 (PKD1) and are involved in adhesive protein-protein and protein-carbohydrate interactions. Most of these domains are found in the extracellular parts of proteins involved in interactions with other proteins. In 2-40 they could be involved in anchoring the protein to the surface of the cell, or act as CBD. They are present in polysaccharides from a member of other organisms where there is anecdotal evidence (in a few of many observations) that it disorders the crystalline part of the polymer making it more accessible to attack.

Carbohydrate-binding modules (CBMs) are a class of protein comprising 32 families classified on the basis of amino acid sequence similarity. CBMs can be grouped into 3 types based on their specificity for crystalline polysaccharides, Type A, glycan chains, Type B, or small soluble sugars, Type C.(Boraston 2003, personal communication).

scaffold on the cell surface. 2-40 alginase protein sequences had a high level of similarity to alginases from 4 *Klebsiella* spp., 5 *Pseudomonas* spp., 1 *Corynebacterium* sp. and 1 *Vibrio* sp., suggesting (among other examples) that 2-40 is unusually adept at horizontal transfer and recombination.

The biochemistry of alginate biosynthesis has been determined in the human pathogen *Pseudomonas aeruginosa* and in *Azotobacter vinelandii* (Rehm and Valla 1997). In both

TABLE 3.12

Alginases produced by 2-40: Stop codon, unusual domain, and amino acid repeats.

| Alginase gene | Stop codon | CBD[a] (# aa) | MMBD[b] (# aa) | Predicted active site position | Active site class | AA Repeat[c] (# aa) |
|---|---|---|---|---|---|---|
| AlgA | TAA | ND | HELICc (114): Helicase, ATP binding, nucleic acid binding | 67-343 (277) | Class 1 | — |
| AlgB | TAA | ND | 7 repeats of Parallel beta-helix (22-35): found in pectate lyases and rhamno-galacturonase A | 220-485 (265) | Class 2 | — |
| AlgC | TAA | ND | — | 295-659 (364) | Class 3 | DVVVVD (6) (SEQ ID NO: 70) |
| AlgD | TAG | FA58C (131) | Ricin-type beta-trefoil (140) | 374-612 (238) | Class 1 | Serine stretch (24) |
| AlgE | TAG | FA58C (135) | — | 259-525 (266) | Class 1 | TP stretch (39) |
| AlgF | TAA | ND | 9 repeats of Parallel beta-helix (21-31) | 781-1080 (299) | Class 1 | — |
|  |  |  |  | 1088-1461 (373) | Class 3 |  |
| AlgG | TAA | FA58C (264), CBM-4-9 (133) | 2 copies of PDK1 | 361-779 (418) | Class 3 | — |
| AlgH | TAA | CBM-4-9 (168) | 4 repeats of Parallel beta-helix (22-32) | 288-553 (265) | Class 2 | EGEP (47) (SEQ ID NO: 69) |
| AlgI | TAG | ND | d1dbga (345), or PDB id (276) Pectin lyase-like domain | 217-517 (300) | Class 2 | — |
| AlgJ | TAA | FA58C (142), CBM-4-9 (122) |  | — | — | TP stretch (22) |
| AlgK | TAA | ND | — | — | — | — |

[a]CBD: Carbohydrate binding domain
[b]MMBD: Macromolecule binding domain.
[c]For more details on repeats and their functions, see Results.
ND: No determined match was identified from the genome annotation.

Genomic analysis showed that 2-40 alginases have molecular weights that vary widely from 37 to 163 kDa. Genomic annotation also showed that all of the eleven alginases of 2-40 have signal peptide, except AlgA and AlgK, which were not amenable to annotation. AlgD, AlgE, AlgG, AlgH and AlgJ have carbohydrate binding domains. Several repeats of the PbH1 domains were found in AlgB, AlgF and AlgH. AlgG contains PDK domain and could bind putative organisms the immediate precursor of polymerization is GDP-mannuronic acid, and the sugar residues in this compound are polymerized into mannuronan. This polymer is then further modified by acetylation at 0-2 and/or 0-3 position (s) of some of the D-mannuronate residues. This results in the formation of alginates with different block structures and degrees of O-acetylation. In brown algae, however, alginates are not acetylated.

Based on the characterized biochemistry pathway of alginate biosynthesis and on the genomic analysis of 2-40 alginase system, a pathway for degradation and transport of alginate in 2-40 can be proposed. Since it grows on alginate as a sole carbon source, arguably 2-40 encodes an enzyme system to depolymerize, transport and metabolize alginate polymers down to monosaccharide 4-deoxy-L-erythro-5-hexoseulose uronic acid. The first stage of depolymerization would occur extracellularly and may be carried out by alginases AlgD, E, G, H and J. Alginate would be epimerized into homopolymers of mannuronic acid residues (in the case where the alginic acid contains both M and G residues). The need for more than one extracellular alginase is explained by the substrate specificities observed for alginases from various sources (Chavagnat et al., 1998, and Rehm 1998). Additionally some alginate lyase may only degrade defined oligomannuronic lengths (Rehm 1998). Other alginases may be extracellular while others may be epicellular.

In the next stage, polymannuronate (poly-M) would then be degraded into alginate-oligosaccharide and unsaturated uronic acid (AOS+UA). The AOS–UA may be transported into the periplasm via a specialized outer-membrane porin, yet to be identified. There, the unsaturated uronic acid residues would further be degraded by AlgC, B, F and I to monosaccharide 4-deoxy-L-erythro-5-hexoseulose uronic acid (MS-DEHL). This would be reduced to 2-keto-3-deoxy-D-gluconic acid (KDG) by AlgA and AlgK. KDG and then catalyzed to GDP-mannose by dehydrogenase to GDP-mannose which would go through serial reaction steps to until it is converted to fructose-6-phosphate.

In various embodiments of this invention, the alginase degrading enzymes, related proteins and systems containing thereof, of this invention, for example including one or more enzymes or alginase-binding proteins, have a number of uses. In fact, many possible uses of the alginases of the present invention are conceivable. For example Table X lists some of the uses of alginates to which the alginases of the present invention can be expected to be useful, for example in cleaning up the alginates and/or to shorten the size of the alginates.

TABLE X

| Application | Type of Alginate | Functions and Benefits |
|---|---|---|
| FOOD | | |
| Bakery Creams | Protanal ® | Instant gelling and thickening; heat stability; range of different textures; good mouthfeel and flavor release |
| Dressings | Protanal Ester | Thickening, stabilizing, emulsifying; good mouthfeel; acid stable |
| Fruit Juices | Protanal Ester | Stabilizing, emulsifying |
| Fruit Fillings and Preparations | Protanal | Gelling, thickening, stabilizing; prevents syneresis; excellent heat stability; cold and hot process; wide range of different textures; available for low to high brix systems |
| Ice Cream and Sorbet | Protanal | Stabilizing; controlled viscosity; prevents crystal formation and shrinkage; contributes to even and slow meltdown |
| Low Fat Spreads | Protanal | Stabilizing; good mouthfeel, texture and flavor release |
| Restructured Foods | Protanal | Excellent gelling ability; heat stability; easy to form |
| Yoghurt | Protanal | Stabilizing; good mouthfeel, texture and flavor release |
| SPECIALTY | | |
| Beer | Profoam ® | Improves and maintains foam levels |
| Petfoods | Protanal | Gelling of heat-resistant and retortable meat-like chunks |
| Textile Printing | Lamitex, ® Scotex ® | Gives the desired rheology to print pastes; is inert to dyes and fibers; has excellent wash-out properties; is extremely pure |
| Paper | Scogin ® | Enhance greaseproof properties, oil resistance, and solvent holdout; improves rheology, water-retention, runability, ink holdout, and printability |
| Welding | Protaweld ™ | Lubricant stabilizer and "green strength" agent in the extrusion of high quality welding rods |

The alginases of this invention have unusual versatility in degrading alginates from a wide variety of sources. Advantages of the alginases of this invention are that they can withstand high salt environments and relatively high pH. The alginases of this invention can also resist detergents.

2-40 has a very high efficiency turnover rate and the alginases produced thereby have unusual enzyme architectures.

The alginases of this invention are useful in degrading alginate polymers to produce shorter chains, for example exoalginases, that are useful as feedstock for land-based animals, as well as for fish and other marine animals.

In one embodiment, these systems can be used to degrade alginate to produce short chain peptides for use in medicine. In another embodiment, the alginase systems can be used to treat cystic fibrosis patients by administering at least one of the alginases of this invention to a patient to degrade viscous polymer produced by *Psudomonas aeruginosa*.

In some embodiments of this invention, alginate or algae may be used to absorb environmental pollutants and waste spills. The alginate may then be degraded by the alginate degrading systems of the present invention. Bacteria that can metabolize environmental pollutants and can degrade alginate may be used in bioreactors that degrade toxic materials. Such a bioreactor would be advantageous since there would be no need to add additional nutrients to maintain the bacteria—they would use alginate as a carbon source.

In some embodiments of this invention, alginate degrading enzyme systems can be supplied in dry form, in buffers, as pastes, paints, micelles, etc. Alginase systems can also comprise additional components such as metal ions, chelators, detergents, organic ions, inorganic ions, additional proteins such as biotin and albumin.

In some embodiments of this invention, the alginate degrading systems of this invention could be applied directly to the alginate material. For example, a system containing one, some or all of the alginases of this invention could be directly applied to algae such that the system would degrade the algae. As another example, 2-40 could be grown on algae, which would allow the 2-40 to produce the alginases of this invention in order to degrade the algae as the 2-40 grows. An advantage of using the 2-40 or systems of this invention is that the degradation of the algae can be conducted in a marine environment, for example under water.

It is one aspect of the present invention to provide a nucleotide sequence that has a homology selected from 100%, 99%, 98%, 97%, 96%, 95%, 90%, 85%, 80%, or 75% to any of the sequences of the alginases of this invention.

The present invention also covers replacement of between 1 and 20 nucleotides of any of the alginases of this invention with non-natural or non-standard nucleotides for example phosphorothioate, deoxyinosine, deoxyuridine, isocytosine, isoguanosine, ribonucleic acids including 2-O-methyl, and replacement of the phosphodiester backbone with, for example, alkyl chains, aryl groups, and protein nucleic acid (PNA).

It is another aspect of some embodiments of this invention to provide a nucleotide sequence that hybridizes to any one of the alginases of this invention under stringency condition of 1×SSC, 2×SSC, 3×SSC1, 4×SSC, 5×SSC, 6×SSC, 7×SSC, 8×SSC, 9×SSC, or 10×SSC.

The scope of this invention covers natural and non-natural alleles of any one of the sequences of the alginases of this invention. In some embodiments of this invention, alleles of any one of any one of the sequences of the alginases can comprise replacement of one, two, three, four, or five naturally occurring amino acids with similarly charged, shaped, sized, or situated amino acids (conservative substitutions). The present invention also covers non-natural or non-standard amino acids for example selenocysteine, pyrrolysine, 4-hydroxyproline, 5-hydroxylysine, phosphoserine, phosphotyrosine, and the d-isomers of the 20 standard amino acids.

It is to be understood that while the invention has been described above using specific embodiments, the description and examples are intended to illustrate the structural and functional principles of the present invention and are not intended to limit the scope of the invention. On the contrary, the present invention is intended to encompass all modifications, alterations, and substitutions within the spirit and scope of the appended claims.

REFERENCES CITED

Akiyama, H., T. Endo, R. Nakakita, K. Murata, Y. Yenemoto, and K. Okayama. 1992. Biosci. Biotechnol. Biochem. 56: 355-356.

Altschul S. F., Gish W., Miller W., Myers E. W., Lipman D. J. 1990. Basic local alignment search tool. J Mol Biol. 215 (3):403-10.

Altschul S. F., Boguski M. S., Gish W., Wootton J. C. 1994. Issues in searching molecular sequence databases. Nat Genet. 6(2):119-29.

Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. Nucleic Acids Res. 25:3389-3402.

Andrykovitch, G. and I. Marx. 1988. Isolation of a new polysaccharide-degrading bacterium from salt marsh. Applied and Environmental Microbiology. 54: 1061-1062.

Bayer, A. S.; S. Park; M. C. Ramos; C. C. Nast; F. Eftekhar and N. L. Schiller. 1992. Effects of Alginase on the Natural History and Antibiotic Therapy of Experimental Endocarditis Caused by Mucoid *Pseudomonas aeruginosa*. Infection and Immunity. 60(10): 3979-3985.

Baba, T., F. Takeuchi, M. Kuroda, H. Yuzawa, K. Aoki, A. Oguchi, Y. Nagai, N. Iwama, K. Asano, T. Naimi, H. Kuroda, L. Cui, K. Yamamoto, and K. Hiramatsu. 2002. Genome and virulence determinants of high virulence community-acquired MRSA. Lancet 359 (9320), 1819-1827.

Boyd, J. and J. R. Truvey. 1977. Isolation of poly-□-L-guluronate lyase from *Klebsiella* aerogenes. Carbohyd. Res. 57:163-171

Boyen C, Bertheau Y, Barbeyron T, Kloareg B. 1990. Preparation of guluronate lyase from *Pseudomonas alginovora* for protoplast isolation in *Laminaria*. Enzyme Microb. Technol. 12:885-90

Caswell R C, Gacesa P, Lutrell K E, Weight- man A J. 1989. Molecular cloning and heterologous expression of *Klebsiella pneumoniae* gene encoding alginate lyase. Gene 75:127-34

Chakravorty, Devi. 1998. Cell Biology of Alginic acid Degradation by Marine Bacterium 2-40. M. S. Thesis. University of Maryland, College Park, Md.

Chavagnat, F., C. Duez, M. Guinard, P. Potin, T. Barbeyron, B. Henrissat, J. Wallach, and J. Ghuysen. 1996. Cloning, sequencing and overexpression in *Escherichia coli* of the alginate-lyase encoding aly gene of *Pseudomonas alginovora*: identification of three classes' alginate lyases. J. Biochem. 319: 575-583.

Chavagnat, F., A. Heyraud, Ph. Colin-Morel, M. Guinand, and J. Wallach. 1998. Catalytic properties and specificity of a recombinant, overexpressed D-mannuronate lyase. Carbohydrate Research 308: 409-415.

Conti, E., A Flaibani, M. O'Regan, and I. W. Sutherland. 1994. Alginate from *Pseudomonas fluorescens* and *P. putida*: production and properties. Mic. 140: 1125-1132.

Crasnier, M., V. Dumay, and A. Danchin. 1994. The catalytic domain of *Escherichia coli* adenylate cyclase as revealed by deletion analysis of the cya gene. Mol. Gen. Genet. 243:409-416.

Cross, A.; J. R. Allen, J. Burke; G. Ducel, A. Haris; J. John; D. Johnson,; M. Law; B. MacMillan; R. Skalova; R. Wenzel; and J. Tenney. 1983. Nosocomial infections due to *Pseudomonas aeruginosa*: review of recent trends. Rev. Infect. Dis. 5(Suppl.): S837-S845.

Da Silva, A. C. R., J. A. Ferro, F. C. Reinach, F. C., Farah, C. S., Furlan, L. R., Quaggio, R. B., Monteiro-Vitorello, C. B., Van Sluys, M. A., Almeida Jr., N. F., Alves, L. M. C., do Amaral, A. M., Bertolini, M. C., Camargo, L. E. A., Camarotte, G., Cannavan, F., Cardozo, J., Chambergo, F., Ciapina, L. P., Cicarelli, R. M. B., Coutinho, L. L., Cursino-Santos, J. R., El-Dorry, H., Faria, J. B., Ferreira, A. J. S., Ferreira, R. C. C., Ferro, M. I. T., Formighieri, E. F., Franco, M. C., Greggio, C. C., Gruber, A., Katsuyama, A. M., Kishi, L. T., Leite Jr., R. P., Lemos, E. G. M., Lemos, M. V. F., Locali, E. C., Machado, M. A., Madeira, A. M. B. N., Martinez-Rossi, N. M., Martins, E. C., Meidanis, J., Menck, C. F. M., Miyaki, C. Y., Moon, D. H., Moreira, L. M., Novo, M. T. M., Okura, V. K., Oliveira, M. C., Oliveira, V. R., Pereira Jr., H. A., Rossi, A., Sena, J. A. D., Silva, C., de Souza, R. F., Spinola, L. A. F., Takita, M. A., Tamura, R. E., Teixeira, E. C., Tezza, R. I. D., Trindade dos Santos, M., Truffi, D., Tsai, S. M., White, F. F., Setubal, J. C. and J. P. Kitajima, 2002. Comparison of the genomes of two *Xanthomonas* pathogens with differing host specificities. Nature 417 (6887), 459-463.

Davidson, I. W.; I. W. Sutherland and C. J. Lawson. 1976. Purification and Properties of an Alginate Lyase from a Marine Bacterium. Biochemistry Journal 159: 707-713.

Davidson, I. W.; C. J. Lawson; and I. W. Sutherland. 1977. An Alginate Lyase From *Azotobacter* vinelandii Phage. J. Gen. Microbiol. 98: 223-229.

Deng, W., V. Burland, G. III Plunkett, A. Boutin, G. F. Mayhew, P. Liss, N. T. Nerna, D. J. Rose, B. Mau, S. Zhou, D. C. Schwartz, J. D. Fetherston, L. E. Lindler, R. R. Brubaker, G. V. Plana, S. C. Straley, K. A. McDonough, M. L. Nilles, J. S. Matson, F. R. Blattner, and R. D. Perry. 2002. Genome Sequence of *Yersinia pestis* KIM. J. Bacteriol. 184 (16), 4601-4611

Dinwiddie R. 1990. Clinical aspects of mucoid *Pseudomonas aeruginosa* infections. In *Pseudomonas* infection and alginates: *Biochemistry, Genetics and Pathology* (Edit by Gacesa P. and Russel N. J.) pp. 13-28. Chapman and Hall, London Doubet, R. S. and R. Quatrano. 1982. Isolation of Marine Bacteria Capable of Producing Specific Lyases for Alginate Degradation. Applied and Environmental Microbiology. 47(4): 704-709.

Doubet, R. S. and R. Quatrano 1984. Properties of Alginate Lyases from Marine Bacteria. Applied and Environmental Microbiology. 47 (4): 699-703.

Egli, T. 1995. The ecological and physiological significance of the growth of heterotrophic microorganisms with mixtures of substrates. Adv. Microbiol. Ecoli. 14: 305-386.

Elyakova, L. A. and V. V. Favorov. 1974. Isolation and certain properties of alginate lyase VI from the mollusk *Littorina* sp. Biochemica et Biophysica Acta, 358: 341-354.

Ertesvåg, H.; H. K. Hoidal; I. K. Hals; A. Rian; B. Doseth and S. Valla. 1995. A family of modular type mannuronan C-5 epimerase genes controls alginate structure in *Azotobacter vinelandii*. Mol. Micb. 16: 719-731.

Ertesvåg, H., F. Erlin, G. Skjåk-Braek, B. H. A. Rehm, and S. Valla. 1998. Biochemical properties and substrate specificities of a recombinantly produced *Azotobacter vinelandii* alginate lyase. J. Bacteriology. 180(15): 3779-3784.

Feucht, B. U., and M. H. Saier, Jr. 1980. Fine control of adenylate cyclase by the phosphoenolpyruvate:sugar phosphotransferase systems in *Escherichia coli* and *Salmonella typhimurium*. J. Bacteriol. 141:603-610.

Ford, T. E. 1993. Aquatic microbiology, an ecological approach. Backwell Scientific Publication, Inc. Cambridge, Mass. P. 239-250.

Gacesa, P. 1987. Alginate-modifying enzymes: a proposed unified mechanism of action for the lyases and epimerases. FEBS Lett. 212: 199-202.

Gacesa, P.1988. Alginates. Carbohydr. Polym. 8: 161-182.

Gacesa, P. 1992. Enzymic Degradation of Alginates. International Journal of Biochemistry. 24(4): 545-552.

Glantz, Stanton A. 2002. Primer of biostatistics. $5^{th}$ ed. McGraw-Hill. pp. 249-256

Goodne, B., Hinkle, G., Gattung, S., Miller, N., Blanchard, M., Qurollo, B., Goldman, B. S., Cao, Y., Askenazi, M., Halling, C., Mullin, L., Houmiel, K., Gordon, J., Vaudin, M., Iartchouk, O., Epp, A., Liu, F., Wollam, C., Allinger, M., Doughty, D., Scott, C., Lappas, C., Markelz, B., Flanagan, C., Crowell, C., Gurson, J., Lomo, C., Sear, C., Strub, G., Cielo, C. and S. Slater. 2001. Genome Sequence of the Plant Pathogen and Biotechnology Agent *Agrobacterium tumefaciens* C58. Science 294 (5550), 2323-2328.

González, J. M. and R. M. Weiner. 2000. Phylogenetic characterization of marine bacterium strain 2-40, a degrader pf complex polysaccharides. International Journal of Systematic and Evolutionary Microbiology. 8: 831-834.

Hansen, J. B; R. Scott Doubet and J Ram. 1984. Alginase Enzyme Production by *Bacillus circulans*. Applied and Environmental Microbiology. 47 (4): 704-709.

Haug, A.; B. Larsen and O. Smidsrød. 1967. Studies on the sequence of uronic acid residues in alginic acid. Acta Chem. Scand. 21: 691-704.

Haugen, Frode; F. Kortner and B. Larsen. 1990. Kinetics and Specificity of Alginate Lyase: Part 1, A Case Study. Carbohydrate Research. 198: 101-109.

Hazes B. 1996. The (Q×W)3 domain: a flexible lectin scaffold. Protein Sci. 1996 August; 5(8): 1490-501

Heyraud, A., Ph. Colin-Morel, C. Gey, F. Chavagnat, M. Guinand, and J. Wallach. 1998. An enzymatic method for preparation of homopolymannuronate blocks and strictly alternating sequences of mannuronic and guluronic units. Carbohydrate Research. 308: 417-422.

Jacober, L. F., C. Rice, and A. G. Rand. 1980. Characterization of the carbohydrate degrading enzymes in the surf clam *Spinula solidissima* crystalline style. J. Food Sci. 45: 381-385.

Kaneko, T., Nakamura, Y., Sato, S., Asamizu, E., Kato, T., Sasamoto, S., Watanabe, A., Idesawa, K., Ishikawa, A., Kawashima, K., Kimura, T., Kishida, Y., Kiyokawa, C., Kohara, M., Matsumoto, M., Matsuno, A., Mochizuki, Y., Nakayama, S., Nakazaki, N., Shimpo, S., Sugimoto, M., Takeuchi, C., Yamada, M. and Tabata, S. 2000. Complete genome structure of the nitrogen-fixing symbiotic bacterium *Mesorhizobium* loti. DNA Res. 7 (6), 331-338.

Karlin S, Altschul SF. 1990. Methods for assessing the statistical significance of molecular sequence features by using general scoring schemes. Proc Natl Acad Sci USA. 87(6):2264-8.

Karlin S, Altschul S F. 1993. Applications and statistics for multiple high-scoring segments in molecular sequences. Proc Natl Acad Sci USA. 1993 Jun. 15; 90(12):5873-7.

Kennedy, L.; K. McDowell and I. W. Sutherland 1992. Alginases from *Azotobacter* species. J. General Microbiol. 138, 2465-2471.

Kjelleberg, S; M. Hermansson and P. Mårdén. 1987. The transient phase between growth and nongrowth of heterotrophic bacteria, with emphasis on the marine environment. Annual Review of Microbiology. 41:25-49

Kiss, J. 1974. □-Eliminative degradation of carbohydrates containing uronic acid residues. Adv. Carbohydr. Chem. Biochem. 29: 229-303.

Kitamikado M, Yamaguchi K, Tseng C-H, Okabe B. 1990. Method designed to detect alginate-degrading bacteria. *Appl. Environ. Microbiol.* 56:2939-40

Kitamikado, M.; C-H. Tseng; K. Yamaguchi and T. Nakamura. 1992. Two Types of Bacterial Alginate Lyases. Applied and Environmental Microbiology. 58(8): 2474-2478.

Kloareg, B. and R. S. Quatrano. 1987. Isolation of protoplasts from zygotes of *Fucus discuss* (L.) Powell (Phaeophyta). Hydrobiologia. 151/152: 123-129.

Kloareg, B.; M. Polne-Fuller and A. Gibor. 1989. Mass production of variable protoplasts from *Macrocystis pyrifera* L. G. Ag. Phaeophyta. Plant Sci. 62: 105-112.

Kraiwattanapong J, Ooi T, Kinoshita S. 1997. Cloning and sequence analysis of the gene (alyII) coding for an alginate lyase of *Pseudomonas* sp. OS-ALG-9. Biosci. Biotechnol. Biochem. 61: 1853-57

Kraiwattanapong J, Tsuruga H, Ooi T, Kinoshita S. 1999. Cloning and sequencing of a *Delaya marina* gene encoding for alginate lyase. Biotechnol. Lett. 21: 169-74

Kundig, W., S. Ghosh, and S. Roseman, 1964. Phosphate bound to histidine in a protein as an intermediate in a novel phospho-transferase system. Proc. Natl. Acad. Sci. USA 52:1067-1074.

Kuroda, M., T Ohta., I. Uchiyama., T. Baba, H. Yuzawa, I. Obayashi, L. Cui, A. Oguchi, K. Aoki, Y. Nagai, J. Lian, T. Ito, M. Kanamori, H. Matsumaru, A. Maruyama, H. Murakami, A. Hosoyama, Y. Mizutani-Ui, N. K. Takahashi, T. Sawano, R. Inoue, C. Kaito, K. Sekimizu, H. Hirakawa, S. Kuhara, S. Goto, J. Yabuzaki, M. Kanehisa, A. Yamashita, K. Oshima, K. Furuya, C. Yoshino, T. Shiba, M. Hattori, N. Ogasawara, H. Hayashi, and K. Hiramatsu. 2001. Whole genome sequencing of meticillin-resistant *Staphylococcus aureus*. Lancet 357 (9264),1225-1240.

Laemmli, U. K. 1970. Cleavage of structural proteins during the assembly of the head of the bacteriophage T4. Nature (London) 227: 680-685.

Lange, B.; J. Wingender and U. K. Winkler. 1989. Isolation and characterization of an alginate lyase from *Klebsiella aerogenes*. Arch. Microbiol. 152: 302-308.

Langille, S. E. 1996. Capsular and holdfast Extracellular polymeric substances of *Hyphomonas* strain VP-6 mediate adhesion to solid substrata. Ph.D. Dissertation. University of Maryland, College Park, Md.

Letunic, L, L. Goodstadt, N. J. Dickens, T. Doerks, J. Schultz, R. Mott, F. Ciecarelli, R. R. Copley, C. P. Pouting, and P. Bork. 2002. Recent improvements to the SMART domain-based sequence annotation resource. Nucleic Acids Res. 30:242-244.

Lineweaver, H. and D. Burk. 1937. J. Am. Chem. Soc. 56:658-666

Linhardt, R. J.; P. M. Galliher and C. L. Cooney. 1986. Polysaccharide Lyases. Applied Biochemistry and Biotechnology, 12: 135-176.

Linker, A. and L. E. Evans. 1984. Isolation and characterization of an alginase from mucoid strains of *Pseudomonas aeruginosa*. J. Bacteriol. 159: 958-964

Lowry, Oliver H. and Janet V. Passonneau. 1972. A Flexible System of Enzymatic Analysis. Academic Press, New York, N.Y. p 21.

Macauley, S. P. and J. F. Preston III. 1990. Catabolite repression of alginase in alginate-degrading bacteria associated with pelagic *Sargassum* species. Abstr. Annual Meet. Am. Microbiol. Soc. p. 212.

Madgwick, J., A Haug, and B. Larsen. 1978. Ionic requirements of alginate modifying enzymes in the marine alga *Pelvetia canalitulata*. Bot. Mar. 21:1-4.

Maki, H., A. Mori, K. Fujiyama, S. Kinoshita and T. Yoshida. 1993. Cloning, sequence analysis and expression in *Escherichia coli* of a gene encoding an alginate lyase from *Pseudomonas* sp. OS-ALG-9. J. Gen. Microbiol. 139 (Pt 5), 987-993

Malissard M, Duez C, Guinand M, Vacheron M-J, Michel G, et al. 1993. Sequence of a gene encoding a (poly ManA) alginate lyase active on *Pseudomonas aeruginosa* alginate. FEMS Microbiol. Lett. 110: 101-6

Malissard M, Chavagnat F, Duez C, Vacheron M-J, Guinand M, et al. 1995. Overproduction and properties of the mannuronate alginate lyase AlXMB FEMS Microbiol. Lett. 126:105-12

Marx, I. 1986. Isolation and Characterization of an Agar-Degrading Bacterium. M. S. Dissertation. George Mason University Library.

Matsubara, Y.; R. Kawada; Ken-ichi Iwasaki; T. Oda and T. Muramatsu. 1998. Extracellular Poly (□-L-guluronate) lyase from *Corynebacterium* sp.: Purification, Characterization, and Conformational Properties. Journal of Protein Chemistry, 17(1): 29-36.

Monday, S. R. and N. L. Schiller. 1996. Alginate synthesis in *Pseudomonas aeruginosa*: the role of AlgL (alginate lyase) and AlgX. Journal of Bacteriology. 178: 625-632.

Monod, J. 1942. Recherches sur la croissance des cultures bacteriennes. Ph.D. thesis, University of Paris, France.

Moore, David. 1995. The Basic Practice of Statistics. W. H. Freeman and Commpany, pp. 630-633 (Table D).

Mounffort, D. O.; F. A. Rainy; J. Burghardt; E. Stackebrandt. 1994. *Clpstridium grantii* sp. nov., a new obligatory anaerobic, alginolytic bacterium isolated from mullet gut. Arch. Microbiol. 162: 173-179.

Muramatsu, T.; S. Hirose and M. Katayose. 1977. Isolation and properties of alginate lyase EC 4.2.2.3 from the mid gut gland wreath shell Turbo cornutus. Agric. Biol. Chem. 41: 1939-1946.

Muramatsu T, and T. Sogi. 1990. Characterization of alginate lyases from a marine bacterium. *Compo Biochem. Physiol*. 97B: 103-8

Narang, Atul. 1998. The Dynamical Analogy between Microbial Growth on Mixtures of Substrates and Population Growth of Competing Species. Biotechnology and Bioengineering, Vol. 59 (1): 116-121.

Natsume, M., Y. Kamo, M. Hirayama, and T. Adachi. 1994. Isolation and characterization of alginate-derived oligosaccharides with root growth-promoting activities. Carbohydrate Research. 258: 187-197.

Nibu Y, Satoh T, Nishi Y, Takeuchi T, Murata K, Kusakabe 1. 1995. Purification and characterization of extracellular alginate lyase from *Enterobacter cloacae* M-1. *Biosci. Biotechnol. Biochem.* 59:632-37

Nishizawa, K.; S. Fushibayashi and Y. Kashiwabara. 1968. Alginate Lyases in the hepatopancreas of a marine mollusk *Dollabella auricular* Solander. J. Biochem. 64: 25-37.

Ott, C. Mark, Donal F. Day, David W. Koenig, Duane L. Pierson. 2001. The Release of Alginate Lyase from Growing *Pseudomonas syringae* pathovar *phaseolicola*. Current Microbiology 42:78-81.

Parkhill, J., G. Dougan, K. D. James, N. R. Thomson, D. Pickard, J. Wain, C. Churcher, K. L. Mungall, S. D. Bentley, M. T. G. Holden, M. Sebaihia, S. Baker, D. Basham, K. Brooks, T. Chillingworth, P. Connerton, A. Cronin, P. Davis, R. M. Davies, L. Dowd, N. White, J. Farrar, T. Feltwell, N. Hamlin, A. Haque, T. T. Hien, S. Holroyd, K. Jagels, A. Krogh, T. S. Larsen, S. Leather, S. Moule, P. O'Gaora, C. Parry, M. Quail, K. Rutherford, M. Simmonds, J. Skelton, K. Stevens, K. S. Whitehead, and B. G. Barrell. 2001. Complete genome sequence of a multiple drug resistant *Salmonella enterica* serovar typhi CT18. Nature 413 (6858), 848-852.

Peciña A, and A. Paneque. 1994. Detection of alginate lyase by activity staining after sodium dodecil sulfate-polyacrylamide gel electrophoresis and subsequent renaturation. *Anal. Biochem.* 217: 124-27

Peciña A, A. Pascual, and A. Paneque. 1999. Cloning and expression of the algL gene, encoding the *Azotobacter chroococcum* alginate lyase: purification and characterization of the enzyme. J. Bacteriol. 181: 1409-14

Peña, C; L. Miranda, D. Segura, C. Nuñez, G. Espin, and E. Galindo. 2002. Alginate production by *Azotobacter vinelandii* mutants altered in poly-□-hydroxybutyrate and alginate biosynthesis. J. Industrial Microbiology and Biotechnology. 29(5): 209-213.

Pindar, D. F., and C. Bucke. 1975. The biosynthesis of alginic acid by *Azotobacter vinelandii*. Biochem. J. 152: 617-622.

Pitt, T. L. and L. C. Raisbeck. 1978. Degradation of the mucoid polysaccharide of *Pseudomonas aeruginosa* by Beneckea pelgia. J. Appl. Bac. 45: 297-300.

Preiss, J. and G. Ashwell. 1962a. Alginic Acid Metabolism in Bacteria: I. Enzymatic Formation of Unsaturated Oligosaccharides and 4-Deoxy-L-Erythro-5-Hexoseulose Uronic Acid. The Journal of Biological Chemistry. 237(2): 309-316.

Preiss, J. and G. Ashwell. 1962b. Alginic Acid Metabolism in Bacteria: II. The Enzymatic Reduction of 4-Deoxy-L-Erythro-5-Hexoseulose Uronic Acid to 2-Keto-3-Deoxy-D-Gluconic Acid. The Journal of Biological Chemistry. 237(2): 317-321.

Preston, Lori A., T. Y. Wong, Carol L. Bender, and Neal L. Schiller. 2000. Characterization of Alginate Lyase from *Pseudomonas syringae pv. syringae*. J. of Bacteriology 182(21): 6268-6271.

Redenbach M, Kieser H M, Denapaite D, Eichner A, Cullum J, et al. 1996. A set of ordered cosmids and a detailed genetic and physical map for the 8 Mb *Streptomyces coelicolor* A3(2) chromosome. *Mol. Microbiol.* 21:77-96.

Rehm, Bern H. A. 1998. Alginate lyase from *Pseudomonas aeruginosa* CF1/M1 prefers the hexameric oligomannuronate as substrate. FEMS Microbiology Letters. 165: 175-180.

Rehm, B. H. A. and S. Valla. 1997. Bacterial alginates: biosynthesis and applications. Applied Microbiology and Biotechnology. 48: 281-288.

Romeo, T. and J. F. Preston, III. 1986a. Purification and Structural Properties of an Extracellular (1-4)-□-D-Mannuronan-Specific Alginate Lyase from a Marine Bacterium. Biochemistry. 25: 8385-8391.

Romeo, T. and J. F. Preston, III. 1986b. Depolymerization of Alginate by an Extracellular Lyase from a Marine Bacterium: Substrate Specificity and Accumulation of Reaction Products. Biochemistry. 25: 8391-8396.

Russel, N. J. and P. Gacesa. 1988. Chemistry and biology of the alginate of mucoid strains of *Pseudomonas aeruginosa* in cystic fibrosis. Molec. Aspect. Med. 19: 1-91.

Rutenber E, Ready M, and Robertus J D. 1987. Structure and evolution of ricin B chain. Nature. 326 (6113): 624-6

Saier, M. H. Jr., and B. U. Feucht. 1975. Coordinate regulation of adenylate cyclase and carbohydrate permeases by the phosphoenolpyruvate:sugar phosphotransferase system in *Salmonella typhimurium*. J. Biol. Chem. 250:7078-7080.

Saier, M. H. Jr., and S. Roseman. 1976. Inducer exclusion and regulation of the melibiose, maltose, glycerol, and lactose transport systems by the phosphoenolpyruvate:sugar phosphotransferase system. J. Biol. Chem. 251:6606-6615.

Salyers, A. A.; A. Reeves and J. D'Elia. 1996. Solving the problem of how to eat something as big as yourself: diverse bacterial strategies for degrading polysaccharides. Journal of Industrial Microbiology 17:470-476

Sawabe T, Ezura Y, Kimura T. 1992. Purification and characterization of an alginate lyase from marine *Alteromonas sp. Nippon Suisan Gakkaishi* 58:521-27

Sawabe, T.; Y. Oda; Y. Shiomi and Y. Ezura. 1995. Alginate Degradation by Bacteria Isolated from the Gut of Sea Urchins and Abalones. Microbial Ecology. 30:193-202.

Sawabe, T., M. Ohtsuka, Y. Ezura. 1997. Novel alginate lyases from marine bacterium *Alteromonas* sr. strain H-4. Carbohydrate Research 304: 69-76.

Sawabe, T., H. Takahashi, a Y. Ezura, P. Gacesab. 2001. Cloning, sequence analysis and expression of *Pseudoalteromonas elyakovii* IAM 14594 gene (alyPEEC) encoding the extracellular alginate lyase. Carbohydrate Research 335: 11-21

Schaumann, K. and G. Weide. 1990. Enzymatic degradation of alginate by marine fungi. Hydrobiologia, 204/205: 589-596.

Schultz, J., R. R. Copley, T. Doerks, C. P. Ponting, and P. Bork. 2000. SMART: a web-based tool for the study of genetically mobile domains. Nucleic Acids Res. 28:231-234

Seiderer, L. J.; R. C. Newell and P. A. Cook. 1982. Quantitative significance of style enzymes from two marine mussels *Choromytilus meridionalis and Perna perna* in relation to diet. Mar. Biol. Lett. 3:257-272.

Shimokawa, T.; S. Yoshida; I. Kusakabe; T. Takeuchi; K. Murata and H. Kobayashi. 1997. Some properties and action mode of (1→4)-□-L-guluronan lyase from *Enterobacter cloacae* M-1. Carbohydrate Research, 304: 125-132.

Stevens, R. A. and R. E. Levin. 1977. Purification and characteristics of an alginase from *Alginovibrio aqualitis*. Appl. Environ. Microbiol. 3: 1156-1161.

Stosz, Sarah K. 1994. An agarose system from a periphytic prokaryote. Ph.D. Dissertation, University of Maryland, College Park, Md.

Suda, Kouji, Yasunori Tanji, Katsutoshi Hori, Hajime Unno. 1999. Evidence for a novel *Chlorella* virus-encoded alginate lyase. FEMS Microbiology Letters. 180: 45-53

Sumner, J. B. and E. B. Sisler. 1944. A simple method for blood sugar. Arch. Biochem. 4: 333-336.

Sutherland, I. W., and G. A Keen. 1981. Alginases from Beneckea pelagia and Pseu-domonas spp. J. Appl. Biochem. 3:48-57

Takami, H., Nakasone, K., Hirama, C., Takaki, Y., Masui, N., Fuji, F., Nakamura, Y. and Inoue, A. 1999. An improved physical and genetic map of the genome of alkaliphilic *Bacillus* sp. C-125. Extremophiles 3 (1), 21-28.

Takeshita S, N. Sato, M. Igarashi, and T. Muramatsu. 1993. A highly denaturant-durable alginate lyase from a marine bacterium: purification and properties. *Biosci. Biotechnol. Biochem.* 57: 1125-28

Takeshita, S; T. Oda, and T. Muramatsu. 1995. Spectroscopic studies on denaturants and guluronate lyase from a marine bacterium. *Biosci. Biotechnol. Biochem.* 59:881-85.

Thompson, J. D., D. G. Higgins and T. J. Gibson. 1994. CLUSTAL W: Improving the sensitivity of progressive multiple sequence alignment through sequence weighting, position specific gap penalties and weight matrix choice. Nucleic Acids Res. 22:4673-4680.

Tseng C-H, Yamaguchi K, and Kitamikado M. 1992. Isolation and some properties of alginate lyase from a marine bacterium *Vibrio* sp. AL-128. *Nippon Suisan Gakkaishi* 58:533-38.

Vilter, H. 1986. Alginate Lyase from *Alteromonas* sp. strain KLIA. A useful aid for isolation of enzymes and other biopolymers from brown algae. Planta Med 417.

Veerland, V. and W. M. Laetsch. 1990. A gelling carbohydrate in algal cell wall formation. In Organization and assembly of plant and animal extracellular matrix. Eds. W. S. Adair and R. P. Mecham. P. 137-171. Academic Press, San Deigo, Ca.

von Riesen V L. 1980. Digestion of alginate by *Pseudomonas maltophilia* and *Pseudomonas putida. Appl. Environ. Microbiol.* 39:92-96

Watanabe, T. and K. Nishizawa. 1982. Enzymatic studies on alginate lyase from *Undaria pinnatifida* in relation to texture softening prevention by ash treatment of haiboshi. Bull. Jap. Soc. Sci. Fish. 48: 243-250.

Weiner, R. M., D. Chakravorty and L. A. Whitehead. 1998. The architecture of degradative complex polysaccharide enzyme arrays in a marine bacterium has implications for bioremediation. In New Developments in Marine technology. Eds. LeGal, Y. and H. Halvorson. Plenum Pub. Corp. New York Weiner, R; L. Taylor; N. Ekborg and L. Whitehead. 2000. Degradosomes: Potential importance in the ocean's carbon cycle in aquaculture and algalculture. In: Recent Advances in Marine Science and Technology. 2000, pp 259-268. Narendra K Saxena. (Ed). Pacon International, Hawaii, USA.

Whitehead, Lynn A. 1997. Complex Polysaccharide Degradation Enzyme Arrays Synthesized by a Marine Bacterium. Ph.D. Dissertation. University of Maryland, College Park, Md.

Wong, T. Y., L. A. Preston and N. L. Schiller. 2000. Alginate Lyase: Review of Major Sources and Enzyme Characteristics, Structure-Function Analysis, Biological Roles, and Applications. Annu. Rev. Microbiol. 54: 289-340.

Yonemoto Y, Murata K, Kimura A, Yamaguchi H, Okayama K. 1991. Bacterial alginate lyase: characterization of alginate lyase-producing bacteria and purification of the enzyme. J: *Ferment. Bioeng.* 72:152-57

Yonemoto Y, Yamaguchi H, Kimura A, Sakaguchi K, Okayama K, Murata K. 1992. Cloning of a gene for intracellular alginate lyase in a bacterium isolated from a ditch. J: *Ferment. Bioeng.* 73:225-27.

Yonemoto Y, Tanaka H, Hisano T, Sakaguchi K, Abe S, et al. 1993. Bacterial alginate lyase gene: nucleotide sequence and molecular route for generation of alginate lyase species. J: *Ferment. Bioeng.* 75:336-42

Yoon, Hye-Jin, Wataru Hashimoto, Yoshio Katsuya, Yoshihiro Mezaki, Kousaku Murata, Bunzo Mikami. 2000. Crystallization and preliminary X-ray crystallographic analysis of alginate lyase AI-II from *Sphingomonas* species AI. Biochimica et Biophysica Acta 1476 (2000) 382-385

Yu, J.; A. Peñaloza-Vázquez; A. Chakrabarty; and C. L. Bender. 1999. Involvement of the exopolysaccharide alginate in the virulence and epiphytic fitness of *Pseudomonas syringae* pv. *syringae*. Mol. Microbiol. 33: 712-720.

LISTING OF AMINO ACID SEQUENCES OF THE AlgA-AlgK (even-numbered SEQ ID NOS 26-46), AND THE CORRESPONDING NUCLEOTIDE SEQUENCES (odd-numbered SEQ ID NOS 25-45)

AlgA

```
LOCUS       ZP_00317800           760 aa      linear   BCT 17-JUN-2004
DEFINITION  COG5651: PPE-repeat proteins [Microbulbifer degradans 2-40].
ACCESSION   ZP_00317800
VERSION     ZP_00317800.1  GI:48863907
DBSOURCE    REFSEQ: accession NZ_AABI03000001.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000001) using gene prediction method: GeneMark.
            Also see:
                Documentation of NCBI's Annotation Process Method: conceptual translation.
FEATURES             Location/Qualifiers
     source          1..760
                     /organism="Microbulbifer degradans 2-40"
                     /strain="2-40"
                     /db_xref="taxon:203122"
     Protein         1..760
                     /product="COG5651: PPE-repeat proteins"
     CDS             1..760
                     /locus_tag="Mdeg02000269"
                     /coded_by="complement(NZ_AABI03000001.1:317816..320098)"
                     /db_xref="COG:COG5651"
ORIGIN
    1 mkkenvniak qgllvvlvsf fmsfslmgca keilvnsqeq yaealssvkp gdtivlange
   61 wkdfeivftg kgtekapitl taqtkgkvli tgesnlalag ehlvvsglvf tngytpsdav
  121 isfraakpva eddystvamh srvtevvidn fsnperfetd swvliygkhn rvdhsnftgk
  181 rnkgvlmavr ldtthsrenh heidhnyfgp rdilgsngge tlrigtshfs lsdsftlven
  241 nyfdrcngel eiisnksgsn kfigntffes rgtltmrhgh gnviennvff gngkdhtggi
  301 rvinerqtvr nnymsdlagy rfggglvvmn gvpnsainry hqvknavien ntlvnvdhiq
  361 laagsdkert atpvdskfsn nlivnddkrn pftvyddvsg itfsnnsisa askelkkgfe
  421 vdaakiaknd qgmvfdasgt ygaskslkpv rkqdvgaswf vksedrkafq sgktvkagag
  481 qnsiydaveq vedggvvela agdyveakti tinktvtvka aagekvnief ykkslfevvd
  541 ggslqlegla isgasspddv gnavvrtsry smlknyrlel knceftdldv nrffnvvsvs
  601 kstladnill envsvkkvtg svlkldlesd dygiynaeyv tiknsqfedv dgplityyrg
  661 gtdestfgph femtgstlkn vgngsknkln aslylhgvqv taisnnkwld skpviiehtv
  721 gepvtsvvdn tfvntakldl qelyskkttt aviknntykk
```

ORIGIN

```
   1 atgaaaaaag agaatgtaaa catcgcgaag cagggcttgc tagttgtttt ggtaagcttc
  61 tttatgagct tttccctaat gggttgcgcc aaagaaattc tggtgaactc gcaggaacaa
 121 tacgcagaag cattgagttc agttaagcct ggcgacacca ttgtgttggc taatggcgaa
 181 tggaaagatt tcgaaattgt atttacaggt aagggcactg aaaaagcgcc aatcacccta
 241 actgcgcaaa caaaaggcaa ggtgttaatt actggcgagt caaacttggc gcttgccggt
 301 gagcatttgg tggtatctgg tttggtgttc actaatggct acacaccaag cgatgccgtt
 361 atctcattta gagctgctaa acccgtagcg gaagacgact acagtacagt tgcaatgcat
 421 tctcgagtca ccgaggtggt gattgataat tttagcaacc cagagcgttt tgaaactgac
 481 tcgtgggtgc ttatctatgg caaacacaac cgtgttgatc acagtaactt caccggcaag
 541 cgcaataaag gtgtgttgat ggctgtgcgt ttagatacca cgcatagccg cgaaaaccat
 601 catgaaattg atcacaacta ctttggtccg cgcgatattc ttggctccaa cggcggagag
 661 actttgcgta ttggcacgag ccacttctct ctttcagact ctttcacttt agtagaaaac
 721 aactatttcg atcgctgtaa cggtgagtta gagattattt ctaacaagtc tgggtctaac
 781 aagtttattg gaaatacctt ctttgaatcg cgtggcacgc taactatgcg tcacggtcat
 841 ggaaacgtaa tcgaaaacaa tgtgttcttt ggtaatggca agatcacac cggtggtatt
 901 cgtgtaatta acgagcgcca acggtacgc aacaactaca tgtctgatct tgcaggctac
 961 cgctttggtg gtggtttagt tgttatgaat ggcgtgccta actcagcgat aaatcgttac
1021 caccaagtaa agaatgccgt tatagaaaac aacacgctgg tgaatgtcga tcacattcag
1081 ctggcagctg gtagcgataa agagcgaaca gctacacccg tggattccaa gttttcaaat
1141 aacttgatcg tcaacgatga taaacgcaac ccgtttaccg tatacgacga tgttagcggc
1201 ataacctttt ctaataacag tattagtgca gcgtccaaag agctaaagaa aggctttgaa
1261 gttgatgccg ctaagattgc taaaaacgat caaggcatgg tgtttgatgc ctccggtact
1321 tacggtgcaa gcaagtcgct aaaacccgtt cgcaagcaag atgtgggcgc tagctggttt
1381 gttaagtcgg aagatcgcaa agcattccaa tcgggtaaaa cagttaaagc tggtgctggc
1441 caaaactcta tctacgatgc agtagagcag gtagaagatg gtggcgttgt cgaactggca
1501 gcgggtgatt atgtagaagc taaaacaatc actattaaca aaaccgtaac cgttaaagca
1561 gcagccggcg aaaaagtaaa tattgagttc tacaaaaagt cgctgtttga agtggttgat
1621 ggcggcagct tacagcttga aggtttggca attagcggtg cgagttcgcc agacgatgta
1681 ggtaatgcgg tcgtgcgtac atcgcgttat tccatgttaa aaaattatcg cttagagctt
1741 aaaaattgcg agttcacaga cctagatgta aacagattct tcaacgttgt atcggttagc
1801 aagtctacgt tagcagataa cattttgtta gaaaacgtaa gcgttaaaaa ggttactggc
1861 tcagtgttga agttagatct tgagtccgat gattacggta tttataacgc agaatacgtc
1921 acgattaaga atagccagtt tgaagatgta gatggcccat tgattactta ctaccgtggt
1981 ggtaccgatg aaagtacttt cggcccacac tttgaaatga ctggcagcac cttaaaaaat
2041 gtaggtaatg gcagcaagaa caagttgaac gcgtcactgt atttacatgg tgtacaggta
2101 acggctcttt caaacaacaa atggctagat agtaagcctg taattattga gcacactgtg
2161 ggtgagcctg taacaagcgt tgtagataac acgtttgtga atacagctaa gttagattta
2221 caagagctgt attctaagaa gacaaccacc gcagtaatta aaaataatac ctataaaaaa
2281 taa
```

AlgB

```
LOCUS       ZP_00317790             892 aa            linear   BCT 17-JUN-2004
DEFINITION  COG2931: RTX toxins and related Ca2+-binding proteins
            [Microbulbifer degradans 2-40].
ACCESSION   ZP_00317790
VERSION     ZP_00317790.1  GI:48863897
DBSOURCE    REFSEQ: accession NZ_AABI03000001.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000001) using gene prediction method: GeneMark.
            Also see:
                Documentation of NCBI's Annotation Process Method: conceptual translation.
FEATURES             Location/Qualifiers
     source          1..892
                     /organism="Microbulbifer degradans 2-40"
                     /strain="2-40"
                     /db_xref="taxon:203122"
     Protein         1..892
                     /product="COG2931: RTX toxins and related Ca2+-binding
                     proteins"
     CDS             1..892
                     /locus_tag="Mdeg02000259"
                     /coded_by="complement(NZ_AABI03000001.1:303978..306656)"
                     /db_xref="CDD:pfam04886"
                     /db_xref="CDD:pfam05887"
                     /db_xref="CDD:pfam06137"
                     /db_xref="CDD:pfam06390"
                     /db_xref="COG:COG2931"
ORIGIN
    1 mkfkslvalf llglltacgg gssnpdpdpd pieepegepe gepegepege pegepegepe
   61 gepegepege pqesnfprgs lgdndtvpdv vctqtvnsts eledavsyem tpgttlclad
  121 gnytnleiqf ggigteanpi tvaaanpgmv tiggevgirm sgeyvvlqgl ifkdgesass
  181 dliqtrgnsn apcnncrite iaiidfdqns dssgkwvhiy gahnrvdhsw fsgkttrgal
  241 lvvdryiedg vdpldaeidy aqidhnyfgd rppvdgkaya ssgdneyegi rigtsdshtg
  301 dsfsviehny feriqgeaev isnksgnnri ehntvrnsyg sittrhgssa titnnfiigd
  361 ghpyagglri iddghtvtnn yiqgarylat thhggivlmg sdgsttngyq qltnvlvahn
  421 tvvdsvnsln vdggqkstnp nnvylvnnii angigpvite aadgmpgssv iagnifygqs
  481 fsdsssltsv dgitwldvaf aadmqgvmra tgsspdltaa aadtgdfaav tldmdglara
  541 attqagaddd iggnpvrgil nsydvgpisy rppmttphva evdvanyafd egaagwtlvd
  601 avvntnaaev fargasvevt gangrasqvv sltantnytl tafvkgtatl aadvggtvyr
  661 sdvnssleyk latvsfnsgd atsatiygev ddfvlnyapi geasldgfpg adttfwsvye
  721 gagigqvqgs dnsaagadgs vkfkledate vgtprisqvl tglelntdyt lsmyalykks
  781 advtvtmgaf vgetdtvlas kvvdfedlva anapkgddsf rqdtltfntg snstitifae
  841 ynantiiadg gdagdtefrv defaltyega paadakayfd efrlvshasl ad
```

ORIGIN

```
   1 atgaagttca aatcattagt ggccctattc ctattgggcc tgcttactgc ttgtgggggc
  61 ggtagttcaa atccagaccc agacccagac ccgattgaag aacctgaagg cgaacctgaa
 121 ggagagccag aaggagagcc tgaaggagaa ccagaaggag agccagaagg agagccagaa
 181 ggggaaccag aaggagagcc agagggtgaa cctcaggagt ctaactttcc gcgtggttca
 241 ctcggtgata acgacactgt gccagacgtg gtatgtacgc aaaccgtaaa cagtacgtca
 301 gaactagaag acgctgtaag ctacgagatg accccaggta caacgctgtg tttggctgac
 361 ggcaactaca ccaacttaga aattcagttc ggtggtattg gtaccgaagc gaaccctatt
 421 actgtggcag cagctaaccc cggtatggtt acaattggcg gcgaagttgg gatccgcatg
 481 agcggtgaat acgttgtgtt gcaagggctt atttttaaag acggtgagag cgcgagtagc
 541 gacttaattc aaactcgcgg caactctaac gcgccttgta ataactgccg tattaccgaa
 601 attgccatta tcgatttcga tcaaaattcc gatagcagcg gcaaatgggt tcacatctac
 661 ggtgcacata accgcgtaga ccacagctgg ttttctggca aaactacccg cggcgcatta
 721 cttgttgtag atcgttacat tgaagatggt gttgacccac tcgatgccga aatagattac
 781 gcgcaaatcg atcacaacta cttcggcgac cgtccaccgg tggatggcaa agcttacgcg
 841 agtagcggcg acaacgaata cgaaggtatt cgcattggta ccagtgattc gcacacaggt
 901 gattcgttct cggtaatcga gcacaactat tttgagcgca tacaaggcga agccgaagtt
 961 atttctaata agtctggcaa caaccgcata gagcacaata ctgtacgtaa cagctatggt
1021 tctattacta cacgtcacgg ctcaagcgcg actattacca ataactttat tattggcgat
1081 ggtcacccat atgcaggcgg cctgcgcatt attgatgacg ccacaccgt aacgaacaac
1141 tacatccaag gtgcgcgtta tttagcaact actcaccatg gcggtattgt gttgatgggc
1201 tccgatggtt caaccaccaa cggttaccag caattaacca atgtacttgt tgcgcacaac
1261 actgtggtag atagcgtgaa cagcttgaac gtagatggcg gccaaaagtc taccaacccc
1321 aataatgttt acctagtgaa taacattatt gctaatggca taggccctgt tattacagaa
1381 gctgcagatg gtatgcctgg tagctctgtg attgcgggca acattttta cggccaaagc
1441 ttttccgact cctctagcct tacctctgta gacggtatta cttggttaga cgttgcgttc
1501 gcagcagata tgcaaggcgt aatgcgcgct acaggcagca gcccagactt aaccgcggca
1561 gctgcagata ctggcgattt gccgccgtt actttggata tggatggctt ggcgcgtgca
1621 gcaaccacac aagctggtgc tgacgacgat ataggtggca acccagttcg cggcattctt
1681 aatagctacg atgttggccc aataagctac cgcccaccaa tgaccacccc acacgttgca
1741 gaagtggatg tcgccaacta tgcgtttgat gaaggtgcag caggttggac tttagttgat
1801 gcagtggtaa acactaacgc tgcagaggtt tttgcccgcg gtgcaagcgt ggaagtaacc
1861 ggtgctaacg gccgcgcttc gcaagttgtt agcttaacgg cgaataccaa ctacacctta
1921 actgcgtttg ttaaaggcac tgcaactctt gcagcagatg taggtggcac ggtttatcgt
1981 tcagatgtga actcttcatt ggagtacaaa ctagcaaccg taagctttaa ttctggtgat
2041 gcaacatcag ccaccatttta cggcgaagtt gatgattttg tacttaacta tgccccaatt
2101 ggcgaagcga gcttagacgg cttccctggc gcagacacca cctttggag tgtgtacgag
2161 ggagcaggta tcggtcaggt tcaaggctct gataactcag cagccggcgc tgatgggtct
2221 gttaagttta aattagaaga cgctacagaa gtgggtaccc gcgtataag ccaagtatta
2281 accggcctag aattaaatac ggactatact ttatctatgt acgccctta caaaaagtct
2341 gccgatgtga ctgtaactat gggggcgttt gttggcgaaa cagacactgt actagcaagc
2401 aaagtggttg attttgaaga ccttgttgca gctaatgcgc cgaaaggcga cgacagtttc
2461 cgtcaagaca cactaacgtt taacacgggt agtaactcaa ctattactat ctttgctgaa
2521 tacaacgcca acacaattat tgctgacggc ggcgacgctg gtgatacgga gtttcgtgta
2581 gatgaatttg cattgacata tgaaggtgca cctgctgcgg atgccaaagc atactttgac
2641 gaattccgtc tagtatcgca tgcatcgcta gcagactaa
```

AlgC

LOCUS       ZP_00317789            509 aa            linear   BCT 17-JUN-2004
DEFINITION  hypothetical protein Mdeg02000258 [Microbulbifer degradans 2-40].
ACCESSION   ZP_00317789
VERSION     ZP_00317789.1  GI:48863896
DBSOURCE    REFSEQ: accession NZ_AABI03000001.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000001) using gene prediction method: GeneMark.
            Also see:
                Documentation of NCBI's Annotation Process Method: conceptual translation.
FEATURES             Location/Qualifiers
     source          1..509
                     /organism="Microbulbifer degradans 2-40"
                     /strain="2-40"
                     /db_xref="taxon:203122"
     Protein         1..509
                     /product="hypothetical protein"
     CDS             1..509
                     /locus_tag="Mdeg02000258"
                     /coded_by="complement(NZ_AABI03000001.1:302282..303811)"
ORIGIN
        1 mcaethiydg kgketwtktd lkpgdvviip ngtyadlkin vqgkgeqakp ivlkaetpgg
       61 vvltgaswlr ywgyfivvdg fdfndvtysm yknkvraiia nrragssses skdmcqacvl
      121 qrvridnend kaidteykwi elygynnvvr ynyfgakksg srvlqvqlkh anaqklpvsh
      181 viqynyfasr nagkavgngg eallvgdsnm qhvdakvtva nnlfydasil gepevisnks
      241 ssniyrsntv rnttasltlr hgnrntvenn wflqdqtegs ggirvigddn iihnnyiags
      301 agggksaayr palgiaagys kkddddaning yqlsernvls nnsviqsaqp vmlstwydrg
      361 klsmtrppmq ttfinnlvyq ldvapstadw vrglaisvdy tpdseygnny gidkaeyvps
      421 fakvkgnitd gkvsplvskg tkaeskkelk gcdafgtgdi vylplkkaga dlskmdeplv
      481 wtdtvksarl gpdwlnanwg gekkaykgc ORIGIN
        1 gtgtgtgccg aaacgcatat ttacgatggc aaaggtaaag aaacctggac caaaacggac
       61 ttaaagccgg gcgatgtggt gattatcccg aatggcacct acgccgactt aaaaattaac
      121 gtgcagggca aaggtgagca ggccaagccg attgtactta agcagaaaac acctgggggc
      181 gttgtgctta caggtgcatc gtggctgcgc tactggggct attttattgt ggtagatggt
      241 ttcgatttta acgacgtaac ctattccatg tataaaaata aagtgcgggc aattattgcc
      301 aaccgccgcg cgggttctag cagtgagtcc tctaaggata tgtgccaagc gtgcgtgtta
      361 cagcgcgtgc gtatagataa cgagaacgat aaagcgatcg atactgaata taatggatt
      421 gagctatacg gttataacaa cgtggtgagg tacaactact tcggtgctaa aaaatcgggc
      481 agccgagttt tacaggttca gttaaagcat gctaatgcgc aaaaattgcc cgtatcccat
      541 gttattcagt acaactattt tgcttcgcgt aacgcgggca aagctgtagg taatggtggt
      601 gaagcattgt tagtgggcga ttcaaatatg cagcatgttg atgctaaggt taccgtggcc
      661 aacaacttat tttacgatgc atccatactt ggcgagccag aggttatttc gaacaaatcc
      721 tcctctaata tttatcgcag caatactgtg cgcaatacaa ccgcgagcct cacgctgcgc

```
 781 cacggcaaca gaaacactgt agagaataac tggtttttgc aggaccaaac agaaggctct
 841 ggtggtatac gtgtcattgg cgacgataat attattcaca acaattacat tgctggctct
 901 gccggtggtg gcaaatcggc cgcgtatcgg ccagcacttg gtattgccgc gggttactcc
 961 aaaaaagatg acgatgccaa tatcaacggt taccagttaa gtgagcgcaa cgtgctttcg
1021 aataatagcg ttattcaatc tgcacagcct gtaatgcttt ctacttggta cgatcgaggt
1081 aagctaagta tgactcgccc ccctatgcaa accacgttta ttaataactt ggtgtaccaa
1141 ctagatgttg caccatctac tgcagattgg gtgcggggct tagccattag tgtagattac
1201 acgccagact ctgaatacgg taacaactat ggcattgata agcggagta tgtaccgtcg
1261 tttgcaaaag taaaaggcaa tattaccgat ggcaaagtgt cgccactggt tagcaaaggc
1321 actaaagctg aatcgaaaaa agaacttaaa gggtgcgatg catttggcac tggcgatatc
1381 gtatatttac cccttaaaaa agcaggcgca gacttatcta aatggatga acccttggtg
1441 tggaccgaca cagtaaaatc tgctcgctta ggaccagatt ggttgaatgc aaattggggc
1501 ggcgagaaaa aagcctataa gggatgttag
```

AlgD

```
LOCUS       ZP_00318426           768 aa         linear   BCT 17-JUN-2004
DEFINITION  COG3291: FOG: PKD repeat [Microbulbifer degradans 2-40].
ACCESSION   ZP_00318426
VERSION     ZP_00318426.1  GI:48864533
DBSOURCE    REFSEQ: accession NZ_AABI03000001.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000001) using gene prediction method: GeneMark.
            Also see:
                Documentation of NCBI's Annotation Process Method: conceptual translation.
FEATURES             Location/Qualifiers
     source          1..768
                     /organism="Microbulbifer degradans 2-40"
                     /strain="2-40"
                     /db_xref="taxon:203122"
     Protein         1..768
                     /product="COG3291: FOG: PKD repeat"
     CDS             1..768
                     /locus_tag="Mdeg02000922"
                     /coded_by="complement(NZ_AABI03000001.1:1068116..1070422)"
                     /db_xref="CDD:cd00057"
                     /db_xref="CDD:pfam05110"
                     /db_xref="CDD:pfam05955"
                     /db_xref="CDD:pfam06112"
                     /db_xref="COG:COG3291"
ORIGIN
    1 mstkltqsik wlapmlmamq vstayaadpv sveastddgn gpsntldndl strwsangsg
   61 qwirynlgts yniesldiaf ykgdqrnasf dvltsgdgqn wntvfsgtqp sstadqqtis
  121 lsdsigqyvq ivgygnssns wnsitevdid tsvvddgntg ggslsasasa ddgnvagnvl
  181 dgdlntrwsa ngngqwlrld lgatqvvgtv niaffkgnqr sanfdieasl dgsnwtrvva
  241 gahssgssvs lepfsfspvn aryiryvgyg nsanswnsit emsvaasggs ssssssssss
  301 sssssstsss sssssssssss sssssssssss sssssssssss snggvpgnty tatpdslndv
  361 latvsggdei vvtgsgeisi knisfnspvl iransiggtt ltnatltncn nislqgfvfg
  421 pndestllki vnstnikilr nlfdhknvte sqtslvmtqa sqyieiayne frdknlgdrs
  481 gtkitgsyik tqfddplmsk nihihhnhfk niapylvdgv pagdsdrevi amgiadsqdv
  541 vtnniveynl fencdgenei vtvktsnnif ryntfknsmg slsfrlgsnn qaygnyfygv
  601 gsgasvandn yetggvrvyg aghtihnnym egltglswrr pilvdsgdts essgndshev
  661 stnvqvydnv ivnslgggih vggdkyskmp tnititnnvv sgsdgilfnn hanqssntws
  721 gnqayatgsa vavaggslga sevvvlssep tinkptplta sdvgpsap
```

ORIGIN
```
    1 atgagcacaa aactaacccca gtcgatcaag tggttggcac ccatgttaat ggccatgcag
   61 gtatcaacgg cgtatgcagc agacccagtt tctgttgaag cgtccaccga tgatggcaat
  121 gggcctagca acacattaga taatgattta tccacgcgtt ggtctgccaa tggtagcggc
  181 cagtggattc gctacaacct tggcactagc tacaatattg aatctttaga tattgcgttt
```

```
 241 tacaaaggcg atcagcgcaa cgcgagcttt gacgttttaa catcaggaga tggccaaaac
 301 tggaataccg tattcagcgg tacgcagcca agcagtacgg cagatcaaca aactatctcc
 361 ctatctgact cgataggtca gtacgtacaa attgttggtt acggcaattc atctaacagc
 421 tggaacagta tcaccgaagt tgatatagat acttcagtgg ttgatgacgg caataccggt
 481 ggcggtagtt taagtgcaag cgccagtgcc gatgatggca atgtggccgg taacgtactt
 541 gatggcgacc taaacacccg ttggtccgcc aatggcaatg gccagtggtt gcgcttagat
 601 cttggtgcta cgcaagtggt tggcactgta atattgctt tctttaaagg taatcaacgc
 661 agtgctaatt ttgatataga agccagtacc gatggttcga actggacccg tgtagtggct
 721 ggtgcacaca gttcaggttc ttctgtaagc ttggagcctt tttcattctc acctgttaac
 781 gcgcgctaca ttcgctacgt tggttatggc aacagtgcca acagctggaa ctcaatcacc
 841 gagatgagtg ttgcagctag tggtggttct agtagttcga gcagttcttc aagcagctca
 901 tcgagttcat ctagctcaac cagttcatct agttcaagca gctcttcaag ttcctcgtct
 961 agctcttcta gcagttcgtc tagttctagt agctcaagca gttcttcaag ttctagctcg
1021 tcgaatggcg gtgtaccagg taatacttat accgcaacac ccgattcgct aaacgatgta
1081 ttggcgacgg tgtctggtgg cgacgaaatt gtggttactg gctccggtga aatatcgata
1141 aaaaatatta gctttaattc acctgtgtta attgcgcaa actctattgg cggcaccacg
1201 ttaaccaatg caaccttac taactgtaat aacattagtt tgcagggttt tgtgtttggt
1261 cctaacgacg agagcacgct gttaaagatt gtgaactcca ccaacatcaa aatattgcgc
1321 aacttgtttg atcacaaaaa cgttaccgaa agccaaacgt ctttagtgat gactcaagcc
1381 agccaatata ttgaaattgc ttacaacgag ttccgcgata aaaatttagg tgaccgcagt
1441 ggtaccaaaa ttacgggtag ctacattaaa acccagttcg acgaccgtt gatgagtaaa
1501 aatattcaca tccatcacaa ccactttaaa aacattgcgc cataccttgt ggacggtgta
1561 ccagcgggtg attcggatcg tgaagtaatt gcaatgggta ttgccgattc gcaagacgta
1621 gtaaccaaca atattgttga gtacaaccct ttcgagaact gcgatggcga aaacgaaatt
1681 gttacagtta aaacctctaa caatattttc cgctacaaca ccttcaaaaa ctccatgggt
1741 tccttgtcgt tccgtttagg ttcgaacaac caagcttatg gcaactattt ttacggtgta
1801 ggttctggtg cgtcggttgc taatgataac tatgaaacag gcggtgtgcg cgtgtacggc
1861 gcgggtcata ctattcacaa caactatatg gaaggcctaa cagggcttag ctggagacgc
1921 ccaattttag tggattcggg tgatacctca gaaagctcgg gtaacgatag ccacgaagtg
1981 tctactaatg tgcaggttta cgataacgtt attgttaata gtttaggtgg cggcattcat
2041 gtaggcggcg acaagtacag caaaatgccc accaatatca ccattactaa caacgtagtt
2101 agcggtagtg acggtatatt atttaacaat cacgctaatc aatcttctaa cacttggtcg
2161 ggcaaccagg cttacgcaac aggttctgct gtagcggttg ctggcggttc attaggtgct
2221 tcggaagttg ttgtgttatc tagcgagcca actattaata agccaacacc gcttaccgca
2281 agtgatgtag gcccaagtgc gccttaa
```

AlgE

LOCUS       ZP_00315844       335 aa       linear   BCT 17-JUN-2004
DEFINITION  hypothetical protein Mdeg02002992 [Microbulbifer degradans 2-40].
ACCESSION   ZP_00315844
VERSION     ZP_00315844.1  GI:48861945
DBSOURCE    REFSEQ: accession NZ_AABI03000007.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000007) using gene prediction method: GeneMark.
            Also see:
               Documentation of NCBI's Annotation Process Protein-coding genes were predicted using GeneMark program (kindly
            provided by M. Borodovsky). Functional annotation is based on CDD
            (Conserved Domain Database) and COG (Clusters of Orthologous
            Groups) assignments, it has not yet been subject to manual review.
            DNA sequence and predicted proteins are available for BLAST at
            http://www.ncbi.nlm.nih.gov/sutils/genom_table.cgi.
               URL -- http://www.jgi.doe.gov
            Contact: Paul Richardson
            microbes@cuba.jgi-psf.org.
            Method: conceptual translation.
FEATURES            Location/Qualifiers
     source          1..335
                     /organism="Microbulbifer degradans 2-40"
                     /strain="2-40"
                     /db_xref="taxon:203122"
     Protein         1..335
                     /product="hypothetical protein"
     CDS             1..335
                     /locus_tag="Mdeg02002992"
                     /coded_by="complement(NZ_AABI03000007.1:235866..236873)"
ORIGIN
        1 mqagdvvlpa maydlshwki tvplddnkdg kvdevdtkal qkymhsdyfy vnsegglvfa
       61 tpnqatttsg ssnsrselrq mirgtntrig tkspgnnfal ashpqakafg diggnlkatl
      121 avnhvalnak ytdkfpaysv vvgqihagkd kdliakgegy gwgnepikiy ykkwpdhktg
      181 svfwtyernl ekanpdrtdi aypvwgntwd nsenpgdkgi aldesfsyei nvykdimhlt
      241 ftaankptvk ysinlannvn aygkvdekdh pkgylgdwly fkagaydqcs vkddpgfwyp
      301 acagtgdwet dkkngdytrv tftklelgkg ysvsk ORIGIN
        1 atgcaagcag gcgatgttgt actgcccgca atggcatacg atttaagcca ttggaaaatt
       61 accgttccgc tagacgacaa caaagatggc aaagttgacg aagtggatac caaggcgctg
      121 caaaagtata tgcactcaga ctatttctat gtaaatagcg agggcggatt ggtatttgct
      181 actcctaacc aagccaccac taccagcggc tcgtcaaact cacgcagtga attgcgccaa
      241 atgattcgcg gcaccaatac tagaattgga actaagtcgc caggcaataa ctttgcattg
      301 gcttcgcacc cacaggcaaa agcatttggc gatataggcg gcaacttaaa agctacttta
      361 gcggtaaacc acgttgccct taatgccaaa tatactgata gtttcctgc atactctgtt

```
421 gtagtggggc aaattcacgc cggcaaagat aaagacctaa tcgccaaagg cgaggggtat
481 ggctggggta acgagcctat caaaatctat tacaaaaaat ggcccgatca taaaacgggg
541 tcagtttttt ggacatacga gcgcaaccta gaaaaagcaa atccagatag aaccgatatt
601 gcttatccag tatggggcaa cacttgggat aattcagaaa acccaggcga caaaggcata
661 gcattagatg aatcttttag ctatgagata aacgtgtaca aagacatcat gcacttaacc
721 tttactgcgg cgaataaacc tacagttaaa tacagcatta acctagcaaa caatgtaaat
781 gcttacggca aggtggatga aaaagatcat cctaaaggtt atttaggcga ttggttgtac
841 tttaaagccg gcgcttacga tcagtgtagt gtgaaagatg accctggctt ttggtaccca
901 gcctgcgctg gtaccggcga ttgggaaacc gacaagaaaa acggtgacta cacacgcgta
961 acatttacaa agcttgagct aggtaaaggc tatagcgtaa gcaagtaa
```

AlgF

LOCUS   ZP_00315261   605 aa   linear   BCT 17-JUN-2004
DEFINITION  hypothetical protein Mdeg02003311 [Microbulbifer degradans 2-40].
ACCESSION  ZP_00315261
VERSION  ZP_00315261.1  GI:48861359
DBSOURCE  REFSEQ: accession NZ_AABI03000010.1
KEYWORDS  .
SOURCE  Microbulbifer degradans 2-40
  ORGANISM  Microbulbifer degradans 2-40
    Bacteria; Proteobacteria; Gammaproteobacteria; Alteromonadales;
    Alteromonadaceae; Microbulbifer.
COMMENT  MODEL REFSEQ: This record is predicted by automated computational
    analysis. This record is derived from an annotated genomic sequence
    (NZ_AABI03000010) using gene prediction method: GeneMark.
    Also see:
      Documentation of NCBI's Annotation Process Protein-coding genes were predicted using GeneMark program (kindly
    provided by M. Borodovsky). Functional annotation is based on CDD
    (Conserved Domain Database) and COG (Clusters of Orthologous
    Groups) assignments, it has not yet been subject to manual review.
    DNA sequence and predicted proteins are available for BLAST at
    http://www.ncbi.nlm.nih.gov/sutils/genom_table.cgi.
       URL -- http://www.jgi.doe.gov
    Contact: Paul Richardson
    microbes@cuba.jgi-psf.org.
    Method: conceptual translation.
FEATURES         Location/Qualifiers
    source       1..605
                 /organism="Microbulbifer degradans 2-40"
                 /strain="2-40"
                 /db_xref="taxon:203122"
    Protein      1..605
                 /product="hypothetical protein"
    CDS          1..605
                 /locus_tag="Mdeg02003311"
                 /coded_by="complement(NZ_AABI03000010.1:18670..20487)"
ORIGIN
  1 mgagaliasa slanaatfvl ekvntgfsvd ggngavearq vylwetntnn vnqnwvqish
 61 gggyysykkq ntnlcldggs ggarlqpvtl evcdssnydq hwnkvkvytg teiyrmekrn
121 apgfsidgng gaaarqaiyl wnsnsnnvnq qwefirtded tgdgklaiat afddgsshss
181 ypaskaidgn tawasrwaas gspvnltiql eqtsrvtevg iawgqggsra ytfeiyarpg
241 tsgswtkvfd dvssgstagi evfditdida qqirvktfen tagttwtnit eveiygadgg
301 sssssssss tsstsstsst ssssggfnln pnappssnfn lsqwylsvpt dtdgsgtads
361 ikegelnsgy ennsyfytgs dggmvfkcpi sgyktstgts ytrtelreml ragntsiats
421 gvnknnwvfg sapssaqaaa ggvdgnmkat lavnyvtttg dssqvgrvii gqihaeknep
481 irlyyrklpg nskggiyyah edadggevwv dmigsrsssa snpsdgialn evfsyeidvt
541 nnmltvkiyr dgkstvtsqy nmvnsgydds ddwmyfkagv ynqnntgngs dyvqatfysl
601 ththd

ORIGIN

```
   1 atgggcgcag gtgcgttaat agcttctgcg tcgctcgcga atgctgcaac ttttgtttta
  61 gaaaaggtaa atacagggtt ttccgtcgac ggtggcaacg gcgctgtgga ggcgcgtcag
 121 gtttaccttt gggaaacaaa taccaataac gtcaaccaga actgggttca aattagccat
 181 ggtggcggtt actactccta taaaaaacaa aatacgaatt tatgcttaga cggtggcagt
 241 ggtggtgccc gccttcagcc tgtcacacta gaggtgtgtg attcgagcaa ttacgaccag
 301 cactggaaca aagtgaaagt atacacgggc accgaaattt atcgcatgga aaagcgcaat
 361 gcaccgggtt tctctataga tggtaacggt ggagcggctg caaggcaggc gatttattta
 421 tggaattcaa acagtaataa cgttaaccag cagtgggaat ttattcgcac agatgaagat
 481 acaggtgatg caagcttgc tattgcaact gcatttgacg acggttcaag tcacagcagc
 541 tacccagcat caaaagccat tgacggcaac accgcttggg cttcgcgctg gctgcttct
 601 ggctcgccag taaatctaac tattcagctt gaacaaacta gccgcgtaac tgaagtgggc
 661 attgcatggg ggcagggcgg ctctcgcgcg tatacgttcg aaatctatgc gcgaccaggc
 721 actagcggct cttggacaaa agtgtttgat gatgtgagta gcggttcgac ggcgggtatt
 781 gaagtgtttg atattactga tattgatgct cagcaaattc gagtaaaaac ttttgagaat
 841 actgctggta ccacttggac gaatattacc gaggttgaaa tttatggggc tgatggcggg
 901 tcatctagca gttctagttc atctagctct acgtctagta ctagttctac ttccagcaca
 961 agttctagct cgggcgggtt taacctgaac cctaacgcgc ctccttcaag taattttaac
1021 ctttctcagt ggtacctcag cgtgcctacc gatacagatg gtagcggtac ggcagacagc
1081 attaaagaag gtgagttgaa ctcgggctac gagaataaca gttacttta cacgggttct
1141 gatggtggca tggtatttaa gtgtccaatt tctggctata aacatctac tggtaccagc
1201 tatacgcgca ccgaattgcg tgaaatgttg cgtgcgggta atacatcaat tgctaccagt
1261 ggtgtaaata aaaataactg ggtgtttggt tcggcaccta gcagtgcgca ggcagcggct
1321 ggcggtgttg acggcaacat gaaagcaacc ctagcagtga attatgtaac aaccacgggc
1381 gatagctcac aggtggggcg cgtcattatc ggtcagattc acgccgaaaa aaacgagcct
1441 attcgcctgt actatcgcaa gctacccggt aactctaaag gcggtattta ttacgctcac
1501 gaagatgccg atggcggtga ggtttgggta gatatgattg gttcgcgcag cagtagtgct
1561 tctaatcctt cagatggcat tgcattgaac gaggtgttta gctacgagat tgatgtaact
1621 aacaatatgt taactgtgaa aatttaccgt gatggtaaat caacagtaac aagccagtac
1681 aacatggtta atagtggtta cgacgactcc gacgattgga tgtatttcaa agcgggcgta
1741 tacaatcaga acaatactgg aaatggttca gactatgtgc aagcgacgtt ctactcgctt
1801 acgcatactc acgactag
```

AlgG

LOCUS       ZP_00317486         524 aa         linear   BCT 17-JUN-2004
DEFINITION  hypothetical protein Mdeg02001684 [Microbulbifer degradans 2-40].
ACCESSION   ZP_00317486
VERSION     ZP_00317486.1  GI:48863592
DBSOURCE    REFSEQ: accession NZ_AABI03000002.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000002) using gene prediction method: GeneMark.
            Also see:
               Documentation of NCBI's Annotation Process Method: conceptual translation.
FEATURES             Location/Qualifiers
     source          1..524
                     /organism="Microbulbifer degradans 2-40"
                     /strain="2-40"
                     /db_xref="taxon:203122"
     Protein         1..524
                     /product="hypothetical protein"
     CDS             1..524
                     /locus_tag="Mdeg02001684"
                     /coded_by="complement(NZ_AABI03000002.1:803278..804852)"
ORIGIN
     1  mlkvvikafv vtlsgliisa cgggdskspe ttptptptpt ptptptptpt ptptptptpt
    61  ptptptptpv ectpalstis safddgsndg yvpantiddd ltdesrwssf gdgkwivfdl
   121  aiakdvreih sawykgdtrt sfydiessld avswstlqtn lqsqgttsle avtldstdar
   181  yirvvgrgnt dntwnsliev diydcgetgt ptedpvvvep peppaptdgd mpattpnppl
   241  vtdaldpdaa pssnfdlwpw ylsvptdtdg sgtadsikes dlnagyesse ffytaadggm
   301  vfkcpvagfk tstntsytrv elremlrrgn ssistqgvng nnwvfgsapq sdlnaaggid
   361  gnlratlavn kvttthgdgf eyqvgrviig qihanddepi rlyyrklpsn skgsiyfahe
   421  lldgddtwhe migsrgdnas dpadgialde tfsyeidvrg ntltvtimre gkpdvtkvld
   481  msasgydegg qymyfkagvy nqnnsgdpdd yvqatfyale athn ORIGIN
     1  atgttaaaag tagttatcaa agcctttgtt gtaaccctgt ctggttaat tattagtgcg
    61  tgtggtggtg gcgatagtaa gtcccctgaa accacgccga caccaacgcc gacgccaacg
   121  ccgacaccaa cgccgacacc aacgccgaca ccaacgccaa cgccgacgcc aacgccaacg
   181  ccaacaccaa caccaacacc tacaccggta gagtgtacgc cagcgttaag cactataagc
   241  tctgccttcg acgatggcag taacgatggc tatgtaccgg caaatacaat agatgacgac
   301  ctaaccgatg agtcgcgttg gtcttcgttt ggcgatggca agtggatagt gtttgatctt
   361  gctatcgcaa aagacgtaag agaaatacac agtgcttggt ataaaggtga tactcgcact
   421  agttttttacg acatagaaag ttcgctagat gcggtatctt ggagcacctt gcaaactaac
   481  cttcagtcac aaggtactac aagcctagag gcggtaacgt tagacagcac cgatgcgcgt
   541  tacattcgcg tggttggccg cggcaacacc gacaacacat ggaacagctt gatagaagta
   601  gatatttacg attgtggtga acaggtacg cctaccgaag atcctgttgt agtagagcca

```
 661 ccagagccgc cagcgccaac agatggtgac atgccagcaa ccacgccaaa tccgccgctc
 721 gtaactgacg cgttagaccc agatgccgcg ccatcgagta acttcgattt atggccttgg
 781 tatttaagtg tgccaaccga tacagatggc agcggcactg cagatagtat taaagagtcc
 841 gacctaaacg cgggctacga aagttcggaa tttttttaca cagctgcaga tggcggtatg
 901 gtatttaaat gcccagttgc gggctttaaa acctctacca atacttctta tacgcgcgtg
 961 gagctaagag aaatgttacg cagagggaac agcagtattt ctacccaagg tgtaaatggt
1021 aacaactggg tgtttggttc tgcaccgcaa agcgatttaa acgcagccgg tggaatagac
1081 ggcaacctgc gagccacatt ggccgtaaac aaggtaacca ccacgcacgg cgatggcttt
1141 gaataccaag ttggccgcgt aattattggt caaatacacg cgaacgacga cgagccaatt
1201 cgcttgtact accgcaaatt accttctaat agcaaaggct caatttactt cgcgcacgag
1261 ttgttagatg gtgacgacac ttggcacgaa atgatcggca gccgtggcga caacgctagc
1321 gacccagccg acggtatagc gctagatgaa acgttcagct acgaaataga tgtacgcggc
1381 aacacgctca ctgtaaccat tatgcgtgaa ggcaaacccg acgtaaccaa agtgctagac
1441 atgagcgcca gcggctacga cgaaggcggc cagtacatgt actttaaagc tggcgtgtac
1501 aaccaaaata actcgggcga ccccgatgac tacgtgcaag caactttcta tgcattagag
1561 gccacccaca actag
```

AlgH

```
LOCUS       ZP_00317801        254 aa         linear   BCT 17-JUN-2004
DEFINITION  hypothetical protein Mdeg02000270 [Microbulbifer degradans 2-40].
ACCESSION   ZP_00317801
VERSION     ZP_00317801.1  GI:48863908
DBSOURCE    REFSEQ: accession NZ_AABI03000001.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000001) using gene prediction method: GeneMark.
            Also see:
                Documentation of NCBI's Annotation Process Method: conceptual translation.
FEATURES            Location/Qualifiers
     source         1..254
                    /organism="Microbulbifer degradans 2-40"
                    /strain="2-40"
                    /db_xref="taxon:203122"
     Protein        1..254
                    /product="hypothetical protein"
     CDS            1..254
                    /locus_tag="Mdeg02000270"
                    /coded_by="NZ_AABI03000001.1:320891..321655"
ORIGIN
        1 mpdateylpd wltagnevan tfytspqtga mvfncpthgs ttssatkysr telremlrgl
       61 ntrpstkgig rnnwvlstap hqnqvsaggi dgtleavlsv dyvsqtgpah migrvivgqi
      121 hgeddepvri yyrklphntk gsvyfasehp ggedvfypmi gsssnsaadp edgialgekw
      181 gyrihiegrq lsvriiredg ryveqsltig eaynndwfyf kagvynqnnd gnpdeyaqas
      241 ffklkathkq ynkq ORIGIN
        1 ttgccagacg ccaccgaata cctacctgat tggttaacag cgggcaacga agtggccaac
       61 accttttaca catcccctca aaccggcgcc atggtgttta attgcccaac acacggcagc
      121 accaccagca gcgcgacaaa atattcacgt acagaattaa gggaaatgtt acgagggctg
      181 aatacacgcc cttcaaccaa gggtataggg cggaacaatt gggtgctatc aaccgctcca
      241 caccaaaacc aagtcagtgc aggcggcatc gatggcacct tagaagcagt tctgagcgtt
      301 gattacgtat cccaaactgg gccagcgcat atgataggcc gcgtgatagt ggggcaaatt
      361 cacggtgaag atgacgagcc tgtgcgaatt tattaccgca aactgccgca caacaccaaa
      421 ggctcggtgt attttgcaag cgagcacccc ggcggcgaag atgtgttcta tccaatgata
      481 ggcagtagta gcaatagcgc ggccgaccca gaagatggta tagcgctagg cgaaaagtgg
      541 gggtatcgca ttcatataga aggcaggcag cttagtgtaa gaattattcg cgaagacggg
      601 cgctatgtgg agcaatcact cactatcggc gaagcgtaca ataacgattg gttttacttt
      661 aaagcggggg tatataacca aataatgat ggcaacccag atgaatatgc ccaagcctct
      721 tttttaaac ttaaagcaac acataaacag tataataaac aataa
```

AlgI

LOCUS       ZP_00314832          409 aa          linear   BCT 17-JUN-2004
DEFINITION  hypothetical protein Mdeg02003845 [Microbulbifer degradans 2-40].
ACCESSION   ZP_00314832
VERSION     ZP_00314832.1  GI:48860925
DBSOURCE    REFSEQ: accession NZ_AABI03000015.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000015) using gene prediction method: GeneMark.
            Also see:
                Documentation of NCBI's Annotation Process Protein-coding genes were predicted using GeneMark program (kindly
            provided by M. Borodovsky). Functional annotation is based on CDD
            (Conserved Domain Database) and COG (Clusters of Orthologous
            Groups) assignments, it has not yet been subject to manual review.
            DNA sequence and predicted proteins are available for BLAST at
            http://www.ncbi.nlm.nih.gov/sutils/genom_table.cgi.
                URL -- http://www.jgi.doe.gov
            Contact: Paul Richardson
            microbes@cuba.jgi-psf.org.
            Method: conceptual translation.
FEATURES             Location/Qualifiers
     source          1..409
                     /organism="Microbulbifer degradans 2-40"
                     /strain="2-40"
                     /db_xref="taxon:203122"
     Protein         1..409
                     /product="hypothetical protein"
     CDS             1..409
                     /locus_tag="Mdeg02003845"
                     /coded_by="NZ_AABI03000015.1:43152..44381"
                     /db_xref="CDD:pfam05110"
                     /db_xref="CDD:pfam05955"
ORIGIN
        1 mkkaklirln llyplvatlg latfsaqaev iysngfdglp lgnasdrdik ntwstryakg
       61 pdegrvttvt dshtgkairi kypananqss psgatwetdi ghsgeelyms ywvkfdydfd
      121 fvkggkmpgl agatefpygd ngfttrlmwr edgklefylh gyeinnsqga epyrvfwnya
      181 gyharvipgq whhieirqkl ntpgqrngvl qgwldgvlvc ndsdnsgvrg aghgstklnh
      241 lyfstffggs sapvsqwqpk tdvyanyddf ivsttrigmn gnpgtgssss sssssstss
      301 sssssssss sssggssnct vvpsgsakhe inlnnssclq fnenlrgktf avwdsdsnps
      361 cdfrgtvtst ngtgslnvpd nyeatdsltg tkvsiqpsng ckylkvral ORIGIN
        1 atgaaaaagg ccaaactcat aaggctaaac ctactctacc cgctagtggc taccctaggg
       61 ctagcaacct tctctgcaca agcagaggta atttattcca acggttttga cggcttgccg

```
 121 cttggtaacg ccagcgacag agatataaaa aacacctgga gcacccgcta tgcaaaaggc
 181 ccagacgagg gcagggtaac caccgttacc gattcacata caggcaaagc catacgcatt
 241 aaatacccag ccaatgccaa tcaatcgtcg ccaagtggcg ccacctggga aaccgacata
 301 ggccatagcg gcgaagagct gtatatgtct tactgggtga aatttgatta cgatttcgat
 361 tttgtgaaag gcggtaaaat gcctggctta gcaggcgcca ccgagttccc ctacggcgac
 421 aacggcttta ccacccgctt aatgtggcgc gaagacggca aacttgagtt ttacttgcac
 481 gggtacgaaa taaacaatag ccaaggcgcc gaaccctacc gtgtattttg gaattacgcc
 541 ggttaccacg cacgtgttat acccggccag tggcaccata ttgaaattcg ccaaaaacta
 601 aacaccccag ggcagcgcaa tggcgtattg cagggttggt tagatggtgt attggtatgt
 661 aacgatagcg acaactctgg tgtgcgtggc gctggccacg gcagcaccaa gctaaaccac
 721 ctttactttt ctacctttt tggcgggtcg agcgcgccgg taagccagtg gcaacctaaa
 781 actgatgtgt acgcaaacta cgatgacttt atcgtatcca ccacgcgtat tggtatgaat
 841 ggcaacccgg gcactggttc ttctagttca tcttcaagtt caagcagttc tacttcgagc
 901 tcgtcgtcca gctcttcatc cagctccagc agttcatcgg gcggcagctc taattgtacg
 961 gtggttccca gtggctcggc taagcacgaa ataaacctca acaattccag ctgcttgcag
1021 tttaacgaaa acttacgcgg taaaaccttt gcggtgtggg atagcgacag caacccttct
1081 tgcgacttta gaggcaccgt aacctccact aatggtactg ggtcgctaaa cgtgcccgac
1141 aactacgaag ccaccgattc gctcaccggc accaaagtaa gtattcaacc cagtaatggc
1201 tgtaaatacc taaaagtaag agcgctataa
```

AlgJ

LOCUS      ZP_00316088           1554 aa         linear   BCT 17-JUN-2004
DEFINITION  COG3210: Large exoproteins involved in heme utilization or adhesion
            [Microbulbifer degradans 2-40].
ACCESSION   ZP_00316088
VERSION     ZP_00316088.1  GI:48862191
DBSOURCE    REFSEQ: accession NZ_AABI03000005.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000005) using gene prediction method: GeneMark.
            Also see:
                Documentation of NCBI's Annotation Process Protein-coding genes were predicted using GeneMark program (kindly
            provided by M. Borodovsky). Functional annotation is based on CDD
            (Conserved Domain Database) and COG (Clusters of Orthologous
            Groups) assignments, it has not yet been subject to manual review.
            DNA sequence and predicted proteins are available for BLAST at
            http://www.ncbi.nlm.nih.gov/sutils/genom_table.cgi.
                URL -- http://www.jgi.doe.gov
            Contact: Paul Richardson
            microbes@cuba.jgi-psf.org.
            Method: conceptual translation.
FEATURES            Location/Qualifiers
     source          1..1554
                     /organism="Microbulbifer degradans 2-40"
                     /strain="2-40"
                     /db_xref="taxon:203122"
     Protein         1..1554
                     /product="COG3210: Large exoproteins involved in heme
                     utilization or adhesion"
     CDS             1..1554
                     /locus_tag="Mdeg02002396"
                     /coded_by="complement(NZ_AABI03000005.1:49372..54036)"
                     /db_xref="COG:COG3210"
ORIGIN
    1 mrsvllpvml lssgvalatn aedtnssnny vsysnngygd hasaltfaae nrcsqvltiw
   61 rpahpracps tvtwgevlpg lsigvatqaf drpnrvmysd isvknetgls iaagsklifa
  121 nsslpllnae gqteagqpyl ittqdlpsgq tvtlraefkp rlrplsfdag fdilqvsdgv
  181 vsiagearvv rtltanvsdp agvssavsyq wqangvdiag atsatykltp edeskvitvt
  241 asyiddagfa eniqsnatta vaarnenteg nlqiqgerla gatlravlgd nngiagnaty
  301 hwyvegqaie gatesilylg selvgktita tasytdydey sespsattsh iatsivsseq
  361 elvaalasas ngewialasg eyanmaeiai angvtltagq dgdavisgat cielsgnqsg
  421 lvgltfdnls plfgsacddn nklnsvwvsg dnvtvshnrf lghaedlgsv aeynyvylrg
  481 synviernvf sgknldikga avsvynkgdg segghvvqyn lfkdmpgtsv qssayalqvg
  541 rstgsdglge gqhvvrfnrf dnvmadrrii kvqasrssvy gntivnstgg isledgyent
  601 vsnnvilsag dnsddsgimf spfghtvtgn yiaglkttss qraalllnte tvansgnsal
  661 svsrvtvann tvinsnnaia tytgskcvad tfvasfennl vangvagqga ngadsyafdn

```
721 gcainslesn fsnetyfasg adlvplagsa geatlvatan gllndansla ganasalivl
781 seldvgpgss fvqpvagayn galnldfthw yitfpsgdaq ynpqwlldgy tsenefyyda
841 dgaavfktpn iagttsantk ysrtelremm rgpeqspkpa dwpstqgink nnwvfsnsyq
901 rvqyeaggvd gvmeatlkvd hvsttvtegy eymmgrvivg qihasddepf rlyyrklpgn
961 slgsvyfate vpglgdnryd migdskedsp npldgialge vwsyrveakg ddltvtimre
1021 gkpdvtrtvk taaayandwm yfkagvynqn nggdpsdyaq atfysivvsh dappvepgng
1081 edegnggttt evtdgpslqt ailaasagdt ieigagdyan mgtvvvtdgv titraegsna
1141 visgefclqv sgdgaritgl efadlivpad sanhcrsngd gnivitgddv vfdhnllsgd
1201 aefptpvddd dhnwlvlkgs nalverntfq nrrgiaadgv sqvrggfisi yvngsatgnt
1261 vqynlfkdml lndqstayai mlgrttglds mldgfntiqy nrfdnidskt rvirvqgssn
1321 tishntvvns qgmlalesgq nnvvsynvil psgtdsndgg isaapyghti vgnyiagsnt
1381 tssergaiyl nndvdepgnl aatpsaveia gntiinskqp ihigakgcev gpafianfsn
1441 nliangvsgv sefyegapvs graairysce ldpahsftge ayfsdllynt sgayggglwf
1501 daastfgydg eatliageng lieatgslag kgapsnslvv veetdvgvgs atnf
```

ORIGIN
```
   1 atgagaagtg tattgcttcc agtaatgctt ctgtcttcgg gggtagctct agctactaat
  61 gctgaagata cgaacagttc aaataattat gtttcttata gtaataacgg ttatggcgat
 121 catgctagcg cattaacatt cgctgccgaa aaccgttgtt cgcaagtgct taccatttgg
 181 cggcctgccc atcctcgagc gtgcccttca acagtaacct ggggtgaagt tctgcctggt
 241 ctgtcaattg gtgtagcaac tcaagcattc gatcgaccta atcgcgtaat gtatagcgat
 301 atttcagtta aaaacgaaac gggtttatct attgctgcag gctctaagtt aattttttgcc
 361 aatagttctt taccactttt aaatgccgaa gggcaaacag aagctgggca gccataccctt
 421 ataaccacgc aagatttacc ctctggcaa accgttacgc tgcgcgcaga atttaagccg
 481 cgccttcgtc cgcttagctt tgatgcaggc tttgatatac tgcaagtaag cgacggtgta
 541 gtaagtatcg ctggtgaagc tagggtagtg cgtaccttaa ctgcaaatgt gagtgaccct
 601 gcaggcgtga gttctgccgt tagctatcaa tggcaggcca atgggggtgga tattgctggt
 661 gcaacttctg caacctataa gcttaccccca gaagacgaaa gcaaagttat tactgtcacg
 721 gcatcttata tagatgacgc gggctttgcg gaaaatatcc aatccaatgc aactacggca
 781 gtggccgccc gcaatgaaaa taccgaaggc aacttgcaaa tacagggcga acgcttagct
 841 ggtgcaactt tgcgagccgt gctgggcgac aataacggta tagccggtaa cgctacttat
 901 cattggtatg tagagggcca agctatagag ggtgcgacgg aatctatttt gtaccttggc
 961 agcgagttgg tgggtaaaac cattacagct acggcaagct ataccgacta cgatgaatat
1021 tcagagtcgc cttccgccac tacttcacat attgcaactt caatagtaag tagtgaacaa
1081 gagttggttg cggccttagc gtctgctagt aacggcgaat ggatagcgct cgcgagtggc
1141 gagtatgcca atatggcaga aattgccatt gccaatggcg ttacattaac tgcggccaa
1201 gatggcgatg cggttattag cggtgcgaca tgtatcgaat taagcggcaa tcagtctggg
1261 ctggttggct taacatttga taacttaagt ccattatttg ctccgcatg tgacgacaat
1321 aacaagttaa acagtgtatg ggtgtctggt gataacgtta ccgttagcca taaccgtttt
1381 cttggtcatg ctgaagacct cggtagtgta gccgagtaca actacgttta tttgcgtggc
1441 tcttataatg ttattgagcg caatgtatttt agcggtaaga atctagatat aaaaggcgca
1501 gcagtttctg tctataacaa aggcgacggc agtgaaggtg gtcatgttgt tcagtacaac
1561 ctgttcaaag atatgcctgg cacgagcgtg caatctagcg cttacgcgtt acaggttggc
1621 cgctctacgg gtagcgacgg cttaggtgaa ggtcagcacg ttgtgcgctt taaccgtttc
1681 gataatgtaa tggcagaccg ccgcattatt aaggttcaag ctagccgcag cagcgtatat
1741 ggcaatacca ttgttaattc aaccggtggt atttcgttgg aagacggtta tgaaaatacc
1801 gttagcaata acgttatact ttctgcgggc gataatagcg acgatagcgg cattatgttc
1861 agcccgtttg gtcacactgt tactggcaat tatatcgcag gattaaaaac cacctcttcg
1921 caacgcgcag cgttattgtt aaatacagaa acggttgcca attctggtaa tagtgcacta
1981 agcgttagcc gagtaactgt tgctaacaac actgtaataa acagtaataa tgcaattgct
2041 acttataccg gcagtaagtg tgtggcagat actttgttg ctagtttcga aaataactta
2101 gttgctaacg gcgttgctgg tcaaggggct aatggtgccg acagctatgc gtttgataac
2161 ggttgtgcaa taaactccct agaaagtaac tttagcaacg aaacctattt tgcttcaggt
```

```
2221 gcagatcttg tgccgctagc gggcagtgct ggtgaagcaa ccttagtggc aacggctaat
2281 ggcttattga acgatgctaa ttcactggcg ggcgcaaatg ccagcgcgtt aatagtactt
2341 agcgaattag atgtggggcc tgggtcgagt tttgtgcaac ctgtagcggg tgcttacaac
2401 ggtgctttaa atcttgattt tactcattgg tacatcactt tccctagtgg cgatgcacag
2461 tacaaccctc agtggttact cgatggctat accagtgaaa acgagtttta ctacgacgcc
2521 gatggcgcag ctgtatttaa aacaccaaat atagcgggca ctacatctgc caatacaaaa
2581 tactcgcgta ccgagttgcg tgaaatgatg cgcgggccag agcaaagccc taagccagca
2641 gattggccaa gtacgcaagg cataaacaaa aacaactggg tgttttctaa ctcgtatcag
2701 cgagtgcaat atgaggccgg tggtgtggat ggcgtgatgg aagccacact caaggttgat
2761 catgtgtcta ccactgttac cgaagggtac gagtacatga tggggcgggt tattgttggc
2821 caaattcatg cgtccgacga tgagccattc cgtttgtact atcgcaaatt accgggcaac
2881 agtttggggt ctgtgtattt tgctaccgag gtgccaggct taggcgataa ccgctacgac
2941 atgattggtg atagcaaaga agactcgcca aacccttag atggcattgc gctgggcgaa
3001 gtttggagtt accgcgtaga agctaagggt gatgatttaa ccgttaccat tatgcgtgaa
3061 ggtaaaccag atgttacgcg cacagtaaaa actgctgccg cttacgccaa cgactggatg
3121 tatttaaag cgggggtgta caaccaaaat aatggtggtg atccatcgga ttacgcgcaa
3181 gcaaccttt attccattgt tgtaagtcac gatgcgcccc cagtagaacc gggtaacgg
3241 gaagatgaag gtaatggtgg aacaaccaca gaagttaccg atggcccatc tttgcaaact
3301 gcaattcttg ctgcttctgc aggcgatact atcgagattg gcgcaggtga ctacgccaat
3361 atgggcacag ttgtggttac cgacggggtg accattacac gcgccgaagg cagtaacgct
3421 gttatttctg gcgagttttg tttgcaggtt agtggtgatg gtgcgcgtat tacagggttg
3481 gaatttgcgg atttaattgt acccgcagat agcgctaatc actgccgcag caatggtgat
3541 ggcaatattg taattaccgg tgatgacgta gtgtttgatc acaaccttct gtcgggtgat
3601 gccgaattcc caacacctgt ggacgacgac gaccacaact ggctagtact aaaaggcagt
3661 aacgcactgg ttgagcgcaa cactttcaa aaccgtcgcg gtatagccgc agatggcgta
3721 agccaagtgc gaggtggttt tatttctatc tacgtaaatg gttctgcaac gggtaatact
3781 gtgcaataca acctgtttaa agacatgttg ttgaatgatc agtctactgc gtatgccatt
3841 atgcttggcc gaaccactgg tttagattca atgttagacg ggtttaatac tattcagtac
3901 aaccgtttcg ataatattga ttccaaaacc cgcgtaattc gagtgcaggg tagtagcaat
3961 actattagcc acaacactgt agtcaattcg caaggtatgc tcgcgttaga aagcggtcaa
4021 aataatgttg ttagctacaa cgttattta ccttctggta ccgacagtaa tgatggcggt
4081 atttctgcag cgccatacgg ccataccatt gtgggtaact atattgcagg ctccaacacc
4141 acttccagtg agcgcggtgc catctaccta aataacgacg tggatgagcc aggtaaccctc
4201 gccgctacgc catcggcagt ggaaatagct ggcaacacga ttattaactc taagcaaccc
4261 attcatattg gtgctaaggg ctgcgaagtg ggcccggcgt ttatagcaaa tttcagtaac
4321 aacctaatag cgaacggtgt tagcggtgta tctgaatttt atgaaggtgc gccagtttca
4381 ggtcgagcgg ctattcgtta cagctgtgag ctagaccctg cacactcgtt taccggcgaa
4441 gcctacttta gcgatttgct ttacaacact tcgggtgcgt atggcggtgg cctatggttc
4501 gatgctgcca gcaccttggg ttacgacggc gaggctacgc taatagcagg cgagaatggc
4561 ttaatagaag ctactggttc tctcgctggt aaaggagcgc caagtaattc attagtagtg
4621 gtagaagaga ccgatgtagg tgtgggctct gccaccaatt tttaa
```

AlgK

LOCUS       ZP_00315844         335 aa       linear   BCT 17-JUN-2004
DEFINITION  hypothetical protein Mdeg02002992 [Microbulbifer degradans 2-40].
ACCESSION   ZP_00315844
VERSION     ZP_00315844.1  GI:48861945
DBSOURCE    REFSEQ: accession NZ_AABI03000007.1
KEYWORDS    .
SOURCE      Microbulbifer degradans 2-40
  ORGANISM  Microbulbifer degradans 2-40
            Bacteria; Proteobacteria; Gammaproteobacteria; Alteromonadales;
            Alteromonadaceae; Microbulbifer.
COMMENT     MODEL REFSEQ: This record is predicted by automated computational
            analysis. This record is derived from an annotated genomic sequence
            (NZ_AABI03000007) using gene prediction method: GeneMark.
            Also see:
              Documentation of NCBI's Annotation Process Protein-coding genes were predicted using GeneMark program (kindly
            provided by M. Borodovsky). Functional annotation is based on CDD
            (Conserved Domain Database) and COG (Clusters of Orthologous
            Groups) assignments, it has not yet been subject to manual review.
            DNA sequence and predicted proteins are available for BLAST at
            http://www.ncbi.nlm.nih.gov/sutils/genom_table.cgi.
                URL -- http://www.jgi.doe.gov
            Contact: Paul Richardson
            microbes@cuba.jgi-psf.org.
            Method: conceptual translation.
FEATURES             Location/Qualifiers
     source          1..335
                     /organism="Microbulbifer degradans 2-40"
                     /strain="2-40"
                     /db_xref="taxon:203122"
     Protein         1..335
                     /product="hypothetical protein"
     CDS             1..335
                     /locus_tag="Mdeg02002992"
                     /coded_by="complement(NZ_AABI03000007.1:235866..236873)"
ORIGIN
        1 mqagdvvlpa maydlshwki tvplddnkdg kvdevdtkal qkymhsdyfy vnsegglvfa
       61 tpnqatttsg ssnsrselrq mirgtntrig tkspgnnfal ashpqakafg diggnlkatl
      121 avnhvalnak ytdkfpaysv vvgqihagkd kdliakgegy gwgnepikiy ykkwpdhktg
      181 svfwtyernl ekanpdrtdi aypvwgntwd nsenpgdkgi aldesfsyei nvykdimhlt
      241 ftaankptvk ysinlannvn aygkvdekdh pkgylgdwly fkagaydqcs vkddpgfwyp
      301 acagtgdwet dkkngdytrv tftklelgkg ysvsk ORIGIN
        1 atgcaagcag gcgatgttgt actgcccgca atggcatacg atttaagcca ttggaaaatt
       61 accgttccgc tagacgacaa caaagatggc aaagttgacg aagtggatac caaggcgctg
      121 caaaagtata tgcactcaga ctatttctat gtaaatagcg agggcggatt ggtatttgct
      181 actcctaacc aagccaccac taccagcggc tcgtcaaact cacgcagtga attgcgccaa
      241 atgattcgcg gcaccaatac tagaattgga actaagtcgc caggcaataa ctttgcattg

```
301 gcttcgcacc cacaggcaaa agcatttggc gatataggcg gcaacttaaa agctacttta
361 gcggtaaacc acgttgccct taatgccaaa tatactgata agtttcctgc atactctgtt
421 gtagtggggc aaattcacgc cggcaaagat aaagacctaa tcgccaaagg cgagggtat
481 ggctggggta acgagcctat caaaatctat tacaaaaaat ggcccgatca taaaacgggg
541 tcagtttttt ggacatacga gcgcaaccta gaaaaagcaa atccagatag aaccgatatt
601 gcttatccag tatggggcaa cacttgggat aattcagaaa acccaggcga caaaggcata
661 gcattagatg aatcttttag ctatgagata aacgtgtaca aagacatcat gcacttaacc
721 tttactgcgg cgaataaacc tacagttaaa tacagcatta acctagcaaa caatgtaaat
781 gcttacggca aggtggatga aaaagatcat cctaaaggtt atttaggcga ttggttgtac
841 tttaaagccg gcgcttacga tcagtgtagt gtgaaagatg accctggctt ttggtaccca
901 gcctgcgctg gtaccggcga ttgggaaacc gacaagaaaa acggtgacta cacacgcgta
961 acatttacaa agcttgagct aggtaaaggc tatagcgtaa gcaagtaa
```

Alignment of 2-40 alginase sequence with their best hit alginase,
* indicates identical amino acid, : indicates similar amino acid (SEQ ID NOS 47-68, in order of appearance).

AlgA

```
AlgA          MSHPAQHLVRRGICSLTTGLIISLVTISGCGVKTEKIGTQTSNKPLTISADSANTPITSR
K. pneumoniae MLKSGVMVAS--LCLFS---VPSRAAVPAPGDKFELSG-----WSLSVPVDSDND-----
              *  :   :    * :*  :   .*    *** *    .:...  **.*

AlgA          GIGPALTHATLDPQKPPAINFALTNWKITLPDATEYLPDWLTAGNEVANT-FYTSPQTGA
K. pneumoniae --GKA------D-Q---------------IKEKT------LAAG--YRNSDFFTLSDAGG
                **      * *                 :.* *      *..*  *.:: *.*.*..

AlgA          MVFNCPTHGSTTSSATKYSRTELREMLRGLNTRPSTKGIGRNNWVLSTAPHQNQVSAGGI
K. pneumoniae MVFKAPISGAKTSKNTTYTRSELREMLRKGDTSIATQGVSRNNWVLSSAPLSEQKKAGGV
              ***:. *:*:**.. * * *:*******:* .*: :: *:.*******:** .:*. ***:

AlgA          DGTLEAVLSVDYVSQTGPAHMIGRVIVGQIHGEDDEPVRIYYRKLPHNTKGSVYFASEH-
K. pneumoniae DGTLEATLSVDHVTTTGVNWQVGRVIIGQIHANNDEPIRLYYRKLPHHQKGSVYFAHEPR
              ****** ****:*: **  :  ****:****. :****:*:****** .******  *

AlgA          PG-GEDVFYPMIG----SSSNSAAD---PEDGIALGEKWGYRIHIEGRQLSVRIIREDGR
K. pneumoniae KGFGDEQWYEMIGTLQPSHGNQTAAPTEPEAGIALGETFSYRIDATGNKLTVTLMRE-GR
              .* *:: :* ***    *  *  *    **.******   :*** : *:*:* ::** **

AlgA          --YVEQSLTIGEAYNND--WFYFKAGVYNQNNDGNPDEYAQASFFKLKATHKQYNKQ
K. pneumoniae PDVVKTVDMSKSGYSEAGQYLYFKAGVYNQNKTGKPDDYVQATFYRLKATHGAQR--
                  :.   :  . *.:   : **********: .:**:*.**:*:****.*:::
```

AlgB

```
algB           MKKENVNIAKQGLLVVLVSFFMSFSLMGCAKEILVNSQEQYAEALSSVKPGDTIVLANGE
Pseudomonas sp -----MNYLKKVVLVSFCAFF-SLSLMAQTHPSIMLT----KANVAAVKKG-VNTYPLLR
                   :* :.*:* ***:.:* *. **.  :  *::      *..*:*  * .:: :.

algB           WKDFEIVFTGKGTEKAPITLTAQTKGKVLITGESNLALAGEHLVVSGLVFTNGYTPSDAV
Pseudomonas sp QSYQAVKNAADKALAQPIVVPVPKDG-----G-GGYTHE-QHKKN----YSNMLNCG---
                  : :. .. :   * *.:     .*     * ..  :  * :     :* :  * algB           ISFRAAKPVAEDDYSTVAMHSRVTEVVIDNFSNPER-FETDSWVLIYGKHNRVDHSNFTG
Pseudomonas sp VAYQISGEKKYADYVKNVMLNYASQYGKWPLH-PKRKSEEDGGRIFWQSLNDFVWQLYTI
              ::::   .*  :* .  .*:..   :  :  :   .:*.*. :*:. :*:.  :  :*
```

```
algB          KRNKGVLMAVRLDTTHSRENHHEIDHNYFGPRDILGSNGGETLRIGTSHFSLSDSFTLVE
Pseudomonas sp   QAYDLVYDGIPATDRKTIEEKLFVPILKFFTEDRYDVFN-KIHNHGTWNLAAVGITGYVL
                 :  .*  .:     ::*: :  :  *..:  . ..   .** :::  .      * algB          NNYFDRCNGELEI-ISNKSGSNKFIG--NTFFESRGTLTMRHGHGNVIEN-NVFFGNGKD
Pseudomonas sp   N---KREYVEMAIKGSKKDGKTGYLAQIDQLFSPDGYYMEGPYYQRYALLPFVLFAKAIN
                 *  .*   *.*.  ***..:  .*      *  .:       *.*.  :

algB          HTGGIRVINERQTVRNNYMSDLAGYRFGGGLVVMNGVPNSAINRYHQVKNAVIENNTLVN
Pseudomonas sp   NYEPSRKIFEY---RDKLLSKAIHTSLQTSYTDKTFFP---LN--DAIKDKTYESVELVY
                 :  * **   *:. *   .  : .:*    .* .:    .* . **

algB          -VDHIQLAAGSDKERTATPVDSKFSNNLIVNDDKRNPFTVYDDVSG--ITFSNNS--ISA
Pseudomonas sp   GVD-LAYA---DIKAEVDLLDIARQQNRVIVSDAGLKVAA-DLAAGKAVPFKYQTLWIRD
                 **: .*  .   *    .*  :.*   ..: ..*  ..:  * * algB          ASKELKKGFEVDAAKIAKNDQGMVFDAS--GT-YGASKSLKPVRKQDVGASWFVKSEDRK
Pseudomonas sp   GGKGDEGGLGILRNGPNTDQQCVVLKAASQGMGHGHFDRLN-LLFYDN-TTEIFPDYGAA
                 .*:.   .*:**.*  * * *. *.:  *   :::.. ::.

algB          AFQSGKTVKAG--AGQNSIYDAVEQVEDGGVVELAAGDYVEAKTITINKTVTVKAAAGEK
Pseudomonas sp   RFLNIDTKNGGGYLPENNTWAKQTVAHNALVVDQTS--HFNAKLGPADKASPTLLYFSNQ
                 * ..*. *.*    *.:*: :.::. .  .:**:    .:.*   .* : *.    :::

algB          VNIEFY-KKSLFEVVDGGSLQLEGLA-ISGASSPDDVGNAVVRTSRYSMLKNYRLELKNC
Pseudomonas sp   PNLKVVSAKEDKAYTDVTMLRTSALVKVEGLDKPLLID---VMQAQSAKSHQYDLPFW--
                 *:.  .  * : * *:  : : . **  :*.      :   * .:  :*: *  :   *:

algB          EFTDLDVNRFFNVVSVS--KSTLADNILLENVSVKKVTGSVLKLDLESDDYGIYNAEYVT
Pseudomonas sp   -YKGQLVNTSFPVTAKANQLTALGDKNGYQHIWLNASN----PLEGKSGMVGLLNKNRFY
                 :  ** **:.  *: .:    ..**:   .:  : *:        **  *::  ..

algB          IKNSQFEDVDGPL-ITYYRGGTDESTFGPHFEMTGSTLKNVGNGSKNKLNASLYLHGVQV
Pseudomonas sp   T--THFVS-DNPLEVKLLSIGAND---PEMNLVDGKAFMLSSSGQNQTFVSITETHGG--
                  ::* ***   *..:  . *:.:    .*:.    .* ..  .. ::.  .       **

algB          TAISNNKWLDSKPVIIEHTVGEPVTSVVDNTF-VNTAKLDLQELYSKKTTTAVIKNNTYK
Pseudomonas sp   TDPINETVSSALPTVSGLKLIKSDAQQTIISFKVNERTYTYQINYTEKQQLYIIKIKE--
                 *  *:: . *::.*:    :. ..:*: . :* . **: :  . *. : :  *.**  :

algB          K
Pseudomonas sp   -

AlgC

AlgC          MLSVNTIKNTLLAAVLVSVPATAQVSGNGHPNLIVTEQDVANIAASWESYDAYAEQLNAD
Pseudomonas sp.   ---MNYLKKVVLVSFCAFFSLSLMAQT--HPSIMLTKANVAAVKKGVNTYPLLRQSYQAV
                 .*  .*:.*  :*:**:   . :**    **.:::*: :**:   . ::*   . *:*

AlgC          KTNLDAFMAEGVVVPMPKDAGGGYTHEQHKRNYKAIRNAGFLYQVTGDEKYLTFAKDLLL
Pseudomonas sp.   KNAADKALAQPIVVPVPKDGGGGYTHEQHKKNYSNMLNCGVAYQISGEKKYADYVKNVML
                 *.   .: *: :***:***.*****************:**..: *.*.:**   .*::*
```

```
AlgC            AYAKMYPSLGEHPNRK-EQSPGRLFWQSLNEAVWLVYSIQGYDAIIDGLAAEEKQEIESG
Pseudomonas sp. NYASQYGKWPLHPKRKSEEDGGRIFWQSLNDFVWQLYTIQAYDLVYDGIPATDRKTIEEK
                **.*  .  ****.*:.**.*******.** .*.** **..**..*. ... **.

AlgC            VFLPMAKFLSVESPETFNKIHNHGTWAVAAVGMTGYVLGNDELVEISLMGLDKTGKAGFM
Pseudomonas sp. LFVPILKFFTEDRYDVFNKIHNHGTWNLAAVGITGYVLNKREYVEMAIKGSKKDGKTGYL
                :*.*. **:*...*   ********** :***:*****...* **.:: * *..**..:

AlgC            KQLDKLFSPDGYYTEGPYYQRYALMPFIWFAKAIETNEPERKIFEYRNNILLKAVYTTID
Pseudomonas sp. AQIDQLFSPDGYYMEGPYYQRYALLPFVLFAKAINNYEPSRKIFEYRDKLLSKAIHTSLQ
                .*:*.******** *********:**: *****:. .**.******:: :*.**.:*: :

AlgC            LSYAG-YFFPINDALKDKGIDTVELVHALAIVYS-ITGDNTLLDIAQEQGRISLTGDGLK
Pseudomonas sp. TSYTDKTFFPLNDAIKDKTYESVELVYGVDLAYADIKAEVDLLDIARQQNRVIVSDAGLK
                 **:.  ***:***:***  ::****:.: :.*:  * .: *****:*:.*:: :*.***

AlgC            VAKAVGEGLTQPYNYRSILLGDGADGDQGALSIHRLGEGHNHMALVAKNTSQGMGHGHFD
Pseudomonas sp. VAADLAAGKAVPFKYQTLWIRDGGKGDEGGLGILRNGPNTDQQCVVLKAASQGMGHGHFD
                ** ..  * : *::*:::::**.:**:*.* *:*.*  .::*  *.:.:*********

AlgC            KLNWLLYDNGNEIVTDYGAARYLNVEAKYGGHYLAENNTWAKQTIAHNTLVVNEQSHFYG
Pseudomonas sp. RLNLLFYDNTTEIFPDYGAARFLNIDTKNGGGYLPENNTWAKQTVAHNALVVDQTSHFNA
                :** *:***. **. ******:**::.* ** **.********:***.***::.*** .

AlgC            DVTTADLHHPEVLSFYSGEDYQLSSAKEANAYDGVEFVRSMLLVNVPSLEHPIVVDVLNV
Pseudomonas sp. KLGPADKASPTLLYFSNQPNLKVVSAKEDKAYTDVTMLRTSALVKVEGLDKPLLIDVMQA
                .:. **  .* :* :*.  : :: ****..**..*.::*: ***:* .*::*::.*::

AlgC            SADKASTFDLPLYFNGQIIDFSFKVKDNKNVMKMLGKRNGYQHLWLRNTAPVGDASERAT
Pseudomonas sp. QSAKSHQYDLPFWYKGQLVNTSFPVTAKANQLTALGDKNGYQHIWLNASNPLEGKSGMVG
                 :** *  *** ::.**:::. ** *. : :: :**.:*****:**..:.*: ..*. .

AlgC            WILDDRFYSYAFVTSTPSKKQNVLIAELGANDPNYNLRQQQVLIRRVEKAKQASFVSVLE
Pseudomonas sp. LLNKNRFYTTHFVSDNPLE---VKLLSIGANDPEMNLVDGKAFMLSSSGQNQ-TFVSITE
                :.:.:***: .**:  * :   *: : :*****: **  .:.::   .:.  :***: *

AlgC            PHGKYDGSLETTSGAYSNVKSVKHVSENGKDVVVVVDLKDGSNVVVALSYNANSEQVHKVN
Pseudomonas sp. THGGTDPINETVSSALPTVSGLKLIKSDAQQTIISFKVNERTYTYQINYTEK-QQLYIIK
                .**. *..:**.*.* ...  :* :.*.....:.. .::. :..  :.*  . .*::.

AlgC            AGEEAIEWKGFSSVVVRRK
Pseudomonas sp. IKE----------------
                  *

AlgD

AlgD            301 YGADGGSSSSSSSSSSTSSTSSTSSTSSSSGGFNLNPNAPPSSNFNLSQW
Klebsiella pneumoniae  --------------MLKSGVMVASLCLFSVPSRAAVP--APGDKFELSGW
                              . *  .*   *    * *.* . .*.**

AlgD            351 YLSVPTDTDGSGTADSIKEGELNSGYENNSYFYTGSDGGMVFKCPISGYK
Klebsiella pneumoniae  SLSVPVDSDNDGKADQIKEKTLAAGYRNSDFFTLSDAGGMVFKAPISGAK
```

```
                      ****.*.*.**.***..*..**.*...*...******.****.*

AlgD              401 TSTGTSYTRTELREMLRAGNTSIATSGVNKNNWVFGSAPSSAQAAAGGVD
Klebsiella pneumoniae TSKNTTYTRSELREMLRKGDTSIATQGVSRNNWVLSSAPLSEQKKAGGVD
                      **.*.***.******.*.*****.**..****..***.*.*..*****

AlgD              451 GNMKATLAVNYVTTTGDSSQVGRVIIGQIHAEKNEPIRLYYRKLPGNSKG
Klebsiella pneumoniae GTLEATLSVDHVTTTGVNWQVGRVIIGQIHANNDEPIRLYYRKLPHHQKG
                      *...***.*..***** .************...************..**

AlgD              501 GIYYAHEDADG-G-EVWVDMIGS-------RSSSASNPSDGIALNEVFSY
Klebsiella pneumoniae SVYFAHEPRKGFGDEQWYEMIGTLQPSHGNQTAAPTEPEAGIALGETFSY
                      .*.***.*.*.*.***.       .....**.****.*.***

AlgD              551 EIDVTNNMLTVKIYRDGKSTVTSQYNMVNSGYDDSDDWMYFKAGVYNQNN
Klebsiella pneumoniae RIDATGNKLTVTLMREGRPDVVKTVDMSKSGYSEAGQYLYFKAGVYNQNK
                      **.*.*.***..*.*.*..*.***..........**********.

AlgD              601 TGNGSDYVQATFYSLTHTHD---
Klebsiella pneumoniae TGKPDDYVQATFYRLKATHGAQR
                      **..********.*..**.

AlgE

AlgE                  MLKVVIKAFVVTLSGLIISACGGGDSKSPETTPTPTPTPTPTPTPTPT
Klebsiella pneumoniae -----------------------------------------------

AlgE                  PTPTPTPTPTPTPTPTPTPVECTPALSTISSAFDDGSNDGYVPANTIDDD
Klebsiella pneumoniae --------------------------------------------------

AlgE                  LTDESRWSSFGDGKWIVFDLAIAKDVREIHSAWYKGDTRTSFYDIESSLD
Klebsiella pneumoniae --------------------------------------------------

AlgE                  AVSWSTLQTNLQSQGTTSLEAVTLDSTDARYIRVVGRGNTDNTWNSLIEV
Klebsiella pneumoniae --------------------------------------------------

AlgE                  DIYDCGETGTPTEDPVVVEPPEPPAPTDGDMPATTPNPPLVTDALDPDAA
Klebsiella pneumoniae -----------------------MLKSGVMVASLCLFSVPSRAAVP--A
                                              .***. ..:.*.*.*

AlgE                  PSSNFDLWPWYLSVPTDTDGSGTADSIKESDLNAGYESSEFFYTAADGGM
Klebsiella pneumoniae PGDKFELSGWSLSVPVDSDNDGKADQIKEKTLAAGYRNSDFFTLSDAGGM
                      *..*.*.****.*.*.**.***.****..***.*.**..*.**
```

```
AlgE                 VFKCPVAGFKTSTNTSYTRVELREMLRRGNSSISTQGVNGNNWVFGSAPQ
Klebsiella pneumoniae VFKAPISGAKTSKNTTYTRSELREMLRKGDTSIATQGVSRNNWVLSSAPL
                     *** *..* *** **.*** *******.*..**.**** .****. ***

AlgE                 SDLNAAGGIDGNLRATLAVNKVTTTHGDGFEYQVGRVIIGQIHANDDEPI
Klebsiella pneumoniae SEQKKAGGVDGTLEATLSVDHVTTT---GVNWQVGRVIIGQIHANNDEPI
                     *..***.** * ***.*..**** *..************.****

AlgE                 RLYYRKLPSNSKGSIYFAHELLD--GDDTWHEMIG----SRG---DNASD
Klebsiella pneumoniae RLYYRKLPHHQKGSVYFAHEPRKGFGDEQWYEMIGTLQPSHGNQTAAPTE
                     ********. ***.***** **.*.**** *.*   :::

AlgE                 PADGIALDETFSYEIDVRGNTLTVTIMREGKPDVTKVLDMSASGYDEGGQ
Klebsiella pneumoniae PEAGIALGETFSYRIDATGNKLTVTLMREGRPDVVKTVDMSKSGYSEAGQ
                     * ****.*****.** ** ****.*****.*** ** *** *.* .*.**

AlgE                 YMYFKAGVYNQNNSGDPDDYVQATFYALEATHN---
Klebsiella pneumoniae YLYFKAGVYNQNKTGKPDDYVQATFYRLKATHGAQR
                     *.**********..* **********  *.***.

AlgF

AlgF              751 GEATLVATANGLLNDANSLAGANASALIVLSELDVGPGSSFVQPVAGAYN
Klebsiella pneumoniae --------------------MLKSGVMVASLCLFSVPSRAAVPAPGDKF
                                          *..* ..  * . *.*

AlgF              801 GALNLDFTHWYITFPSG-DAQYNPQWLLDGYTSENEFYYDADGAAVFKTP
Klebsiella pneumoniae ELSGWSLSVPVDSDNDGKADQIKEKTLAAGYRNSDFFTLSDAGGMVFKAP
                       ..: .  * :.  **  ..:  . . * ***.*

AlgF              851 NIAGTTSANTKYSRTELREMMRGPEQSPKPADWPSTQGINKNNWVFSNSY
Klebsiella pneumoniae ISGAKTSKNTTYTRSELREMLRKGDTS-----I-ATQGVSRNNWVLSSAP
                     . ** **.*.*.******.*  *    .***. ****.*  ..

AlgF              901 QRVQYEAGGVDGVMEATLKVDHVSTTVTEGYEYMMGRVIVGQIHASDDEP
Klebsiella pneumoniae LSEQKKAGGVDGTLEATLSVDHVTTT---GVNWQVGRVIIGQIHANNDEP
                     * .****** **.**** **** *.:: .***.***** *****

AlgF              951 FRLYYRKLPGNSLGSVYFATEVP-GLGDNR-YDMIGDSKEDSPN------
Klebsiella pneumoniae IRLYYRKLPHHQKGSVYFAHEPRKGFGDEQWYEMIGTLQPSHGNQTAAPT
                      ********. ****** *  *.**.. *.***   . *

AlgF             1001 -PLDGIALGEVWSYRVEAKGDDLTVTIMREGKPDVTRTVKT-AAAY--AN
Klebsiella pneumoniae EPEAGIALGETFSYRIDATGNKLTVTLMREGRPDVVKTVDMSKSGYSEAG
                     * ******.**.* *. **** ***** *** . . * *

AlgF             1051 DWMYFKAGVYNQNNGGDPSDYAQATFYSIVVSHDAPPVEPGNGEDEGNGG
Klebsiella pneumoniae QYLYFKAGVYNQNKTGKPDDYVQATFYRLKATHPGAQR------------
                     ...**********. * ** ***** .  .* *
```

AlgF            1101 TTTEVTDGPSLQTAILAASAGDTIEIGAGDYANMGTVVVTDGVTITRAEG
Klebsiella pneumoniae   -------------------------------------------------

AlgG

AlgG             501 NVVSMNGTSNPQPPEGGRLLVIDGDGGIIKQAIYKPIAGHVYEITAYVYG
Corynebacterium sp. ALY-1  --------------------------------------------------

AlgG             551 HGTIGIQDLGSDNVYETSTAHGNSWQQISVTYVSTGSPAMLYAKYGPGSG
Corynebacterium sp. ALY-1  ------------------------------------MTLTRKRGLTAA
                                                            *  **  :

AlgG             601 DSYFDVFDAKDISTAEDLSKQPPAPIMRYASQVIDLSWWKITLPINN---
Corynebacterium sp. ALY-1  LTATALLVGSMVVGGSGAAAAEPC---DYPAQQLDLTDWKVTLPIGSSGK
                           :  ::..: ....:  *.  *.*  .. .****..

AlgG             651 AMEIYTPELLTYEIDPWFKLVEDEDGYAVQFRANHGGSTTGGSSNPRSEL
Corynebacterium sp. ALY-1  PSEIEQPALDTFATAPWFQVNAKCTG--VQFRAAVNGVTTSGSGYPRSEL
                           .** .*.*.  ***.    *  *****  *   *****

AlgG             701 RELTQNYHYRNSKSAAAWSNTSGTHEMWIKQKVTHLTYVKPHVVVGQIHD
Corynebacterium sp. ALY-1  REMTD-----GGEEKASWSATSGTHTMVFREAFNHLPEVKPHLVGAQIHD
                           **.*.   .. *. *** * ...   **.*  ****

AlgG             751 SGDDVTVFRVEGHLGQGGDWDNNGTVGVMDTHANIWITNGNDRHGYLVDD
Corynebacterium sp. ALY-1  GDDDVTVFRLE---G-----------------TS-LYITKGDDTHHKLVTS
                           .. *******.*  *          . ...**.*.* * **.

AlgG             801 NYELGTVFTVKFIARDGKVEYEYNGRKLDYVHEESFSGAYFKLGNYTQSH
Corynebacterium sp. ALY-1  DYKLNTVFEGKFVVSGGKIKVYYNG-VLQTTISHTSSGNYFKAGAYTQAN
                           :*.*.* ..  ***.*: .:  ....  * * ***::

AlgG             851 NGTAPGETDDAYAETYVVYDYYIKHTE
Corynebacterium sp. ALY-1  CSNSSPCSSSNYGQVSLYKLQVTHS-
                           ..:. ....:* ..:* ..*:

AlgH

AlgH              1 MKFKSLVALFLLGLLTACGGGSSNPDPDPDPIEEPEGEPEGEPEGEPEGEPEGEPEGEPE
Pseudomonas sp.     -----------------------------------------------------------

AlgH             61 GEPEGEPEGEPQESNFPRGSLGDNDTVPDVVCTQTVNSTSELEDAVSYEMTPGTTLCLAD
Pseudomonas sp.     ---------------------------------------MPGDKVIMKS
                                                              **  :: .

AlgH            121 GNYTNLEIQFGGIGTEANPITVAAANPGMVTIGGEVGIRMSGEYVVLQGLIFKDGESASS
Pseudomonas sp.     GEWKSQFIHFKGKGTAEKPITLTAETKGSVLLTGNSNLKIDGEWLVVDGLSFKNGFSLKD

```
                  *...  *.* * **  .***..*  .* *..*.  .... **..*..** **.* * ..

AlgH           181 D-LIQTRGNSNAPCNNCRITEIAIIDFDQNSDSSGKWVHIYGAHNRVDHSWFSGKTTRGA
Pseudomonas sp.    DVVVFTKTTTNSRLTNTSIENYNPVDK--TLDY--KWVSLYGHHNRVDHCSITGKNHQGT
                   *.::*.:.:*:. * *.: .* * ***.** ******..:**..:**..:.*:.

AlgH           241 LLVVDRYIEDGVDPLDAEIDYAQIDHNYFGDRPPVDGKAYASSGDNEYEGIRIGTSDSHT
Pseudomonas sp.    TLVV--WLDD--KP-----NYHQIDHNYFGPRP-------E-LGANGGETIRIGTSAFSM
                   ***.:..*.  .*  .* ******** **         * *  ******

AlgH           301 GDSFSVIEHNYFERIQGEAEVISNKSGNNRIEHNTVRNSYGSITTRHGSSATITNNFIIG
Pseudomonas sp.    NDSYRTVQNNIFDKCDGEVEIISIKSGFNKILNNLFYECAGTVTFRHGNNSEVSNNYFIA
                    **..:...*.:**.*.**  *** *.** .*  . * *..* ***  ..**..*.

AlgH           361 DGHPYAGGLRIIDDGHTVTNNYIQGARYLATTHHGGIVLMGSDGSTTNGYQQLTNVLVAH
Pseudomonas sp.    NNVTNSGGVRIIGENQKVYGNYLYKVA-GRTLRSAISVMNAYEKPALNDYWQVKNADIQN
                   : . .**:****:...* .**:  .*.   *: .*:.: *. * ::.* *. : :

AlgH           421 NTVVDSVNSLNVDGGQ---KSTNPNNVYLVNNIIANGIGPVITEAADGMPGSSVIAGNIF
Pseudomonas sp.    NIIVGAREAFVLGSGKDNDRTLAPDGVNISNNYIIN---PTTLLVTQDEPKNLKMQNNQV
                   *.*.: .....:. :.*:. *:.** .* **  ....*   * .  .*.

AlgH           481 YGQSFSDSSSSLTSVDGITWLDVAFAADMQGVMRATGSSPDLTAAAADTGDFAAVTLDMDG
Pseudomonas sp.    EGASIVTGFVKMGND-------LQMSDGIWQKKTEIKKPFWLATAIGP----EWKKDHRS
                   * *: .  *     . :* ::..*.  *    ..*..        *   .

AlgH           541 LARAATTQAGADDDIGGNPVRGILNSYDVGPISYRPPMTTPHVAEVDVANYAFDEGAAGW
Pseudomonas sp.    FIFK--------------------------------------------------------
                   :

AlgH           601 TLVDAVVNTNAAEVFARGASVEVTGANGRASQVVSLTANTNYTLTAFVKGTATLAADVGG
Pseudomonas sp.    ------------------------------------------------------------

AlgH           661 TVYRSDVNSSLEYKLATVSFNSGDATSATIYGEVDDFVLNYAPIGEASLDGFPGADTTFW
Pseudomonas sp.    ------------------------------------------------------------

AlgH           721 SVYEGAGIGQVQGSDNSAAGADGSVKFKLEDATEVGTPRISQVLTGLELNTDYTLSMYAL
Pseudomonas sp.    ------------------------------------------------------------

AlgH           781 YKKSADVTVTMGAFVGETDTVLASKVVDFEDLVAANAPKGDDSFRQDTLTFNTGSNSTIT
Pseudomonas sp.    ------------------------------------------------------------

AlgH           841 IFAEYNANTIIADGGDAGDTEFRVDEFALTYEGAPAADAKAYFDEFRLVSHASLAD
Pseudomonas sp.    -------------------------------------------------------
```

AlgI

```
AlgI              MKKIVASLLIGLCSLAVCAETHIYDGKGKETWTKTDLKPGDVVIIPNGTYADLKINVQGK
Pseudomonas sp.   -----------------------------------MPGDKVIMKSGEWKSQFIHFKGK
                                                     ***  **.  *  .   *.  **

AlgI              GEQAKPIVLKAETPGGVVLTGASWLRYWGYFIVVDGFDFNDVTYSMYKNKVRAIIANRRA
Pseudomonas sp.   GTAEKPITLTAETKGSVLLTGNSNLKIDGEWLVVDGLSFKNG-FS-LKDDV--VVFTK--
                  *  *** * ***  * ** ** * *  ..*****.  *  *  * * .   ..  ..

AlgI              GSSSESSKDMCQACVLQRVRIDNENDKAIDTEYKWIELYGYNNVVRYN-YFGAKKSGSRV
Pseudomonas sp.   -TTTNS---R---LTNTSIENYNPVDKTLD--YKWVSLYGHHNRVDHCSITGKNHQGT-T
                   ....*      .  ..  * **.* ***. ***.* * *   *:  . *... .

AlgI              LQVQLKHANAQKLPVSHVIQYNYFASRNAGKAVGNGGEALLVGDSNMQHVDAKVTVANNL
Pseudomonas sp.   LVVWLDDK-----PNYHQIDHNYFGPR--PELGANGGETIRIGTSAFSMNDSYRTVQNNI
                  *  *        *  .   *  *.****..*   **  ***..***. .*   ..**  **. ** **

AlgI              FYDASILGEPEVISNKSSSNIYRSNTVRNTTASLTLRHGNRNTVENNWFLQDQTEGSGGI
Pseudomonas sp.   F-DK-CDGEVEIISIKSGFNKILNNLFYECAGTVTFRHGNNSEVSNNYFIANNVTNSGGV
                  * *  **  ** ** **  *   .  .   ..*****  * **.*   ..  ** *

AlgI              RVIGDDNIIHNNYIAGSAGGGKSAAYRPALGIAAGYSKKDDDANINGYQLSERNVLSNNS
Pseudomonas sp.   RIIGENQKVYGNYLYKVAG----RTLRSAISVMNAYEKP----ALNDYWQVKNADIQNNI
                  *.**..  ** . **   **         * *..  **       * **   .   **

AlgI              VIQSAQPVMLSTWYDRGKLSMTRPPMQTTFINNLVYQLDVAPSTADVVRGLAISVDYTPD
Pseudomonas sp.   IVGAREAFVLGSGKDN--D-RTLAPDGVNISNNYI----INPTT------LLVTQDEPKN
                  .. ....*.  *  .   *  .*  ..**     . **    * .. *    .

AlgI              SEYGNNYGIDKAEYVPSFAKVKGNITDGKVSPLVSKGTKAESKKELKGCDAFGTGDIVYL
Pseudomonas sp.   LKMQNNQ-VEGASIVTGFVK-MGN--DLQMS----------------------DGIWQ
                   .  **  .  *   *  ** **  .  *                          * ..

AlgI              PLKKAGADLSKMDEPLVWTDTVKSARLGPDWLNANWGGEKKAYKGC
Pseudomonas sp.   --KKT-----EIKKP-FWLATA----IGPEWKKDHR---SFIFK--
                  **.   ...  *  *   .**.*         .*
```

AlgJ

```
AlgJ                           -----------------MLA---LSASLTQAATISNSGFESGFDGWTDTD
Pseudoalteromonas sp. IAM14594  MYRFGEIKIMINQKSLFMLAAMTASSSFVQAATINNAGFEDGWSNWNETE
                                                 ***  *.*. ***** .****.*.**..* .*.

AlgJ                           PSALSSDANNGSRSAKITGSAGRVDQDVAVTPNTNYQLTAYVLGSGRVGV
Pseudoalteromonas sp. IAM14594  PAAISGSAYKGSKSLKIQGSPGRVYQNVDVDRNTQYTLSAYVLGKGQIGI
                                *.*.*  *  **.*  ** ** *** *:*.*  **.*  ******.*..*.
```

```
AlgJ                         NTGTAVY-DEAVNTSSWSKVTVNFNSGSANSVEVFGKYNSGTG--RFDDF
Pseudoalteromonas sp. IAM14594  NDLNGLFKNEKFNVSSWTKVSRTFTTANTGTLQVFAKHDKSSNDVRFDNF
                              *   . *  ***.**  *.  .**.** ..    ***.*

AlgJ                         SLVETGTPTPTPTPTPTPAGCNSLNTIDISSATDDGSHDGHGPHLA
Pseudoalteromonas sp. IAM14594  SLTK-GT-----------------------------SG-----G----
                              **. **                                *   *

AlgJ                         VDGDLSADSRWSSKGDGKAITLDLGAEATVRQLKTAWYKGDSRTAYFDVE
Pseudoalteromonas sp. IAM14594  --GDT-----------G-------G--------------GD--T------
                                **         *           ** *              ** *

AlgJ                         TSTDKSNWSTALSNVQSQGSTGLKSNSIDDVTARYVRIVGHGNSSNTWNS
Pseudoalteromonas sp. IAM14594  -------------------GS-----------------GSGIAS---N-
                                                 **            * * .*  *

AlgJ                         LIEAQVLGCAGTVTPTPTPTPTPTPTPTPTPTPSGSKIPESITNSDVW
Pseudoalteromonas sp. IAM14594  ------------------------------------------ITNGSIF
                                                                        ***  .::

AlgJ                         DLEGENPHPLVDPYTLEFVPLEARVTTPNGNGWRHEYKIASSERTAMTAT
Pseudoalteromonas sp. IAM14594  DLEGNNPHPLVNSNTLEFVPLEARHITPNGNGWRHEYKVKESARAAMTET
                              ****.******. ********** . ************. * .*** *

AlgJ                         YEDFSATIKVDLSTGGKTIVAQHHAGDTGTIMKLYVSDTSESGFFDSVAA
Pseudoalteromonas sp. IAM14594  YEVFEATVKVEMSDGGKTIISQHHASDTGTISKVYVSDTDESGFDDSVAG
                              ** * **.**..* *****..**** .***** * .***** **** ****.

AlgJ                         NGIFDVYVRIRNTSGVEEKKPLGTIRSGDSFSFHVLNNYGVVKVSAFGKN
Pseudoalteromonas sp. IAM14594  NGIFDVYVRLRNTSGKEEKHALGTIRSGGSFNLKVVNNYGDVDVTALGTT
                              *********.***** *** .******* **. . **** . *..  ..

AlgJ                         LETEVEDDSASYLKFGNYLQSQYPQGSKDCGSHGDSDSFRACYEDIGITE
Pseudoalteromonas sp. IAM14594  FGIPVEDDSESYFKFGNYLQSQDPYTLDECGESGNSDSFKECFKDLGITK
                               :  *****.**.********* .**  *.  *.*.* .*  *..*:.:

AlgJ                         AKITMTNVSYTRITK
Pseudoalteromonas sp. IAM14594  AKVTMTDVSYTRRTN
                              **.***.***** *.

AlgK

AlgK               MQAGDVVLPAMAYDLSHWKITVPLDDNKDGKVDEVDTKALQKYMHSDYFYVNSEGGLVFA
Vibrio halioticoli  ------MIKKHQITLFIVATVVAVSAN----AASVDYR--QEYKHNDKSYASR----VKV
                          :  *.. .    * . . ** . ** **.* *   *   *   *.

AlgK               TPNQATTTSGSSNSRSELRQMIRGTNTRIGTKSPGNNFALASHPQAKAFGDIGGNLKATL
Vibrio halioticoli  G-----SSVGHHFFSLEAKQTGKPISDWQAAD---NEFVYGYNFKVNKKWRITPSMPITF
                    .*     *.*  :  ..   **.:: ::    *  : * . *  :.: *:

AlgK               AVNHVALNAKYTDKFPAYSVVVGQIHAGKDKDLIAKGEGYGWGNEPIKIYYKKWPDHKTG
```

```
Vibrio halioticoli    G------NDRVTYK-P-------QVRVQYKFD-----SGL-----TSKLRYR----HE--
                       *.***   *:..  *     .*       .*.*.   *:

AlgK              SVFWTYERNLEKANPDRTDIAYPVWGNTWDNSENPGDKGIALDESFSYEINVYKDIMHLT
Vibrio halioticoli  --FRNYTG--DKSDKDSIDRS-KITGN-LD------YKVGALQLGF--EANYAEDFFHD-
                    *.*  .*:.* *  :.**  *   **.* * *.*:..*

AlgK              FTAANKPTVKYSINLANNVNAYGKVDEKDHPKGYLGDWLYFKAGAYDQCSVKDDPGFWYP
Vibrio halioticoli  ----N----EW----------FGGKSAKRH-----NEWDYNVKIGY-KETDWD----WRP
                       *  ::        .*  .**  .*   *   ** **

AlgK              -ACAGTGDWETDKKNGDYTRVTFTKLELGKGYSVSK
Vibrio halioticoli  YIELGNVQYSNGPSVTNSNRQLRTR--VGLTYSF--
                    *.:..... ..* *. *  :* **.
```

What is claimed is:

1. Isolated AlgF comprising SEQ ID NO: 44.
2. A kit comprising a sealed containing AlgF comprising SEQ ID NO:44.

* * * * *